US005872135A

United States Patent [19]
deSolms

[11] Patent Number: 5,872,135
[45] Date of Patent: Feb. 16, 1999

[54] INHIBITORS OF FARNESYL-PROTEIN TRANSFERASE

[75] Inventor: S. Jane deSolms, Norristown, Pa.

[73] Assignee: Merk & Co., Inc., Rahway, N.J.

[21] Appl. No.: 824,936

[22] Filed: Mar. 26, 1997

Related U.S. Application Data

[63] Continuation-in-part of PCT/US95/12474, filed Oct. 27, 1995, and a continuation-in-part of Ser. No. 527,972, Sep. 14, 1995, Pat. No. 5,661,161, which is a continuation-in-part of Ser. No. 472,077, Jun. 6, 1995, abandoned, which is a continuation-in-part of Ser. No. 399,282, Mar. 6, 1995, abandoned, which is a continuation-in-part of Ser. No. 315,161, Sep. 29, 1994, abandoned.

[51] Int. Cl.$^6$ ................ A61K 31/445; C07D 211/32; C07D 211/60; C07D 401/06
[52] U.S. Cl. ................ 514/326; 514/330; 546/210; 546/226
[58] Field of Search ................ 546/210, 225; 514/326, 330

[56] References Cited

U.S. PATENT DOCUMENTS

| | | | |
|---|---|---|---|
| 5,043,268 | 8/1991 | Stock | 435/15 |
| 5,141,851 | 8/1992 | Brown et al. | 435/15 |
| 5,238,922 | 8/1993 | Graham et al. | 514/18 |
| 5,326,773 | 7/1994 | Desolms et al. | 514/331 |
| 5,340,828 | 8/1994 | Graham et al. | 514/357 |
| 5,352,705 | 10/1994 | Deana | 514/630 |
| 5,420,245 | 5/1995 | Brown et al. | 530/328 |
| 5,504,212 | 4/1996 | Desolms et al. | 564/162 |
| 5,686,472 | 11/1997 | Anthony et al. | 514/357 |

FOREIGN PATENT DOCUMENTS

| | | |
|---|---|---|
| 0 456 180 A1 | 11/1991 | European Pat. Off. . |
| 0 618 221 A2 | 10/1994 | European Pat. Off. . |
| 0 675 112 A1 | 10/1995 | European Pat. Off. . |
| 7-112930 | 5/1995 | Japan . |
| 2 130 590 | 6/1984 | United Kingdom . |
| WO 91/16340 | 10/1991 | WIPO . |
| WO 95/09000 | 4/1995 | WIPO . |
| WO 95/09001 | 4/1995 | WIPO . |
| WO 95/11917 | 5/1995 | WIPO . |

OTHER PUBLICATIONS

Gibbs, J.B. et al., "Selective Inhibition of Farnesyl–Protein Transferase Blocks Ras Procesing in Vivo," The Journal of Biological Chemistry, vol. 268, No. 11, pp. 7617–7620 (1993).

Goldstein, J.L. et al., "Nonfarnesylated Tetrapeptide Inhibitors of Protein Farnesyltransferase," The Journal of Biological Chemistry, vol. 266, No. 24, pp.15575–15578 (1991).

James, G.L. et al. Benzodiazepine Peptidomimetic BZA–5B Interrupts the MAP Kinase Activation Pathway in H–Ras–transformed Rat–1 Cells, but Not in Untransformed Cells, The Journal of Biological Chemistry, vol. 269, No. 44, pp. 27705–27714 (1994).

James, G.L. et al., "Benzodiazepine Peptidomimetics: Potent Inhibitors of Ras Farnesylation in Animal Cells", Science, vol. 260, pp. 1937–1942 (1993).

James, G., et al., Polylysine and CVIM Sequences of K–RasB Dictate Specificity of Prenylation and Confer Resistance to Benzodiaepine Peptidomimetic in Vitro, The Journal of Biological Chemistry, vol. 270, No. 11, pp. 6221–6226 (1995).

Kohl, N.E. et al., "Selective Inhibition of ras–Dependent Transformation by a Farnesyltransferase Inhibitor", Science, vol. 260, pp. 1934–1937 (1993)

Kohl, N.E. et al., "Protein farneyltransferase inhibitors block the growth of ras–dependent tumors in nude mice", Proc. Natl. Acad. Sci. USA, Med. Sciences, vol. 91, pp. 9141–9145 (1994).

Kohl, N.E. et al., "Inhibition of farnesyltransferase induces regression of mammary and salivary carcinomas in ras transgenic mice," Nature Medicine, vol. 1, No. 8, pp. 792–797 (1995).

Lorenzino, L.S., et al., "A Peptimomimetic Inhibtor of Farnesyl:Protein Transferase Blocks the Anchorage–dependent and independent Growth of Human Tumor Cell Lines," Cancer Research, 55, pp. 5302–5309 (1995).

Pompliano, D.L., "Steady–State Kinetic Mechanism of Ras Farnesyl:Protein Transferase," Biochemistry, vol. 31, pp. 3800–3807 (1992).

*Primary Examiner*—Richard L. Raymond
*Attorney, Agent, or Firm*—Dianne Pecoraro; David A. Muthard; Mark R. Daniel

[57] ABSTRACT

The present invention comprises analogs of the CAAX motif of the protein Ras that is modified by farnesylation in vivo. These CAAX analogs inhibit farnesyl-protein transferase. Furthermore, these CAAX analogues differ from those previously described as inhibitors of farnesyl-protein transferase in that they do not have a thiol moiety. The lack of the thiol offers unique advantages in terms of improved pharmacokinetic behavior in animals, prevention of thiol-dependent chemical reactions, such as rapid autoxidation and disulfide formation with endogenous thiols, and reduced systemic toxicity. Further contained in this invention are chemotherapeutic compositions containing these farnesyl transferase inhibitors and methods for their production.

26 Claims, No Drawings

INHIBITORS OF FARNESYL-PROTEIN TRANSFERASE

RELATED APPLICATIONS

The present patent application is a continuation-in-part of copending PCT Application No. PCT/US95/12474, filed Oct. 27, 1995, and a continuation-in-part application of application Ser. No. 08/527,972, filed Sep. 14, 1995, now U.S. Pat. No. 5,661,161, which is a continuation-in-part application of Ser. No. 08/472,077, filed Jun. 6, 1995, now abandoned, which is a continuation-in-part application of Ser. No. 08/399,282, filed Mar. 6, 1995, now abandoned, which is a continuation-in-part application Ser. No. 08/315,161, filed Sep. 29, 1994, now abandoned.

BACKGROUND OF THE INVENTION

The Ras protein is part of a signalling pathway that links cell surface growth factor receptors to nuclear signals initiating cellular proliferation. Biological and biochemical studies of Ras action indicate that Ras functions like a G-regulatory protein. In the inactive state, Ras is bound to GDP. Upon growth factor receptor activation Ras is induced to exchange GDP for GTP and undergoes a conformational change. The GTP-bound form of Ras propagates the growth stimulatory signal until the signal is terminated by the intrinsic GTPase activity of Ras, which returns the protein to its inactive GDP bound form (D. R. Lowy and D. M. Willumsen, *Ann. Rev. Biochem.* 62:851–891 (1993)). Mutated ras genes are found in many human cancers, including colorectal carcinoma, exocrine pancreatic carcinoma, and myeloid leukemias. The protein products of these genes are defective in their GTPase activity and constitutively transmit a growth stimulatory signal.

Ras must be localized to the plasma membrane for both normal and oncogenic functions. At least 3 post-translational modifications are involved with Ras membrane localization, and all 3 modifications occur at the C-terminus of Ras. The Ras C-terminus contains a sequence motif termed a "CAAX" or "Cys-Aaa$^1$-Aaa$^2$-Xaa" box (Cys is cysteine, Aaa is an aliphatic amino acid, the Xaa is any amino acid) (Willumsen et al., *Nature* 310:583–586 (1984)). Depending on the specific sequence, this motif serves as a signal sequence for the enzymes farnesyl-protein transferase or geranylgeranyl-protein transferase, which catalyze the alkylation of the cysteine residue of the CAAX motif with a $C_{15}$ or $C_{20}$ isoprenoid, respectively. (S. Clarke., *Ann. Rev. Biochem.* 61:355–386 (1992); W. R. Schafer and J. Rine, *Ann. Rev. Genetics* 30:209–237 (1992)). The Ras protein is one of several proteins that are known to undergo post-translational farnesylation. Other farnesylated proteins include the Ras-related GTP-binding proteins such as Rho, fungal mating factors, the nuclear lamins, and the gamma subunit of transducin. James, et al., *J. Biol. Chem.* 269, 14182 (1994) have identified a peroxisome associated protein Pxf which is also farnesylated. James, et al., have also suggested that there are farnesylated proteins of unknown structure and function in addition to those listed above.

Inhibition of farnesyl-protein transferase has been shown to block the growth of Ras-transformed cells in soft agar and to modify other aspects of their transformed phenotype. It has also been demonstrated that certain inhibitors of farnesyl-protein transferase selectively block the processing of the Ras oncoprotein intracellularly (N. E. Kohl et al., *Science,* 260:1934–1937 (1993) and G. L. James et al., *Science,* 260:1937–1942 (1993). Recently, it has been shown that an inhibitor of farnesyl-protein transferase blocks the growth of ras-dependent tumors in nude mice (N. E. Kohl et al., *Proc. Natl. Acad. Sci U.S.A.,* 91:9141–9145 (1994) and induces regression of mammary and salivary carcinomas in ras transgenic mice (N. E. Kohl et al., *Nature Medicine,* 1:792–797 (1995).

Indirect inhibition of farnesyl-protein transferase in vivo has been demonstrated with lovastatin (Merck & Co., Rahway, N.J.) and compactin (Hancock et al., ibid; Casey et al., ibid; Schafer et al., *Science* 245:379 (1989)). These drugs inhibit HMG-CoA reductase, the rate limiting enzyme for the production of polyisoprenoids including farnesyl pyrophosphate. Farnesyl-protein transferase utilizes farnesyl pyrophosphate to covalently modify the Cys thiol group of the Ras CAAX box with a farnesyl group (Reiss et al., *Cell,* 62:81–88 (1990); Schaber et al., *J. Biol. Chem.,* 265:14701–14704 (1990); Schafer et al., *Science,* 249:1133–1139 (1990); Manne et al., *Proc. Natl. Acad. Sci USA,* 87:7541–7545 (1990)). Inhibition of farnesyl pyrophosphate biosynthesis by inhibiting HMG-CoA reductase blocks Ras membrane localization in cultured cells. However, direct inhibition of farnesyl-protein transferase would be more specific and attended by fewer side effects than would occur with the required dose of a general inhibitor of isoprene biosynthesis.

Inhibitors of farnesyl-protein transferase (FPTase) have been described in two general classes. The first are analogs of farnesyl diphosphate (FPP), while the second class of inhibitors is related to the protein substrates (e.g., Ras) for the enzyme. The peptide derived inhibitors that have been described are generally cysteine containing molecules that are related to the CAAX motif that is the signal for protein prenylation. (Schaber et al., ibid; Reiss et. al., ibid; Reiss et al., *PNAS,* 88:732–736 (1991)). Such inhibitors may inhibit protein prenylation while serving as alternate substrates for the farnesyl-protein transferase enzyme, or may be purely competitive inhibitors (U.S. Pat. No. 5,141,851, University of Texas; N. E. Kohl et al., *Science,* 260:1934–1937 (1993); Graham, et al., *J. Med. Chem.,* 37, 725 (1994)). In general, deletion of the thiol from a CAAX derivative has been shown to dramatically reduce the inhibitory potency of the compound. However, the thiol group potentially places limitations on the therapeutic application of FPTase inhibitors with respect to pharmacokinetics, pharmacodynamics and toxicity. Therefore, a functional replacement for the thiol is desirable.

It has recently been shown that farnesyl-protein transferase inhibitors are inhibitors of proliferation of vascular smooth muscle cells and are therefore useful in the prevention and thereapy of arteriosclerosis and diabetic disturbance of blood vessels (JP H7-112930).

With the exception of the pepticinnamins, non-thiol FPTase inhibitors that are competitive with the Ras substrate have not been described and are the subject of this invention.

It is, therefore, an object of this invention to develop tetrapeptide-based compounds which do not have a thiol moiety, and which will inhibit farnesyl transferase and the post-translational functionalization of the oncogene Ras protein. It is a further object of this invention to develop chemotherapeutic compositions containing the compounds of this invention and methods for producing the compounds of this invention.

SUMMARY OF THE INVENTION

The present invention comprises analogs of the CAAX motif of the protein Ras that is modified by farnesylation in vivo. These CAAX analogs inhibit the farnesyl-protein transferase. Furthermore, these CAAX analogues differ from those previously described as inhibitors of farnesyl-protein transferase in that they do not have a thiol moiety. The lack of the thiol offers unique advantages in terms of improved pharmacokinetic behavior in animals, prevention of thiol-dependent chemical reactions, such as rapid autoxidation and disulfide formation with endogenous thiols, and reduced systemic toxicity. The compounds of the instant invention also incorporate a cyclic amine moiety in the second amino acid position of the motif. Further contained in this invention are chemotherapeutic compositions containing these farnesyl transferase inhibitors and methods for their production.

The compounds of this invention are illustrated by the formulae:

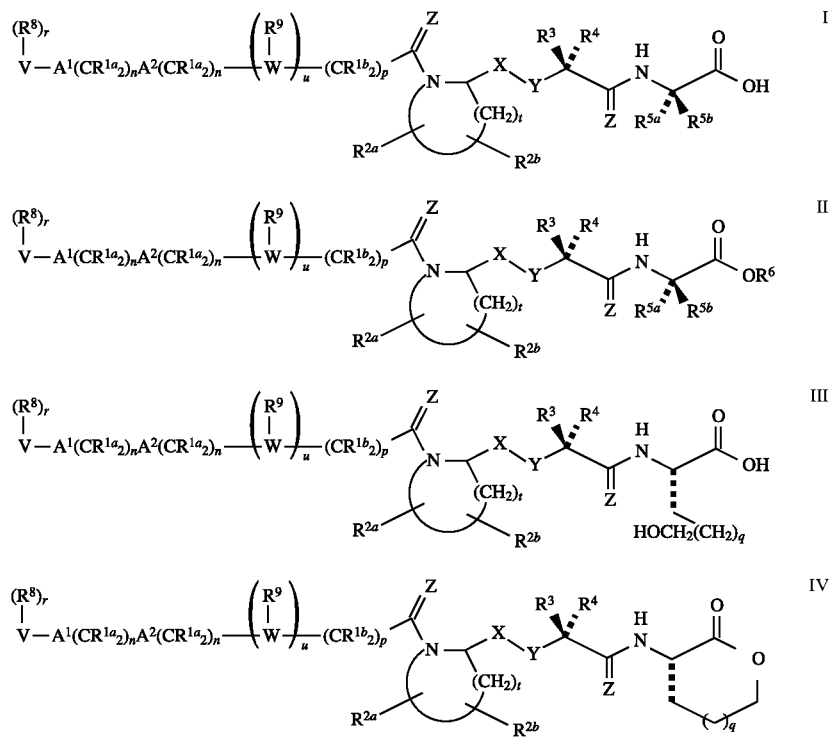

DETAILED DESCRIPTION OF THE INVENTION

The compounds of this invention inhibit farnesyl-protein transferase. In a first embodiment of this invention, the farnesyl-protein transferase inhibitors are illustrated by the formula I:

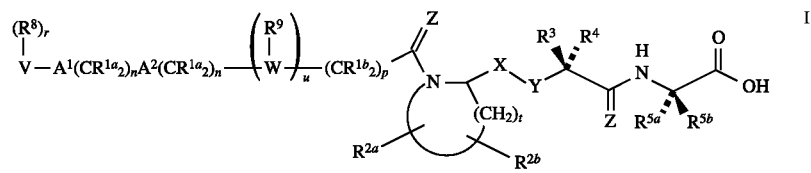

wherein:

$R^{1a}$ and $R^{1b}$ are independently selected from:
 a) hydrogen,
 b) aryl, heterocycle, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)$ $NR^{10}$—, CN, $NO_2$, $(R^{10})_2N$—$C(NR^{10})$—, $R^{10}C(O)$ —, $R^{10}OC(O)$—, $N_3$, —$N(R^{10})_2$, or $R^{11}OC(O)$ $NR^{10}$—, c) $C_1$–$C_6$ alkyl unsubstituted or substituted by aryl, heterocyclic, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)$ $NR^{10}$—, CN, $(R^{10})_2N$—$C(NR^{10})$—, $R^{10}C(O)$—, $R^{10}OC(O)$—, $N_3$, —$N(R^{10})_2$, or $R^{11}OC(O)$— $NR^{10}$—;

$R^{2a}$ and $R^{2b}$ are independently selected from:
 a) hydrogen,
 b) $C_1$–$C_6$ alkyl unsubstituted or substituted by $C_2$–$C_6$ alkenyl, $R^{10}O$—, $R^{11}S(O)_m$—, $R^{10}C(O)NR^{10}$—, CN, $N_3$, $(R^{10})_2N$—$C(NR^{10})$—, $R^{10}C(O)$—, $R^{10}OC(O)$—, —$N(R^{10})_2$, or $R^{11}OC(O)NR^{10}$—, c) aryl, heterocycle, $C_3$–$C_{10}$ cycloalkyl, $C_2$–$C_6$ alkenyl, $R^{10}O$—, $R^{11}S(O)_m$—, $R^{10}C(O)NR^{10}$—, CN, $NO_2$, $(R^{10})_2N$—$C(NR^{10})$—, $R^{10}C(O)$—, $R^{10}OC(O)$—, $N_3$, —$N(R^{10})_2$, or $R^{11}OC(O)NR^{10}$—, and
 d) $C_1$–$C_6$ alkyl substituted with an unsubstituted or substituted group selected from aryl, heterocyclic and $C_3$–$C_{10}$ cycloalkyl;

$R^3$ and $R^4$ are independently selected from:
 a) a side chain of a naturally occurring amino acid,
 b) an oxidized form of a side chain of a naturally occurring amino acid which is:
  i) methionine sulfoxide, or ii) methionine sulfone, and
c) substituted or unsubstituted $C_1$–$C_{20}$ alkyl, $C_2$–$C_{20}$ alkenyl, $C_3$–$C_{10}$ cycloalkyl, aryl or heterocyclic group,
wherein the substituent is selected from F, Cl, Br, $N(R^{10})_2$, $NO_2$, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, $N_3$, —$N(R^{10})_2$, $R^{11}OC(O)NR^{10}$— and $C_1$–$C_{20}$ alkyl, and
d) $C_1$–$C_6$ alkyl substituted with an unsubstituted or substituted group selected from aryl, heterocycle and $C_3$–$C_{10}$ cycloalkyl; or $R^3$ and $R^4$ are combined to form —$(CH_2)_s$—;

$R^{5a}$ and $R^{5b}$ are independently selected from:
a) a side chain of a naturally occurring amino acid,
b) an oxidized form of a side chain of a naturally occurring amino acid which is:
i) methionine sulfoxide, or
ii) methionine sulfone,
c) substituted or unsubstituted $C_1$–$C_{20}$ alkyl, $C_2$–$C_{20}$ alkenyl, $C_3$–$C_{10}$ cycloalkyl, aryl or heterocycle group,
wherein the substituent is selected from F, Cl, Br, $CF_3$, $N(R^{10})_2$, $NO_2$, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, $N_3$, —$N(R^{10})_2$, $R^{11}OC(O)NR^{10}$— and $C_1$–$C_{20}$ alkyl,
d) $C_1$–$C_6$ alkyl substituted with an unsubstituted or substituted group selected from aryl, heterocycle and $C_3$–$C_{10}$ cycloalkyl; or $R^{5a}$ and $R^{5b}$ are combined to form —$(CH_2)_s$— wherein one of the carbon atoms is optionally replaced by a moiety selected from: O, $S(O)_m$, —NC(O)—, and —$N(COR^{10})$—;

X—Y is

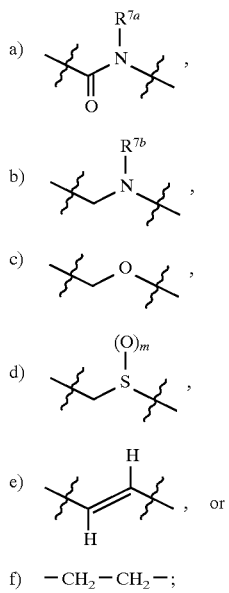

f) —$CH_2$—$CH_2$—;

$R^{7a}$ is selected from
a) hydrogen,
b) unsubstituted or substituted aryl,
c) unsubstituted or substituted heterocycle,
d) unsubstituted or substituted $C_3$–$C_{10}$ cycloalkyl, and
e) $C_1$–$C_6$ alkyl substituted with hydrogen or an unsubstituted or substituted group selected from aryl, heterocycle and $C_3$–$C_{10}$ cycloalkyl;

$R^{7b}$ is selected from
a) hydrogen,
b) unsubstituted or substituted aryl,
c) unsubstituted or substituted heterocycle,
d) unsubstituted or substituted $C_3$–$C_{10}$ cycloalkyl,
e) $C_1$–$C_6$ alkyl substituted with hydrogen or an unsubstituted or substituted group selected from aryl, heterocycle and $C_3$–$C_{10}$ cycloalkyl,
f) a carbonyl group which is bonded to an unsubstituted or substituted group selected from aryl, heterocycle, $C_3$–$C_{10}$ cycloalkyl and $C_1$–$C_6$ alkyl substituted with hydrogen or an unsubstituted or substituted group selected from aryl, heterocycle and $C_3$–$C_{10}$ cycloalkyl, and
g) a sulfonyl group which is bonded to an unsubstituted or substituted group selected from aryl, heterocycle, $C_3$–$C_{10}$ cycloalkyl and $C_1$–$C_6$ alkyl substituted with hydrogen or an unsubstituted or substituted group selected from aryl, heterocycle and $C_3$–$C_{10}$ cycloalkyl;

$R^8$ is independently selected from:
a) hydrogen,
b) aryl, heterocycle, $C_3$–$C_{10}$ cycloalkyl, $C_2$–$C_6$ alkenyl, $C_2$–$C_6$ alkynyl, perfluoroalkyl, F, Cl, Br, $R^{10}O$—, $R^{11}S(O)_m$—, $R^{10}C(O)NR^{10}$—, CN, $NO_2$, $R^{10}_2N$—$C(NR^{10})$—, $R^{10}C(O)$—, $R^{10}OC(O)$—, $N_3$, —$N(R^{10})_2$, or $R^{11}OC(O)NR^{10}$—, and
c) $C_1$–$C_6$ alkyl unsubstituted or substituted by aryl, heterocycle, $C_3$–$C_{10}$ cycloalkyl, $C_2$–$C_6$ alkenyl, $C_2$–$C_6$ alkynyl, perfluoroalkyl, F, Cl, Br, $R^{10}O$—, $R^{11}S(O)_m$—, $R^{10}C(O)NH$—, CN, $H_2N$—$C(NH)$—, $R^{10}C(O)$—, $R^{10}OC(O)$—, $N_3$, —$N(R^{10})_2$, or $R^{10}OC(O)NH$—;

$R^9$ is selected from:
a) hydrogen,
b) $C_2$–$C_6$ alkenyl, $C_2$–$C_6$ alkynyl, perfluoroalkyl, F, Cl, Br, $R^{10}O$—, $R^{11}S(O)_m$—, $R^{10}C(O)NR^{10}$—, CN, $NO_2$, $(R^{10})_2N$—$C$—$(NR^{10})$—, $R^{10}C(O)$—, $R^{10}OC(O)$—, $N_3$, —$N(R^{10})_2$, or $R^{11}OC(O)NR^{10}$—, and
c) $C_1$–$C_6$ alkyl unsubstituted or substituted by perfluoroalkyl, F, Cl, Br, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, $N_3$, —$N(R^{10})_2$, or $R^{11}OC(O)NR^{10}$—;

$R^{10}$ is independently selected from H, $C_1$–$C_6$ alkyl, benzyl, substituted aryl and $C_1$–$C_6$ alkyl substituted with substituted aryl;

$R^{11}$ is independently selected from $C_1$–$C_6$ alkyl and aryl;

$A^1$ and $A^2$ are independently selected from: a bond, —CH═CH—, —C≡C—, —C(O)—, —C(O)NR$^{10}$—, —NR$^{10}$C(O)—, O, —N(R$^{10}$)—, —S(O)$_2$N(R$^{10}$)—, —N(R$^{10}$)S(O)$_2$—, or S(O)$_m$;

V is selected from:
a) hydrogen,
b) heterocycle,
c) aryl,
d) $C_1$–$C_{20}$ alkyl wherein from 0 to 4 carbon atoms are replaced with a a heteroatom selected from O, S, and N, and
e) $C_2$–$C_{20}$ alkenyl, provided that V is not hydrogen if $A^1$ is $S(O)_m$ and V is not hydrogen if
$A^1$ is a bond, n is 0 and $A^2$ is $S(O)_m$;

W is a heterocycle;

Z is independently $H_2$ or O;

m is 0, 1 or 2;

n is 0, 1, 2, 3 or 4;

p is 0, 1, 2, 3 or 4;

r is 0 to 5, provided that r is 0 when V is hydrogen;

s is 4 or 5;

t is 3, 4 or 5; and u is 0 or 1;

or the pharmaceutically acceptable salts thereof.

In a second embodiment of this invention the prodrugs of compounds of formula I are illustrated by the formula II:

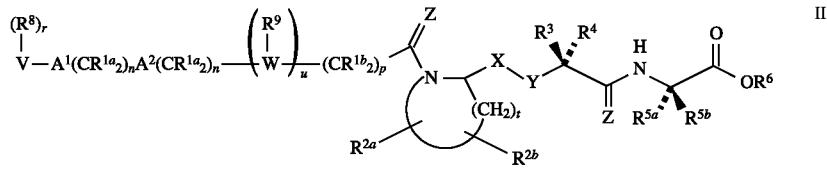

wherein:

$R^{1a}$ and $R^{1b}$ are independently selected from:
a) hydrogen,
b) aryl, heterocycle, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, CN, $NO_2$, $(R^{10})_2N$—$C(NR^{10})$—, $R^{10}C(O)$—, $R^{10}OC(O)$—, $N_3$, —$N(R^{10})_2$, or $R^{11}OC(O)NR^{10}$—,
c) $C_1$–$C_6$ alkyl unsubstituted or substituted by aryl, heterocyclic, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, $N_3$, —$N(R^{10})_2$, or $R^{11}OC(O)NR^{10}$—;

$R^{2a}$ and $R^{2b}$ are independently selected from:
a) hydrogen,
b) $C_1$–$C_6$ alkyl unsubstituted or substituted by $C_2$–$C_6$ alkenyl, $R^{10}O$—, $R^{11}S(O)_m$—, $R^{10}C(O)NR^{10}$—, CN, $N_3$, $(R^{10})_2N$—$C(NR^{10})$—, $R^{10}C(O)$—, $R^{10}OC(O)$—, —$N(R^{10})_2$, or $R^{11}OC(O)NR^{10}$—,
c) aryl, heterocycle, $C_3$–$C_{10}$ cycloalkyl, $C_2$–$C_6$ alkenyl, $R^{10}O$—, $R^{11}S(O)_m$—, $R^{10}C(O)NR^{10}$—, CN, $NO_2$, $(R^{10})_2N$—$C(NR^{10})$—, $R^{10}C(O)$—, $R^{10}OC(O)$—, $N_3$, —$N(R^{10})_2$, or $R^{11}OC(O)NR^{10}$—, and
d) $C_1$–$C_6$ alkyl substituted with an unsubstituted or substituted group selected from aryl, heterocyclic and $C_3$–$C_{10}$ cycloalkyl;

$R^3$ and $R^4$ are independently selected from:
a) a side chain of a naturally occurring amino acid,
b) an oxidized form of a side chain of a naturally occurring amino acid which is:
i) methionine sulfoxide, or
ii) methionine sulfone,
c) substituted or unsubstituted $C_1$–$C_{20}$ alkyl, $C_2$–$C_{20}$ alkenyl, $C_3$–$C_{10}$ cycloalkyl, aryl or heterocyclic group,
wherein the substituent is selected from F, Cl, Br, $N(R^{10})_2$, $NO_2$, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, $N_3$, —$N(R^{10})_2$, $R^{11}OC(O)NR^{10}$— and $C_1$–$C_{20}$ alkyl, and
d) $C_1$–$C_6$ alkyl substituted with an unsubstituted or substituted group selected from aryl, heterocyclic and $C_3$–$C_{10}$ cycloalkyl; or $R^3$ and $R^4$ are combined to form —$(CH_2)_s$—;

$R^{5a}$ and $R^{5b}$ are independently selected from:
a) a side chain of a naturally occurring amino acid,
b) an oxidized form of a side chain of a naturally occurring amino acid which is:
i) methionine sulfoxide, or
ii) methionine sulfone,
c) substituted or unsubstituted $C_1$–$C_{20}$ alkyl, $C_2$–$C_{20}$ alkenyl, $C_3$–$C_{10}$ cycloalkyl, aryl or heterocycle group,
wherein the substituent is selected from F, Cl, Br, $CF_3$, $N(R^{10})_2$, $NO_2$, $R^{10}O$—, $R^{11}S(O)_m$—, $R^{10}C(O)(O)NR^{10}$—, CN, $(R^{10})_2N$—$C(NR^{10})$—, $R^{10}C(O)$—, $R^{10}OC(O)$—, $N_3$, —$N(R^{10})_2$, $R^{11}OC(O)NR^{10}$— and $C_1$–$C_{20}$ alkyl, and
d) $C_1$–$C_6$ alkyl substituted with an unsubstituted or substituted group selected from aryl, heterocycle and $C_3$–$C_{10}$ cycloalkyl; or $R^{5a}$ and $R^{5b}$ are combined to form —$(CH_2)_s$— wherein one of the carbon atoms is optionally replaced by a moiety selected from: O, $S(O)_m$, —$NC(O)$—, and —$N(COR^{10})$—;

$R^6$ is
a) substituted or unsubstituted $C_1$–$C_8$ alkyl, substituted or unsubstituted $C_5$–$C_8$ cycloalkyl, or substituted or unsubstituted cyclic amine, wherein the substituted alkyl, cycloalkyl or cyclic amine is substituted with 1 or 2 substituents independently selected from:
1) $C_1$–$C_6$ alkyl,
2) aryl,
3) heterocycle,
4) —$N(R^{11})_2$,
5) —$OR^{10}$, or
b)

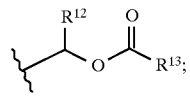

X—Y is a) 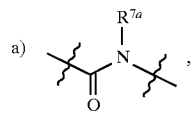

b) 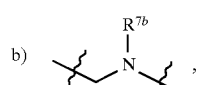

c) 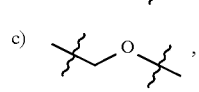

d) 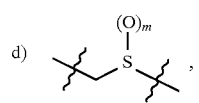

-continued e)

, or f) —CH$_2$—CH$_2$—;

R$^{7a}$ is selected from
  a) hydrogen,
  b) unsubstituted or substituted aryl,
  c) unsubstituted or substituted heterocycle,
  d) unsubstituted or substituted C$_3$–C$_{10}$ cycloalkyl, and
  e) C$_1$–C$_6$ alkyl substituted with hydrogen or an unsubstituted or substituted group selected from aryl, heterocycle and C$_3$–C$_{10}$ cycloalkyl;

R$^{7b}$ is selected from
  a) hydrogen,
  b) unsubstituted or substituted aryl,
  c) unsubstituted or substituted heterocycle,
  d) unsubstituted or substituted C$_3$–C$_{10}$ cycloalkyl,
  e) C$_1$–C$_6$ alkyl substituted with hydrogen or an unsubstituted or substituted group selected from aryl, heterocycle and C$_3$–C$_{10}$ cycloalkyl,
  f) a carbonyl group which is bonded to an unsubstituted or substituted group selected from aryl, heterocycle, C$_3$–C$_{10}$ cycloalkyl and C$_1$–C$_6$ alkyl substituted with hydrogen or an unsubstituted or substituted group selected from aryl, heterocycle and C$_3$–C$_{10}$ cycloalkyl, and
  g) a sulfonyl group which is bonded to an unsubstituted or substituted group selected from aryl, heterocycle, C$_3$–C$_{10}$ cycloalkyl and C$_1$–C$_6$ alkyl substituted with hydrogen or an unsubstituted or substituted group selected from aryl, heterocycle and C$_3$–C$_{10}$ cycloalkyl;

R$^8$ is independently selected from:
  a) hydrogen,
  b) aryl, heterocycle, C$_3$–C$_{10}$ cycloalkyl, C$_2$–C$_6$ alkenyl, C$_2$–C$_6$ alkynyl, perfluoroalkyl, F, Cl, Br, R$^{10}$O—, R$^{11}$S(O)$_m$—, R$^{10}$C(O)NR$^{10}$—, CN, NO$_2$, R$^{10}{}_2$N—C(NR$^{10}$)—, R$^{10}$C(O)—, R$^{10}$OC(O)—, N$_3$, —N(R$^{10}$)$_2$, or R$^{11}$OC(O)NR$^{10}$—, and
  c) C$_1$–C$_6$ alkyl unsubstituted or substituted by aryl, heterocycle, C$_3$–C$_{10}$ cycloalkyl, C$_2$–C$_6$ alkenyl, C$_2$–C$_6$ alkynyl, perfluoroalkyl, F, Cl, Br, R$^{10}$O—, R$^{11}$S(O)$_m$—, R$^{10}$C(O)NH—, CN, H$_2$N—C(NH)—, R$^{10}$C(O)—, R$^{10}$OC(O)—, N$_3$, —N(R$^{10}$)$_2$, or R$^{10}$OC(O)NH—;

R$^9$ is selected from:
  a) hydrogen,
  b) C$_2$–C$_6$ alkenyl, C$_2$–C$_6$ alkynyl, perfluoroalkyl, F, Cl, Br, R$^{10}$O—, R$^{11}$S(O)$_m$—, R$^{10}$C(O)NR$^{10}$—, CN, NO$_2$, (R$^{10}$)$_2$N—C—(NR$^{10}$)—, R$^{10}$C(O)—, R$^{10}$OC(O)—, N$_3$, —N(R$^{10}$)$_2$, or R$^{11}$OC(O)NR$^{10}$—, and
  c) C$_1$–C$_6$ alkyl unsubstituted or substituted by perfluoroalkyl, F, Cl, Br, R$^{10}$O—, R$^{11}$S(O)$_m$—, R$^{10}$C(O)NR$^{10}$—, CN, (R$^{10}$)$_2$N—C(NR$^{10}$)—, R$^{10}$C(O)—, R$^{10}$OC(O)—, N$_3$, —N(R$^{10}$)$_2$, or R$^{11}$OC(O)NR$^{10}$—;

R$^{10}$ is independently selected from H, C$_1$–C$_6$ alkyl, benzyl, substituted aryl and C$_1$–C$_6$ alkyl substituted with substituted aryl;

R$^{11}$ is independently selected from C$_1$–C$_6$ alkyl and aryl;

R$^{12}$ is hydrogen or C$_1$–C$_6$ alkyl;

R$^{13}$ is C$_1$–C$_6$ alkyl;

A$^1$ and A$^2$ are independently selected from: a bond, —CH=CH—, —C≡C—, —C(O)—, —C(O)NR$^{10}$—, —NR$^{10}$C(O)—, O, —N(R$^{10}$)—, —S(O)$_2$N(R$^{10}$)—, —N(R$^{10}$)S(O)$_2$—, or S(O)$_m$;

V is selected from:
  a) hydrogen,
  b) heterocycle,
  c) aryl,
  d) C$_1$–C$_{20}$ alkyl wherein from 0 to 4 carbon atoms are replaced with a a heteroatom selected from O, S, and N, and
  e) C$_2$–C$_{20}$ alkenyl,
provided that V is not hydrogen if A$^1$ is S(O)$_m$ and V is not hydrogen if A$^1$ is a bond, n is 0 and A$^2$ is S(O)$_m$;

W is a heterocycle;

Z is independently H$_2$ or O;

m is 0, 1 or 2;

n is 0, 1, 2, 3 or 4;

p is 0, 1, 2, 3 or 4;

r is 0 to 5, provided that r is 0 when V is hydrogen;

s is 4 or 5;

t is 3, 4 or 5; and u is 0 or 1;

or the pharmaceutically acceptable salts thereof.

In a third embodiment of this invention, the inhibitors of farnesyl-protein transferase are illustrated by the formula III:

wherein:

R$^{1a}$ and R$^{1b}$ are independently selected from:
  a) hydrogen,
  b) aryl, heterocycle, C$_3$–C$_{10}$ cycloalkyl, C$_2$–C$_6$ alkenyl, C$_2$–C$_6$ alkynyl, R$^{10}$O—, R$^{11}$S(O)$_m$—, R$^{10}$C(O)NR$^{10}$—, CN, NO$_2$, (R$^{10}$)$_2$N—C(NR$^{10}$)—, R$^{10}$C(O)—, R$^{10}$OC(O)—, N$_3$, —N(R$^{10}$)$_2$, or R$^{11}$OC(O)NR$^{10}$—,
  c) C$_1$–C$_6$ alkyl unsubstituted or substituted by aryl, heterocyclic, C$_3$–C$_{10}$ cycloalkyl, C$_2$–C$_6$ alkenyl, C$_2$–C$_6$ alkynyl, R$^{10}$O—, R$^{11}$S(O)$_m$—, R$^{10}$C(O)NR$^{10}$—, CN, (R$^{10}$)$_2$N—C(NR$^{10}$)—, R$^{10}$C(O)—, R$^{10}$OC(O)—, N$_3$, —N(R$^{10}$)$_2$, or R$^{11}$OC(O)—NR$^{10}$—;

R$^{2a}$ and R$^{2b}$ are independently selected from:
  a) hydrogen,
  b) C$_1$–C$_6$ alkyl unsubstituted or substituted by C$_2$–C$_6$ alkenyl, R$^{10}$O—, R$^{11}$S(O)$_m$—, R$^{10}$C(O)NR$^{10}$—, CN, N$_3$, (R$^{10}$)$_2$N—C(NR$^{10}$)—, R$^{10}$C(O)—, R$^{10}$OC(O)—, —N(R$^{10}$)$_2$, or R$^{11}$OC(O)NR$^{10}$—, c) aryl, heterocycle, $C_3$–$C_{10}$ cycloalkyl, $C_2$–$C_6$ alkenyl, $R^{10}O$—, $R^{11}S(O)_m$—, $R^{10}C(O)NR^{10}$—, CN, $NO_2$, $(R^{10})_2N$—$C(NR^{10})$—, $R^{10}C(O)$—, $R^{10}OC(O)$—, $N_3$, $N(R^{10})_2$, or $R^{11}OC(O)NR^{10}$—, and d) $C_1$–$C_6$ alkyl substituted with an unsubstituted or substituted group selected from aryl, heterocyclic and $C_3$–$C_{10}$ cycloalkyl;

$R^3$ and $R^4$ are independently selected from:
  a) a side chain of a naturally occurring amino acid,
  b) an oxidized form of a side chain of a naturally occurring amino acid which is:
    i) methionine sulfoxide, or
    ii) methionine sulfone, and
  c) substituted or unsubstituted $C_1$–$C_{20}$ alkyl, $C_2$–$C_{20}$ alkenyl, $C_3$–$C_{10}$ cycloalkyl, aryl or heterocyclic group,
    wherein the substituent is selected from F, Cl, Br, $N(R^{10})_2$, $NO_2$, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, $N_3$, —$N(R^{10})_2$, $R^{11}OC(O)NR^{10}$— and $C_1$–$C_{20}$ alkyl, and
  d) $C_1$–$C_6$ alkyl substituted with an unsubstituted or substituted group selected from aryl, heterocycle and $C_3$–$C_{10}$ cycloalkyl; or $R^3$ and $R^4$ are combined to form —$(CH_2)_s$—;

X—Y is a) 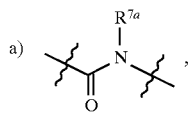, b) 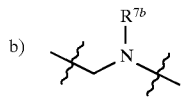, c) 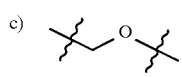, d) 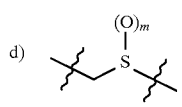, e) 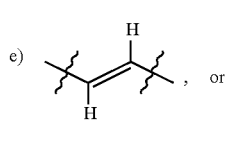, or f) —$CH_2$—$CH_2$—;

$R^{7a}$ is selected from
  a) hydrogen,
  b) unsubstituted or substituted aryl,
  c) unsubstituted or substituted heterocycle,
  d) unsubstituted or substituted $C_3$–$C_{10}$ cycloalkyl, and
  e) $C_1$–$C_6$ alkyl substituted with hydrogen or an unsubstituted or substituted group selected from aryl, heterocycle and $C_3$–$C_{10}$ cycloalkyl;

$R^{7b}$ is selected from
  a) hydrogen,
  b) unsubstituted or substituted aryl,
  c) unsubstituted or substituted heterocycle,
  d) unsubstituted or substituted $C_3$–$C_{10}$ cycloalkyl,
  e) $C_1$–$C_6$ alkyl substituted with hydrogen or an unsubstituted or substituted group selected from aryl, heterocycle and $C_3$–$C_{10}$ cycloalkyl,
  f) a carbonyl group which is bonded to an unsubstituted or substituted group selected from aryl, heterocycle, $C_3$–$C_{10}$ cycloalkyl and $C_1$–$C_6$ alkyl substituted with hydrogen or an unsubstituted or substituted group selected from aryl, heterocycle and $C_3$–$C_{10}$ cycloalkyl, and
  g) a sulfonyl group which is bonded to an unsubstituted or substituted group selected from aryl, heterocycle, $C_3$–$C_{10}$ cycloalkyl and $C_1$–$C_6$ alkyl substituted with hydrogen or an unsubstituted or substituted group selected from aryl, heterocycle and $C_3$–$C_{10}$ cycloalkyl;

$R^8$ is independently selected from:
  a) hydrogen,
  b) aryl, heterocycle, $C_3$–$C_{10}$ cycloalkyl, $C_2$–$C_6$ alkenyl, $C_2$–$C_6$ alkynyl, perfluoroalkyl, F, Cl, Br, $R^{10}O$—, $R^{11}S(O)_m$—, $R^{10}C(O)NR^{10}$—, CN, $NO_2$, $R^{10}_2N$—$C(NR^{10})$—, $R^{10}C(O)$—, $R^{10}OC(O)$—, $N_3$, —$N(R^{10})_2$, or $R^{11}OC(O)NR^{10}$—, and
  c) $C_1$–$C_6$ alkyl unsubstituted or substituted by aryl, heterocycle, $C_3$–$C_{10}$ cycloalkyl, $C_2$–$C_6$ alkenyl, $C_2$–$C_6$ alkynyl, perfluoroalkyl, F, Cl, Br, $R^{10}O$—, $R^{11}S(O)_m$—, $R^{10}C(O)NH$—, CN, $H_2N$—$C(NH)$—, $R^{10}C(O)$—, $R^{10}OC(O)$—, $N_3$, —$N(R^{10})_2$, or $R^{10}OC(O)NH$—;

$R^9$ is selected from:
  a) hydrogen,
  b) $C_2$–$C_6$ alkenyl, $C_2$–$C_6$ alkynyl, perfluoroalkyl, F, Cl, Br, $R^{10}O$—, $R^{11}S(O)_m$—, $R^{10}OC(O)NR^{10}$—, CN, $NO_2$, $(R^{10})_2N$—C—$(NR^{10})$—, $R^{10}C(O)$—, $R^{10}OC(O)$—, $N_3$, —$N(R^{10})_2$, or $R^{11}OC(O)NR^{10}$—, and
  c) $C_1$–$C_6$ alkyl unsubstituted or substituted by perfluoroalkyl, F, Cl, Br, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, $N_3$, —$N(R^{10})_2$, or $R^{11}OC(O)NR^{10}$—;

$R^{10}$ is independently selected from H, $C_1$–$C_6$ alkyl, benzyl, substituted aryl and $C_1$–$C_6$ alkyl substituted with substituted aryl;

$R^{11}$ is independently selected from $C_1$–$C_6$ alkyl and aryl;

$R^{12}$ is hydrogen or $C_1$–$C_6$ alkyl;

$R^{13}$ is $C_1$–$C_6$ alkyl;

$A^1$ and $A^2$ are independently selected from: a bond, —CH=CH—, —C≡C—, —C(O)—, —C(O)NR$^{10}$—, —NR$^{10}$C(O)—, O, —N(R$^{10}$)—, —S(O)$_2$N(R$^{10}$)—, —N(R$^{10}$)S(O)$_2$—, or S(O)$_m$;

V is selected from:
  a) hydrogen,
  b) heterocycle,
  c) aryl,
  d) $C_1$–$C_{20}$ alkyl wherein from 0 to 4 carbon atoms are replaced with a a heteroatom selected from O, S, and N, and
  e) $C_2$–$C_{20}$ alkenyl, provided that V is not hydrogen if $A^1$ is $S(O)_m$ and V is not hydrogen if $A^1$ is a bond, n is 0 and $A^2$ is $S(O)_m$;

W is a heterocycle;

Z is independently $H_2$ or O;

m is 0, 1 or 2;

n is 0, 1, 2, 3 or 4;

p is 0, 1, 2, 3 or 4;

q is 0, 1 or 2;

r is 0 to 5, provided that r is 0 when V is hydrogen;

s is 4 or 5;

t is 3, 4 or 5; and u is 0 or 1;

or the pharmaceutically acceptable salts thereof.

In a fourth embodiment of this invention the prodrugs of compounds of formula III are illustrated by the formula IV:

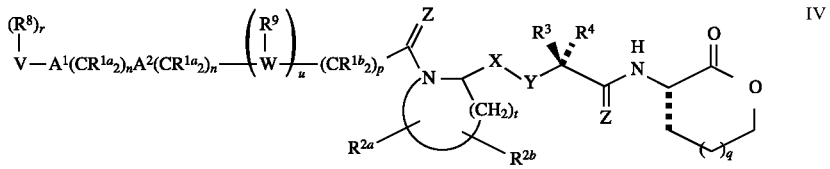

wherein:

$R^{1a}$ and $R^{1b}$ are independently selected from:
a) hydrogen,
b) aryl, heterocycle, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, CN, $NO_2$, $(R^{10})_2N$—$C(NR^{10})$—, $R^{10}C(O)$—, $R^{10}OC(O)$—, $N_3$, —$N(R^{10})_2$, or $R^{11}OC(O)NR^{10}$—,
c) $C_1$–$C_6$ alkyl unsubstituted or substituted by aryl, heterocycle, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, $N_3$, —$N(R^{10})_2$, or $R^{11}OC(O)NR^{10}$—;

$R^{2a}$ and $R^{2b}$ are independently selected from:
a) hydrogen,
b) $C_1$–$C_6$ alkyl unsubstituted or substituted by $C_2$–$C_6$ alkenyl, $R^{10}O$—, $R^{11}S(O)_m$—, $R^{10}C(O)NR^{10}$—, CN, $N_3$, $(R^{10})_2N$—$C(NR^{10})$—, $R^{10}C(O)$—, $R^{10}OC(O)$—, —$N(R^{10})_2$, or $R^{11}OC(O)NR^{10}$—,
c) aryl, heterocycle, $C_3$–$C_{10}$ cycloalkyl, $C_2$–$C_6$ alkenyl, $R^{10}O$—, $R^{11}S(O)_m$—, $R^{10}C(O)NR^{10}$—, CN, $NO_2$, $(R^{10})_2N$—$C(NR^{10})$—, $R^{10}C(O)$—, $R^{10}OC(O)$—, $N_3$, —$N(R^{10})_2$, or $R^{11}OC(O)NR^{10}$—, and
d) $C_1$–$C_6$ alkyl substituted with an unsubstituted or substituted group selected from aryl, heterocyclic and $C_3$–$C_{10}$ cycloalkyl;

$R^3$ and $R^4$ are independently selected from:
a) a side chain of a naturally occurring amino acid,
b) an oxidized form of a side chain of a naturally occurring amino acid which is:
i) methionine sulfoxide, or
ii) methionine sulfone,
c) substituted or unsubstituted $C_1$–$C_{20}$ alkyl, $C_2$–$C_{20}$ alkenyl, $C_3$–$C_{10}$ cycloalkyl, aryl or heterocycle group,
wherein the substituent is selected from F, Cl, Br, $N(R^{10})_2$, $NO_2$, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}C(O)$—, $N_3$, —$N(R^{10})_2$, $R^{11}OC(O)NR^{10}$— and $C_1$–$C_{20}$ alkyl, and
d) $C_1$–$C_6$ alkyl substituted with an unsubstituted or substituted group selected from aryl, heterocycle and $C_3$–$C_{10}$ cycloalkyl; or $R^3$ and $R^4$ are combined to form —$(CH_2)_s$—;

X—Y is a) 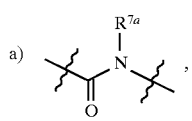

b) 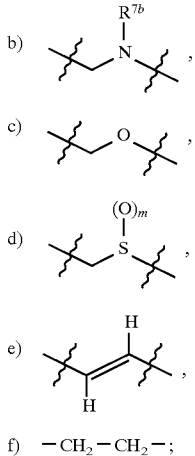

c)

d)

e) , or f) —$CH_2$—$CH_2$—;

$R^{7a}$ is selected from
a) hydrogen,
b) unsubstituted or substituted aryl,
c) unsubstituted or substituted heterocycle,
d) unsubstituted or substituted $C_3$–$C_{10}$ cycloalkyl, and
e) $C_1$–$C_6$ alkyl substituted with hydrogen or an unsubstituted or substituted group selected from aryl, heterocycle and $C_3$–$C_{10}$ cycloalkyl;

$R^{7b}$ is selected from
a) hydrogen,
b) unsubstituted or substituted aryl,
c) unsubstituted or substituted heterocycle,
d) unsubstituted or substituted $C_3$–$C_{10}$ cycloalkyl,
e) $C_1$–$C_6$ alkyl substituted with hydrogen or an unsubstituted or substituted group selected from aryl, heterocycle and $C_3$–$C_{10}$ cycloalkyl,
f) a carbonyl group which is bonded to an unsubstituted or substituted group selected from aryl, heterocycle, $C_3$–$C_{10}$ cycloalkyl and $C_1$–$C_6$ alkyl substituted with hydrogen or an unsubstituted or substituted group selected from aryl, heterocycle and $C_3$–$C_{10}$ cycloalkyl, and
g) a sulfonyl group which is bonded to an unsubstituted or substituted group selected from aryl, heterocycle, $C_3$–$C_{10}$ cycloalkyl and $C_1$–$C_6$ alkyl substituted with hydrogen or an unsubstituted or substituted group selected from aryl, heterocycle and $C_3$–$C_{10}$ cycloalkyl;

$R^8$ is independently selected from:
a) hydrogen,
b) aryl, heterocycle, $C_3$–$C_{10}$ cycloalkyl, $C_2$–$C_6$ alkenyl, $C_2$–$C_6$ alkynyl, perfluoroalkyl, F, Cl, Br, $R^{10}O$—, $R^{11}S(O)_m$—, $R^{10}C(O)NR^{10}$—, CN, $NO_2$, $R^{10}_2N$—$C(NR^{10})$—, $R^{10}C(O)$—, $R^{10}OC(O)$—, $N_3$, —$N(R^{10})_2$, or $R^{11}OC(O)NR^{10}$—, and
c) $C_1$–$C_6$ alkyl unsubstituted or substituted by aryl, heterocycle, $C_3$–$C_{10}$ cycloalkyl, $C_2$–$C_6$ alkenyl, $C_2$–$C_6$ alkynyl, perfluoroalkyl, F, Cl, Br, $R^{10}O$—, $R^{11}S(O)_m$—, $R^{10}C(O)NH$—, CN, $H_2N$—$C(NH)$—, $R^{10}C(O)$—, $R^{10}OC(O)$—, $N_3$, $N(R^{10})_2$, or $R^{10}OC(O)NH$—;

$R^9$ is selected from:
a) hydrogen,
b) $C_2$–$C_6$ alkenyl, $C_2$–$C_6$ alkynyl, perfluoroalkyl, F, Cl, Br, $R^{10}O$—, $R^{11}S(O)_m$—, $R^{10}C(O)NR^{10}$—, CN, $NO_2$, $(R^{10})_2N$—$C$—$(NR^{10})$—, $R^{10}C(O)$—, $R^{10}OC(O)$—, $N_3$, —$N(R^{10})_2$, or $R^{11}OC(O)NR^{10}$—, and
c) $C_1$–$C_6$ alkyl unsubstituted or substituted by perfluoroalkyl, F, Cl, Br, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, $N_3$, —$N(R^{10})_2$, or $R^{11}OC(O)NR^{10}$—;

$R^{10}$ is independently selected from H, $C_1$–$C_6$ alkyl, benzyl, substituted aryl and $C_1$–$C_6$ alkyl substituted with substituted aryl;

$R^{11}$ is independently selected from $C_1$–$C_6$ alkyl and aryl;

$R^{12}$ is hydrogen or $C_1$–$C_6$ alkyl;

$R^{13}$ is $C_1$–$C_6$ alkyl;

$A^1$ and $A^2$ are independently selected from: a bond, —CH=CH—, —C≡C—, —C(O)—, —C(O)$NR^{10}$—, —$NR^{10}C(O)$—, O, —$N(R^{10})$—, —$S(O)_2N(R^{10})$—, —$N(R^{10})S(O)_2$—, or $S(O)_m$;

V is selected from:
a) hydrogen,
b) heterocycle,
c) aryl,
d) $C_1$–$C_{20}$ alkyl wherein from 0 to 4 carbon atoms are replaced with a a heteroatom selected from O, S, and N, and
e) $C_2$–$C_{20}$ alkenyl, provided that V is not hydrogen if $A^1$ is $S(O)_m$ and V is not hydrogen if $A^1$ is a bond, n is 0 and $A^2$ is $S(O)_m$;

W is a heterocycle;

Z is independently $H_2$ or O;

m is 0, 1 or 2;

n is 0, 1, 2, 3 or 4;

p is 0, 1, 2, 3 or 4;

q is 0, 1 or 2;

r is 0 to 5, provided that r is 0 when V is hydrogen;

s is 4 or 5;

t is 3, 4 or 5; and u is 0 or 1;

or the pharmaceutically acceptable salts thereof.

In a more preferred embodiment of this invention, the farnesyl-protein transferase inhibitors are illustrated by the Formula I:

b) aryl, heterocycle, $C_3$–$C_{10}$ cycloalkyl, $R^{10}O$—, —$N(R^{10})_2$ or alkenyl,
c) $C_1$–$C_6$ alkyl unsubstituted or substituted by aryl, heterocycle, cycloalkyl, alkenyl, $R^{10}O$—, or —$N(R^{10})_2$;

$R^{2a}$ is selected from:
a) hydrogen,
b) $C_1$–$C_6$ alkyl unsubstituted or substituted by $C_2$–$C_6$ alkenyl, $R^{10}O$—, $R^{11}S(O)_m$—, $R^{10}C(O)NR^{10}$—, CN, $N_3$, $(R^{10})_2N$— $C(NR^{10})$—, $R^{10}C(O)$—, $R^{10}OC(O)$—, —$N(R^{10})_2$, or $R^{11}OC(O)NR^{10}$—,
c) aryl, heterocycle, $C_3$–$C_{10}$ cycloalkyl, $C_2$–$C_6$ alkenyl, $R^{10}O$—, $R^{11}S(O)_m$—, $R^{10}C(O)NR^{10}$—, CN, $NO_2$, $(R^{10})_2N$—$C(NR^{10})$—, $R^{10}C(O)$—, $R^{10}OC(O)$—, $N_3$, —$N(R^{10})_2$, or $R^{11}OC(O)NR^{10}$—, and
d) $C_1$–$C_6$ alkyl substituted with an unsubstituted or substituted group selected from aryl, heterocyclic and $C_3$–$C_{10}$ cycloalkyl;

$R^{2b}$ is hydrogen;

$R^3$ and $R^4$ are independently selected from:
a) a side chain of a naturally occurring amino acid,
b) an oxidized form of a side chain of a naturally occurring amino acid which is:
 i) methionine sulfoxide, or
 ii) methionine sulfone,
c) substituted or unsubstituted $C_1$–$C_{10}$ alkyl, $C_2$–$C_{10}$ alkenyl, $C_3$–$C_{10}$ cycloalkyl, aryl or heterocyclic group,
 wherein the substituent is selected from F, Cl, Br, $NO_2$, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, $N_3$, —$N(R^{10})_2$, $R^{11}OC(O)NR^{10}$— and $C_1$–$C_{20}$ alkyl, and
d) $C_1$–$C_6$ alkyl substituted with an unsubstituted or substituted group selected from aryl, heterocycle and $C_3$–$C_{10}$ cycloalkyl;

$R^{5a}$ is selected from:
a) a side chain of a naturally occurring amino acid, wherein the amino acid is selected from methionine and glutamine,
b) an oxidized form of a side chain of a naturally occurring amino acid which is:
 i) methionine sulfoxide, or
 ii) methionine sulfone, and
c) substituted or unsubstituted $C_1$–$C_{10}$ alkyl, $C_2$–$C_{10}$ alkenyl, $C_3$–$C_{10}$ cycloalkyl, aryl or heterocyclic group,
 wherein the substituent is selected from F, Cl, Br, $CF_3$, $NO_2$, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, $N_3$, —$N(R^{10})_2$, $R^{11}OC(O)NR^{10}$— and $C_1$–$C_{20}$ alkyl, and

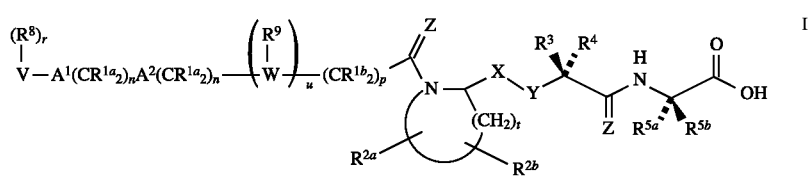

wherein:
$R^{1a}$ is independently selected from: hydrogen or $C_1$–$C_6$ alkyl;
$R^{1b}$ is independently selected from:
a) hydrogen, d) $C_1$–$C_6$ alkyl substituted with an unsubstituted or substituted group selected from aryl, heterocycle and $C_3$–$C_{10}$ cycloalkyl;

$R^{5b}$ is selected from:
a) hydrogen, and b) $C_1$–$C_3$ alkyl;

X—Y is

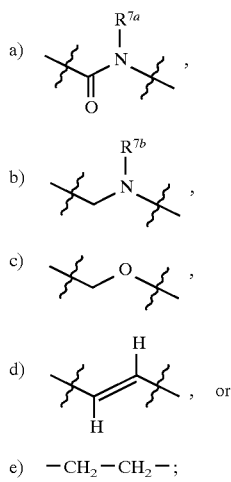

a)

b)

c)

d)

e) $-CH_2-CH_2-$;

$R^{7a}$ is selected from
a) hydrogen,
b) unsubstituted or substituted aryl,
c) unsubstituted or substituted heterocycle,
d) unsubstituted or substituted $C_3$–$C_{10}$ cycloalkyl, and
e) $C_1$–$C_6$ alkyl substituted with hydrogen or an unsubstituted or substituted group selected from aryl, heterocycle and $C_3$–$C_{10}$ cycloalkyl;
wherein heterocycle is selected from pyrrolidinyl, imidazolyl, pyridinyl, thiazolyl, pyridonyl, 2-oxopiperidinyl, indolyl, quinolinyl, isoquinolinyl, and thienyl;

$R^{7b}$ is selected from
a) hydrogen,
b) unsubstituted or substituted aryl,
c) unsubstituted or substituted heterocycle,
d) unsubstituted or substituted $C_3$–$C_{10}$ cycloalkyl,
e) $C_1$–$C_6$ alkyl substituted with hydrogen or an unsubstituted or substituted group selected from aryl, heterocycle and $C_3$–$C_{10}$ cycloalkyl,
f) a carbonyl group which is bonded to an unsubstituted or substituted group selected from aryl, heterocycle, $C_3$–$C_{10}$ cycloalkyl and $C_1$–$C_6$ alkyl substituted with hydrogen or an unsubstituted or substituted group selected from aryl, heterocycle and $C_3$–$C_{10}$ cycloalkyl, and
g) a sulfonyl group which is bonded to an unsubstituted or substituted group selected from aryl, heterocycle, $C_3$–$C_{10}$ cycloalkyl and $C_1$–$C_6$ alkyl substituted with hydrogen or an unsubstituted or substituted group selected from aryl, heterocycle and $C_3$–$C_{10}$ cycloalkyl; wherein heterocycle is selected from pyrrolidinyl, imidazolyl, pyridinyl, thiazolyl, pyridonyl, 2-oxopiperidinyl, indolyl, quinolinyl, isoquinolinyl, and thienyl;

$R^8$ is independently selected from:
a) hydrogen,
b) $C_1$–$C_6$ alkyl, $C_2$–$C_6$ alkenyl, $C_2$–$C_6$ alkynyl, $C_1$–$C_6$ perfluoroalkyl, F, Cl, $R^{10}O$—, $R^{10}C(O)NR^{10}$—, CN, $NO_2$, $(R^{10})_2N$—$C(NR^{10})$—, $R^{10}C(O)$—, $R^{10}OC(O)$—, —$N(R^{10})_2$, or $R^{11}OC(O)NR^{10}$—, and
c) $C_1$–$C_6$ alkyl substituted by $C_1$–$C_6$ perfluoroalkyl, $R^{10}O$—, $R^{10}C(O)NR^{10}$—, $(R^{10})_2N$—$C(NR^{10})$—, $R^{10}C(O)$—, $R^{10}OC(O)$—, —$N(R^{10})_2$, or $R^{11}OC(O)NR^{10}$—;

$R^9$ is selected from:
a) hydrogen,
b) $C_2$–$C_6$ alkenyl, $C_2$–$C_6$ alkynyl, $C_1$–$C_6$ perfluoroalkyl, F, Cl, $R^{10}O$—, $R^{11}S(O)_m$—, $R^{10}C(O)NR^{10}$—, CN, $NO_2$, $(R^{10})_2N$—$C(NR^{10})$—, $R^{10}C(O)$—, $R^{10}OC(O)$—, —$N(R^{10})_2$, or $R^{11}OC(O)NR^{10}$—, and
c) $C_1$–$C_6$ alkyl unsubstituted or substituted by $C_1$–$C_6$ perfluoroalkyl, F, Cl, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, —$N(R^{10})_2$, or $R^{11}OC(O)NR^{10}$—;

$R^{10}$ is independently selected from hydrogen, $C_1$–$C_6$ alkyl, benzyl and aryl;

$R^{11}$ is independently selected from $C_1$–$C_6$ alkyl and aryl;

$A^1$ and $A^2$ are independently selected from: a bond, —CH═CH—, —C≡C—, —C(O)—, C—(O)$NR^{10}$—, O, —$N(R^{10})$—, or $S(O)_m$;

V is selected from:
a) hydrogen,
b) heterocycle selected from pyrrolidinyl, imidazolyl, pyridinyl, thiazolyl, pyridonyl, 2-oxopiperidinyl, indolyl, quinolinyl, isoquinolinyl, and thienyl,
c) aryl,
d) $C_1$–$C_{20}$ alkyl wherein from 0 to 4 carbon atoms are replaced with a a heteroatom selected from O, S, and N, and
e) $C_2$–$C_{20}$ alkenyl, and provided that V is not hydrogen if $A^1$ is $S(O)_m$ and V is not hydrogen if $A^1$ is a bond, n is 0 and $A^2$ is $S(O)_m$;

W is a heterocycle selected from pyrrolidinyl, imidazolyl, pyridinyl, thiazolyl, pyridonyl, 2-oxopiperidinyl, indolyl, quinolinyl, or isoquinolinyl;

Z is independently $H_2$ or O;

m is 0, 1 or 2;

n is 0, 1, 2, 3 or 4;

p is 0, 1, 2, 3 or 4;

r is 0 to 5, provided that r is 0 when V is hydrogen;

t is 3, 4 or 5; and u is 0 or 1;

or the pharmaceutically acceptable salts thereof.

In a second more preferred embodiment of this invention, the prodrugs of the preferred compounds of Formula I are illustrated by the Formula II:

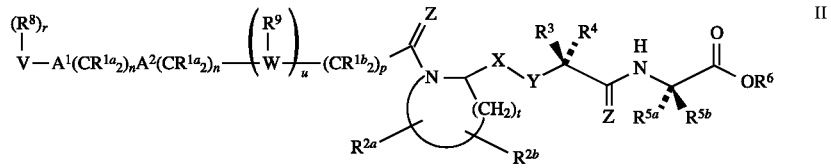

wherein:

$R^{1a}$ is independently selected from: hydrogen or $C_1$–$C_6$ alkyl;

$R^{1b}$ is independently selected from:
a) hydrogen,
b) aryl, heterocycle, $C_3$–$C_{10}$ cycloalkyl, $R^{10}O$—, —$N(R^{10})_2$ or $C_2$–$C_6$ alkenyl,
c) $C_1$–$C_6$ alkyl unsubstituted or substituted by aryl, heterocycle, $C_3$–$C_{10}$ cycloalkyl, $C_2$–$C_6$ alkenyl, $R^{10}O$—, or —$N(R^{10})_2$;

$R^{2a}$ is selected from:
a) hydrogen,
b) $C_1$–$C_6$ alkyl unsubstituted by $C_2$–$C_6$ alkenyl, $R^{10}O$—, $R^{11}S(O)_m$—, $R^{10}C(O)NR^{10}$—, CN, $N_3$, $(R^{10})_2N$—$C(NR^{10})$—, $R^{10}C(O)$—, $R^{10}OC(O)$—, —$N(R^{10})_2$, or $R^{11}OC(O)NR^{10}$—,
c) aryl, heterocycle, $C_3$–$C_{10}$ cycloalkyl, $C_2$–$C_6$ alkenyl, $R^{10}O$—, $R^{11}S(O)_m$—, $R^{10}C(O)NR^{10}$—, CN, $NO_2$, $(R^{10})_2N$—$C(NR^{10})$—, $R^{10}C(O)$—, $R^{10}OC(O)$—, $N_3$, —$N(R^{10})_2$, or $R^{11}OC(O)NR^{10}$—, and
d) $C_1$–$C_6$ alkyl substituted with an unsubstituted or substituted group selected from aryl, heterocyclic and $C_3$–$C_{10}$ cycloalkyl;

$R^{2b}$ is hydrogen;

$R^3$ and $R^4$ are independently selected from:
a) a side chain of a naturally occurring amino acid,
b) an oxidized form of a side chain of a naturally occurring amino acid which is:
 i) methionine sulfoxide, or
 ii) methionine sulfone,
c) substituted or unsubstituted $C_1$–$C_{10}$ alkyl, $C_2$–$C_{10}$ alkenyl, $C_3$–$C_{10}$ cycloalkyl, aryl or heterocyclic group,
wherein the substituent is selected from F, Cl, Br, $NO_2$, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, $N_3$, —$N(R^{10})_2$, $R^{11}OC(O)NR^{10}$— and $C_1$–$C_{20}$ alkyl, and
d) $C_1$–$C_6$ alkyl substituted with an unsubstituted or substituted group selected from aryl, heterocycle and $C_3$–$C_{10}$ cycloalkyl;

$R^{5a}$ is selected from:
a) a side chain of a naturally occurring amino acid, wherein the amino acid is selected from methionine and glutamine,
b) an oxidized form of a side chain of a naturally occurring amino acid which is:
 i) methionine sulfoxide, or
 ii) methionine sulfone, and
c) substituted or unsubstituted $C_1$–$C_{10}$ alkyl, $C_2$–$C_{10}$ alkenyl, $C_3$–$C_{10}$ cycloalkyl, aryl or heterocyclic group,
wherein the substituent is selected from F, Cl, Br, $CF_3$, $NO_2$, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, $N_3$, —$N(R^{10})_2$, $R^{11}OC(O)NR^{10}$— and $C_1$–$C_{20}$ alkyl, and
d) $C_1$–$C_6$ alkyl substituted with an unsubstituted or substituted group selected from aryl, heterocycle and $C_3$–$C_{10}$ cycloalkyl;

$R^{5b}$ is selected from:
a) hydrogen, and
b) $C_1$–$C_3$ alkyl;

$R^6$ is
a) substituted or unsubstituted $C_1$–$C_8$ alkyl, substituted or unsubstituted $C_5$–$C_8$ cycloalkyl, or substituted or unsubstituted cyclic amine wherein the substituted alkyl, cycloalkyl or cyclic amine is substituted with 1 or 2 substituents independently selected from:
1) $C_1$–$C_6$ alkyl,
2) aryl,
3) heterocycle,
4) —$N(R^{11})_2$,
5) –$OR^{10}$, or

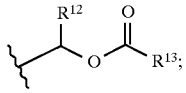

X—Y is

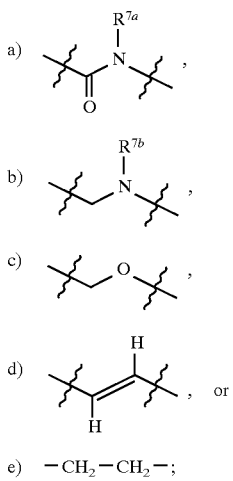

e) —$CH_2$—$CH_2$—;

$R^{7a}$ is selected from
a) hydrogen,
b) unsubstituted or substituted aryl,
c) unsubstituted or substituted heterocycle, d) unsubstituted or substituted $C_3$–$C_{10}$ cycloalkyl, and
e) $C_1$–$C_6$ alkyl substituted with hydrogen or an unsubstituted or substituted group selected from aryl, heterocycle and $C_3$–$C_{10}$ cycloalkyl; wherein heterocycle is selected from pyrrolidinyl, imidazolyl, pyridinyl, thiazolyl, pyridonyl, 2-oxopiperidinyl, indolyl, quinolinyl, isoquinolinyl, and thienyl;

$R^{7b}$ is selected from
a) hydrogen,
b) unsubstituted or substituted aryl,
c) unsubstituted or substituted heterocycle,
d) unsubstituted or substituted $C_3$–$C_{10}$ cycloalkyl,
e) $C_1$–$C_6$ alkyl substituted with hydrogen or an unsubstituted or substituted group selected from aryl, heterocycle and $C_3$–$C_{10}$ cycloalkyl,
f) a carbonyl group which is bonded to an unsubstituted or substituted group selected from aryl, heterocycle, $C_3$–$C_{10}$ cycloalkyl and $C_1$–$C_6$ alkyl substituted with hydrogen or an unsubstituted or substituted group selected from aryl, heterocycle and $C_3$–$C_{10}$ cycloalkyl, and
g) a sulfonyl group which is bonded to an unsubstituted or substituted group selected from aryl, heterocycle, $C_3$–$C_{10}$ cycloalkyl and $C_1$–$C_6$ alkyl substituted with hydrogen or an unsubstituted or substituted group selected from aryl, heterocycle and $C_3$–$C_{10}$ cycloalkyl; wherein heterocycle is selected from pyrrolidinyl, imidazolyl, pyridinyl, thiazolyl, pyridonyl, 2-oxopiperidinyl, indolyl, quinolinyl, isoquinolinyl, and thienyl;

$R^8$ is independently selected from:
a) hydrogen,
b) $C_1$–$C_6$ alkyl, $C_2$–$C_6$ alkenyl, $C_2$–$C_6$ alkynyl, $C_1$–$C_6$ perfluoroalkyl, F, Cl, $R^{10}O$—, $R^{10}C(O)NR^{10}$—, CN, $NO_2$, $(R^{10})_2N$—$C(NR^{10})$—, $R^{10}C(O)$—, $R^{10}OC(O)$—, —$N(R^{10})_2$, or $R^{11}OC(O)NR^{10}$—, and
c) $C_1$–$C_6$ alkyl substituted by $C_1$–$C_6$ perfluoroalkyl, $R^{10}O$—, $R^{10}C(O)NR^{10}$—, $(R^{10})_2N$—$C(NR^{10})$—, $R^{10}C(O)$—, $R^{10}OC(O)$—, —$N(R^{10})_2$, or $R^{11}OC(O)NR^{10}$—;

$R^9$ is selected from:
a) hydrogen,
b) $C_2$–$C_6$ alkenyl, $C_2$–$C_6$ alkynyl, $C_1$–$C_6$ perfluoroalkyl, F, Cl, $R^{10}O$—, $R^{11}S(O)_m$—, $R^{10}C(O)NR^{10}$—, CN, $NO_2$, $(R^{10})_2N$—$C(NR^{10})$—, $R^{10}C(O)$—, $R^{10}OC(O)$—, —$N(R^{10})_2$, or $R^{11}OC(O)NR^{10}$—, and
c) $C_1$–$C_6$ alkyl unsubstituted or substituted by $C_1$–$C_6$ perfluoroalkyl, F, Cl, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, —$N(R^{10})_2$, or $R^{11}OC(O)NR^{10}$—;

$R^{10}$ is independently selected from hydrogen, $C_1$–$C_6$ alkyl, benzyl and aryl;
$R^{11}$ is independently selected from $C_1$–$C_6$ alkyl and aryl;
$R^{12}$ is hydrogen or $C_1$–$C_6$ alkyl;
$R^{13}$ is 1,1-dimethylethyl;
$A^1$ and $A^2$ are independently selected from: a bond, —CH=CH—, —C≡C—, —C(O)—, —C(O)NR^{10}—, O, —N(R^{10})—, or $S(O)_m$;

V is selected from:
a) hydrogen,
b) heterocycle selected from pyrrolidinyl, imidazolyl, pyridinyl, thiazolyl, pyridonyl, 2-oxopiperidinyl, indolyl, quinolinyl, isoquinolinyl, and thienyl,
c) aryl,
d) $C_1$–$C_{20}$ alkyl wherein from 0 to 4 carbon atoms are replaced with a a heteroatom selected from O, S, and N,
e) $C_2$–$C_{20}$ alkenyl, and
provided that V is not hydrogen if $A^1$ is $S(O)_m$ and V is not hydrogen if
$A^1$ is a bond, n is 0 and $A^2$ is $S(O)_m$;

W is a heterocycle selected from pyrrolidinyl, imidazolyl, pyridinyl, thiazolyl, pyridonyl, 2-oxopiperidinyl, indolyl, quinolinyl, or isoquinolinyl;
Z is independently $H_2$ or O;
m is 0, 1 or 2;
n is 0, 1, 2, 3 or 4;
p is 0, 1, 2, 3 or 4;
r is 0 to 5, provided that r is 0 when V is hydrogen;
t is 3, 4 or 5; and
u is 0 or 1;
or the pharmaceutically acceptable salts thereof.

In a third more preferred embodiment of this invention, the inhibitors of farnesyl-protein transferase are illustrated by the formula III:

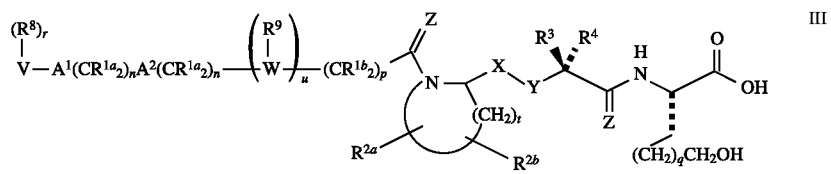

wherein:
$R^{1a}$ is independently selected from: hydrogen or $C_1$–$C_6$ alkyl;
$R^{1b}$ is independently selected from:
a) hydrogen,
b) aryl, heterocycle, $C_3$–$C_{10}$ cycloalkyl, $R^{10}O$—, —$N(R^{10})_2$ or $C_2$–$C_6$ alkenyl,
c) $C_1$–$C_6$ alkyl unsubstituted or substituted by aryl, heterocycle, cycloalkyl, alkenyl, $R^{10}O$—, or —$N(R^{10})_2$;

$R^{2a}$ is selected from:
a) hydrogen,
b) $C_1$–$C_6$ alkyl unsubstituted or substituted by $C_2$–$C_6$ alkenyl, $R^{10}O$—, $R^{11}S(O)_m$—, $R^{10}C(O)NR^{10}$—, CN, $N_3$, $(R^{10})_2N$—$C(NR^{10})$—, $R^{10}C(O)$—, $R^{10}OC(O)$—, —$N(R^{10})_2$, or $R^{11}OC(O)NR^{10}$—,
c) aryl, heterocycle, $C_3$–$C_{10}$ cycloalkyl, $C_2$–$C_6$ alkenyl, $R^{10}O$—, $R^{11}S(O)_m$—, $R^{10}C(O)NR^{10}$—, CN, $NO_2$, $(R^{10})_2N$—$C(NR^{10})$—, $R^{10}C(O)$—, $R^{10}OC(O)$—, $N_3$, —$N(R^{10})_2$, or $R^{11}OC(O)NR^{10}$—, and
d) $C_1$–$C_6$ alkyl substituted with an unsubstituted or substituted group selected from aryl, heterocyclic and $C_3$–$C_{10}$ cycloalkyl;

$R^{2b}$ is hydrogen;
$R^3$ and $R^4$ are independently selected from:
a) a side chain of a naturally occurring amino acid,
b) an oxidized form of a side chain of a naturally occurring amino acid which is:
i) methionine sulfoxide, or
ii) methionine sulfone,
c) substituted or unsubstituted $C_1$–$C_{10}$ alkyl, $C_2$–$C_{10}$ alkenyl, $C_3$–$C_{10}$ cycloalkyl, aryl or heterocycle group,
wherein the substituent is selected from F, Cl, Br, —$NO_2$, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, $N_3$, —$N(R^{10})_2$, $R^{11}OC(O)NR^{10}$— and $C_1$–$C_{20}$ alkyl, and
d) $C_1$–$C_6$ alkyl substituted with an unsubstituted or substituted group selected from aryl, heterocycle and $C_3$–$C_{10}$ cycloalkyl;

X—Y is a) 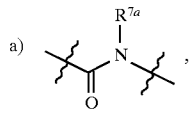

b) 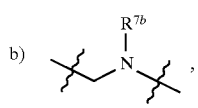

-continued c) [structure: CH2-O-C branched]

d) [structure: C=C with H's, trans alkene]

e) —CH$_2$—CH$_2$—;

R$^{7a}$ is selected from
  a) hydrogen,
  b) unsubstituted or substituted aryl,
  c) unsubstituted or substituted heterocycle,
  d) unsubstituted or substituted C$_3$–C$_{10}$ cycloalkyl, and
  e) C$_1$–C$_6$ alkyl substituted with hydrogen or an unsubstituted or substituted group selected from aryl, heterocycle and C$_3$–C$_{10}$ cycloalkyl;
    wherein heterocycle is selected from pyrrolidinyl, imidazolyl, pyridinyl, thiazolyl, pyridonyl, 2-oxopiperidinyl, indolyl, quinolinyl, isoquinolinyl, and thienyl;

R$^{7b}$ is selected from
  a) hydrogen,
  b) unsubstituted or substituted aryl,
  c) unsubstituted or substituted heterocycle,
  d) unsubstituted or substituted C$_3$–C$_{10}$ cycloalkyl,
  e) C$_1$–C$_6$ alkyl substituted with hydrogen or an unsubstituted or substituted group selected from aryl, heterocycle and C$_3$–C$_{10}$ cycloalkyl,
  f) a carbonyl group which is bonded to an unsubstituted or substituted group selected from aryl, heterocycle, C$_3$–C$_{10}$ cycloalkyl and C$_1$–C$_6$ alkyl substituted with hydrogen or an unsubstituted or substituted group selected from aryl, heterocycle and C$_3$–C$_{10}$ cycloalkyl, and
  g) a sulfonyl group which is bonded to an unsubstituted or substituted group selected from aryl, heterocycle, C$_3$–C$_{10}$ cycloalkyl and C$_1$–C$_6$ alkyl substituted with hydrogen or an unsubstituted or substituted group selected from aryl, heterocycle and C$_3$–C$_{10}$ cycloalkyl; wherein heterocycle is selected from pyrrolidinyl, imidazolyl, pyridinyl, thiazolyl, pyridonyl, 2-oxopiperidinyl, indolyl, quinolinyl, isoquinolinyl, and thienyl;

R$^8$ is independently selected from:
  a) hydrogen,
  b) C$_1$–C$_6$ alkyl, C$_2$–C$_6$ alkenyl, C$_2$–C$_6$ alkynyl, C$_1$–C$_6$ perfluoroalkyl, F, Cl, R$^{10}$O—, R$^{10}$C(O)NR$^{10}$—, CN, NO$_2$, (R$^{10}$)$_2$N—C(NR$^{10}$)—, R$^{10}$C(O)—, R$^{10}$OC(O)—, —N(R$^{10}$)$_2$, or R$^{11}$OC(O)NR$^{10}$—, and
  c) C$_1$–C$_6$ alkyl substituted by C$_1$–C$_6$ perfluoroalkyl, R$^{10}$O—, R$^{10}$C(O)NR$^{10}$—, (R$^{10}$)$_2$N—C(NR$^{10}$)—, R$^{10}$C(O)—, R$^{10}$OC(O)—, —N(R$^{10}$)$_2$, or R$^{11}$OC(O)NR$^{10}$—;

R$^9$ is selected from:
  a) hydrogen,
  b) C$_2$–C$_6$ alkenyl, C$_2$–C$_6$ alkynyl, C$_1$–C$_6$ perfluoroalkyl, F, Cl, R$^{10}$O—, R$^{11}$S(O)$_m$—, R$^{10}$C(O)NR$^{10}$—, CN, NO$_2$, (R$^{10}$)$_2$N—C(NR$^{10}$)—, R$^{10}$C(O)—, R$^{10}$OC(O)—, —N(R$^{10}$)$_2$, or R$^{11}$OC(O)NR$^{10}$—, and
  c) C$_1$–C$_6$ alkyl unsubstituted or substituted by C$_1$–C$_6$ perfluoroalkyl, F, Cl, R$^{10}$O—, R$^{11}$S(O)$_m$—, R$^{10}$C(O)NR$^{10}$—, CN, (R$^{10}$)$_2$N—C(NR$^{10}$)—, R$^{10}$C(O)—, R$^{10}$OC(O)—, —N(R$^{10}$)$_2$, or R$^{11}$OC(O)NR$^{10}$—;

R$^{10}$ is independently selected from hydrogen, C$_1$–C$_6$ alkyl, benzyl and aryl;

R$^{11}$ is independently selected from C$_1$–C$_6$ alkyl and aryl;

A$^1$ and A$^2$ are independently selected from: a bond, —CH=CH—, —C≡C—, —C(O)—, —C(O)NR$^{10}$—, O, —N(R$^{10}$)—, or S(O)$_m$;

V is selected from:
  a) hydrogen,
  b) heterocycle selected from pyrrolidinyl, imidazolyl, pyridinyl, thiazolyl, pyridonyl, 2-oxopiperidinyl, indolyl, quinolinyl, isoquinolinyl, and thienyl,
  c) aryl,
  d) C$_1$–C$_{20}$ alkyl wherein from 0 to 4 carbon atoms are replaced with a a heteroatom selected from O, S, and N, and
  e) C$_2$–C$_{20}$ alkenyl, and
provided that V is not hydrogen if A$^1$ is S(O)$_m$ and V is not hydrogen if A$^1$ is a bond, n is 0 and A$^2$ is S(O)$_m$;

W is a heterocycle selected from pyrrolidinyl, imidazolyl, pyridinyl, thiazolyl, pyridonyl, 2-oxopiperidinyl, indolyl, quinolinyl, or isoquinolinyl;

Z is independently H$_2$ or O;

m is 0, 1 or 2;

n is 0, 1, 2, 3 or 4;

p is 0, 1, 2, 3 or 4;

q is 0,1 or 2;

r is 0 to 5, provided that r is 0 when V is hydrogen;

t is 3, 4 or 5; and u is 0 or 1;

or the pharmaceutically acceptable salts thereof.

In a fourth more preferred embodiment of this invention, the prodrugs of the preferred compounds of Formula III are illustrated by the Formula IV:

[Structure of Formula IV: V—A$^1$(CR$^{1a}$$_2$)$_n$A$^2$(CR$^{1a}$$_2$)$_n$—(W)$_u$ with (R$^8$)$_r$ and R$^9$ substituents—(CR$^{1b}$$_2$)$_p$—N connected to a ring with (CH$_2$)$_t$, R$^{2a}$, R$^{2b}$, then —X—Y— with R$^3$, R$^4$, Z groups—C(=O)—NH—cyclic lactam with (CH$_2$)$_q$, Z]

wherein:

R$^{1a}$ is independently selected from: hydrogen or C$_1$–C$_6$ alkyl;

R$^{1b}$ is independently selected from:
  a) hydrogen,
  b) aryl, heterocycle, C$_3$–C$_{10}$ cycloalkyl, R$^{10}$O—, —N(R$^{10}$)$_2$ or C$_2$–C$_6$ alkenyl,
  c) C$_1$–C$_6$ alkyl unsubstituted or substituted by aryl, heterocycle, C$_3$–C$_{10}$ cycloalkyl, C$_2$–C$_6$ alkenyl, R$^{10}$O—, or —N(R$^{10}$)$_2$;

$R^{2a}$ is selected from:
a) hydrogen,
b) $C_1$–$C_6$ alkyl unsubstituted or substituted by $C_2$–$C_6$ alkenyl, $R^{10}O$—, $R^{11}S(O)_m$—, $R^{10}C(O)NR^{10}$—, CN, $N_3$, $(R^{10})_2N$—$C(NR^{10})$—, $R^{10}C(O)$—, $R^{10}OC(O)$—, —$N(R^{10})_2$, or $R^{11}OC(O)NR^{10}$—,
c) aryl, heterocycle, $C_3$–$C_{10}$ cycloalkyl, $C_2$–$C_6$ alkenyl, $R^{10}O$—, $R^{11}S(O)_m$—, $R^{10}C(O)NR^{10}$—, CN, $NO_2$, $(R^{10})_2N$—$C(NR^{10})$—, $R^{10}C(O)$—, $R^{10}OC(O)$—, $N_3$, —$N(R^{10})_2$, or $R^{11}OC(O)NR^{10}$—, and
d) $C_1$–$C_6$ alkyl substituted with an unsubstituted or substituted group selected from aryl, heterocyclic and $C_3$–$C_{10}$ cycloalkyl;

$R^{2b}$ is hydrogen;

$R^3$ and $R^4$ are independently selected from:
a) a side chain of a naturally occurring amino acid,
b) an oxidized form of a side chain of a naturally occurring amino acid which is:
i) methionine sulfoxide, or
ii) methionine sulfone,
c) substituted or unsubstituted $C_1$–$C_{10}$ alkyl, $C_2$–$C_{10}$ alkenyl, $C_3$–$C_{10}$ cycloalkyl, aryl or heterocycle group,
wherein the substituent is selected from F, Cl, Br, $NO_2$, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, $N_3$, —$N(R^{10})_2$, $R^{11}OC(O)NR^{10}$— and $C_1$–$C_{20}$ alkyl, and
d) $C_1$–$C_6$ alkyl substituted with an unsubstituted or substituted group selected from aryl, heterocycle and $C_3$–$C_{10}$ cycloalkyl;

X—Y is

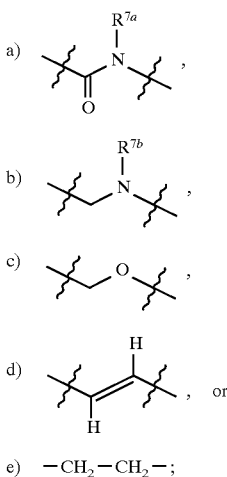

e) —$CH_2$—$CH_2$—;

$R^{7a}$ is selected from
a) hydrogen,
b) unsubstituted or substituted aryl,
c) unsubstituted or substituted heterocycle,
d) unsubstituted or substituted $C_3$–$C_{10}$ cycloalkyl, and
e) $C_1$–$C_6$ alkyl substituted with hydrogen or an unsubstituted or substituted group selected from aryl, heterocycle and $C_3$–$C_{10}$ cycloalkyl;
wherein heterocycle is selected from pyrrolidinyl, imidazolyl, pyridinyl, thiazolyl, pyridonyl, 2-oxopiperidinyl, indolyl, quinolinyl, isoquinolinyl, and thienyl;

$R^{7b}$ is selected from
a) hydrogen,
b) unsubstituted or substituted aryl,
c) unsubstituted or substituted heterocycle,
d) unsubstituted or substituted $C_3$–$C_{10}$ cycloalkyl,
e) $C_1$–$C_6$ alkyl substituted with hydrogen or an unsubstituted or substituted group selected from aryl, heterocycle and $C_3$–$C_{10}$ cycloalkyl,
f) a carbonyl group which is bonded to an unsubstituted or substituted group selected from aryl, heterocycle, $C_3$–$C_{10}$ cycloalkyl and $C_1$–$C_6$ alkyl substituted with hydrogen or an unsubstituted or substituted group selected from aryl, heterocycle and $C_3$–$C_{10}$ cycloalkyl, and
g) a sulfonyl group which is bonded to an unsubstituted or substituted group selected from aryl, heterocycle, $C_3$–$C_{10}$ cycloalkyl and $C_1$–$C_6$ alkyl substituted with hydrogen or an unsubstituted or substituted group selected from aryl, heterocycle and $C_3$–$C_{10}$ cycloalkyl; wherein heterocycle is selected from pyrrolidinyl, imidazolyl, pyridinyl, thiazolyl, pyridonyl, 2-oxopiperidinyl, indolyl, quinolinyl, isoquinolinyl, and thienyl;

$R^8$ is independently selected from:
a) hydrogen,
b) $C_1$–$C_6$ alkyl, $C_2$–$C_6$ alkenyl, $C_2$–$C_6$ alkynyl, $C_1$–$C_6$ perfluoroalkyl, F, Cl, $R^{10}O$—, $R^{10}C(O)NR^{10}$—, CN, $NO_2$, $(R^{10})_2N$—$C(NR^{10})$—, $R^{10}C(O)$—, $R^{10}OC(O)$—, —$N(R^{10})_2$, or $R^{11}OC(O)NR^{10}$—, and
c) $C_1$–$C_6$ alkyl substituted by $C_1$–$C_6$ perfluoroalkyl, $R^{10}O$—, $R^{10}C(O)NR^{10}$—, $(R^{10})_2N$—$C(NR^{10})$—, $R^{10}C(O)$—, $R^{10}OC(O)$—, —$N(R^{10})_2$, or $R^{11}OC(O)NR^{10}$—;

$R^9$ is selected from:
a) hydrogen,
b) $C_2$–$C_6$ alkenyl, $C_2$–$C_6$ alkynyl, $C_1$–$C_6$ perfluoroalkyl, F, Cl, $R^{10}O$—, $R^{11}S(O)_m$—, $R^{10}C(O)NR^{10}$—, CN, $NO_2$, $(R^{10})_2N$—$C(NR^{10})$—, $R^{10}C(O)$—, $R^{10}OC(O)$—, —$N(R^{10})_2$, or $R^{11}OC(O)NR^{10}$—, and
c) $C_1$–$C_6$ alkyl unsubstituted or substituted by $C_1$–$C_6$ perfluoroalkyl, F, Cl, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, —$N(R^{10})_2$, or $R^{11}OC(O)NR^{10}$—;

$R^{10}$ is independently selected from hydrogen, $C_1$–$C_6$ alkyl, benzyl and aryl;

$R^{11}$ is independently selected from $C_1$–$C_6$ alkyl and aryl;

$A^1$ and $A^2$ are independently selected from: a bond, —CH=CH—, —C≡C—, —C(O)—, —C(O)$NR^{10}$—, O, —$N(R^{10})$—, or $S(O)_m$;

V is selected from:
a) hydrogen,
b) heterocycle selected from pyrrolidinyl, imidazolyl, pyridinyl, thiazolyl, pyridonyl, 2-oxopiperidinyl, indolyl, quinolinyl, isoquinolinyl, and thienyl,
c) aryl,
d) $C_1$–$C_{20}$ alkyl wherein from 0 to 4 carbon atoms are replaced with a a heteroatom selected from O, S, and N, and
e) $C_2$–$C_{20}$ alkenyl, and
provided that V is not hydrogen if $A^1$ is $S(O)_m$ and V is not hydrogen if $A^1$ is a bond, n is 0 and $A^2$ is $S(O)_m$;

W is a heterocycle selected from pyrrolidinyl, imidazolyl, pyridinyl, thiazolyl, pyridonyl, 2-oxopiperidinyl, indolyl, quinolinyl, or isoquinolinyl;

Z is independently H₂ or O;

| | |
|---|---|
| m is | 0, 1 or 2; |
| n is | 0, 1, 2, 3 or 4; |
| p is | 0, 1, 2, 3 or 4; |
| q is | 0, 1 or 2; |
| r is | 0 to 5, provided that r is 0 when V is hydrogen; |
| t is | 3, 4 or 5; and |
| u is | 0 or 1; | or the pharmaceutically acceptable salts thereof.

The preferred compounds of this invention are as follows:

N-[1-(4-Imidazoleacetyl)pyrrolidin-2(S)-ylmethyl]-N-(1-naphthylmethyl)glycyl-methionine N-[1-(4-Imidazoleacetyl)pyrrolidin-2(S)-ylmethyl]-N-(1-naphthylmethyl)glycyl-methionine methyl ester N-[1-(2(S),3-Diaminopropionyl)pyrrolidin-2(S)-ylmethyl]-N-(1-naphthylmethyl)glycyl-methionine N-[1-(2(S),3-Diaminopropionyl)pyrrolidin-2(S)-ylmethyl]-N-(1-naphthylmethyl)glycyl-methionine methyl ester N-[1-(3-Aminopropionyl)pyrrolidin-2(S)-ylmethyl]-N-(1-naphthylmethyl)glycyl-methionine N-[1-(3-Aminopropionyl)pyrrolidin-2(S)-ylmethyl]-N-(1-naphthylmethyl)glycyl-methionine methyl ester N-[1-(2(S)-Amino-3-benzyloxycarbonylaminopropionyl) pyrrolidin-2(S)- ylmethyl]-N-(1-naphthylmethyl)glycyl-methionine N-[1-(2(S)-Amino-3-benzyloxycarbonylaminopropionyl) pyrrolidin-2(S)- ylmethyl]-N-(1-naphthylmethyl)glycyl-methionine methyl ester N-[1-(3-Amino-2(S)-benzyloxycarbonylaminopropionyl) pyrrolidin-2(S)- ylmethyl]-N-(1-naphthylmethyl)glycyl-methionine N-[1-(3-Amino-2(S)-benzyloxycarbonylaminopropionyl) pyrrolidin-2(S)- ylmethyl]-N-(1-naphthylmethyl)glycyl-methionine methyl ester N-[1-(L-Glutaminyl)pyrrolidin-2(S)- ylmethyl]-N-(1-naphthylmethyl)glycyl-methionine N-[1-(L-Glutaminyl)pyrrolidin-2(S)- ylmethyl]-N-(1-naphthylmethyl)glycyl-methionine methyl ester N-[1-(L-Histidyl)pyrrolidin-2(S)-ylmethyl]-N-(1-naphthylmethyl)glycyl-methionine N-[1-(L-Histidyl)pyrrolidin-2(S)-ylmethyl]-N-(1-naphthylmethyl)glycyl-methionine methyl ester N-[1-(D-Histidyl)pyrrolidin-2(S)-ylmethyl]-N-(1-naphthylmethyl)glycyl-methionine N-[1-(D-Histidyl)pyrrolidin-2(S)-ylmethyl]-N-(1-naphthylmethyl)glycyl-methionine methyl ester N-[1-(L-Pyroglutamyl)pyrrolidin-2(S)-ylmethyl]-N-(1-naphthylmethyl)glycyl-methionine N-[1-(L-Pyroglutamyl)pyrrolidin-2(S)-ylmethyl]-N-(1-naphthylmethyl)glycyl-methionine methyl ester 2(S)-[1-(2(S)-Pyroglutamyl)pyrrolidin-2(S)-ylmethyloxy]-3-phenylpropionyl-methionine 2(S)-[1-(2(S)-Pyroglutamyl)pyrrolidin-2(S)-ylmethyloxy]-3-phenylpropionyl-methionine methyl ester 2(S)-[1-(2(S)-Pyroglutamyl)pyrrolidin-2(S)-ylmethyloxy]-3-phenylpropionyl-methionine isopropyl ester 2(S)-[1-(1H-Imidazol-4-ylacetyl)pyrrolidin-2(S)-ylmethyloxy]-3-phenylpropionyl-methionine 2(S)-[1-(1H-Imidazol-4-ylacetyl)pyrrolidin-2(S)-ylmethyloxy]-3-phenylpropionyl-methionine methyl ester 2(S)-[1-(2(S)-Pyroglutamyl)pyrrolidin-2(S)-ylmethyloxy]-3-phenylpropionyl-methionine sulfone 2(S)-[1-(2(S)-Pyroglutamyl)pyrrolidin-2(S)-ylmethyloxy]-3-phenylpropionyl-methionine sulfone methyl ester 2(S)-[1-(Pyrid-3-ylcarboxy)pyrrolidin-2(S)-ylmethyloxy]-3-phenylpropionyl-methionine 2(S)-[1-(Pyrid-3-ylcarboxy)pyrrolidin-2(S)-ylmethyloxy]-3-phenylpropionyl-methionine methyl ester 2(R)-{2-[1-(Naphth-2-yl)-1-H-imidazol-5-ylacetyl] pyrrolidin-2(S)-ylmethoxy}-3-phenylpropionyl-methionine 2(R)-{2-[1-(Naphth-2-yl)-1H-imidazol-5-ylacetyl] pyrrolidin-2(S)-ylmethoxy}-3-phenylpropionyl-methionine methyl ester 2(S)-[1-(Pyrid-3-ylmethyl)pyrrolidin-2(S)-ylmethyloxy]-3-phenylpropionyl-methionine 2(S)-[1-(Pyrid-3-ylmethyl)pyrrolidin-2(S)-ylmethyloxy]-3-phenylpropionyl-methionine methyl ester N-[1-(1H-imidazol-4-ylacetyl)pyrrolidin-2(S)-ylmethyl]-N-(1-naphthylmethyl)glycyl-methionine isopropyl ester N-[1-(1H-imidazol-4-ylacetyl)pyrrolidin-2(S)-ylmethyl]-N-(1-naphthylmethyl)glycyl-methionine sulfone isopropyl ester N-[1-(1H-imidazol-4-ylacetyl)pyrrolidin-2(S)-ylmethyl]-N-(1-naphthylmethyl)glycyl-methionine sulfone N-[1-(Glycyl) pyrrolidin-2(S)-ylmethyl]-N-(1-naphthylmethyl)glycyl-methionine methyl ester N-[1-(Glycyl) pyrrolidin-2(S)-ylmethyl]-N-(1-naphthylmethyl)glycyl-methionine isopropyl ester N-[1-(Glycyl) pyrrolidin-2(S)-ylmethyl]-N-(1-naphthylmethyl)glycyl-methionine N-[1-(Glycyl) pyrrolidin-2(S)-ylmethyl]-N-(1-naphthylmethyl)glycyl-methionine sulfone methyl ester N-[1-(Glycyl) pyrrolidin-2(S)-ylmethyl]-N-(1-naphthylmethyl)glycyl-methionine sulfone N-[1-(Sarcosyl) pyrrolidin-2(S)-ylmethyl]-N-(1-naphthylmethyl)glycyl-methionine methyl ester N-[1-(Sarcosyl) pyrrolidin-2(S)-ylmethyl]-N-(1-naphthylmethyl)glycyl-methionine N-[1-(N,N-Dimethylglycyl) pyrrolidin-2(S)-ylmethyl]-N-(1-naphthylmethyl)glycyl-methionine methyl ester N-[1-(N,N-Dimethylglycyl) pyrrolidin-2(S)-ylmethyl]-N-(1-naphthylmethyl)glycyl-methionine N-[1-(1H-imidazol-4-ylacetyl)pyrrolidin-3(S)-ethyl-2(S)-ylmethyl]-N-(1-naphthylmethyl)glycyl-methionine methyl ester N-[1-(1H-imidazol-4-ylacetyl)pyrrolidin-3(S)-ethyl-2(S)-ylmethyl]-N-(1-naphthylmethyl)glycyl-methionine N-[1-(Glycyl) pyrrolidin-3(S)-ethyl-2(S)-ylmethyl]-N-(1-naphthylmethyl)glycyl-methionine methyl ester N-[1-(Glycyl) pyrrolidin-3(S)-ethyl-2(S)-ylmethyl]-N-(1-naphthylmethyl)glycyl-methionine N-[1-(4-Cyanobenzyl)-1H-imidazol-5-ylacetyl)pyrrolidin-2 (S)-ylmethyl]-N-(1-naphthylmethyl)glycyl-methionine methyl ester N-[1-(4-Cyanobenzyl)-1H-imidazol-5-ylacetyl)pyrrolidin-2 (S)-ylmethyl]-N-(1-naphthylmethyl)glycyl-methionine N-[1-(2-Acetylamino-3(S)-benzyloxycarbonylaminopropionyl)pyrrolidin-2(S)-ylmethyl]-N-(1-naphthylmethyl)glycyl-methionine N-[1-(2-Acetylamino-3(S)-aminopropionyl)pyrrolidin-2(S)-ylmethyl]-N-(1-naphthylmethyl)glycyl-methionine N-[1-(2-Amino-3(S)-acetylaminopropionyl)pyrrolidin-2(S)-ylmethyl]-N-(1-naphthylmethyl)glycyl-methionine 2(S)-[1-(1H-Imidazol-4-ylacetyl)pyrrolidin-3(S)-ethyl-2(S)-ylmethyloxy]-3-phenylpropionyl-methionine methyl ester 2(S)-[1-(1H-imidazol-4-ylacetyl)pyrrolidin-3 (S)-ethyl-2-(S)-ylmethyloxy]-3-phenylpropionyl-methionine 2(R)-{2-[1-(4-Cyanobenzyl)-1H-imidazol-5-ylacetyl] pyrrolidin-2(S)-ylmethoxy}-3-phenyl propionyl-methionine methyl ester 2(R)-{2-[1-(4-Cyanobenzyl)-1H-imidazol-5-ylacetyl] pyrrolidin-2(S)-ylmethoxy}-3-phenyl propionyl-methionine 2(R)-{2-[1-(4-Nitrobenzyl)-1H-imidazol-5-ylacetyl] pyrrolidin-2(S)-ylmethoxy}-3-phenyl propionyl-methionine methyl ester 2(R)-{2-[1-(4-Nitrobenzyl)-1H-imidazol-5-ylacetyl] pyrrolidin-2(S)-ylmethoxy}-3-phenyl propionyl-methionine 2(R)-{2-[1-(4-Methoxybenzyl)-1H-imidazol-5-ylacetyl] pyrrolidin-2(S)-ylmethoxy}-3-phenyl propionyl-methionine methyl ester 2(R)-{2-[1-(4-Methoxybenzyl)-1H-imidazol-5-ylacetyl] pyrrolidin-2(S)-ylmethoxy}-3-phenyl propionyl-methionine 2(R)-{2-[1-(4-Cyanobenzyl)-1H-imidazol-5-ylacetyl] pyrrolidin-3(S)-ethyl-2(S)-ylmethoxy}-3-phenyl propionyl-methionine methyl ester 2(R)-{2-[1-(4-Cyanobenzyl)-1H-imidazol-5-ylacetyl] pyrrolidin-3(S)-ethyl-2(S)-ylmethoxy}-3-phenyl propionyl-methionine N-[1-(1H-imidazol-4-ylacetyl)pyrrolidin-2(S)-ylmethyl]-N-(1-naphthylmethyl)glycyl-(β-acetylamino)alanine methyl ester N-[1-(1H-imidazol-4-ylacetyl)pyrrolidin-2(S)-ylmethyl]-N-(1-naphthylmethyl)glycyl-(β-acetylamino)alanine N-[1-(Glycyl) pyrrolidin-2(S)-ylmethyl]-N-(1-naphthylmethyl)glycyl-(β-acetylamino)alanine methyl ester N-[1-(Glycyl) pyrrolidin-2(S)-ylmethyl]-N-(1-naphthylmethyl)glycyl-(β-acetylamino)alanine N-[1-(Seryl)pyrrolidin-2(S)-ylmethyl]-N-(1-naphthylmethyl)glycyl-methionine methyl ester N-[1-(D-Alanyl) pyrrolidin-2(S)-ylmethyl]-N-(1-naphthylmethyl)glycyl-methionine methyl ester N-[1-(1H-imidazol-4-carbonyl)pyrrolidin-2(S)-ylmethyl]-N-(1-naphthylmethyl)glycyl-methionine methyl ester N-[1-(Isoasparagyl) pyrrolidin-2(S)-ylmethyl]-N-(1-naphthylmethyl)glycyl-methionine methyl ester N-[1-(1H-Imidazol-4-propionyl) pyrrolidin-2(S)-ylmethyl]-N-(1-naphthylmethyl)glycyl-methionine methyl ester N-[1-(3-Pyridylacetyl) pyrrolidin-2(S)-ylmethyl]-N-(1-naphthylmethyl)glycyl-methionine methyl ester N-[1-(2-Pyridylacetyl) pyrrolidin-2(S)-ylmethyl]-N-(1-naphthylmethyl)glycyl-methionine methyl ester N-[1-(4-Pyridylglycyl) pyrrolidin-2(S)-ylmethyl]-N-(1-naphthylmethyl)glycyl-methionine methyl ester N-[1-(Seryl)pyrrolidin-2(S)-ylmethyl]-N-(1-naphthylmethyl)glycyl-methionine N-[1-(D-Alanyl) pyrrolidin-2(S)-ylmethyl]-N-(1-naphthylmethyl)glycyl-methionine N-[1-(1H-Imidazol-4-carbonyl)pyrrolidin-2(S)-ylmethyl]-N-(1-naphthylmethyl)glycyl-methionine N-[1-(Isoasparagyl) pyrrolidin-2(S)-ylmethyl]-N-(1-naphthylmethyl)glycyl-methionine N-[1-(1H-Imidazol-4-propionyl) pyrrolidin-2(S)-ylmethyl]-N-(1-naphthylmethyl)glycyl-methionine N-[1-(3-Pyridylacetyl) pyrrolidin-2(S)-ylmethyl]-N-(1-naphthylmethyl)glycyl-methionine N-[1-(2-Pyridylacetyl) pyrrolidin-2(S)-ylmethyl]-N-(1-naphthylmethyl)glycyl-methionine N-[1-(4-Pyridylglycyl) pyrrolidin-2(S)-ylmethyl]-N-(1-naphthylmethyl)glycyl-methionine N-[1-(1H-Imidazol-4-ylmethyl)pyrrolidin-2(S)-ylmethyl]-N-(1-naphthylmethyl)glycyl-methionine N-[1-(2-Aminoethyl)pyrrolidin-2(S)-ylmethyl]-N-(1-naphthylmethyl)glycyl-methionine N-[1-(Glycyl) pyrrolidin-2(S)-ylmethyl]-N-(1-naphthylmethyl)glycyl-(2-thienyl)alanine N-[1-(1H-Imidazol-4-ylacetyl)pyrrolidin-2(S)-ylmethyl]-N-(1-naphthylmethyl)glycyl-(trifluoromethyl)alanine N-[1-(1H-Imidazol-4-ylacetyl)pyrrolidin-2(S)-ylmethyl]-N-(1-naphthylmethyl)glycyl-(2(S)-amino-4-acetylamino) butyric acid N-[1-(1H-Imidazol-4-ylacetyl)pyrrolidin-2(S)-ylmethyl]-N-(1-naphthylmethyl)glycyl-(N,N-dimethyl)glutamine N-[1-(1H-Imidazol-4-ylacetyl)pyrrolidin-2(S)-ylmethyl]-N-(benzyl)glycyl-methionine N-[1-(Glycyl)pyrrolidin-2(S)-ylmethyl]-N-(benzyl)glycyl-methionine N-[1-(1H-Imidazol-4-ylacetyl)pyrrolidin-2(S)-ylmethyl]-N-(4-methoxybenzyl)glycyl-methionine N-[1-(Glycyl)pyrrolidin-3(S)-ethyl-2(S)-ylmethyl]-N-(benzyl)glycyl-methionine N-[1-(1H-Imidazol-4-ylacetyl)pyrrolidin-3(S)-ethyl-2(S)-ylmethyl]-N-(benzyl)glycyl-methionine N-((4-Imidazolyl)methyl-(2S)-pyrrolidinylmethyl)-N-(1-naphthylmethyl)glycyl-methionine methyl ester N-[1-(Glycyl) pyrrolidin-2(S)-ylmethyl]-N-(1-naphthylmethyl)glycyl-(2-thienyl)alanine methyl ester N-[1-(1H-imidazol-4-ylacetyl)pyrrolidin-2(S)-ylmethyl]-N-(1-naphthylmethyl)glycyl-(N,N-dimethyl)glutamine methyl ester N-[1-(1H-Imidazol-4-ylacetyl)pyrrolidin-2(S)-ylmethyl]-N-(1-naphthylmethyl)glycyl-(trifluoromethyl)alanine methyl ester N-[1-(1H-Imidazol-4-ylacetyl)pyrrolidin-2(S)-ylmethyl]-N-(1-naphthylmethyl)glycyl-(2(S)-amino-4-acetylamino) butyric acid methyl ester N-[1-(1H-Imidazol-4-ylacetyl)pyrrolidin-2(S)-ylmethyl]-N-(benzyl)glycyl-methionine methyl ester N-[1-(Glycyl)pyrrolidin-2(S)-ylmethyl]-N-(benzyl)glycyl-methionine methyl ester N-[1-(1H-Imidazol-4-ylacetyl)pyrrolidin-2(S)-ylmethyl]-N-(4-methoxybenzyl)glycyl-methionine methyl ester N-[1-(1H-Imidazol-4-ylacetyl)pyrrolidin-3(S)-ethyl-2(S)-ylmethyl]-N-(benzyl)glycyl-methionine methyl ester N-[1-(Glycyl) pyrrolidin-3(S)-ethyl-2(S)-ylmethyl]-N-(benzyl)glycyl-methionine methyl ester N-[1-(Glycyl) pyrrolidin-2(S)-ylmethyl]-N-(1-naphthylmethyl)glycyl-methionine isopropyl ester N-[1-(Glycyl) pyrrolidin-2(S)-ylmethyl]-N-(1-naphthylmethyl)glycyl-methionine cyclohexyl ester N-[1-(Glycyl) pyrrolidin-2(S)-ylmethyl]-N-(1-naphthylmethyl)glycyl-methionine benzyl ester N-[1-(Glycyl) pyrrolidin-2(S)-ylmethyl]-N-(1-naphthylmethyl)glycyl-methionine ethyl ester N-[1-(Sarcosyl) pyrrolidin-2(S)-ylmethyl]-N-(1-naphthylmethyl)glycyl-methionine isopropyl ester N-[1-(N,N-Dimethylglycyl) pyrrolidin-2(S)-ylmethyl]-N-(1-naphthylmethyl)glycyl-methionine isopropyl ester N-[1-(Glycyl) pyrrolidin-2(S)-ylmethyl]-N-(1-naphthylmethyl)glycyl-methionine (2-pyridylmethyl) ester N-[1-(Glycyl) pyrrolidin-2(S)-ylmethyl]-N-(1-naphthylmethyl)glycyl-methionine (1-glyceryl) ester N-[1-L-Prolylpyrrolidin-2(S)-ylmethyl]-N-(1-naphthylmethyl)glycyl-methionine methyl ester N-[1-(L-Prolyl)pyrrolidin-2(S)-ylmethyl]-N-(1-naphthylmethyl)glycyl-methionine N-[1-(1-Morpholinoacetyl)pyrrolidin-2(S)-ylmethyl]-N-(1-naphthylmethyl)glycyl-methionine methyl ester N-[1-(1-Morpholinoacetyl)pyrrolidin-2(S)-ylmethyl]-N-(1-naphthylmethyl)glycyl-methionine N-[1-(4-Piperidinecarbonyl)pyrrolidin-2(S)-ylmethyl]-N-(1-naphthylmethyl)glycyl-methionine methyl ester
N-[1-(4-Piperidinecarbonyl)pyrrolidin-2(S)-ylmethyl]-N-(1-naphthylmethyl)glycyl-methionine
N-[1-(3-Piperidinecarbonyl)pyrrolidin-2(S)-ylmethyl]-N-(1-naphthylmethyl)glycyl-methionine methyl ester
N-[1-(3-Piperidinecarbonyl)pyrrolidin-2(S)-ylmethyl]-N-(1-naphthylmethyl)glycyl-methionine
N-[1-(2-Pyridylglycyl)pyrrolidin-2(S)-ylmethyl]-N-(1-naphthylmethyl)glycyl-methionine methyl ester
N-[1-(2-Pyridylglycyl)pyrrolidin-2(S)-ylmethyl]-N-(1-naphthylmethyl)glycyl-methionine
N-[1-(4-Pyridylglycyl)pyrrolidin-2(S)-ylmethyl]-N-(1-naphthylmethyl)glycyl-methionine methyl ester
N-[1-(4-Pyridylglycyl)pyrrolidin-2(S)-ylmethyl]-N-(1-naphthylmethyl)glycyl-methionine
N-[1-(4-Pyridyl(N-methyl)glycyl)pyrrolidin-2(S)-ylmethyl]-N-(1-naphthylmethyl)glycyl-methionine methyl ester
N-[1-(4-Pyridyl(N-methyl)glycyl)pyrrolidin-2(S)-ylmethyl]-N-(1-naphthylmethyl)glycyl-methionine
N-[1-(1H-Imidazol-4-ylpropionyl) pyrrolidin-2(S)-ylmethyl]-N-(1-naphthylmethyl)glycyl-(β-acetylamino)alanine
N-[1-(1H-Imidazol-4-ylpropionyl) pyrrolidin-2(S)-ylmethyl]-N-(1-naphthylmethyl)glycyl-(β-acetylamino)alanine methyl ester
N-[1-(4-Pyridylglycyl) pyrrolidin-2(S)-ylmethyl]-N-(1-naphthylmethyl)glycyl-(β-acetylamino)alanine
N-[1-(4-Pyridylglycyl) pyrrolidin-2(S)-ylmethyl]-N-(1-naphthylmethyl)glycyl-(β-acetylamino)alanine methyl ester
N-[1-(Glycyl) pyrrolidin-2(S)-ylmethyl]-N-(1-naphthylmethyl)glycyl-(β-acetylamino)alanine cyclohexyl ester
N-[1-(1H-Imidazol-4-ylacetyl)pyrrolidin-2(S)-ylmethyl]-N-(1-naphthylmethyl)glycyl-(N-methyl)glutamine
N-[1-(1H-Imidazol-4-ylacetyl)pyrrolidin-2(S)-ylmethyl]-N-(1-naphthylmethyl)glycyl-(N-methyl)glutamine methyl ester
N-[1-(1H-Imidazol-4-ylacetyl) pyrrolidin-2(S)-ylmethyl]-N-(1-naphthylmethyl)glycyl-(β-methylcarbonylamino)alanine
N-[1-(1H-Imidazol-4-ylacetyl) pyrrolidin-2(S)-ylmethyl]-N-(1-naphthylmethyl)glycyl-(β-methylcarbonylamino)alanine methyl ester
N-[1-(1H-Imidazol-4-ylacetyl) pyrrolidin-2(S)-ylmethyl]-N-(1-naphthylmethyl)glycyl-(β-methylsulfonylamino)alanine
N-[1-(1H-Imidazol-4-ylacetyl) pyrrolidin-2(S)-ylmethyl]-N-(1-naphthylmethyl)glycyl-(β-methylsulfonylamino)alanine methyl ester
N-[1-(1H-Imidazol-4-ylacetyl) pyrrolidin-2(S)-ylmethyl]-N-(1-naphthylmethyl)glycyl-(β-propionylamino)alanine
N-[1-(1H-Imidazol-4-ylacetyl) pyrrolidin-2(S)-ylmethyl]-N-(1-naphthylmethyl)glycyl-(β-propionylamino)alanine methyl ester
N-[1-(1H-Imidazol-4-ylacetyl) pyrrolidin-2(S)-ylmethyl]-N-(1-naphthylmethyl)glycyl-(β-pyrrolidinon-1-ylamino)alanine
N-[1-(1H-Imidazol-4-ylacetyl) pyrrolidin-2(S)-ylmethyl]-N-(1-naphthylmethyl)glycyl-(β-pyrrolidinon-1-ylamino)alanine methyl ester
N-[1-(1H-Imidazol-4-ylacetyl)pyrrolidin-2(S)-ylmethyl]-N-(3-methoxybenzyl)glycyl-methionine
N-[1-(1H-Imidazol-4-ylacetyl)pyrrolidin-2(S)-ylmethyl]-N-(3-methoxybenzyl)glycyl-methionine methyl ester
N-[1-(1H-Imidazol-4-ylacetyl)pyrrolidin-2(S)-ylmethyl]-N-(2-methoxybenzyl)glycyl-methionine
N-[1-(1H-Imidazol-4-ylacetyl)pyrrolidin-2(S)-ylmethyl]-N-(2-methoxybenzyl)glycyl-methionine methyl ester
N-[1-(Glycyl)pyrrolidin-2(S)-ylmethyl]-N-(3-methoxybenzyl)glycyl-methionine
N-[1-(Glycyl)pyrrolidin-2(S)-ylmethyl]-N-(3-methoxybenzyl)glycyl-methionine methyl ester
N-[1-(Glycyl)pyrrolidin-2(S)-ylmethyl]-N-(2-methoxybenzyl)glycyl-methionine
N-[1-(Glycyl)pyrrolidin-2(S)-ylmethyl]-N-(2-methoxybenzyl)glycyl-methionine methyl ester
N-[1-(1H-Imidazol-4-ylpropionyl)pyrrolidin-2(S)-ylmethyl]-N-(2-methoxybenzyl)glycyl-methionine
N-[1-(1H-Imidazol-4-ylpropionyl)pyrrolidin-2(S)-ylmethyl]-N-(2-methoxybenzyl)glycyl-methionine methyl ester
N-[1-(1H-Imidazol-4-ylacetyl)pyrrolidin-2(S)-ylmethyl]-N-(3-cyanobenzyl)glycyl-methionine
N-[1-(1H-Imidazol-4-ylacetyl)pyrrolidin-2(S)-ylmethyl]-N-(3-cyanobenzyl)glycyl-methionine methyl ester
N-[1-(1H-Imidazol-4-ylacetyl)pyrrolidin-2(S)-ylmethyl]-N-(4-cyanobenzyl)glycyl-methionine
N-[1-(1H-Imidazol-4-ylacetyl)pyrrolidin-2(S)-ylmethyl]-N-(2-cyanobenzyl)glycyl-methionine
N-[1-(1H-Imidazol-4-ylacetyl)pyrrolidin-2(S)-ylmethyl]-N-(2-cyanobenzyl)glycyl-methionine methyl ester
N-[1-(Glycyl)pyrrolidin-2(S)-ylmethyl]-N-(2-cyanobenzyl)glycyl-methionine
N-[1-(Glycyl)pyrrolidin-2(S)-ylmethyl]-N-(2-cyanobenzyl)glycyl-methionine methyl ester
N-[1-(1H-Imidazol-4-ylpropionyl)pyrrolidin-2(S)-ylmethyl]-N-(2-cyanobenzyl)glycyl-methionine
N-[1-(1H-Imidazol-4-ylpropionyl)pyrrolidin-2(S)-ylmethyl]-N-(2-cyanobenzyl)glycyl-methionine methyl ester
N-[1-(1H-Imidazol-4-ylacetyl)pyrrolidin-2(S)-ylmethyl]-N-(2-methylbenzyl)glycyl-methionine
N-[1-(1H-Imidazol-4-ylacetyl)pyrrolidin-2(S)-ylmethyl]-N-(2-methylbenzyl)glycyl-methionine methyl ester
N-[1-(1H-Imidazol-4-ylacetyl)pyrrolidin-2(S)-ylmethyl]-N-(2-trifluoromethylbenzyl)glycyl-methionine
N-[1-(1H-Imidazol-4-ylacetyl)pyrrolidin-2(S)-ylmethyl]-N-(2-trifluoromethylbenzyl)glycyl-methionine methyl ester
N-[1-(1H-Imidazol-4-ylacetyl)pyrrolidin-2(S)-ylmethyl]-N-(1-naphthylsulfonyl)glycyl-methionine
N-[1-(1H-Imidazol-4-ylacetyl)pyrrolidin-2(S)-ylmethyl]-N-(1-naphthylsulfonyl)glycyl-methionine methyl ester
N-[1-(Glycyl) pyrrolidin-2(S)-ylmethyl]-N-(1-naphthylmethyl)glycyl-methionine 4-N-methylpiperidinyl ester
N-[1-(Glycyl) pyrrolidin-2(S)-ylmethyl]-N-(1-naphthylmethyl)glycyl-methionine tert-butyl ester
N-[1-(Glycyl) pyrrolidin-2(S)-ylmethyl]-N-(1-naphthylmethyl)glycyl-methionine 3-pentyl ester
N-[1-(4-Pyridylglycyl) pyrrolidin-2(S)-ylmethyl]-N-(1-naphthylmethyl)glycyl-methionine isopropyl ester
N-[1-(1H-Imidazol-4-ylpropionyl)pyrrolidin-2(S)-ylmethyl]-N-(1-naphthylmethyl)glycyl-methionine isopropyl ester
N-[1-(1H-Imidazol-4-ylacetyl)piperidin-2(S)-ylmethyl]-N-(1-naphthylmethyl)glycyl-methionine methyl ester
N-[1-(1H-Imidazol-4-ylacetyl)piperidin-2(S)-ylmethyl]-N-(1-naphthylmethyl)glycyl-methionine
N-[1-(1H-Imidazol-4-ylacetyl)piperidin-2(S)-ylmethyl]-N-(1-naphthylmethyl)glycyl-methionine isopropyl ester
N-[1-(1H-Imidazol-4-ylacetyl)piperidin-2(S)-ylmethyl]-N-(2-methoxybenzyl)glycyl-methionine
N-[1-(1H-Imidazol-4-ylacetyl)piperidin-2(S)-ylmethyl]-N-(2-methoxybenzyl)glycyl-methionine isopropyl ester N-[1-(1H-Imidazol-4-ylpropionyl)piperidin-2(S)-ylmethyl]
-N-(2-methoxybenzyl)glycyl-methionine methyl ester N-[1-(1H-Imidazol-4-ylpropionyl)piperidin-2(S)-ylmethyl]
-N-(2-methoxybenzyl)glycyl-methionine or the pharmaceutically acceptable salts thereof.

Representative compounds of the invention are:

N-[1-(4-Imidazoleacetyl)pyrrolidin-2(S)-ylmethyl]-N-(1-naphthylmethyl)glycylmethionine

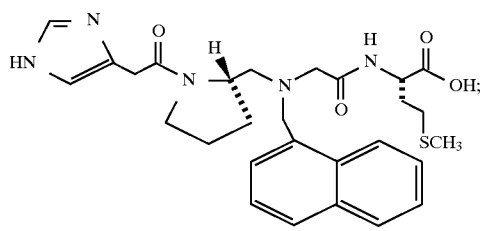

N-[1-(4-Imidazoleacetyl)pyrrolidin-2(S)-ylmethyl]-N-(1-naphthylmethyl)glycyl-methionine methyl ester

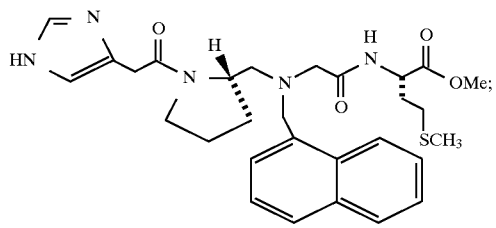

N-[1-(4-Imidazoleacetyl)pyrrolidin-2(S)-ylmethyl]-N-(1-naphthylmethyl)glycyl-methionine isopropyl ester

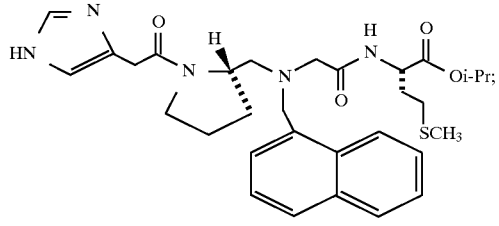

N-[1-(Glycyl)pyrrolidin-2(S)-ylmethyl]-N-(1-naphthylmethyl)glycyl-methionine

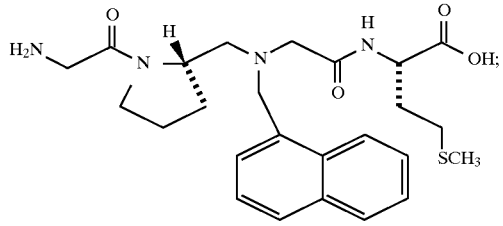

N-[1-(Glycyl)pyrrolidin-2(S)-ylmethyl]-N-(1-naphthylmethyl)glycyl-methionine methyl ester

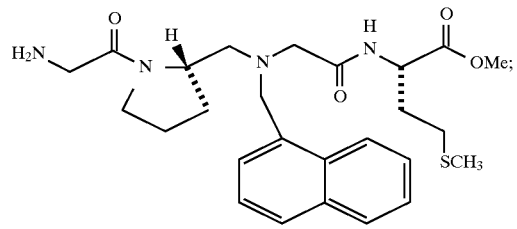

N-[1-(Glycyl)pyrrolidin-2(S)-ylmethyl]-N-(1-naphthylmethyl)glycyl-methionine isopropyl ester

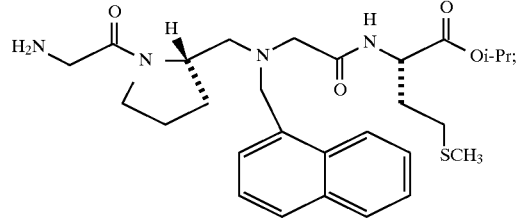

N-[1-(L-Pyroglutamyl)pyrrolidin-2(S)-ylmethyl]-N-(1-naphthylmethyl)glycyl-methionine

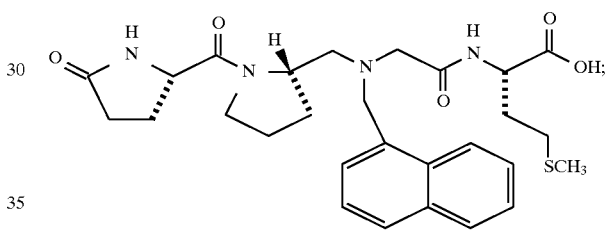

N-[1-(L-Pyroglutamyl)pyrrolidin-2(S)-ylmethyl]-N-(1-naphthylmethyl)glycyl-methionine methyl ester

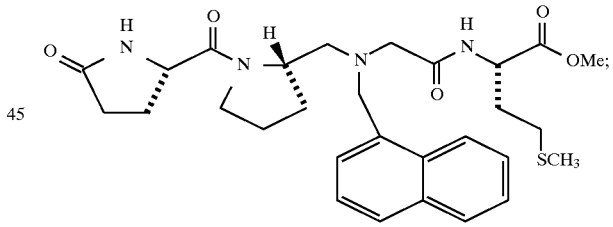

2(S)-[1-(1H-Imidazol-4-ylacetyl)pyrrolidin-3(S)-ethyl-2(S)-ylmethyloxyl]-3-phenylpropionyl-methionine methyl ester

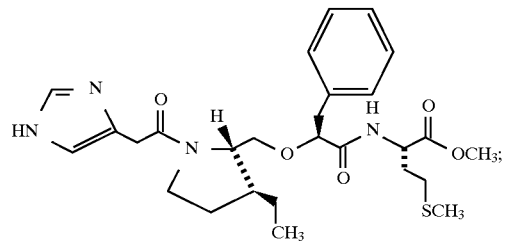

2(S)-[1-(1H-Imidazol-4-ylacetyl)pyrrolidin-3(S)-ethyl-2(S)-ylmethyloxy]-3-phenylpropionyl-methionine

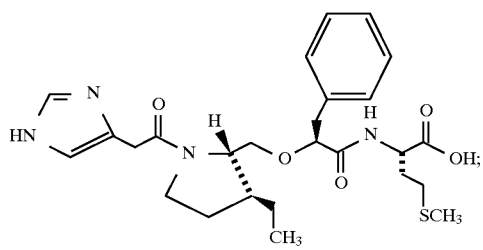

N-[1-(Sarcosyl)pyrrolidin-2(S)-ylmethyl]-N-(1-naphthylmethyl)glycyl-methionine

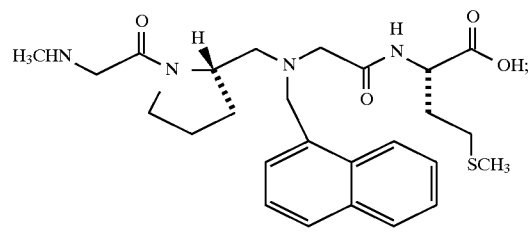

N-[1-(Sarcosyl)pyrrolidin-2(S)-ylmethyl]-N-(1-naphthylmethyl)glycyl-methionine methyl ester

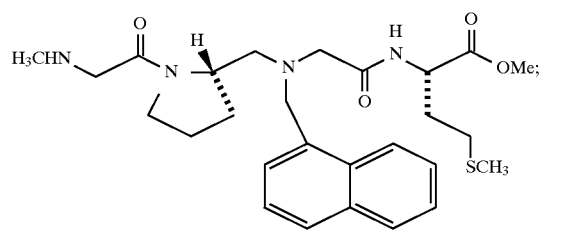

N-[1-(N,N-Dimethylglycyl)pyrrolidin-2(S)-ylmethyl]-N-(1-naphthylmethyl)glycyl-methionine

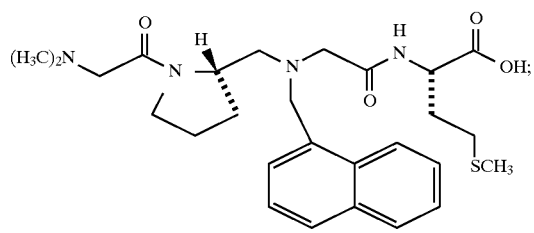

N-[1-(N,N-Dimethylglycyl)pyrrolidin-2(S)-ylmethyl]-N-(1-naphthylmethyl)glycyl-methionine methyl ester

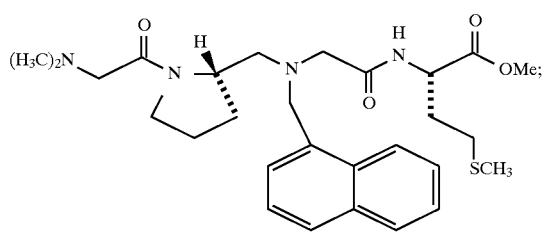

N-[1-(1H-Imidazol-4-ylacetyl)pyrrolidin-2(S)-ylmethyl]-N-(1-naphthylmethyl)glycyl-(β-acetylamino)alanine methyl ester

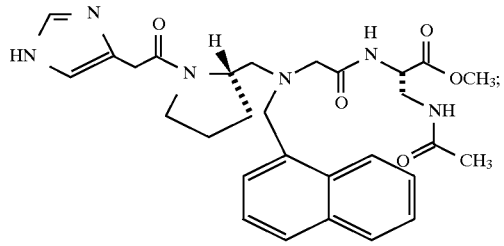

N-[1-(1H-Imidazol-4-ylacetyl)pyrrolidin-2(S)-ylmethyl]-N-(1-naphthylmethyl)glycyl-(β-acetylamino)alanine

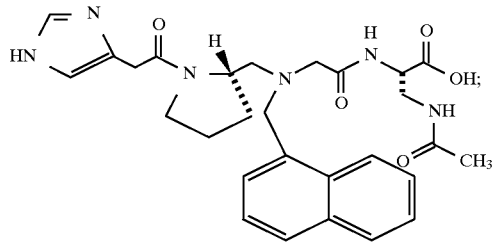

N-[1-(Glycyl) pyrrolidin-2(S)-ylmethyl]-N-(1-naphthylmethyl)glycyl-(β-acetylamino)alanine cyclohexyl ester

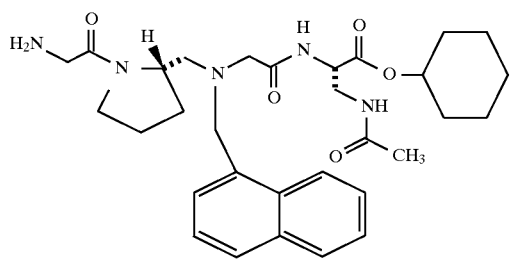

N-[1-(Glycyl) pyrrolidin-2(S)-ylmethyl]-N-(1-naphthylmethyl)glycyl-(β-acetylamino)alanine

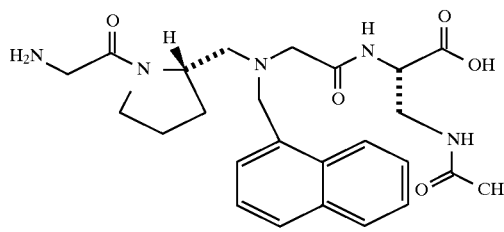

N-[1-(4-Pyridylglycyl)pyrrolidin-2(S)-ylmethyl]-N-(1-naphthylmethyl)glycyl-methionine isopropyl ester

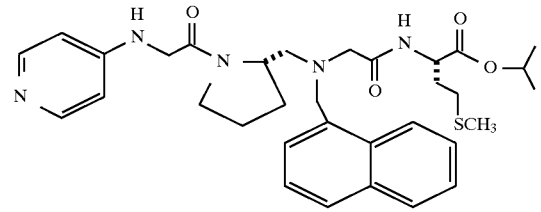

N-[1-(4-Pyridylglycyl)pyrrolidin-2(S)-ylmethyl]-N-(1-naphthylmethyl)glycyl-methionine

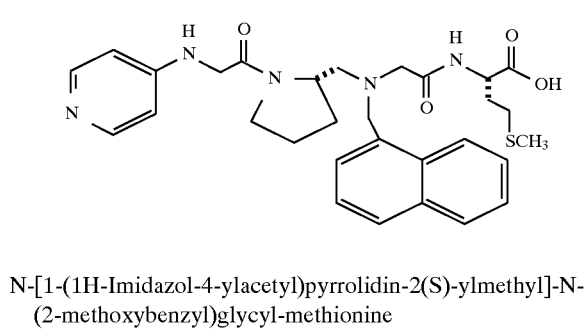

N-[1-(1H-Imidazol-4-ylacetyl)pyrrolidin-2(S)-ylmethyl]-N-(2-methoxybenzyl)glycyl-methionine

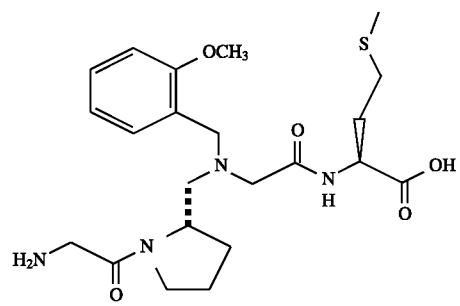

N-[1-(1H-Imidazol-4-ylpropionyl)pyrrolidin-2(S)-ylmethyl]-N-(2-methoxybenzyl)glycyl-methionine methyl ester

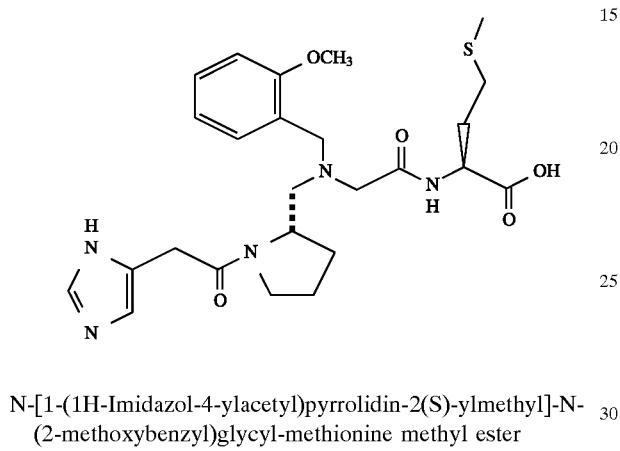

N-[1-(1H-Imidazol-4-ylacetyl)pyrrolidin-2(S)-ylmethyl]-N-(2-methoxybenzyl)glycyl-methionine methyl ester

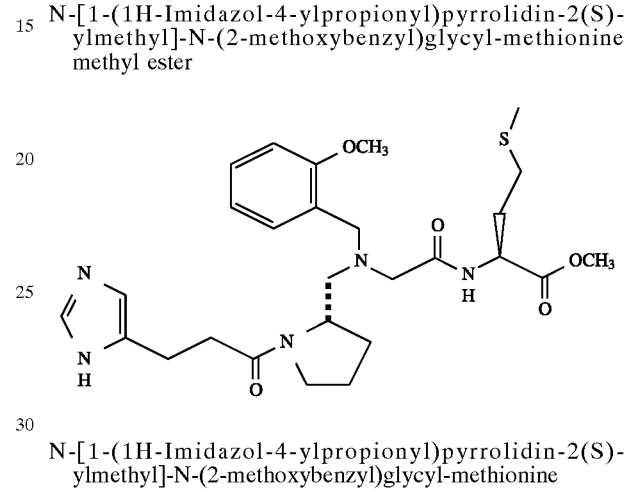

N-[1-(1H-Imidazol-4-ylpropionyl)pyrrolidin-2(S)-ylmethyl]-N-(2-methoxybenzyl)glycyl-methionine

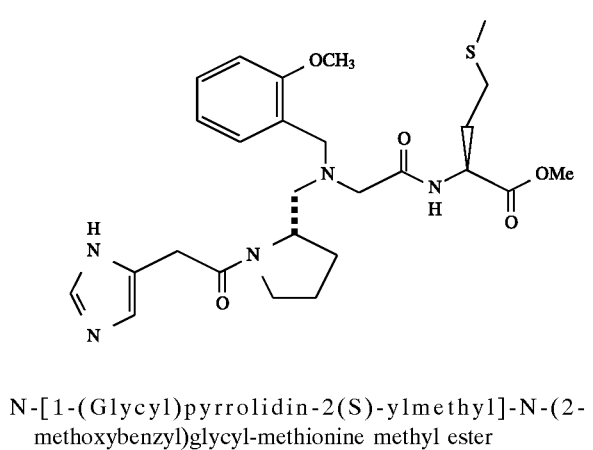

N-[1-(Glycyl)pyrrolidin-2(S)-ylmethyl]-N-(2-methoxybenzyl)glycyl-methionine methyl ester

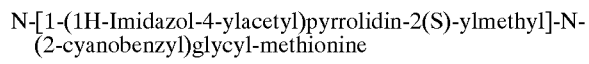

N-[1-(1H-Imidazol-4-ylacetyl)pyrrolidin-2(S)-ylmethyl]-N-(2-cyanobenzyl)glycyl-methionine

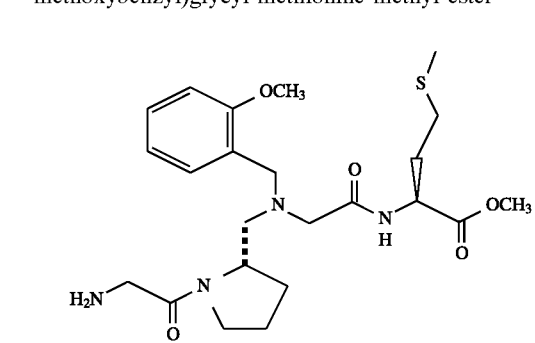

N-[1-(Glycyl)pyrrolidin-2(S)-ylmethyl]-N-(2-methoxybenzyl)glycyl-methionine

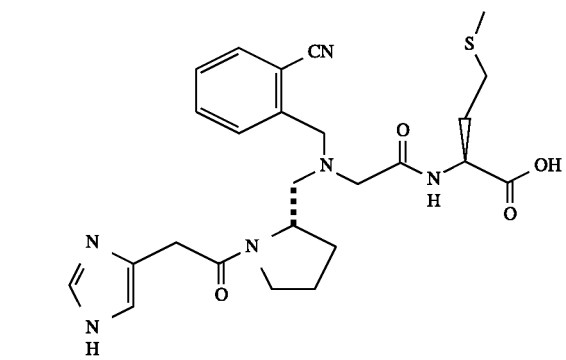

N-[1-(1H-Imidazol-4-ylacetyl)pyrrolidin-2(S)-ylmethyl]-N-(2-cyanobenzyl)glycyl-methionine methyl ester

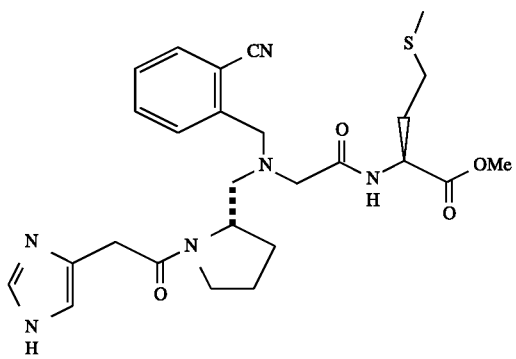

N-[1-(Glycyl) pyrrolidin-2(S)-ylmethyl]-N-(1-naphthylmethyl)glycyl-methionine 4-N-methylpiperidinyl ester

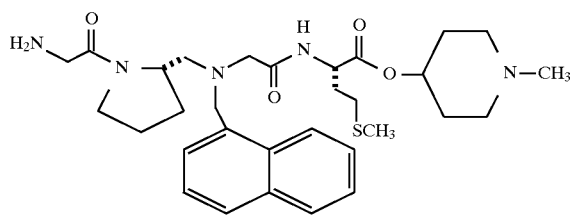

N-[1-(1H-Imidazol-4-ylpropionyl)pyrrolidin-2(S)-ylmethyl]-N-(1-naphthylmethyl)glycyl-methionine isopropyl ester

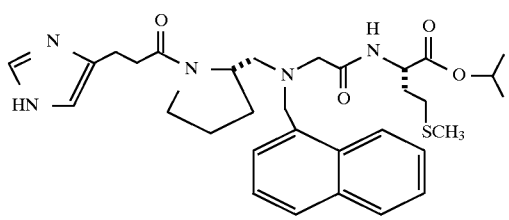

N-[1-(1H-Imidazol-4-ylacetyl)piperidin-2(S)-ylmethyl]-N-(2-methoxybenzyl)glycyl-methionine

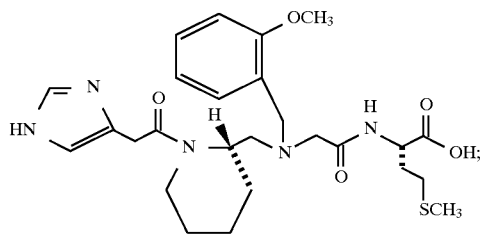

N-[1-(1H-Imidazol-4-ylacetyl)piperidin-2(S)-ylmethyl]-N-(2-methoxybenzyl)glycyl-methionine isopropyl ester

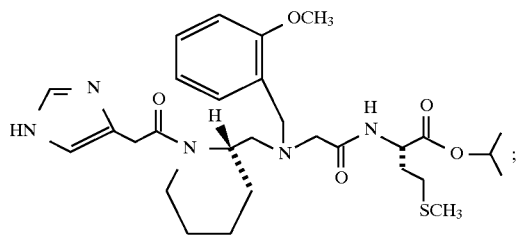

or the pharmaceutically acceptable salts thereof.

In the present invention, the amino acids which are disclosed are identified both by conventional 3 letter and single letter abbreviations as indicated below:

| | | |
|---|---|---|
| Alanine | Ala | A |
| Arginine | Arg | R |
| Asparagine | Asn | N |
| Aspartic acid | Asp | D |
| Asparagine or Aspartic acid | Asx | B |
| Cysteine | Cys | C |
| Glutamine | Gln | Q |
| Glutamic acid | Glu | E |
| Glutamine or Glutamic acid | Glx | Z |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

The compounds of the present invention may have asymmetric centers and occur as racemates, racemic mixtures, and as individual diastereomers, with all possible isomers, including optical isomers, being included in the present invention. Unless otherwise specified, named amino acids are understood to have the natural "L" stereoconfiguration As used herein, "alkyl" is intended to include both branched and straight-chain saturated aliphatic hydrocarbon groups having the specified number of carbon atoms.

As used herein, "cycloalkyl" is intended to include non-aromatic cyclic hydrocarbon groups having the specified number of carbon atoms. Examples of cycloalkyl groups include cyclopropyl, cyclobutyl, cyclopentyl, cyclohexyl and the like.

"Alkenyl" groups include those groups having the specified number of carbon atoms and having one or several double bonds. Examples of alkenyl groups include vinyl, allyl, isopropenyl, pentenyl, hexenyl, heptenyl, cyclopropenyl, cyclobutenyl, cyclopentenyl, cyclohexenyl, 1-propenyl, 2-butenyl, 2-methyl-2-butenyl, isoprenyl, farnesyl, geranyl, geranylgeranyl and the like.

As used herein, "aryl" is intended to include any stable monocyclic, bicyclic or tricyclic carbon ring(s) of up to 7 members in each ring, wherein at least one ring is aromatic.

Examples of aryl groups include phenyl, naphthyl, anthracenyl, biphenyl, tetrahydronaphthyl, indanyl, phenanthrenyl and the like.

The term heterocycle or heterocyclic, as used herein, represents a stable 5- to 7-membered monocyclic or stable 8- to 11-membered bicyclic or stable 11–15 membered tricyclic heterocycle ring which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. Examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, 2-oxopiperazinyl, 2-oxopiperidinyl, 2-oxopyrrolidinyl, piperidyl, piperazinyl, pyridyl, pyridyl N-oxide, pyridonyl, pyrazinyl, pyrazolidinyl, pyrazolyl, pyrimidinyl, pyrrolidinyl, pyrrolyl, quinazolinyl, quinolinyl, quinolinyl N-oxide, quinoxalinyl, tetrahydrofuryl, tetrahydroisoquinolinyl, tetrahydro-quinolinyl, thiamorpholinyl, thiamorpholinyl sulfoxide, thiazolyl, thiazolinyl, thienofuryl, thienothienyl, and thienyl. Preferably, heterocycle is selected from imidazolyl, 2-oxopyrrolidinyl, piperidyl, pyridyl and pyrrolidinyl.

As used herein, the terms "substituted aryl", "substituted heterocycle" and "substituted cycloalkyl" are intended to include the cyclic group which is substituted with 1 or 2 substitutents selected from the group which includes but is not limited to F, Cl, Br, $CF_3$, $NH_2$, $N(C_1-C_6$ alkyl$)_2$, $NO_2$, CN, $(C_1-C_6$ alkyl)O—, —OH, $(C_1-C_6$ alkyl)S(O)$_m$—, $(C_1-C_6$ alkyl)C(O)NH—, $H_2N$—C(NH)—, $(C_1-C_6$ alkyl)C(O)—, $(C_1-C_6$ alkyl)OC(O)—, $N_3$, $(C_1-C_6$ alkyl)OC(O)NH— and $C_1-C_{20}$ alkyl.

The following structure:

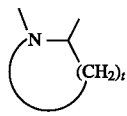

represents a cyclic amine moiety having 5 or 6 members in the ring, such a cyclic amine which may be optionally fused to a phenyl or cyclohexyl ring. Examples of such a cyclic amine moiety include, but are not limited to, the following specific structures:

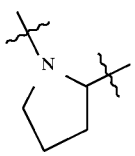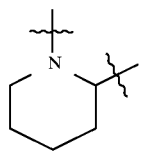

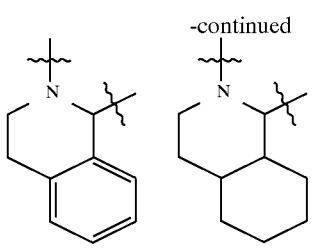

It is also understood that substitution on the cyclic amine moiety by $R^{2a}$ and $R^{2b}$ may be on different carbon atoms or on the same carbon atom.

When $R^3$ and $R^4$ are combined to form —$(CH_2)_s$—, cyclic moieties are formed. Examples of such cyclic moieties include, but are not limited to:

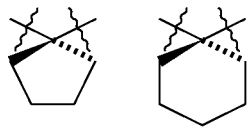

When $R^{5a}$ and $R^{5b}$ are combined to form —$(CH_2)_s$—, cyclic moieties as described hereinabove for $R^3$ and $R^4$ are formed. In addition, such cyclic moieties may optionally include a heteroatom(s). Examples of such heteroatom-containing cyclic moieties include, but are not limited to:

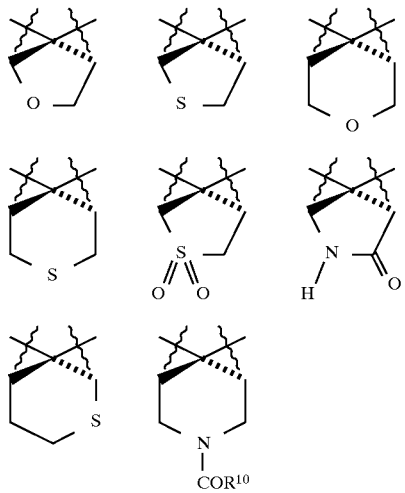

Preferably, $R^{1a}$ and $R^{1b}$ are independently selected from: hydrogen, —$N(R^{10})_2$, $R^{10}C(O)NR^{10}$— or $C_1-C_6$ alkyl unsubstituted or substituted by —$N(R^{10})_2$, $R^{10}O$— or $R^{10}C(O)NR^{10}$—.

Preferably, $R^{2a}$ and $R^{2b}$ are independently selected from: hydrogen and $C_1-C_6$ alkyl.

Preferably, $R^3$ and $R^4$ are independently selected from: a side chain of a naturally occurring amino acid and $C_1-C_6$ alkyl unsubstituted or substituted group selected from aryl, heterocycle and $C_3-C_{10}$ cycloalkyl.

Preferably, $R^{5a}$ and $R^{5b}$ are independently selected from: a side chain of a naturally occurring amino acid, methionine sulfoxide, methionine sulfone and unsubstituted or substituted $C_1-C_6$ alkyl.

Preferably, X—Y is selected from:

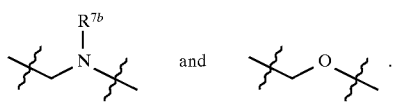

Preferably, $R^{7b}$ is $C_1$–$C_6$ alkyl substituted with hydrogen or an unsubstituted or substituted aryl group.

Preferably, $R^8$ is selected from: hydrogen, perfluoroalkyl, F, Cl, Br, $R^{10}O$—, $R^{11}S(O)_m$—, CN, $NO_2$, $R^{10}{}_2N$—$C(NR^{10})$—, $R^{10}C(O)$—, $R^{10}OC(O)$—, $N_3$, —$N(R^{10})_2$, or $R^{11}OC(O)NR^{10}$— and $C_1$–$C_6$ alkyl.

Preferably, $R^9$ is hydrogen.

Preferably, $R^{10}$ is selected from H, $C_1$–$C_6$ alkyl and benzyl.

Preferably, $A^1$ and $A^2$ are independently selected from: a bond, —$C(O)NR^{10}$—, —$NR^{10}C(O)$—, O, —$N(R^{10})$—, —$S(O)_2N(R^{10})$— and —$N(R^{10})S(O)_2$—.

Preferably, V is selected from hydrogen, heterocycle and aryl.

Preferably, n, p and r are independently 0, 1, or 2.

Preferably t is 3.

The pharmaceutically acceptable salts of the compounds of this invention include the conventional non-toxic salts of the compounds of this invention as formed, e.g., from non-toxic inorganic or organic acids. For example, such conventional non-toxic salts include those derived from inorganic acids such as hydrochloric, hydrobromic, sulfuric, sulfamic, phosphoric, nitric and the like: and the salts prepared from organic acids such as acetic, propionic, succinic, glycolic, stearic, lactic, malic, tartaric, citric, ascorbic, pamoic, maleic, hydroxymaleic, phenyl-acetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like.

It is intended that the definition of any substituent or variable (e.g., $R^{10}$, Z, n, etc.) at a particular location in a molecule be independent of its definitions elsewhere in that molecule. Thus, —$N(R^{10})_2$ represents —NHH, —$NHCH_3$, —$NHC_2H_5$, etc. It is understood that substituents and substitution patterns on the compounds of the instant invention can be selected by one of ordinary skill in the art to provide compounds that are chemically stable and that can be readily synthesized by techniques known in the art as well as those methods set forth below.

The pharmaceutically acceptable salts of the compounds of this invention can be synthesized from the compounds of this invention which contain a basic moiety by conventional chemical methods. Generally, the salts are prepared by reacting the free base with stoichiometric amounts or with an excess of the desired salt-forming inorganic or organic acid in a suitable solvent or various combinations of solvents.

The compounds of the invention can be synthesized from their constituent amino acids by conventional peptide synthesis techniques, and the additional methods described below. Standard methods of peptide synthesis are disclosed, for example, in the following works: Schroeder et al., "*The Peptides*", Vol. I, Academic Press 1965, or Bodanszky et al., "*Peptide Synthesis*", Interscience Publishers, 1966, or McOmie (ed.) "*Protective Groups in Organic Chemistry*", Plenum Press, 1973, or Barany et al., "*The Peptides: Analysis, Synthesis, Biology*" 2, Chapter 1, Academic Press, 1980, or Stewart et al., "*Solid Phase Peptide Synthesis*", Second Edition, Pierce Chemical Company, 1984. Also useful in exemplifying syntheses of specific unnatural amino acid residues are European Pat. Appl. No. 0 350 163 A2 (particularly page 51–52) and J. E. Baldwin et al. *Tetrahedron*, 50:5049–5066 (1994). With regards to the synthesis of instant compounds containing a (β-acetylamino)alanine residue at the C-terminus, use of the commercially available $N_\alpha$-Z-L-2,3-diaminopropionic acid (Fluka) as a starting material is preferred. The teachings of these works are hereby incorporated by reference.

Abbreviations used in the description of the chemistry and in the Examples that follow are:

| | |
|---|---|
| $Ac_2O$ | Acetic anhydride; |
| Boc | t-Butoxycarbonyl; |
| DBU | 1,8-diazabicyclo[5.4.0]undec-7-ene; |
| DMAP | 4-Dimethylaminopyridine; |
| DME | 1,2-Dimethoxyethane; |
| DMF | Dimethylformamide; |
| EDC | 1-(3-dimethylaminopropyl)-3-ethyl-carbodiimide-hydrochloride; |
| HOBT | 1-Hydroxybenzotriazole hydrate; |
| $Et_3N$ | Triethylamine; |
| EtOAc | Ethyl acetate; |
| FAB | Fast atom bombardment; |
| HOOBT | 3-Hydroxy-1,2,2-benzotriazin-4(3H)-one; |
| HPLC | High-performance liquid chromatography; |
| MCPBA | m-Chloroperoxybenzoic acid; |
| MsCl | Methanesulfonyl chloride; |
| NaHMDS | Sodium bis(trimethylsilyl)amide; |
| Py | Pyridine; |
| TFA | Trifluoroacetic acid; |
| THF | Tetrahydrofuran. |

Compounds of this invention are prepared by employing the reactions shown in the following Reaction Schemes A–J, in addition to other standard manipulations such as ester hydrolysis, cleavage of protecting groups, etc., as may be known in the literature or exemplified in the experimental procedures. Some key bond-forming and peptide modifying reactions are:

Reaction A Amide bond formation and protecting group cleavage using standard solution or solid phase methodologies.

Reaction B Preparation of a reduced peptide subunit by 1 reductive alkylation of an amine by an aldehyde using sodium cyanoborohydride or other reducing agents.

Reaction C Alkylation of a reduced peptide subunit with an alkyl or aralkyl halide or, alternatively, reductive alkylation of a reduced peptide subunit with an aldehyde using sodium cyanoborohydride or other reducing agents.

Reaction D Peptide bond formation and protecting group cleavage using standard solution or solid phase methodologies.

Reaction E Preparation of a reduced subunit by borane reduction of the amide moiety.

Reaction Schemes A–E illustrate bond-forming and peptide modifying reactions incorporating acyclic peptide units. It is well understood that such reactions are equally useful when the —$NHC(R^4)$— moiety of the reagents and compounds illustrated is replaced with the following moiety:

These reactions may be employed in a linear sequence to provide the compounds of the invention or they may be used to synthesize fragments which are subsequently joined by the alkylation reactions described in the Reaction Schemes.

REACTION SCHEME A
Reaction A. Coupling of residues to form an amide bond

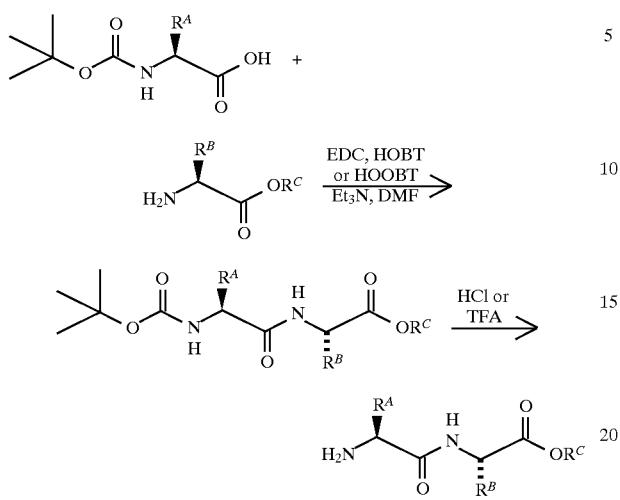

REACTION SCHEME B
Reaction B. Preparation of reduced peptide subunits by reductive alkylation

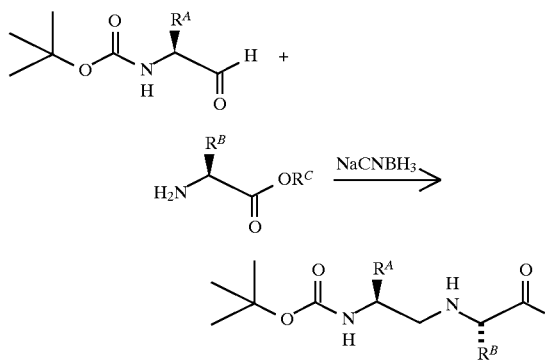

REACTION SCHEME C
Reaction C. Alkylation/reductive alkylation of reduced peptide subunits

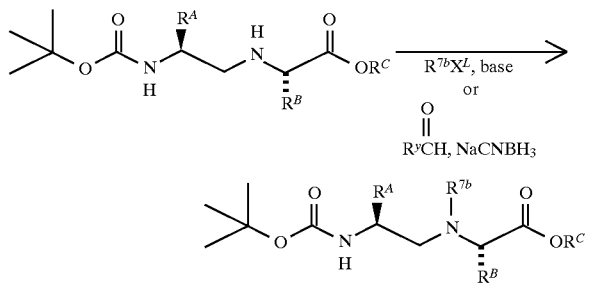

REACTION SCHEME D
Reaction D. Coupling of residues to form an amide bond

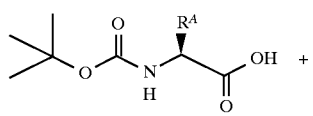

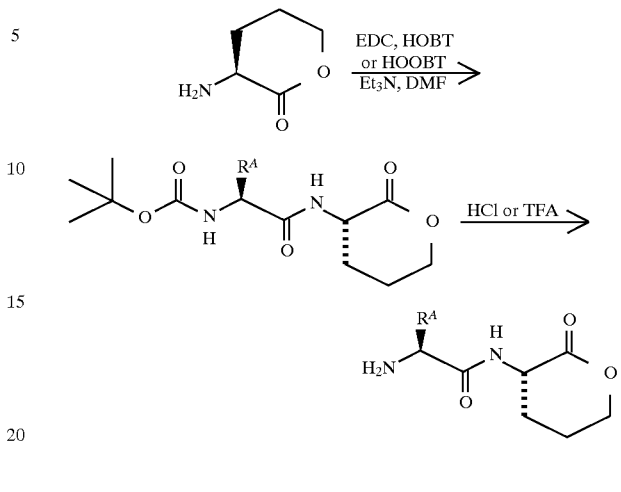

REACTION SCHEME E
Reaction E. Preparation of reduced dipeptides from peptides

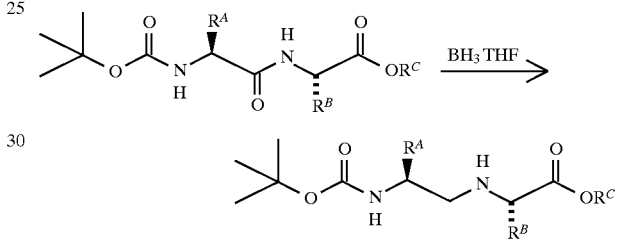

where $R^A$ and $R^B$ are $R^3$, $R^4$, $R^{5a}$ or $R^{5b}$ as previously defined; $R^C$ is $R^6$ as previously defined or a carboxylic acid protecting group; $X^L$ is a leaving group, e.g., $Br^-$, $I^-$ or $MsO^-$; and $R^y$ is defined such that $R^{7b}$ is generated by the reductive alkylation process.

Certain compounds of this invention wherein X—Y is an ethenylene or ethylene unit are prepared by employing the reaction sequences shown in Reaction Schemes F and G. Reaction Scheme F outlines the preparation of the alkene isosteres utilizing standard manipulations such as Weinreb amide formation, Grignard reaction, acetylation, ozonolysis, Wittig reaction, ester hydrolysis, peptide coupling reaction, mesylation, cleavage of peptide protecting groups, reductive alkylation, etc., as may be known in the literature or exemplified in the Experimental Procedure. For simplicity, substituents $R^{2a}$ and $R^{2b}$ on the cyclic amine moiety are not shown. It is, however, understood that the reactions illustrated are also applicable to appropriately substituted cyclic amine compounds. The key reactions are: stereoselective reduction of the Boc-amino-enone to the corresponding syn amino-alcohol (Scheme F, Step B, Part 1), and stereospecific boron triflouride or zinc chloride activated organo-magnesio, organo-lithio, or organo-zinc copper(1) cyanide $S_N2'$ displacement reaction (Scheme F, Step G). Through the use of optically pure N-Boc amino acids as starting material and these two key reactions, the stereo-chemistry of the final products is well defined. In Step H of Scheme F, the amino terminus sidechain, designated $R^x$ is incorporated using coupling reaction A and $R^xCOOH$; the alkylation reaction C using $R^xCHO$ and a reducing agent; or alkylation reaction C using $R^xCH_2X^L$. Such reactions as described in Step H are described in more detail in Reaction Schemes J–X hereinbelow.

47
The alkane analogs are prepared in a similar manner by including an additional catalytic hydrogenation step as outlined in Reaction Scheme G.
REACTION SCHEME F
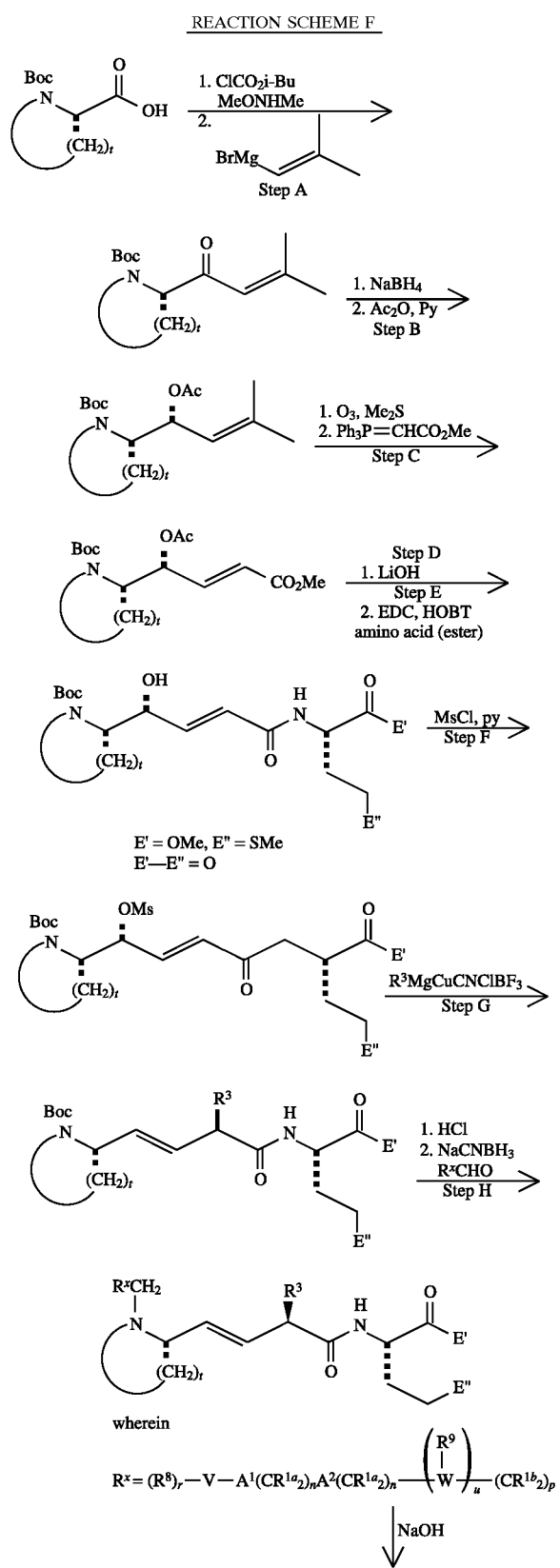
48
-continued
REACTION SCHEME F
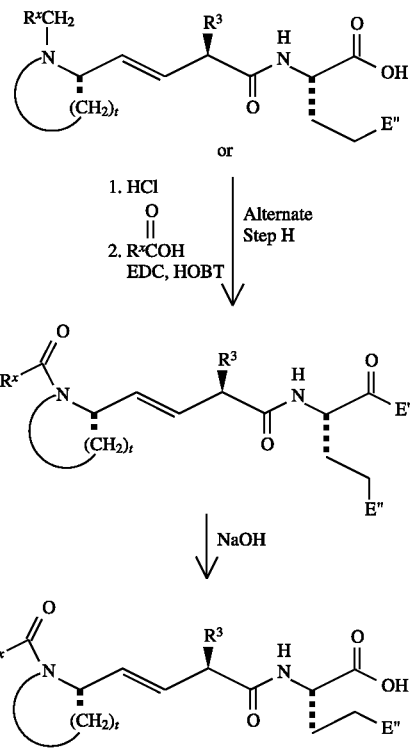
REACTION SCHEME G
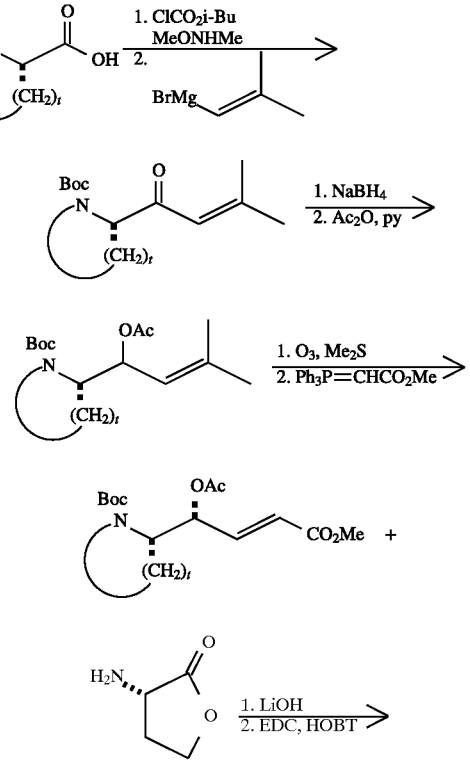

-continued
REACTION SCHEME G

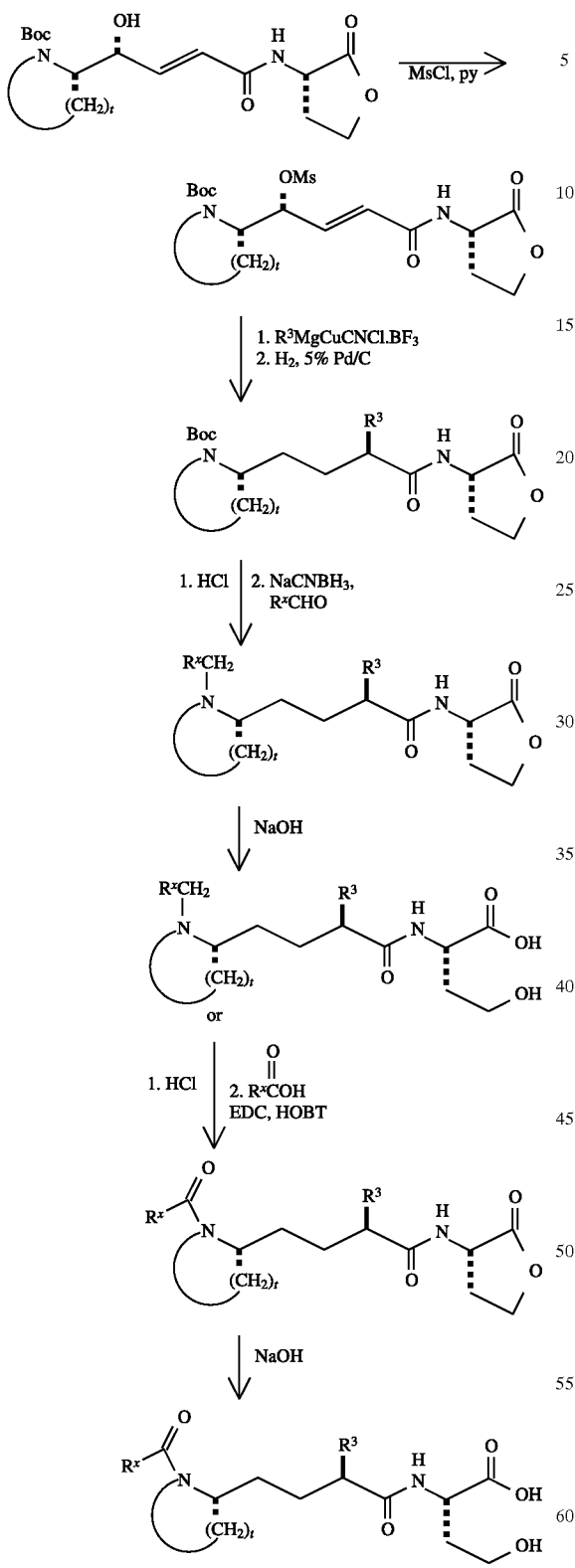

The oxa isostere compounds of this invention are prepared according to the route outlined in Scheme H. An aminoalcohol 1 is acylated with alpha-chloroacetyl chloride in the presence of trialkylamines to yield amide 2. Subsequent reaction of 2 with a deprotonation reagent (e.g., sodium hydride or potassium t-butoxide) in an ethereal solvent such as THF provides morpholinone 3. Alkylation of 3 with $R^3X^L$, where $X^L$ is a leaving group such as $Br^-$, $I^-$ or $Cl^-$ in THF/DME (1,2-dimethoxyethane) in the presence of a suitable base, preferably NaHMDS [sodium bis (trimethylsilyl)amide], affords 4, which is retreated with NaHMDS followed by either protonation or the addition of an alkyl halide $R^4X$ to give 5a or 5b, respectively, as a enantiomeric mixture. Alternatively, 5a can be prepared from 3 via an aldol condensation approach. Namely, deprotonation of 3 with NaHMDS followed by the addition of a carbonyl compound $R^yR^zCO$ gives the adduct 6. Dehydration of 6 can be effected by mesylation and subsequent elimination catalyzed by DBU (1,8-diazabicyclo[5.4.0] undec-7-ene) or the direct treatment of 6 with phosphorus oxychloride in pyridine to give olefin 7. Then, catalytic hydrogenation of 7 yields 5a (wherein —$CHR^yR^z$ constitutes $R^3$). Direct hydrolysis of 5 with lithium hydrogen peroxide in aqueous THF, or aqueous HCl, produces acid 8a. Compound 8a is then derivatized with BOC—ON or BOC anhydride to give 8b. The peptide coupling of acid 8b with either an alpha-aminolactone (e.g., homoserine lactone, etc.) or the ester of an amino acid is carried out under the conditions exemplified in the previously described references to yield derivative 9. Treatment of 9 with gaseous hydrogen chloride gives 10, which undergoes further elaboration as described in Reaction Schemes J-hereinbelow.

An alternative method for the preparation of the prolyl oxa isostere (compounds 23 and 24) is shown in Scheme H-1. Referring to Scheme H-1, the aminoalcohol 1 is protected with trifluoroacetic anhydride and the blocked compound 15 treated with diphenyl disulfide in the presence of tributylphosphine to provide the thioether 16. Chlorination of compound 16 provides compound 17 which can be reacted with the appropriate carboxylic acid alcohol in the presence of silver perchlorate and tin (II) chloride, to afford the mixed acetal 18. Removal of the phenylmercapto moiety with Raney nickel provides compound 19. Compound 19 is doubly deprotected, then selectively BOC protected to provide the acid 20, which undergoes the steps previously described for incorporating terminal amino acid. Still another alternative method for the preparation of the prolyl oxa isostere (compounds 23 and 24 ) is described in the literature [Ruth E. TenBrink, J. Org. Chem., 52, 418–422 (1987)].

SCHEME H
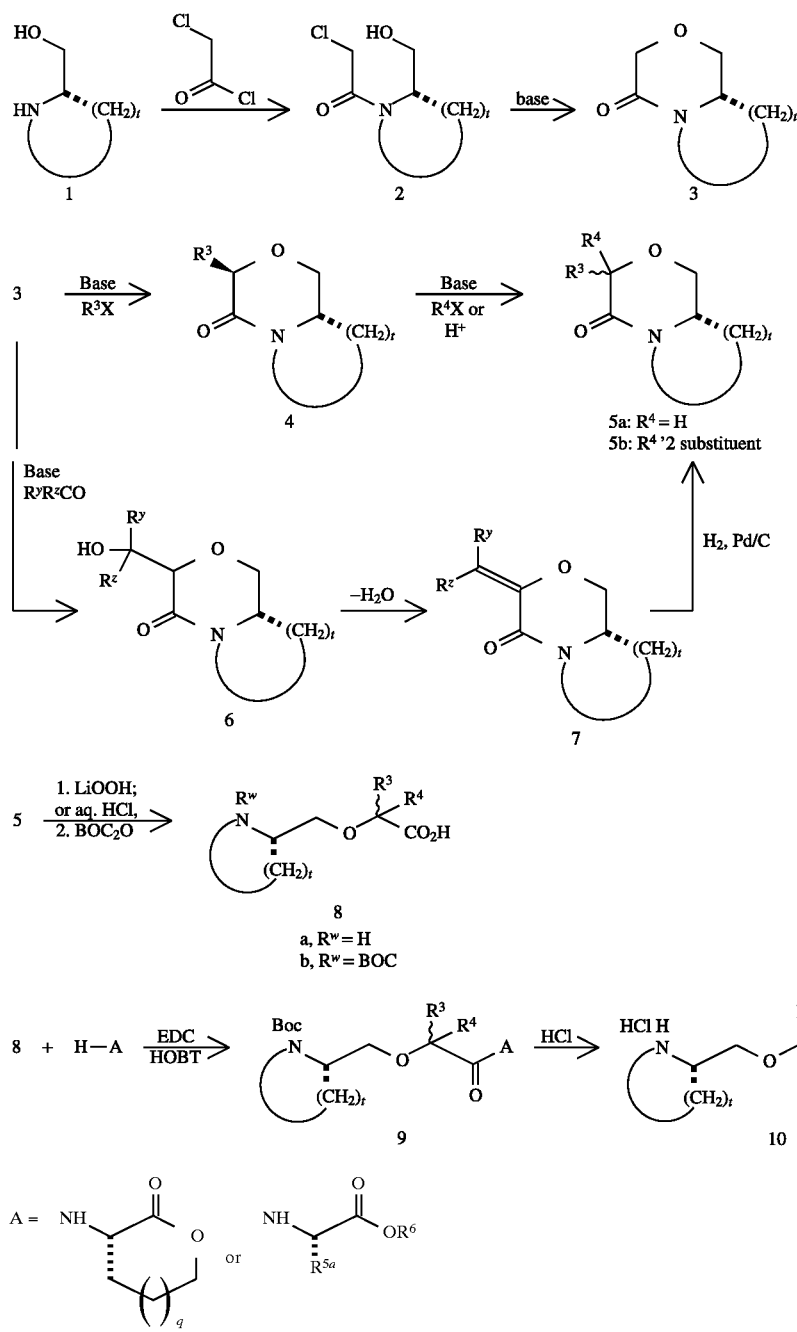
SCHEME H-1
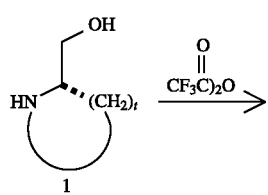
-continued
SCHEME H-1
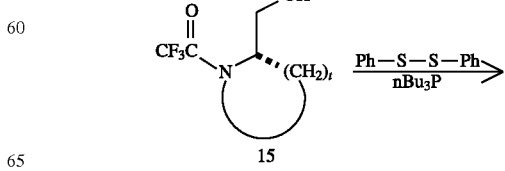

-continued
SCHEME H-1

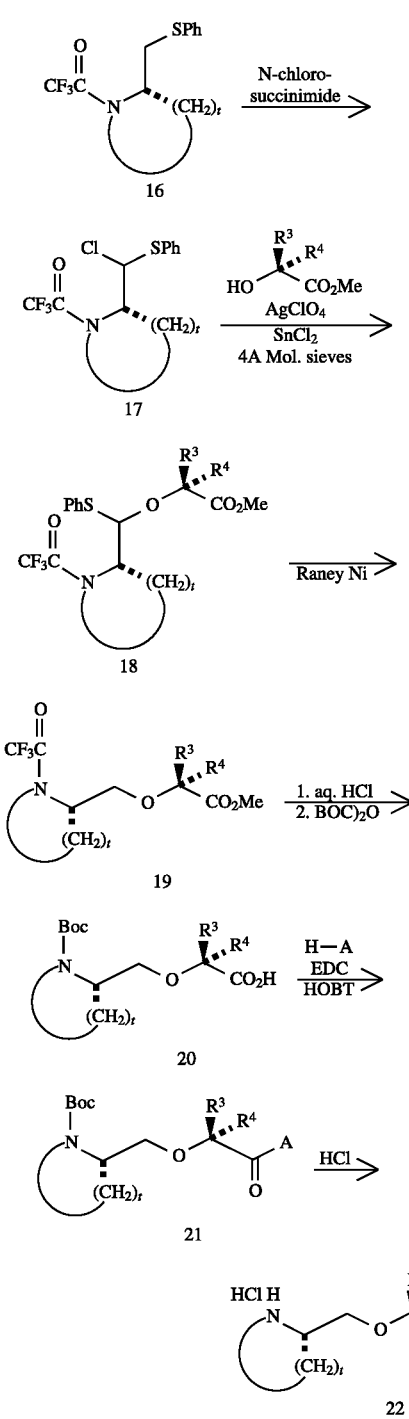

The thia, oxothia and dioxothia isostere compounds of this invention are prepared in accordance to the route depicted in Scheme I. Aminoalcohol 1 is derivatized with $BOC_2O$ to give 25. Mesylation of 25 followed by reaction with methyl alpha-mercaptoacetate in the presence of cesium carbonate gives sulfide 26. Removal of the BOC group in 26 with TFA followed by neutralization with di-isopropylethylamine leads to lactam 27. Sequential alkylation of 27 with the alkyl halides $R^3X$ and $R^4X$ in THF/DME using NaHDMS as the deprotonation reagent produces 28. Hydrolysis of 28 in hydrochloride to yield 29a, which is derivatized with Boc anhydride to yield 29b. The coupling of 29b with an alpha-aminolactone (e.g., homoserine lactone, etc.) or the ester of an amino acid is carried out under conventional conditions as exemplified in the previously described references to afford 30. Sulfide 30 is readily oxidized to sulfone 31 by the use of MCPBA (m-chloroperoxybenzoic acid). The N—BOC group of either 30 or 31 is readily removed by treatment with gaseous hydrogen chloride.

SCHEME I

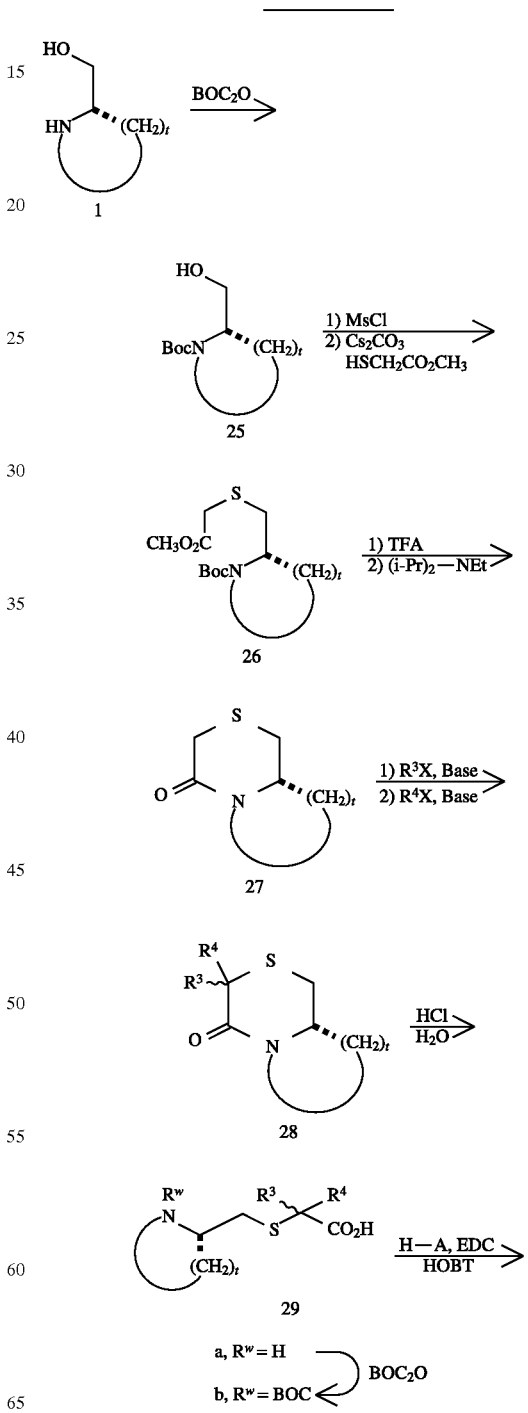

-continued
SCHEME I

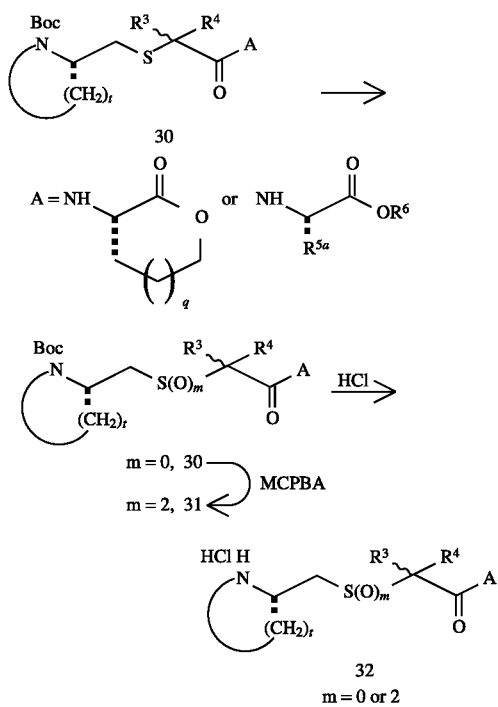

Reaction Schemes J–R illustrate reactions wherein the non-sulfhydryl-containing moiety at the N-terminus of the compounds of the instant invention is attached to the fully elaborated cyclic amino peptide unit, prepared as described in Reaction Schemes A–I. It is understood that the reactions illustrated may also be performed on a simple cyclic amino acid, which may then be further elaborated utilizing reactions described in Reaction Schemes A–I to provide the instant compounds.

The intermediates whose synthesis are illustrated in Reaction Schemes A–I can be reductively alkylated with a variety of aldehydes, such as V, as shown in Reaction Scheme J. The aldehydes can be prepared by standard procedures, such as that described by O. P. Goel, U. Krolls, M. Stier and S. Kesten in *Organic Syntheses*, 1988, 67, 69–75, from the appropriate amino acid (Reaction Scheme F). The reductive alkylation can be accomplished at pH 5–7 with a variety of reducing agents, such as sodium triacetoxyborohydride or sodium cyanoborohydride in a solvent such as dichloroethane, methanol or dimethylformamide. The product VI can be deprotected with trifluoroacetic acid in methylene chloride to give the final compounds VII. The final product VII is isolated in the salt form, for example, as a trifluoroacetate, hydrochloride or acetate salt, among others. The product diamine VII can further be selectively protected to obtain VIII, which can subsequently be reductively alkylated with a second aldehyde to obtain IX. Removal of the protecting group, and conversion to cyclized products such as the dihydroimidazole XI can be accomplished by literature procedures.

Alternatively, the protected cyclic aminopeptidyl intermediate can be reductively alkylated with other aldehydes such as 1-trityl-4-carboxaldehyde or 1-trityl-4-imidazolylacetaldehyde, to give products such as XII (Reaction Scheme K). The trityl protecting group can be removed from XII to give XIII, or alternatively, XII can first be treated with an alkyl halide then subsequently deprotected to give the alkylated imidazole XIV. Alternatively, the dipeptidyl analog intermediate can be acylated or sulfonylated by standard techniques.

The imidazole acetic acid XV can be converted to the protected acetate XVII by standard procedures, and XVII can be first reacted with an alkyl halide, then treated with refluxing methanol to provide the regiospecifically alkylated imidazole acetic acid ester XVIII. Hydrolysis and reaction with the protected dipeptidyl analog intermediate in the presence of condensing reagents such as 1-(3-dimethylaminopropyl)-3-ethylcarbodiimide (EDC) leads to acylated products such as XIX.

If the protected dipeptidyl analog intermediate is reductively alkylated with an aldehyde which also has a protected hydroxyl group, such as XX in Reaction Scheme N, the protecting groups can be subsequently removed to unmask the hydroxyl group (Reaction Schemes N, P). The alcohol can be oxidized under standard conditions to e.g. an aldehyde, which can then be reacted with a variety of organometallic reagents such as Grignard reagents, to obtain secondary alcohols such as XXIV. In addition, the fully deprotected amino alcohol XXV can be reductively alkylated (under conditions described previously) with a variety of aldehydes to obtain secondary amines, such as XXVI (Reaction Scheme P), or tertiary amines.

The Boc protected amino alcohol XXII can also be utilized to synthesize 2-aziridinylmethylpiperazines such as XXVII (Reaction Scheme Q). Treating XXII with 1,1'-sulfonyldiimidazole and sodium hydride in a solvent such as dimethylformamide led to the formation of aziridine XXVII. The aziridine may be reacted in the presence of a nucleophile, such as a thiol, in the presence of base to yield the ring-opened product XXVIII.

In addition, the protected dipeptidyl analog intermediate can be reacted with aldehydes derived from amino acids such as O-alkylated tyrosines, according to standard procedures, to obtain compounds such as XXXIV, as shown in Reaction Scheme R. When R' is an aryl group, XXXIV can first be hydrogenated to unmask the phenol, and the amine group deprotected with acid to produce XXXV. Alternatively, the amine protecting group in XXXIV can be removed, and O-alkylated phenolic amines such as XXXVI produced.

REACTION SCHEME J
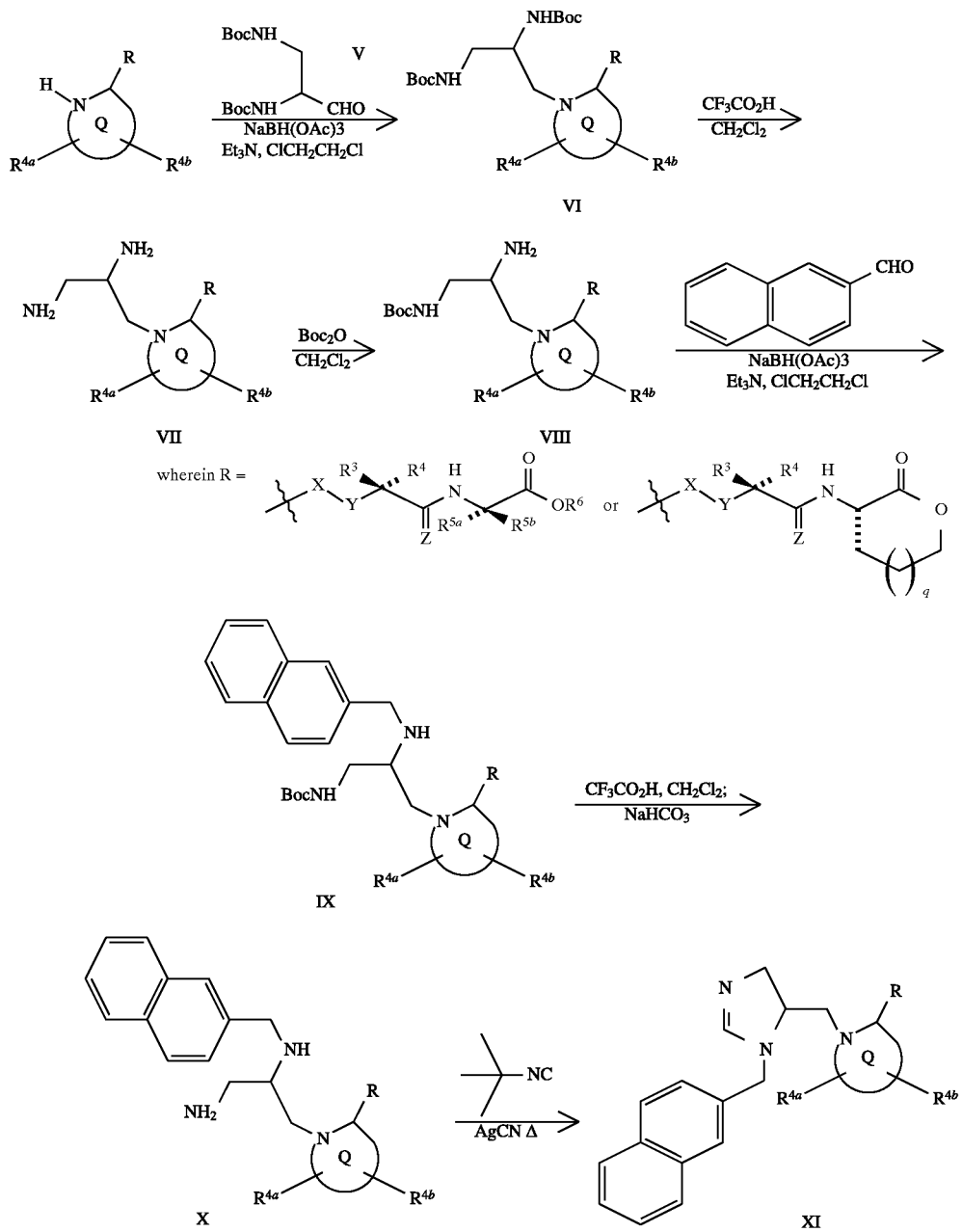
REACTION SCHEME K
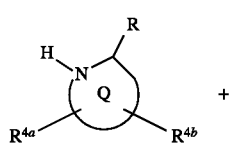 + 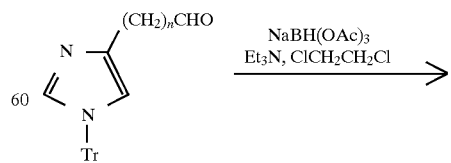

REACTION SCHEME K
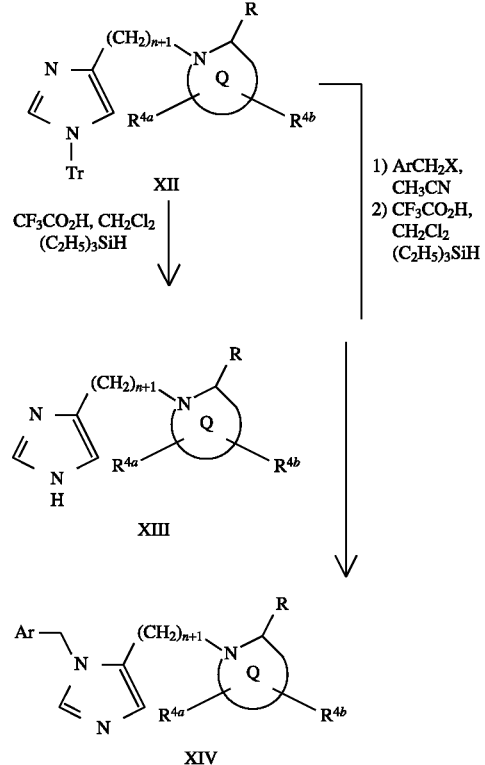
REACTION SCHEME L
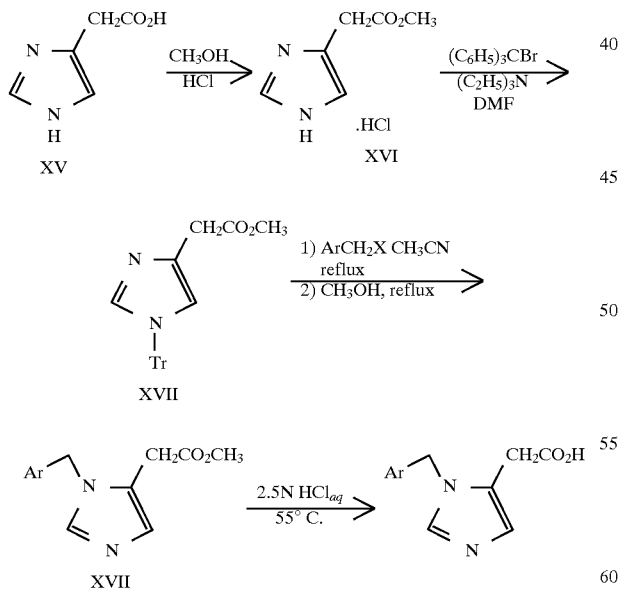
REACTION SCHEME M
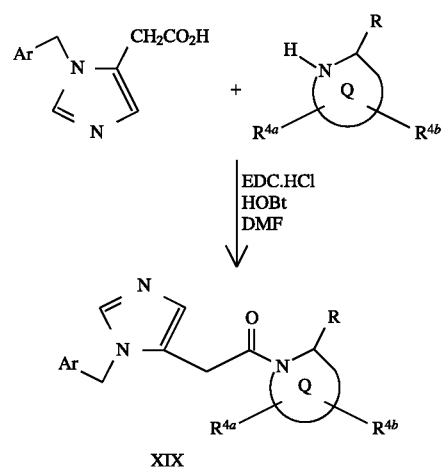
REACTION SCHEME N
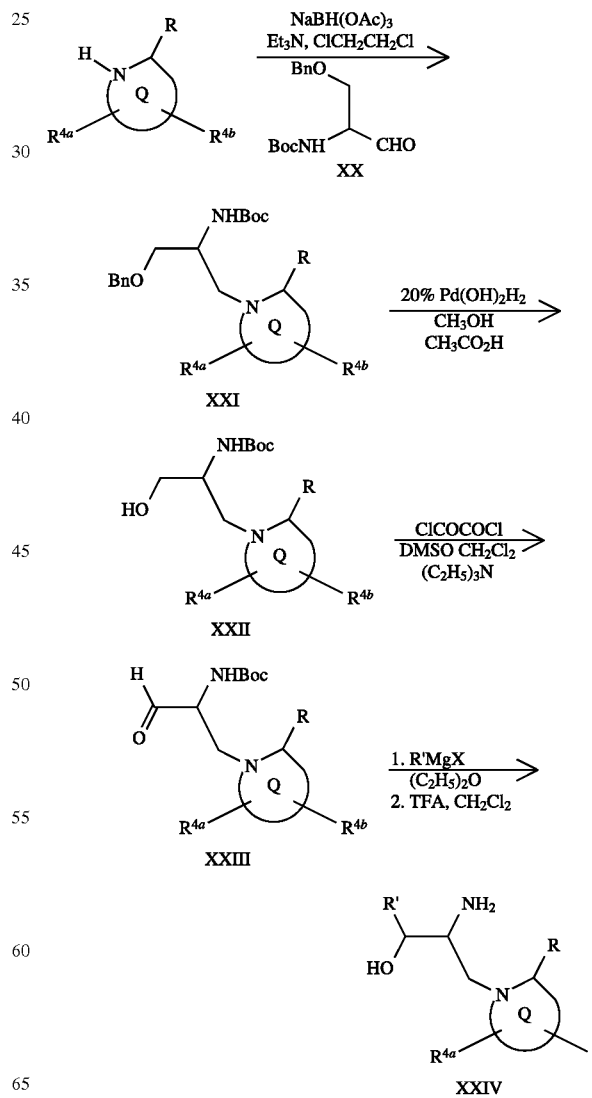

REACTION SCHEME P
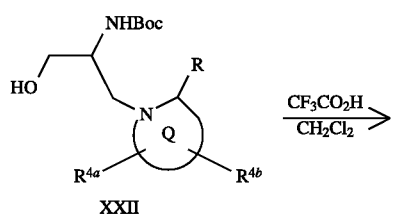
XXII
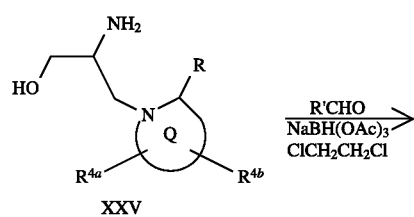
XXV
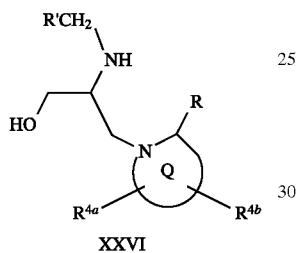
XXVI
REACTION SCHEME Q
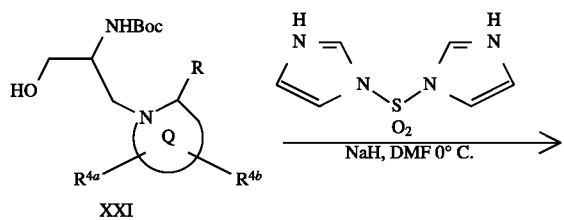
XXI
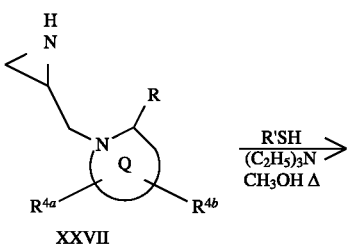
XXVII
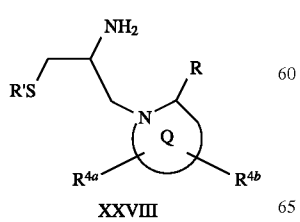
XXVIII
REACTION SCHEME R
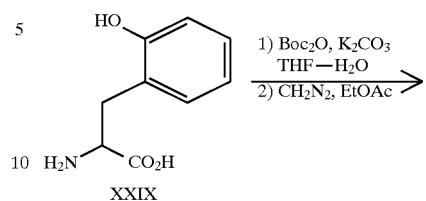
XXIX
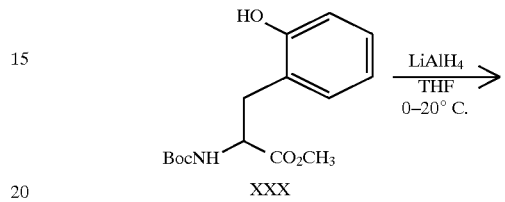
XXX
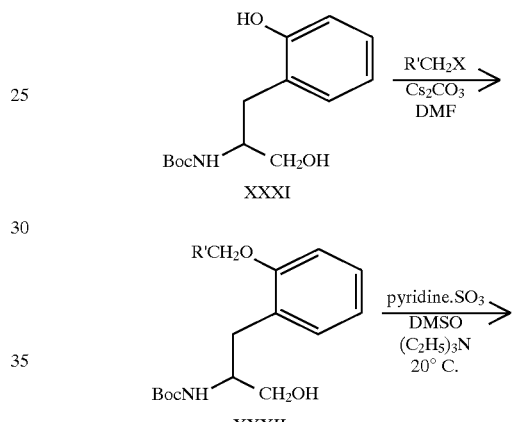
XXXI
XXXII
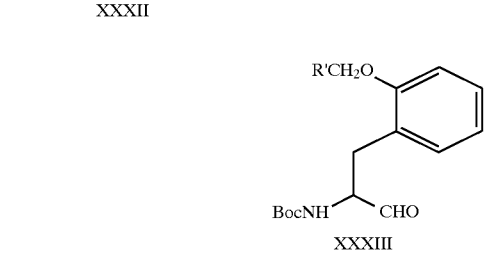
XXXIII
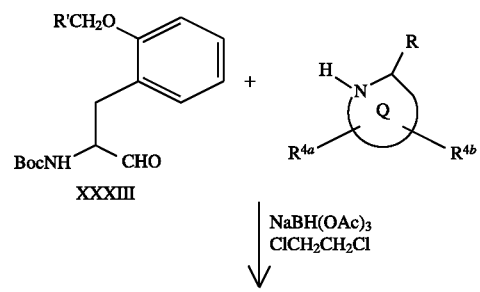
XXXIII
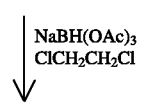

-continued
REACTION SCHEME R

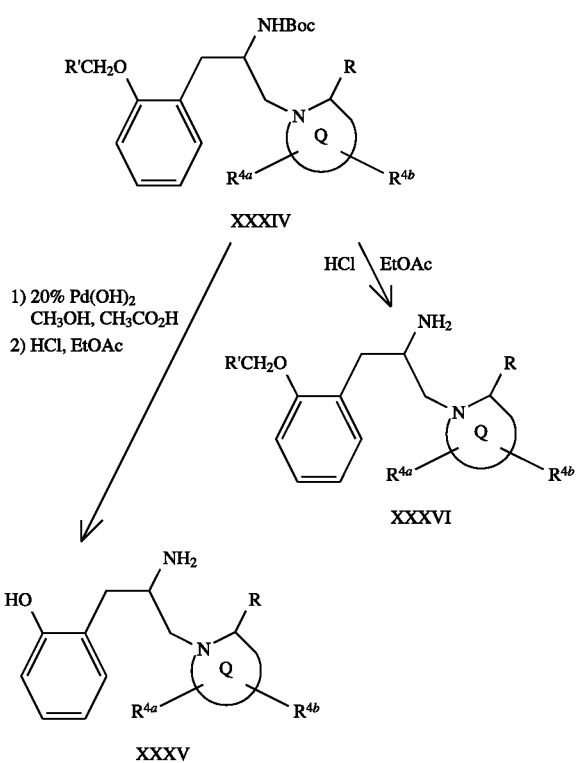

The compounds of this invention inhibit Ras farnesyl transferase which catalyzes the first step in the post-translational processing of Ras and the biosynthesis of functional Ras protein. These compounds are useful as pharmaceutical agents for mammals, especially for humans. These compounds may be administered to patients for use in the treatment of cancer. Examples of the type of cancer which may be treated with the compounds of this invention include, but are not limited to, colorectal carcinoma, exocrine pancreatic carcinoma, and myeloid leukemias.

The compounds of this invention are also useful for inhibiting proliferative diseases, both benign and malignant, wherein Ras proteins are aberrantly activated as a result of oncogenic mutation in other genes (i.e., the Ras gene itself is not activated by mutation to an oncogenic form) with said inhibition being accomplished by the administration of an effective amount of the compounds of the invention to a mammal in need of such treatment. For example, the benign proliferative disorder neurofibromatosis, or tumors in which the Ras is activated due to mutation or overexpression of tyrosine kinase oncogenes (e.g., neu, src, abl, lck, and fyn) may be inhibited by the compounds of this invention. Furthermore, arteriosclerosis and diabetic disturbance of blood vessels may be prevented or treated by use of the instant compounds to inhibit proliferation of vascular smooth muscle cells.

The compounds of this invention may be administered to mammals, preferably humans, either alone or, preferably, in combination with pharmaceutically acceptable carriers or diluents, optionally with known adjuvants, such as alum, in a pharmaceutical composition, according to standard pharmaceutical practice. The compounds can be administered orally or parenterally, including the intravenous, intramuscular, intraperitoneal, subcutaneous, rectal and topical routes of administration.

For oral use of a chemotherapeutic compound according to this invention, the selected compound may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

The present invention also encompasses a pharmaceutical composition useful in the treatment of cancer, comprising the administration of a therapeutically effective amount of the compounds of this invention, with or without pharmaceutically acceptable carriers or diluents. Suitable compositions of this invention include aqueous solutions comprising compounds of this invention and pharmacologically acceptable carriers, e.g., saline, at a pH level, e.g., 7.4. The solutions may be introduced into a patient's intramuscular bloodstream by local bolus injection.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a mammal undergoing treatment for cancer. Administration occurs in an amount between about 0.1 mg/kg of body weight to about 20 mg/kg of body weight per day, preferably of between 0.5 mg/kg of body weight to about 10 mg/kg of body weight per day.

The compounds of the instant invention are also useful as a component in an assay to rapidly determine the presence and quantity of farnesyl-protein transferase (FPTase) in a composition. Thus the composition to be tested may be divided and the two portions contacted with mixtures which comprise a known substrate of FPTase (for example a tetrapeptide having a cysteine at the amine terminus) and farnesyl pyrophosphate and, in one of the mixtures, a compound of the instant invention. After the assay mixtures are incubated for an sufficient period of time, well known in the art, to allow the FPTase to farnesylate the substrate, the chemical content of the assay mixtures may be determined by well known immunological, radiochemical or chromatographic techniques. Because the compounds of the instant invention are selective inhibitors of FPTase, absence or quantitative reduction of the amount of substrate in the assay mixture without the compound of the instant invention relative to the presence of the unchanged substrate in the assay containing the instant compound is indicative of the presence of FPTase in the composition to be tested.

It would be readily apparent to one of ordinary skill in the art that such an assay as described above would be useful in identifying tissue samples which contain farnesyl-protein transferase and quantitating the enzyme. Thus, potent inhibitor compounds of the instant invention may be used in an active site titration assay to determine the quantity of enzyme in the sample. A series of samples composed of aliquots of a tissue extract containing an unknown amount of farnesyl-protein transferase, an excess amount of a known substrate of FPTase (for example a tetrapeptide having a cysteine at the amine terminus) and farnesyl pyrophosphate are incubated for an appropriate period of time in the presence of varying concentrations of a compound of the instant invention. The concentration of a sufficiently potent inhibitor (i.e., one that has a Ki substantially smaller than the concentration of enzyme in the assay vessel) required to inhibit the enzymatic activity of the sample by 50% is approximately equal to half of the concentration of the enzyme in that particular sample.

EXAMPLES

Examples provided are intended to assist in a further understanding of the invention. Particular materials employed, species and conditions are intended to be further illustrative of the invention and not limitative of the reasonable scope thereof.

The standard workup referred to in the examples refers to solvent extraction and washing the organic solution with 10% citric acid, 10% sodium bicarbonate and brine as appropriate. Solutions were dried over sodium sulfate and evaporated in vacuo on a rotary evaporator.

Example 1

Preparation of N-[1-(4-imidazoleacetyl)pyrrolidin-2 (S)-ylmethyl]-N-(1-naphthylmethyl)glycyl-methionine methyl ester Step A: Preparation of N-(t-Butoxycarbonylpyrrolidin-2(S)-ylmethyl) glycine methyl ester N-(t-Butoxycarbonyl)-L-prolinal (9.16 g, 0.046 mol) and glycine methyl ester hydrochloride salt (5.78 g, 0.046 mol) were dissolved in MeOH (180 mL) at 0° C. under nitrogen, treated with sodium cyanoborohydride (4.34 g, 0.069 mol), and stirred for 18 h. The mixture was concentrated, and the residue was partitioned between EtOAc (100 mL) and satd aq NaHCO$_3$ soln (100 mL). The basic layer was washed with EtOAc (2×50 mL), the organics combined, washed with brine, and dried over Na$_2$SO$_4$. Filtration and concentration to dryness gave the title compound as a pale yellow oil. $^1$H NMR (CDCl$_3$) δ3.7–3.9 (m, 1H), 3.72 (s, 3H), 3.43 (s, 2H), 3.33 (s, 2H), 2.7–2.9 (m, 1H), 2.5–2.65 (m, 1H), 1.75–2.0 (m, 4H), 1.47 (s, 9H).

Step B: Preparation of N-(t-Butoxycarbonylpyrrolidin-2(S)-ylmethyl)-N-(1-naphthylmethyl) glycine methyl ester N-(t-Butoxycarbonylpyrrolidin-(2S)-ylmethyl) glycine methyl ester (3.0 g, 0.011 mol) was dissolved in 1,2-dichloroethane (100 ml) and 3A molecular sieves (3 g) were added followed by 1-naphthaldehyde (1.63 ml, 0.012 mol) and sodium triacetoxyborohydride (4.64 g, 0.022 mol). The mixture was stirred at ambient temperature for 5 h, and filtered through glass fiber paper and concentrated. The residue was partitioned between EtOAc and sat. NaHCO$_3$ (100 ml/25 ml). The aqueous layer was washed with EtOAc (3×50 ml). The organic layers were combined, dried with Na$_2$SO$_4$, filtered, and concentrated to give 5.2 g of crude product which was purified by chromatography (silica gel 1:6 EtOAc/hexane) to give the title compound. $^1$H NMR (CDCl$_3$) δ8.24–8.4 (m, 1H), 7.7–7.9 (m, 2H), 7.35–7.5 (m, 4H), 4.43 (d, 1H, J=12 Hz), 3.8–4.1 (m, 2H). 3.68 (s, 3H), 3.15–3.5 (m, 4H), 2.94 (t, 1H, J=12 Hz), 2.44 (t, 1H, J=11 Hz), 1.7–1.8 (m, 2H), 1.5–1.7 (m, 2H), 1.47 (s, 9H).

Step C: Preparation of N-(t-Butoxycarbonylpyrrolidin-2(S)-ylmethyl)-N-(1-naphthylmethyl)glycine N-(t-Butoxycarbonylpyrrolidin-(2S)-ylmethyl)-N-(1-naphthylmethyl)glycine methyl ester (2.91 g, 7.10 mmol) was dissolved in MeOH (60 ml) and 1N NaOH (21.3 ml, 21.3 mmol) was added. The mixture was stirred at ambient temperature for 5 h and concentrated. The resulting residue was dissolved in H$_2$O (25 ml) and neutralized with 1N HCl (21.3 ml). The aqueous layer was washed with EtOAc (3×50 ml). The organic layers were combined, dried with Na$_2$SO$_4$, filtered, and concentrated to give the product. $^1$H NMR (CD$_3$OD); δ8.57 (d, 1H, J=9 Hz), 7.5–8.0 (m, 6H), 5.13 (d, 1H, J=12 Hz), 4.71 (d, 1H, J=12 Hz), 4.05–4.15 (m, 1H), 3.71 (ABq, 2H), 3.2–3.4 (m, 3H), 3.0–3.1 (m, 1H), 2.0–2.1 (m, 1H), 1.6–1.75 (m, 2H), 1.5–1.6 (m, 1H), 1.30 (s, 9H).

Step D: Preparation of N-(t-Butoxycarbonylpyrrolidin-2(S)-ylmethyl)-N-(1-naphthylmethyl)glycine-methionine methyl ester N-(t-Butoxycarbonylpyrrolidin(-2S)-ylmethyl)-N-(1-naphthylmethyl) glycine (1.44 g, 3.6 mmol), dissolved in CH$_2$Cl$_2$ (30 mL), was treated with HOBT (0.581 g, 4.3 mmol), EDC (0.831 g, 4.3 mmol), and methionine methyl ester hydrochloride (0.859 g, 4.3 mmol). The pH was adjusted to 7.5 with Et$_3$N (1.1 mL, 7.9 mmol) and the mixture was stirred at ambient temperature for 18 h. The mixture was concentrated, and the residue was partitioned between CH$_2$Cl$_2$ (50 mL) and saturated NaHCO$_3$ solution (25 mL). The aqueous layer was extracted with CH$_2$Cl$_2$ (2×50 mL). The organic layers were combined, washed with brine (1×25 mL), dried (Na$_2$SO$_4$), filtered, and concentrated to give 2.0 g of crude product which was purified by chromatography (silica gel eluting with 1:3 to 1:1 ethyl acetate in hexane) to give pure product. $^1$H NMR (CDCl$_3$); δ8.22 (d, 1H, J=9 Hz), 7.8–7.95 (m, 2H), 7.4–7.6 (m, 4H), 4.54 (d, 1H, J=16 Hz), 4.3–4.5 (m, 2H), 4.07–4.15 (m, 1H), 3.7–3.9 (m, 2H), 3.68 (s, 3H), 3.25–3.4 (m, 3H), 3.04–3.15 (m, 1H), 2.85–3.0 (m, 1H), 2.4–2.5 (m, 1H), 1.89 (s, 3H). 1.53–2.5 (m, 5H), 1.48 (s. 9H), 1.2–1.45 (m, 2H).

Step E: Preparation of N-(pyrrolidin-(2S)-ylmethyl)-N-(1-naphthylmethyl)-glycyl-methionine methyl ester hydrochloride N-(t-Butoxycarbonylpyrrolidin-(2S)-ylmethyl)-N-(1-naphthylmethyl)-glycyl-methionine methyl ester (1.5 g, 2.76 mmol) was dissolved in EtOAc (50 mL) and cooled to 0° C. HCl was bubbled through the mixture until TLC (95:5 CH$_2$Cl$_2$:MeOH) indicated complete reaction. Argon was bubbled through the mixture to remove excess HCl and the mixture was then concentrated to give the title compound. $^1$H NMR (CD$_3$OD) δ8.23 (d, 1H, J=8 Hz), 7.9–7.95 (m, 2H), 7.45–7.65 (m, 4H), 4.4–4.6 (m, 4H). 3.7–3.8 (m, 1H), 3.71 (s, 3H), 3.5–3.7 (m, 2H), 3.12–3.28 (m, 2H), 2.9–3.05 (m, 1H), 2.35–2.5 (m, 2H), 1.93–2.15 (m, 4H), 2.02 (s, 3H), 1.77–1.89 (m, 1H), 1.6–1.7 (m, 1H).

Anal. Calcd for C$_{24}$H$_{33}$N$_3$O$_3$S.2 HCl.0.5 H$_2$O: C, 54.85; H, 6.90; N, 8.00. Found: C, 54.77; H, 6.72; N, 7.79.

Step F: Preparation of N-[1-(4-imidazoleacetyl)pyrrolidin-2(S)-ylmethyl]-N-(1-naphthylmethyl)glycyl-methionine methyl ester N-(pyrrolidin-2(S)-ylmethyl)-N-(1-naphthylmethyl)-glycyl-methionine methyl ester hydrochloride (0.200 g, 0.387 mmol), imidazoleacetic acid hydrochloride (0.094 g, 0.581 mmol), hydroxybenzotriazole hydrate (0.086 g, 0.639 mmol), EDC hydrochloride (0.134 g, 0.697 mmol) and TEA (0.340 mL, 2.44 mmol) were dissolved in dry DMF (4 mL) and stirred under Ar for 3 h. The mixture was concentrated in vacuo and the residue taken up in aq satd NaHCO$_3$ soln and extracted with EtOAc (2×40 mL). The organics were washed with H$_2$O and brine, dried over MgSO$_4$, filtered and the solvent removed in vacuo to give an oil which was chromatographed on silica gel (5:95 MeOH:CH$_2$Cl$_2$) to give the title compound. $^1$H NMR (CD$_3$OD) δ8.32 (d, 1H, J=8

Hz), 7.90 (d, 1H, J=8 Hz), 7.83 (d, 1H, J=8 Hz), 7.39 –7.62 (m, 5H), 6.92 (br s, 1H), 4.34–4.52 (m, 3H), 3.94 (d, 1H, J=13 Hz), 3.59–3.78 (m, 2H), 3.67 (s, 3H), 3.21–3.56 (m, 6H), 2.93 (dd, 1H, J=4, 13 Hz), 2.51 (dd, 1H, J=9, 13 Hz), 2.02–2.14 (m, 1H), 1.68–2.02 (m, 6H), 1.92 (s, 3H), 1.39–1.52 (m, 1H).

Anal. Calcd for $C_{29}H_{37}N_5O_4S.0.4\ CH_2Cl_2$: C, 60.29; H, 6.51; N, 11.93. Found: C, 60.39; H, 6.57; N, 11.99.

Using the methods outlined in Example 1, the following esters were prepared:

N-[1-(2(S),3-Diaminopropionyl) pyrrolidin-2(S)-ylmethyl]-N-(1-naphthylmethyl)glycyl-methionine methyl ester tris hydrochloride salt Anal. Calcd for $C_{27}H_{39}N_5O_4S.3.95\ HCl.0.95\ H_2O$: C, 46.94; H, 6.54; N, 10.14; Found: C, 46.84; H, 6.42; N, 10.20.

N-[1-(2(S)-Amino-3-benzyloxycarbonylaminopropionyl)pyrrolidin-2(S)-ylmethyl]-N-(1-naphthylmethyl)glycyl-methionine methyl ester bis hydrochloride Anal. Calcd for $C_{35}H_{45}N_5O_6S.2.8\ HCl$: C, 54.89; H, 6.29; N, 9.14; Found: C, 54.95; H, 6.35; N, 8.84.

N-[1-(3-Amino-2(S)-benzyloxycarbonylaminopropionyl) pyrrolidin-2(S)-ylmethyl]-N-(1-naphthylmethyl)glycyl-methionine methyl ester bis trifluoroacetate

FAB MS 664 (M+1).

N-[1-(L-Glutaminyl)pyrrolidin-2(S)-ylmethyl]-N-(1-naphthylmethyl)glycyl-methionine methyl ester bis trifluoroacetate Anal. Calcd for $C_{29}H_{41}N_5O_5S.2.85\ CF_3CO_2H$: C, 46.48; H, 4.93; N, 7.81; Found: C, 46.40; H, 5.29; N, 8.16.

N-[1-L-Histidinylpyrrolidin-2(S)-ylmethyl]-N-(1-naphthylmethyl)glycyl-methionine methyl ester tris trifluoroacetate

FAB MS 581 (M+1).

N-[1-(Glycyl) pyrrolidin-2(S)-ylmethyl]-N-(1-naphthylmethyl)glycyl-methionine methyl ester bis hydrochloride Anal. Calcd for $C_{26}H_{36}N_4O_4S.2\ HCl.0.95\ H_2O$: C, 52.87; H, 6.81; N, 9.48; Found: C, 52.63; H, 6.64; N, 9.26.

N-[1-(Glycyl) pyrrolidin-2(S)-ylmethyl]-N-(1-naphthylmethyl)glycyl-methionine sulfone methyl ester trifluoroacetate Anal. Calcd for $C_{26}H_{36}N_4O_6S.2.3\ CF_3CO_2H.0.3\ H_2O$: C, 45.92; H, 4.90; N, 7.00; Found: C, 45.91; H, 4.91; N, 7.29.

N-[1-(β-Alanyl) pyrrolidin-2(S)-ylmethyl]-N-(1-naphthylmethyl)glycyl-methionine methyl ester bis hydrochloride Anal. Calcd for $C_{27}H_{38}N_4O_4S.2\ HCl.0.9\ H_2O$: C, 53.71; H, 6.98; N, 9.28; Found: C, 53.69; H, 6.74; N, 9.19.

N-[1-(Sarcosyl) pyrrolidin-2(S)-ylmethyl]-N-(1-naphthylmethyl)glycyl-methionine methyl ester bis hydrochloride Anal. Calcd for $C_{27}H_{38}N_4O_4S.2\ HCl.1.6\ H_2O$: C, 52.61; H, 7.06; N, 9.09; Found: C, 52.61; H, 6.74; N, 8.79.

N-[1-(N,N-Dimethylglycyl) pyrrolidin-2(S)-ylmethyl]-N-(1-naphthylmethyl)glycyl-methionine methyl ester bis hydrochloride Anal. Calcd for $C_{28}H_{40}N_4O_4S.2\ HCl.0.85\ H_2O$: C, 54.51; H, 7.14; N, 9.08; Found: C, 54.50; H, 7.10; N, 8.71.

N-[1-(4-Cyanobenzyl)-1H-imidazol-5-ylacetyl) pyrrolidin-2(S)-ylmethyl]-N-(1-naphthylmethyl) glycyl-methionine methyl ester trifluoroacetate Anal. Calcd for $C_{37}H_{42}N_6O_4S.2.9\ CF_3CO_2H.0.45\ H_2O$: C, 51.12; H, 4.59; N, 8.36; Found: C,51.11; H, 4.60; N, 8.52.

N-[1-(Seryl)pyrrolidin-2(S)-ylmethyl]-N-(1-naphthylmethyl)glycyl-methionine methyl ester trifluoroacetate Anal. Calcd for $C_{27}H_{38}N_4O_5S.2.95\ CF_3CO_2H.0.8\ H_2O$: C, 44.83; H, 4.87; N, 6.36; Found: C, 44.82; H, 4.67; N, 6.61.

N-[1-(D-Alanyl) pyrrolidin-2(S)-ylmethyl]-N-(1-naphthylmethyl)glycyl-methionine methyl ester hydrochloride Anal. Calcd for $C_{27}H_{38}N_4O_4S.2.95\ HCl.0.25\ EtOAc$: C, 52.20; H, 6.72; N, 8.70; Found: C, 52.10H, 6.60; N, 8.70.

N-[1-(1H-imidazol-4-carbonyl)pyrrolidin-2(S)-ylmethyl]-N-(1-naphthylmethyl)glycyl-methionine methyl ester Anal. Calcd for $C_{28}H_{35}N_5O_4S.0.95\ H_2O$: C, 60.62; H, 6.70; N, 12.62; Found: C, 60.24; H, 6.42; N, 12.23.

N-[1-(Isoasparagyl) pyrrolidin-2(S)-ylmethyl]-N-(1-naphthylmethyl)glycyl-methionine methyl ester trifluoro acetate Anal. Calcd for $C_{28}H_{39}N_5O_5S.2.5\ CF_3CO_2H.0.3\ H_2O$: C, 46.73; H, 5.00; N, 8.26; Found: C, 46.71; H, 5.00; N, 8.26.

N-[1-(1H-Imidazol-4-propionyl) pyrrolidin-2(S)-ylmethyl]-N-(1-naphthylmethyl)glycyl-methionine methyl ester Anal. Calcd for $C_{30}H_{39}N_5O_4S.0.3\ H_2O$: C, 63.09; H, 6.99; N, 12.26; Found: C, 63.05; H, 6.88; N, 12.21.

N-[1-(3-Pyridylacetyl) pyrrolidin-2(S)-ylmethyl]-N-(1-naphthylmethyl)glycyl-methionine methyl ester hydrochloride Anal. Calcd for $C_{31}H_{38}N_4O_4S.2.65\ HCl.0.7\ EtOAc$: C, 56.30; H, 6.47; N, 7.77; Found: C,56.35; H, 6.44; N, 7.77.

N-[1-(2-Pyridylacetyl) pyrrolidin-2(S)-ylmethyl]-N-(1-naphthylmethyl)glycyl-methionine methyl ester Anal. Calcd for $C_{31}H_{38}N_4O_4S.0.35\ CH_2Cl_2$: C, 63.56; H, 6.58; N, 9.46; Found: C,63.63; H, 6.55; N, 9.46.

N-[1-(4-Pyridylglycyl) pyrrolidin-2(S)-ylmethyl]-N-(1-naphthylmethyl)glycyl-methionine methyl ester Anal. Calcd for $C_{31}H_{39}N_5O_4S.0.65\ CH_2Cl_2$: C, 60.06; H, 6.42; N, 11.06; Found: C, 60.02; H, 6.52; N, 11.33.

N-[1-L-Prolylpyrrolidin-2(S)-ylmethyl]-N-(1-naphthylmethyl)glycyl-methionine methyl ester bis hydrochloride Anal. Calcd for $C_{29}H_{40}N_4O_4S.2\ HCl.1.5\ H_2O$: C, 54.36; H, 7.08; N, 8.75; Found: C, 54.50; H, 6.84; N, 8.40.

N-[1-(1-morpholinoacetyl)pyrrolidin-2(S)-ylmethyl]-N-(1-naphthylmethyl)glycyl-methionine methyl ester tris trifluoroacetate Anal. Calcd for $C_{30}H_{42}N_4O_5S.3.5\ CF_3CO_2H$: C, 45.82; H, 4.73; N, 5.78; Found: C, 45.74; H, 5.00; N, 6.02.

N-[1-(4-Piperidinecarbonyl)pyrrolidin-2(S)-ylmethyl]-N-(1-naphthylmethyl)glycyl-methionine methyl ester trifluoroacetate Anal. Calcd for $C_{30}H_{42}N_4O_4S.3.2\ CF_3CO_2H.0.4\ H_2O$: C, 47.17; H, 5.00; N, 6.05; Found: C, 47.14; H, 5.01; N, 6.19.

N-[1-(3-Piperidinecarbonyl)pyrrolidin-2(S)-ylmethyl]-N-(1-naphthylmethyl)glycyl-methionine methyl ester tris trifluoroacetate Anal. Calcd for $C_{30}H_{42}N_4O_4S.3.2\ CF_3CO_2H.0.8\ H_2O$: C, 46.81; H, 5.05; N, 6.00; Found: C, 46.81; H, 5.02; N, 6.12.

N-[1-(2-Pyridylglycyl)pyrrolidin-2(S)-ylmethyl]-N-(1-naphthylmethyl)glycyl-methionine methyl ester tris trifluoroacetate Anal. Calcd for $C_{31}H_{39}N_5O_4S.2.9\ CF_3CO_2H$: C, 48.66; H, 4.65; N, 7.7 1; Found: C, 48.66; H, 4.65; N, 7.94.

N-[1-(4-Pyridylglycyl)pyrrolidin-2(S)-ylmethyl]-N-(1-naphthylmethyl)glycyl-methionine methyl ester Anal. Calcd for $C_{31}H_{39}N_5O_4S.0.65\ CH_2Cl_2$: C, 60.06; H, 6.42; N, 11.06; Found: C, 60.02; H, 6.52; N, 11.33.

N-[1-(4-Pyridyl(N-methyl)glycyl)pyrrolidin-2(S)-ylmethyl]-N-(1-naphthylmethyl)glycyl-methionine methyl ester Anal. Calcd for $C_{32}H_{41}N_5O_4S.0.45\ CH_2Cl_2$: C, 61.87; H, 6.70; N, 11.12; Found: C, 61.79; H, 6.75; N, 11.44.

Example 2

Preparation of N-[1-(4-Imidazoleacetyl)pyrrolidin-2(S)-ylmethyl]-N-(1-naphthylmethyl)glycyl-methionine bis trifluoroacetate salt N-[1-(4-Imidazoleacetyl)pyrrolidin-2(S)-ylmethyl]-N-(1-naphthylmethyl)glycyl-methionine methyl ester (0.053 g, 0.096 mmol) was dissolved in MeOH (1 mL) with cooling in an ice bath. 1N NaOH (0.384 mL, 0.384 mmol) was added, the bath was removed, and stirred for 2 h. The mixture was cooled in an ice bath and treated with 1N HCl (0.384 mL, 0.384 mmol) with stirring. After 0.5 h $H_2O$ (20 mL) was added, and the mixture was extracted with EtOAc (2×20 mL), dried over $MgSO_4$, filtered, and concentrated to give the title compound after chromatography on RP HPLC (0.1% TFA in $CH_3CN$/0.1% TFA in $H_2O$) and lyophilization. $^1H$ NMR ($CD_3OD$) δ8.84 (d, 1H, J=8 Hz), 8.33 (d, 1H, J=8 Hz), 7.98 (d, 1H, J=8 Hz), 7.94 (d, 1H, J=8 Hz), 7.73 (d, 1H, J=7 Hz), 7.63–7.44 (m, 3H), 7.29 (br s, 1H), 4.38–4.56 (m, 3H), 3.76–4.05 (m, 4H), 3.55–3.74 (m, 3H), 3.34–3.51 (m, 3H), 2.41–2.50 (m, 1H), 2.30–2.41 (m, 1H), 1.70–2.22 (m, 5H), 2.03 (s, 3H). FAB MS 538 (M+1).

Using the methods described in Example 2, but substituting the esters described in Examples 1, 9, 10, 11 and 12, the following acids were prepared:

N-[1-(2(S),3-Diaminopropionyl) pyrrolidin-2(S)-ylmethyl]-N-(1-naphthylmethyl)glycyl-methionine tris trifluoroacetate

FAB MS 516 (M+1).

N-[1-(2-(S)Amino-3-benzyloxycarbonylaminopropionyl)pyrrolidin-2(S)-ylmethyl]-N-(1-naphthylmethyl)glycyl-methionine bis trifluoroacetate Anal. Calcd for $C_{34}H_{43}N_5O_6S.2.8\ CF_3CO_2H$: C, 49.08; H, 4.76; N, 7.23; Found: C, 48.97; H, 4.83; N, 7.26.

N-[1-(3-Amino-2(S)-benzyloxycarbonylaminopropionyl)pyrrolidin-2(S)-ylmethyl]-N-(1-naphthylmethyl)glycyl-methionine bis trifluoroacetate

FAB MS 650 (M+1).

N-[1-(L-Glutaminyl)pyrrolidin-2(S)-ylmethyl]-N-(1-naphthylmethyl)-glycyl-methionine bis hydrochloride Anal. Calcd for $C_{28}H_{39}N_5O_5S.3.5\ HCl$: C, 49.07; H, 6.25; N, 10.22; Found: C, 49.11; H, 6.24; N, 10.08.

N-[1-(L-Histidinyl)pyrrolidin-2(S)-ylmethyl]-N-(1-naphthylmethyl)-glycyl-methionine tris trifluoroacetate

FAB MS 567 (M+1).

N-[1-(D-Histidinyl)pyrrolidin-2(S)-ylmethyl]-N-(1-naphthylmethyl)-glycyl-methionine tris trifluoroacetate

FAB MS 567 (M+1).

N-[1-(1H-Imidazol-4-ylacetyl)pyrrolidin-2(S)-ylmethyl]-N-(1-naphthylmethyl)glycyl-methionine sulfone trifluoroacetate Anal. Calcd for $C_{28}H_{35}N_5O_6S.3\ CF_3CO_2H.1.65\ H_2O$: C, 43.38; H, 4.42; N, 7.44; Found: C, 43.35; H, 4.19; N, 7.78.

N-[1-(Glycyl) pyrrolidin-2(S)-ylmethyl]-N-(1-naphthylmethyl)glycyl-methionine trifluoroacetate Anal. Calcd for $C_{25}H_{34}N_4O_4S.2.9\ CF_3CO_2H$: C, 45.26; H, 4.55; N, 6.86; Found: C, 45.05; H, 4.66; N, 7.23.

N-[1-(Glycyl) pyrrolidin-2(S)-ylmethyl]-N-(1-naphthylmethyl)glycyl-methionine sulfone trifluoroacetate Anal. Calcd for $C_{25}H_{34}N_4O_6S.2.5\ CF_3CO_2H.0.6\ H_2O$: C, 44.24; H, 4.67; N, 6.88; Found: C, 44.25; H, 4.58; N, 6.90.

N-[1-(β-Alanyl) pyrrolidin-2(S)-ylmethyl]-N-(1-naphthylmethyl)glycyl-methionine trifluoroacetate Anal. Calcd for $C_{26}H_{36}N_4O_4S.3.25\ CF_3CO_2H$: C, 44.80; H, 4.54; N, 6.43; Found: C, 44.74; H, 4.66; N, 6.63.

N-[1-(Sarcosyl) pyrrolidin-2(S)-ylmethyl]-N-(1-naphthylmethyl)glycyl-methionine hydrochloride Anal. Calcd for $C_{26}H_{36}N_4O_4S.2.95\ HCl.0.75\ H_2O$: C, 50.23; H, 6.56; N, 9.01; Found: C, 50.23; H, 6.32; N, 8.87.

N-[1-(N,N-Dimethylglycyl) pyrrolidin-2(S)-ylmethyl]-N-(1-naphthylmethyl)glycyl-methionine trifluoroacetate Anal. Calcd for $C_{27}H_{38}N_4O_4S.3.8\ CF_3CO_2H$: C, 43.84; H, 4.44; N, 5.91; Found: C, 43.73; H, 4.66; N, 6.30.

N-[1-(4-Cyanobenzyl)-1H-imidazol-5-ylacetyl)pyrrolidin-2(S)-ylmethyl]-N-(1-naphthylmethyl) glycyl-methionine trifluoroacetate Anal. Calcd for $C_{36}H_{40}N_6O_4S.3.10\ CF_3CO_2H.0.25\ H_2O$: C, 50.15; H, 4.35; N, 8.31; Found: C, 50.15; H, 4.38; N, 8.09.

N-[1-(2-Acetylamino-3(S)-benzyloxycarbonylaminopropionyl)pyrrolidin-2(S)-ylmethyl]-N-(1-naphthylmethyl)glycyl-methionine

FAB MS 692 (M+1)

N-[1-(2-Acetylamino-3(S)-aminopropionyl)pyrrolidin-2(S)-ylmethyl]-N-(1-naphthylmethyl)glycyl-methionine trifluoroacetate Anal. Calcd for $C_{28}H_{39}N_5O_5S.2.9\ CF_3CO_2H.1.85\ H_2O$: C, 42.33; H, 4.44; N, 6.91; Found: C, 42.33; H, 4.43; N, 7.17.

N-[1-(2-Amino-3(S)-acetylaminopropionyl)pyrrolidin-2(S)-ylmethyl]-N-(1-naphthylmethyl)glycyl-methionine trifluoroacetate

FAB MS 558 (M+1)

N-[1-(Seryl)pyrrolidin-2(S)-ylmethyl]-N-(1-naphthylmethyl)glycyl-methionine trifluoroacetate Anal. Calcd for $C_{26}H_{36}N_4O_5S.3.15\ CF_3CO_2H$: C, 44.30; H, 4.51; N, 6.40; Found: C, 43.98; H, 4.44; N, 6.77.

N-[1-(D-Alanyl) pyrrolidin-2(S)-ylmethyl]-N-(1-naphthylmethyl)glycyl-methionine hydrochloride Anal. Calcd for $C_{26}H_{36}N_4O_4S.2.85\ HCl.0.4\ EtOAc$: C, 51.81; H, 6.62; N, 8.76; Found: C, 51.88H, 6.51; N, 8.76.

N-[1-(1H-Imidazol-4-carbonyl)pyrrolidin-2(S)-ylmethyl]-N-(1-naphthylmethyl)glycyl-methionine trifluoroacetate Anal. Calcd for $C_{27}H_{33}N_5O_4S.3.5\ CF_3CO_2H$: C, 44.26; H, 3.99; N, 7.59; Found: C, 43.93; H, 4.25; N, 7.98.

N-[1-(Isoasparagyl) pyrrolidin-2(S)-ylmethyl]-N-(1-naphthylmethyl)glycyl-methionine trifluoroacetate Anal. Calcd for $C_{27}H_{37}N_5O_5S.2.5\ CF_3CO_2H.0.4\ H_2O$: C, 45.98; H, 4.86; N, 8.38; Found: C, 45.97; H, 4.88; N, 8.36.

N-[1-(1H-Imidazol-4-propionyl) pyrrolidin-2(S)-ylmethyl]-N-(1-naphthylmethyl)glycyl-methionine trifluoroacetate Anal. Calcd for $C_{29}H_{37}N_5O_4S.2.8\ CF_3CO_3H$: C, 47.71; H, 4.61; N, 8.04; Found: C, 47.60; H, 4.61; N, 8.04.

N-[1-(3-Pyridylacetyl) pyrrolidin-2(S)-ylmethyl]-N-(1-naphthylmethyl)glycyl-methionine trifluoroacetate Anal. Calcd for $C_{30}H_{36}N_4O_4S.3.45\ CF_3CO_2H.1.3\ H_2O$: C, 45.90; H, 4.39; N, 5.80; Found: C, 45.86; H, 4.11; N, 6.20.

N-[1-(2-Pyridylacetyl) pyrrolidin-2(S)-ylmethyl]-N-(1-naphthylmethyl)glycyl-methionine trifluoroacetate Anal. Calcd for $C_{30}H_{36}N_4O_4S.2.85\ CF_3CO_2H$: C, 49.08; H, 4.48; N, 6.41; Found: C, 49.02; H, 4.66; N, 6.75.

N-[1-(4-Pyridylglycyl) pyrrolidin-2(S)-ylmethyl]-N-(1-naphthylmethyl)glycyl-methionine trifluoroacetate Anal. Calcd for $C_{30}H_{37}N_5O_4S.2.95\ CF_3CO_2H$: C, 47.91; H, 4.47; N, 7.78; Found: C, 47.67; H, 4.58; N, 8.15.

N-[1-(1H-Imidazol-4-ylmethyl)pyrrolidin-2(S)-ylmethyl]-N-(1-naphthylmethyl)glycyl-methionine trifluoroacetate

FAB MS 510 (M+1).

N-[1-(2-Aminoethyl)pyrrolidin-2(S)-ylmethyl]-N-(1-naphthylmethyl)glycyl-methionine trifluoroacetate Anal. Calcd for $C_{25}H_{36}N_4O_3S.3\ CF_3CO_2H.1.45\ H_2O$: C, 44.28; H, 5.02; N, 6.66; Found: C, 44.26; H, 4.78; N, 6.99.

N-[1-(1H-Imidazol-4-ylacetyl)pyrrolidin-2(S)-ylmethyl]-N-(1-naphthylmethyl)glycyl(β-acetylamino)alanine trifluoroacetate Anal. Calcd for $C_{28}H_{34}N_6O_5.2.6\ CF_3CO_2H.0.7\ H_2O$: C, 47.26; H, 4.54; N, 9.96; Found: C, 47.29; H, 4.47; N, 9.96.

FAB MS 535 (M+1).

N-[1-(Glycyl) pyrrolidin-2(S)-ylmethyl]-N-(1-naphthylmethyl)glycyl(β-acetylamino)alanine trifluoroacetate Anal. Calcd for $C_{25}H_{33}N_5O_5.3.0\ CF_3CO_2H.1.0\ H_2O$: C, 44.13; H, 4.54; N, 8.30; Found: C, 44.13; H, 4.49; N, 8.59.

FAB MS 484 (M+1).

N-[1-(Glycyl) pyrrolidin-2(S)-ylmethyl]-N-(1-naphthylmethyl)glycyl-(2-thienyl)alanine trifluoroacetate Anal. Calcd for $C_{27}H_{32}N_4O_4S.2.4\ CF_3CO_2H.0.5\ H_2O$: C, 48.27; H, 4.51; N, 7.08; Found: C, 48.26; H, 4.51; N, 7.09.

N-[1-(1H-Imidazol-4-ylacetyl)pyrrolidin-2(S)-ylmethyl]-N-(1-naphthylmethyl)glycyl-(N,N-dimethyl)glutamine trifluoroacetate Anal. Calcd for $C_{30}H_{38}N_6O_5.3.1\ CF_3CO_2H.0.9\ H_2O$: C, 46.63; H, 4.64; N, 9.01; Found: C, 46.59; H, 4.59; N, 9.22.

N-[1-(1H-Imidazol-4-ylacetyl)pyrrolidin-2(S)-ylmethyl]-N-(1-naphthylmethyl)glycyl-(trifluoromethyl)alanine sodium salt N-[1-(1H-Imidazol-4-ylacetyl)pyrrolidin-2(S)-ylmethyl]-N-(1-naphthylmethyl)glycyl-(2(S)-amino-4-acetylamino)butyric acid sodium salt N-[1-(1H-Imidazol-4-ylacetyl)pyrrolidin-2(S)-ylmethyl]-N-(benzyl)glycyl-methionine trifluoroacetate Anal. Calcd for $C_{24}H_{33}N_5O_4S.2.2\ CF_3CO_2H.2.0\ H_2O$: C, 44.04; H, 5.10; N, 9.04; Found: C, 44.03; H, 5.10; N, 8.95.

N-[1-(Glycyl)pyrrolidin-2(S)-ylmethyl]-N-(benzyl)glycyl-methionine trifluoroacetate Anal. Calcd for $C_{21}H_{32}N4O_4S.3.5\ CF_3CO_2H.1.0\ H_2O$: C, 39.40; H, 4.43; N, 6.56; Found: C, 39.37; H, 4.41; N, 6.82.

N-[1-(1H-Imidazol-4-ylacetyl)pyrrolidin-2(S)-ylmethyl]-N-(4-methoxybenzyl)glycyl-methionine

FAB MS 518 (M+1)

N-[1-(1H-Imidazol-4-ylacetyl)pyrrolidin-3(S)-ethyl-2(S)-ylmethyl]-N-(1-naphthylmethyl)glycyl-methionine trifluoroacetate Anal. Calcd for $C_{30}H_{39}N_5O_4S.3.45\ CF_3CO_2H$: C, 46.21; H, 4.46; N, 7.30; Found: C, 46.24; H, 4.61; N, 7.53.

N-[1-(Glycyl) pyrrolidin-3(S)-ethyl-2(S)-ylmethyl]-
N-(1-naphthylmethyl)glycyl-methionine
trifluoroacetate Anal. Calcd for $C_{27}H_{38}N_4O_4S.3.15\ CF_3CO_2H.1.55\ H_2O$: C, 44.35; H, 4.95; N, 6.21; Found: C, 44.36; H, 4.69; N, 6.61.

N-[1-(Glycyl)pyrrolidin-3(S)-ethyl-2(S)-ylmethyl]-
N-(benzyl)glycyl-methionine bis hydrochloride Anal. Calcd for $C_{23}H_{36}N_4O_4S.2\ HCl.1.0\ H_2O$: C, 49.72; H, 7.26; N, 10.09; Found: C, 49.92; H, 7.07; N, 9.59.

N-[1-(1H-Imidazol-4-ylacetyl)pyrrolidin-3(S)-ethyl-
2(S)-ylmethyl]-N-(benzyl)glycyl-methionine
trifluoroacetate Anal. Calcd for $C_{26}H_{37}N_5O_4S.3.2\ CF_3CO_2H$: C, 44.19; H, 4.60; N, 7.95; Found: C, 44.13; H, 4.98; N, 8.35.

N-[1-(L-Prolyl)pyrrolidin-2(S)-ylmethyl]-N-(1-
naphthylmethyl)glycyl-methionine

FAB MS 527 (M+1)

N-[1-(1-Morpholinoacetyl)pyrrolidin-2(S)-ylmethyl]
-N-(1-naphthylmethyl)glycyl-methionine

FAB MS 557 (M+1)

N-[1-(4-Piperidinecarbonyl)pyrrolidin-2(S)-
ylmethyl]-N-(1-naphthylmethyl)glycyl-methionine
bis trifluoroacetate Anal. Calcd for $C_{29}H_{40}N_4O_4S.2.3\ CF_3CO_2H.0.9\ H_2O$: C, 49.26; H, 5.42; N, 6.84; Found: C, 49.29; H, 5.39; N, 6.95.

N-[1-(3-Piperidinecarbonyl)pyrrolidin-2(S)-
ylmethyl]-N-(1-naphthylmethyl)glycyl-methionine
trifluoroacetate Anal. Calcd for $C_{29}H_{40}N_4O_4S.2.6\ CF_3CO_2H.1.7\ H_2O$: C, 47.34; H, 5.34; N, 6.46; Found: C, 47.37; H, 5.33; N, 6.72.

N-[1-(2-Pyridylglycyl)pyrrolidin-2(S)-ylmethyl]-N-
(1-naphthylmethyl)glycyl-methionine
trifluoroacetate Anal. Calcd for $C_{30}H_{37}N_5O_4S.2.5\ CF_3CO_2H.0.8\ H_2O$: C, 48.70; H, 4.80; N, 8.11; Found: C, 48.72; H, 4.73; N, 8.35.

N-[1-(4-Pyridylglycyl)pyrrolidin-2(S)-ylmethyl]-N-
(1-naphthylmethyl)glycyl-methionine
trifluoroacetate Anal. Calcd for $C_{30}H_{37}N_5O_4S.2.95\ CF_3CO_2H$: C, 47.91; H, 4.47; N, 7.78; Found: C, 47.67; H, 4.58; N, 8.15.

N-[1-(4-Pyridyl(N-methyl)glycyl)pyrrolidin-2(S)-
ylmethyl]-N-(1-naphthylmethyl)glycyl-methionine
trifluoroacetate Anal. Calcd for $C_{31}H_{39}N_5O_4S.2.95\ CF_3CO_2H.0.7\ H_2O$: C, 47.83; H, 4.72; N, 7.56; Found: C, 47.63; H, 4.80; N, 7.95.

N-[1-(1H-Imidazol-4-ylpropionyl) pyrrolidin-2(S)-
ylmethyl]-N-(1-naphthylmethyl)glycyl-(β-
acetylamino)alanine trifluoroacetate Anal. Calcd for $C_{29}H_{36}N_6O_5.4.1\ CF_3CO_2H.2.1\ H_2O$: C, 42.87; H, 4.31; N, 8.15; Found: C, 42.87; H, 4.25; N, 8.26.

N-[1-(4-Pyridylglycyl) pyrrolidin-2(S)-ylmethyl]-N-
(1-naphthylmethyl)glycyl-(β-acetylamino)
alaninetrifluoroacetate Anal. Calcd for $C_{29}H_{36}N_6O_5.3.1\ CF_3CO_2H.0.9\ H_2O$: C, 46.74; H, 4.43; N, 9.03; Found: C, 46.71; H, 4.41; N, 9.27.

N-[1-(1H-Imidazol-4-ylacetyl)pyrrolidin-2(S)-
ylmethyl]-N-(1-naphthylmethyl)glycyl-(N-methyl)
glutamine trifluoroacetate Anal. Calcd for $C_{290}H_{36}N_6O_5.1.7\ CF_3CO_2H.0.9\ H_2O$: C, 44.31; H, 4.29; N, 8.52; Found: C, 44.33; H, 4.28; N, 8.40.

N-[1-(1H-Imidazol-4-ylacetyl) pyrrolidin-2(S)-
ylmethyl]-N-(1-naphthylmethyl)glycyl-(β-
methylcarbonylamino)alanine trifluoroacetate Anal. Calcd for $C_{28}H_{35}N_7O_5.1.2\ CF_3CO_2H.0.6\ H_2O$: C, 44.65; H, 4.29; N, 10.60; Found: C, 44.66; H, 4.40; N, 9.63.

N-[1-(1H-Imidazol-4-ylacetyl) pyrrolidin-2(S)-
ylmethyl]-N-(1-naphthylmethyl)glycyl-(β-
methylsulfonylamino)alanine trifluoroacetate Anal. Calcd for $C_{27}H_{34}N_6O_6S.2.8\ CF_3CO_2H.0.9\ H_2O$: C, 43.21; H, 4.29; N, 9.27; Found: C, 43.21; H, 4.30; N, 9.40.

N-[1-(1H-Imidazol-4-ylacetyl) pyrrolidin-2(S)-
ylmethyl]-N-(1-naphthylmethyl)glycyl-(β-
propionylamino)alanine trifluoroacetate Anal. Calcd for $C_{29}H_{36}N_6O_5.3.1\ CF_3CO_2H.2.0\ H_2O$: C, 45.07; H, 4.63; N, 8.96; Found: C, 45.06; H, 4.56; N, 9.08.

N-[1-(1H-Imidazol-4-ylacetyl) pyrrolidin-2(S)-
ylmethyl]-N-(1-naphthylmethyl)glycyl-(β-
pyrrolidinon-1-ylamino)alanine trifluoroacetate Anal. Calcd for $C_{30}H_{36}N_6O_5.3.4\ CF_3CO_2H.2.7\ H_2O$: C, 44.34; H, 4.53; N, 8.43; Found: C, 44.32; H, 4.47; N, 8.74.

N-[1-(1H-Imidazol-4-ylacetyl)pyrrolidin-2(S)-
ylmethyl]-N-(3-methoxybenzyl)glycyl-methionine
trifluoroacetate Anal. Calcd for $C_{25}H_{35}N_5O_5S.2.75\ CF_3CO_2H$: C, 44.07; H, 4.58; N, 8.43; Found: C, 43.98; H, 4.82; N, 8.62.

N-[1-(1H-Imidazol-4-ylacetyl)pyrrolidin-2(S)-
ylmethyl]-N-(2-methoxybenzyl)glycyl-methionine
trifluoroacetate Anal. Calcd for $C_{25}H_{35}N_5O_5S.2.95\ CF_3CO_2H.0.95\ H_2O$: C, 42.60; H, 4.61; N, 8.04; Found: C, 42.56; H, 4.48; N, 8.00.

N-[1-(Glycyl)pyrrolidin-2(S)-ylmethyl]-N-(3-
methoxybenzyl)glycyl-methionine hydrochloride Anal. Calcd for $C_{22}H_{34}N_4O_5S.3.65\ HCl$: C, 44.06; H, 6.33; N, 9.34; Found: C, 43.99; H, 6.46; N, 9.36.

N-[1-(Glycyl)pyrrolidin-2(S)-ylmethyl]-N-(2-
methoxybenzyl)glycyl-methionine trifluoroacetate Anal. Calcd for $C_{22}H_{34}N_4O_5S.3.1\ CF_3CO_2H.0.6\ H_2O$: C, 40.77; H, 4.65; N, 6.74; Found: C, 40.74; H, 4.67; N, 7.00.

N-[1-(1H-Imidazol-4-ylpropionyl)pyrrolidin-2(S)-
ylmethyl]-N-(2-methoxybenzyl)glycyl-methionine
trifluoroacetate Anal. Calcd for $C_{26}H_{37}N_5O_5S.2.9\ CF_3CO_2H.1.1\ H_2O$: C, 43.30; H, 4.81; N, 7.94; Found: C, 43.28; H, 4.75; N, 7.98.

N-[1-(1H-Imidazol-4-ylacetyl)pyrrolidin-2(S)-ylmethyl]-N-(3-cyanobenzyl)glycyl-methionine trifluoroacetate Anal. Calcd for $C_{25}H_{32}N_6O_4S.4.3$ $CF_3CO_2H.0.8$ $H_2O$: C, 39.67; H, 3.76; N, 8.26; Found: C, 39.65; H, 3.75; N, 8.62.

N-[1-(1H-Imidazol-4-ylacetyl)pyrrolidin-2(S)-ylmethyl]-N-(4-cyanobenzyl)glycyl-methionine trifluoroacetate Anal. Calcd for $C_{25}H_{32}N_6O_4S.2.5$ $CF_3CO_2H.1.4$ $H_2O$: C, 43.79; H, 4.57; N, 10.21; Found: C, 43.85; H, 4.57; N, 10.13.

N-[1-(1H-Imidazol-4-ylacetyl)pyrrolidin-2(S)-ylmethyl]-N-(2-cyanobenzyl)glycyl-methionine trifluoroacetate Anal. Calcd for $C_{25}H_{32}N_6O_4S.3.5$ $CF_3CO_2H.1.4$ $H_2O$: C, 41.02; H, 4.12; N, 8.97; Found: C, 41.03; H, 4.05; N, 9.01.

N-[1-(Glycyl)pyrrolidin-2(S)-ylmethyl]-N-(2-cyanobenzyl)glycyl-methionine trifluoroacetate Anal. Calcd for $C_{22}H_{31}N_5O_4S.3.0$ $CF_3CO_2H$ $.0.6$ $H_2O$: C, 41.29; H, 4.36; N, 8.60; Found: C, 41.29; H, 4.33; N, 8.67.

N-[1-(1H-Imidazol-4-ylpropionyl)pyrrolidin-2(S)-ylmethyl]-N-(2-cyanobenzyl)glycyl-methionine trifluoroacetate Anal. Calcd for $C_{26}H_{34}N_6O_4S.4.1$ $CF_3CO_2H.1.0$ $H_2O$: C, 40.23; H, 4.06; N, 8.23; Found: C, 40.20; H, 4.01; N, 8.50.

N-[1-(1H-Imidazol-4-ylacetyl)pyrrolidin-2(S)-ylmethyl]-N-(2-methylbenzyl)glycyl-methionine trifluoroacetate Anal. Calcd for $C_{25}H_{35}N_5O_4S.3.2$ $CF_3CO_2H$: C, 43.52; H, 4.44; N, 8.08; Found: C, 43.54; H, 4.62; N, 8.20.

N-[1-(1H-Imidazol-4-ylacetyl)pyrrolidin-2(S)-ylmethyl]-N-(2-trifluoromethylbenzyl)glycyl-methionine N-[1-(1H-Imidazol-4-ylacetyl)pyrrolidin-2(S)-ylmethyl]-N-(1-naphthylsulfonyl)glycyl-methionine trifluoroacetate Anal. Calcd for $C_{27}H_{33}N_5O_6S_2.1.8$ $CF_3CO_2H$: C, 46.35; H, 4.42; N, 8.83; Found: C, 46.39; H, 4.48; N, 9.20.

Example 3

Preparation of N-[1-(L-Pyroglutamyl)pyrrolidin-2(S)-ylmethyl]-N-(1-naphthylmethyl)glycyl-methionine methyl ester N-(Pyrrolidin-2(S)-ylmethyl)-N-(1-naphthylmethyl)-glycyl-methionine methyl ester hydrochloride(0.200 g, 0.387 mmol), L-pyroglutamic acid (0.060 g, 0.465 mmol) and diisopropylethylamine (0.300 mL, 2.32 mmol) were dissolved in dry DMF (2 mL). BOP-chloride (0.355 mg, 1.39 mmol) was added and the mixture stirred under Ar for 18 h. The solvent was removed in vacuo and the residue partitioned between saturated $NaHCO_3$ soln and EtOAc. The layers were separated and the organics were washed with $H_2O$, brine, dried over $MgSO_4$, filtered and the solvent removed in vacuo to give an oil which was chromatographed on silica gel (3:97 MeOH:$CH_2Cl_2$) to give the title compound. $^1H$ NMR ($CD_3OD$) δ8.33 (d, 1H, J=8 Hz), 7.91 (d, 1H, J=7 Hz), 7.85 (d, 1H, J=8 Hz), 7.43–7.64 (m, 4H), 4.36–4.54 (m, 3H), 3.98 (d, 1H, J=13 Hz), 3.69 (s, 3H), 3.49–3.58 (m, 1H), 3.21–3.49 (m, 5H), 2.92 (dd,1H, J=4, 12 Hz), 2.50–2.59 (m, 1H), 2.25–2.50 (m, 3H), 2.08–2.25 (m, 1H), 1.79–2.08 (m, 5H), 1.95 (s, 3H), 1.70–1.79 (m, 1H), 1.46–1.57 (m, 1H). FAB MS 555 (M+1).

Anal. Calcd for $C_{29}H_{38}N_4O_5S.0.95$ $H_2O$: C, 60.91; H, 7.03; N, 9.80. Found: C, 60.89; H, 6.67; N, 9.59.

Example 4

Preparation of N-[1-(L-Pyroglutamyl)pyrrolidin-2(S)-ylmethyl]-N-(1-naphthylmethyl)glycyl-methionine N-[1-(L-Pyroglutamyl)pyrrolidin-2(S)-ylmethyl]-N-(1-naphthylmethyl)glycyl-methionine methyl ester from Example 3 was hydrolyzed to give the title compound. $^1H$ NMR ($CD_3OD$) δ8.34–8.48 (m, 1H), 8.04 (d, 1H, J=8 Hz ), 7.99 (d, 1H, J=8 Hz), 7.70 (t, 1H, J=8 Hz), 7.52–7.66 (m, 3H), 4.33–4.77 (m, 3H), 3.35–3.84 (m, 4H), 2.26– 2.54 (m, 3H), 2.14–2.26 (m, 1H), 1.78–2.14 (m, 4H), 2.03 (s, 3H), 1.64–1.78 (m, 1H).

Anal. Calcd for $C_{28}H_{36}N_4O_5S.1.75$ $CF_3CO_2H$: C, 51.11; H, 5.14; N, 7.57. Found: C, 50.98; H, 5.42; N, 7.77.

Example 5

Preparation of 2(S)-[1-(2(S)-Pyroglutamyl)pyrrolidin-2(S)-ylmethyloxyl]-3-phenylpropionyl-methionine methyl ester Step A: Preparation of N-Chloroacetyl-2(S)-hydroxymethypyrrolidine To a solution of 2(S)-hydroxymethylpyrrolidine (25.32 g, 250.3 mmol) in $CH_2Cl_2$ (720 mL) under argon was added $Et_3N$ (38.0 mL, 273 mmol). After cooling this mixture to −20° C., chloroacetyl chloride (20.0 mL, 251 mmol) was added dropwise over 0.75 h maintaining the reaction temperature at −20 ±3° C. The reaction was stirred at ambient temperature for 18 h and evaporated in vacuo. An impurity which precipitated during concentration was removed by filtration. The crude product was purified by chromatography (silica gel, 1:39 to 1:19 MeOH/$CH_2Cl_2$) to give the title compound as a yellow oil. $^1H$ NMR ($CDCl_3$, 400 MHz): δ4.37 (dd, J=8, 3 Hz, 1H), 4.22 (qd, J=7, 3 Hz, 1H), 4.08 (s, 2H), 3.71 (td, J=8, 3 Hz, 1H), 3.68–3.50 (m, 3H), 2.14–1.86 (m, 3H), 1.72–1.62 (m, 1H).

Step B: Preparation of 6(S)-$_2$-Oxo-1-aza-4-oxabicyclo-[4.3.0]-nonane

To a solution of N-chloroacetyl-2(S)-hydroxymethypyrrolidine (12.8 g, 71.9 mmol) in THF (240 mL, distilled from Na/benzophenone) under argon at 0° C. was added NaH (3.16 g of a 60% dispersion in mineral oil, 78.9 mmol) slowly in several portions. After complete addition, the reaction was stirred at ambient temperature for 18 h. The reaction was quenched by adding HOAc (400 μL), diluted with toluene, and evaporated in vacuo to give a thick gray liquid. Water was cautiously added dropwise until no further gas evolution was observed. This mixture was diluted with MeOH and $CH_2Cl_2$ and dried ($Na_2SO_4$). Since filtration was unsuccessful, silica gel (60 g) was added and the mixture was evaporated in vacuo. The crude product was purified by chromatography (silica gel, 7:13 to 1:1 EtOAc/$CH_2Cl_2$) to give the title compound as a white solid. $^1H$ NMR ($CDCl_3$, 400 MHz): δ4.25 (d, J=17 Hz, 1H), 4.19 (dd, J=12, 4 Hz, 1H), 4.02 (d, J=17 Hz, 1H), 3.76–3.64 (m, 2H), 3.50 (td, J=10, 2.5 Hz, 1H), 3.24 (dd, J=12, 10 Hz, 1H), 2.09–1.99 (m, 2H), 1.92–1.78 (m, 1H), 1.39 (qd, J=12, 8 Hz, 1H).

Step C: Preparation of 3(R),6(S)-2-Oxo-3-(phenylmethyl)-1-aza-4-oxabicyclo-[4.3.0]-nonane and 3(S),6(S)-2-Oxo-3-(phenylmethyl)-1-aza-4-oxabicyclo-[4.3.0]-nonane (93:7 respectively)

A solution of 6(S)-2-oxo-1-aza-4-oxabicyclo-[4.3.0]-nonane (6.013 g, 42.60 mmol) in THF (170 mL, distilled from Na/benzophenone) was cooled to −78° C. under argon and transferred via cannula to a second flask containing 1.0M lithium bis(trimethylsilyl)amide in THF (52 mL, 52 mmol) also at −78° C. under argon. After stirring for 0.5 h at −78° C., benzyl bromide (7.20 mL, 60.5 mmol) was added dropwise over 5 min. The reaction was stirred for 1 h at −78° C. followed by 1 h at −50 ° C. The reaction was quenched by adding saturated aq $NH_4Cl$ (60 mL) and warming to ambient temperature. The reaction was diluted with $H_2O$ (60 mL) and saturated aq NaCl (180 mL), and the layers were separated. The aqueous layer was extracted twice with EtOAc (300, 200 mL). The organic extracts were washed in succession with saturated aq NaCl (150 mL), combined, dried ($Na_2SO_4$), and evaporated in vacuo. The crude product was purified by chromatography (silica gel, 1:4 EtOAc/$CH_2Cl_2$) to give the title compound as a yellow oil. $^1$H NMR ($CDCl_3$, 400 MHz) δ7.31–7.19 (m, 5H), 4.44 (dd, J=10, 4 Hz, 0.07H), 4.27 (dd, J=8, 4 Hz, 0.93H), 4.12 (dd, J=12, 4 Hz, 0.93H), 3.94 (dd, J=12, 5 Hz, 0.07H), 3.72–3.62 (m, 1H), 3.54–3.18 (m, 4H), 3.01 (dd, J=15, 8 Hz, 0.93H), 3.00 (dd, J=14, 8 Hz, 0.07H), 2.04–1.91 (m, 2H), 1.83–1.69 (m, 1H), 1.33 (qd, J=11, 8 Hz, 1H).

Step D: Preparation of 3(R),6(S)-2-Oxo-3-(phenylmethyl)-1-aza-4-oxabicyclo-[4.3.0]-nonane and 3(S),6(S)-2-Oxo-3-(phenylmethyl)-1-aza-4-oxabicyclo-[4.3.0]-nonane (2:1 respectively)

A solution of 3(R,S),6(S)-2-oxo-3-(phenylmethyl)-1-aza-4-oxabicyclo-[4.3.0]-nonane (8.818 g, 38.12 mmol) in THF (170 mL, distilled from Na/benzophenone) was cooled to −78° C. under argon and transferred via cannula to a second flask containing 1.0M lithium bis(trimethylsilyl)amide in tetrahydrofuran (57 mL, 57 mmol) also at −78° C. under argon. After stirring for 10 min at −78° C., the reaction was placed in an ice bath for 0.5 h. The reaction was again cooled to −78° C. for 10 min, quenched by adding HOAc (3.30 mL), and allowed to warm to ambient temperature. The reaction was diluted with $H_2O$ (50 mL) and saturated aq NaCl (100 mL) and extracted twice with EtOAc (300, 200 mL). The organic extracts were combined, washed with saturated aq NaCl (200 mL), dried ($Na_2SO_4$), and evaporated in vacuo to give the title compound as a golden orange oil. $^1$H NMR ($CDCl_3$, 400 MHz) δ7.34–7.15 (m, 5H), 4.43 (dd, J=10, 3 Hz, 0.33H), 4.27 (dd, J=8, 3 Hz, 0.67H), 4.11 (dd, J=11, 4 Hz, 0.67H), 3.94 (dd, J=11, 4 Hz, 0.33H), 3.74–3.17 (m, 5H), 3.07 (dd, J=14, 10 Hz, 0.33H), 3.01 (dd, J=14, 8 Hz, 0.67H), 2.06–1.91 (m, 2H), 1.89–1.71 (m, 1H), 1.39–1.24 (m, 1H).

Step E: Preparation of 2(R)-[Pyrrolidin-2(S)-ylmethyloxy]-3-phenylpropionic acid hydrochloride and 2(S)-[Pyrrolidin-2(S)-ylmethyloxy]-3-phenylpropionic acid hydrochloride (2:1 mixture)

3(R and S),6(S)-2-Oxo-3-(phenylmethyl)-1-aza-4-oxabicyclo-[4.3.0]-nonane (8.569 g, 37.05 mmol) was dissolved in 6N aq HCl (400 mL) and stirred at reflux under argon for 24 h. The reaction was cooled to ambient temperature, evaporated in vacuo, diluted with toluene, evaporated in vacuo, diluted with toluene, and evaporated in vacuo to give the title compound as an orange oil. $^1$H NMR ($CD_3OD$, 400 MHz) δ7.35–7.10 (m, 5H), 4.33–4.26 (m, 1H), 3.84–3.53 (m, 3H), 3.30–3.09 (m, 3H), 3.05–2.96 (m, 1H), 2.17–1.88 (m, 3H), 1.80–1.65 (m, 1H).

Step F: Preparation of 2(R)-[1-(t-Butoxycarbonyl)pyrrolidin-2(S)-ylmethyloxy]-3-phenylpropionic acid and 2(S)-[1-(t-Butoxycarbonyl)pyrrolidin-2(S)-ylmethyloxy]-3-phenylpropionic acid (2:1 mixture)

2(R,S)-(Pyrrolidin-2(S)-ylmethyloxy)-3-phenylpropionic acid hydrochloride (9.48 g, 33.2 mmol) was dissolved in $H_2O$ (70 mL) and neutralized with 1.0N aq NaOH (approx. 40 mL). To this mixture was added a solution of $Na_2CO_3$ (7.304 g, 68.91 mmol) in $H_2O$ (40 mL). The resulting mixture (pH=11.5) was cooled to 0° C. under argon; di-tert-butyl dicarbonate (8.2 mL, 36 mmol) was added followed by THF (50 mL). The reaction was stirred at ambient temperature for 18 h, cooled to 0° C., acidified to pH=3 with 10% aq citric acid, and extracted with EtOAc (2×250 mL). The organic extracts were washed in succession with saturated aq NaCl (250 mL), combined, dried ($Na_2SO_4$), and evaporated in vacuo to give the title compound as an orangish-brown oil. $^1$H NMR ($CD_3OD$, 400 MHz) δ7.29–7.17 (m, 5H), 4.05–3.99 (m, 1H), 3.82–3.77 (m, 1H), 3.69–3.59 (m, 1H), 3.54–3.16 (m, 2H), 3.13–2.97 (m, 2H), 2.94–2.85 (m, 1H), 1.88–1.62 (m, 4H), 1.42 (s, 9H).

Step G: Preparation of 2(S)-[1-(t-Butoxycarbonyl)pyrrolidin-2(S)-ylmethyloxyl]-3-phenylpropionyl-methionine methyl ester To a solution of 2(R and S)-[1-(t-butoxycarbonyl)-pyrrolidin-2(S)-ylmethyloxy]-3-phenylpropionic acid (263.6 mg, 0.754 mmol) in DMF (8.0 mL) were added 3-hydroxy-1,2,3-benzotriazin-4(3H)-one (HOOBT, 137 mg, 0.840 mmol), 1-(3-dimethylaminopropyl)-3-ethylcarbodiimide hydrochloride (EDC, 164 mg, 0.855 mmol), L-methionine methyl ester hydrochloride (176 mg, 0.881 mmol), and $Et_3N$ (0.35 mL, 2.5 mmol). The reaction was stirred under argon at ambient temperature for 18 h, diluted with EtOAc (70 mL), and washed with 10% aq citric acid (70 mL), saturated aq $NaHCO_3$ (40, 20 mL), and saturated aq NaCl (40 mL). The organic layer was dried ($Na_2SO_4$) and evaporated in vacuo. The diastereomeric crude products were purified and separated by chromatography (silica gel, 1:19 to 1:2 EtOAc/$CH_2Cl_2$) to give the title compound. $^1$H NMR ($CD_3OD$, 400 MHz) δ7.35–7.17 (m, 5H), 4.63–4.55 (m, 1H), 4.08–3.90 (m, 2H), 3.72 (s, 3H), 3.55–3.46 (m, 2H), 3.34–3.22 (m, 1H), 3.09 (dd, J=14, 4 Hz, 1H), 2.91 (dd, J=14, 7 Hz, 1H), 2.38–2.20 (m, 2H), 2.10–2.00 (m, 1H), 2.04 (br s, 3H), 1.97–1.86 (m, 6H), 1.44 (s, 9H).

Step H: Preparation of 2(S)-[1-Pyrrolidin-2(S)-ylmethyloxy]-3-phenylpropionyl-methionine methyl ester hydrochloride 2(S)-[N-(tert-Butoxycarbonyl)-2(S)-(pyrrolidinyl)-methyloxy]-3-phenylpropionyl-methionine methyl ester (2.138 g, 4.322 mmol) was dissolved in EtOAc (80 mL). The mixture was cooled to 0° C. and HCl gas was bubbled in until saturated. The mixture was stirred at ambient temperature for 1.25 h and evaporated in vacuo to give the title compound as a yellow foam which was used without further purification. $^1$H NMR ($CD_3OD$, 400 MHz) δ7.35–7.20 (m, 5H), 4.67 (dd, J=10, 5 Hz, 1H), 4.21 (dd, J=8, 5 Hz, 1H), 3.81–3.75 (m, 2H), 3.75 (s, 3H), 3.58 (q, J=6 Hz, 1H), 3.30–3.11 (m, 3H), 2.99 (dd, J=14, 8 Hz, 1H), 2.53–2.36 (m, 2H), 2.19–2.10 (m, 1H), 2.08 (s, 3H), 2.07–1.88 (m, 4H), 1.79–1.68 (m, 1H).

Step I: Preparation of 2(S)-[1-(2(S)-Pyroglutamyl)pyrrolidin-2(S)-ylmethyloxy]-3-phenylpropionyl-methionine methyl ester 2(S)-(Pyrrolidin-2(S)-ylmethyloxy)-3-phenylpropionyl-methionine methyl ester hydrochloride (1.892 g, 4.390 mmol) was dissolved in $CH_2Cl_2$ (33 mL). To this solution were added (S)-(−)-2-pyrrolidone-5-carboxylic acid (853.1 mg, 6.607 mmol) and Et$_3$N (3.0 mL, 21.5 mmol). This mixture was cooled to 0° C. under argon and treated with bis(2-oxo-3-oxazolidinyl)phosphinic chloride (BOP—Cl, 1.70 g, 6.68 mmol). After stirring for 18 h at ambient temperature, the reaction was diluted with EtOAc (250 mL) and washed with 10% aq citric acid (200 mL), saturated aq NaHCO$_3$ (200 mL), and saturated aq NaCl (200 mL). The organic layer was dried (Na$_2$SO$_4$) and evaporated in vacuo. The crude product was purified by chromatography (silica gel, 3:97 to 1:19 MeOH/CH$_2$Cl$_2$,) and filtered through a Whatman 0.45 μm PTFE membrane filter to give the title compound as a colorless foam. $^1$H NMR (CD$_3$OD, 400 MHz) δ7.33–7.17 (m, 5H), 4.66–4.57 (m, 1.2H), 4.50 (dd, J=9, 5 Hz, 0.8H), 4.28–4.21 (m, 0.8H), 4.16–4.04 (m, 1.2H), 3.76–3.30 (m, 4H), 3.75 (s, 0.6H), 3.71 (s, 2.4H), 3.16–3.05 (m, 1H), 3.01–2.91 (m, 1H), 2.50–2.18 (m, 5H), 2.16–1.78 (m, 7H), 2.06 (s, 0.6H), 2.03 (s, 2.4H). FAB HRMS exact mass calcd for C$_{25}$H$_{36}$N$_3$O$_6$S: 506.232483 (MH$^+$); found 506.232889.

Anal. Calcd for C$_{25}$H$_{35}$N$_3$O$_6$S: C, 59.39; H, 6.98; N, 8.31. Found: C, 59.56; H, 6.84; N, 8.30.

Using the procedures outlined in Example 5 the following esters were prepared:

2(S)-[1-(1H-Imidazol-4-ylacetyl)pyrrolidin-2(S)-ylmethyloxy]-3-phenylpropionyl-methionine methyl ester trifluoroacetate $^1$H NMR (CD$_3$OD, 400 MHz): δ8.81 (br d, J=1.5 Hz, 0.8H), 8.76 (br d, J=1.5 Hz, 0.2H), 7.38 (br s, 0.8H), 7.30–7.13 (m, 5.2H), 4.63 (dd, J=9, 5 Hz, 0.2H), 4.57 (dd, J=9, 5 Hz, 0.8H), 4.34–4.24 (m, 0.2H), 4.20–4.11 (m, 1H), 4.06 (dd, J=8, 4 Hz, 0.8H), 3.93 (br d, J=5 Hz, 0.4H), 3.91–3.86 (m, 1.6H), 3.75–3.48 (m, 4H), 3.73 (s, 0.6H), 3.70 (s, 2.4H), 3.15–3.04 (m, 1H), 3.00–2.88 (m, 1H), 2.46–2.20 (m, 2H), 2.15–1.84 (m, 6H), 2.05 (s, 0.6H), 2.02 (s, 2.4H). FAB HRMS exact mass Calcd for C$_{25}$H$_{35}$N$_4$O$_5$S: 503.232817 (MH$^+$); found 503.233360.

Anal. Calcd for C$_{25}$H$_{34}$N$_4$O$_5$S.1.40 TFA.0.45 H$_2$O: C, 49.81; H, 5.46; N, 8.36. Found: C, 49.83; H, 5.47; N, 8.52.

2(S)-[1-(-2(S)-Pyroglutamyl)pyrrolidin-2(S)-ylmethyloxy]-3-phenylpropionyl-methionine isopropyl ester $^1$H NMR (CD$_3$OD, 400 MHz) δ7.33–7.17 (m, 5H), 5.08–4.96 (m, 1H), 4.60–4.47 (m, 2H), 4.28–4.20 (m, 1H), 4.14–4.06 (m, 1H), 3.73–3.45 (m, 3H), 3.41–3.33 (m, 1H), 3.09 (dd, J=14, 5 Hz, 1H), 3.00–2.90 (m, 1H), 2.50–2.18 (m, 5H), 2.08–1.80 (m, 7H), 2.04 (s, 3H), 1.29–1.23 (m, 6H). FAB HRMS exact mass calcd for C$_{27}$H$_{40}$N$_3$O$_6$S: 534.263783 (MH$^+$); found 534.264446.

2(S)-[1-(2(S)-Pyroglutamyl)pyrrolidin-2(S)-ylmethyloxy]-3-phenylpropionyl-methionine sulfone methyl ester FAB HRMS exact mass calcd for C$_{25}$H$_{35}$N$_3$O$_8$S: 538.222312 (MH$^+$); found 538.221847.

2(S)-[1-(Pyrid-3-ylcarboxy)pyrrolidin-2(S)-ylmethyloxy]-3-phenylpropionyl-methionine methyl ester trifluoroacetate $^1$H NMR (CD$_3$OD, 400 MHz) δ8.81–8.71 (m, 2H), 8.23–8.15 (m, 1H), 7.78–7.70 (m, 1H), 7.29–7.18 (m, 5H), 4.58 (dd, J=9, 5 Hz, 1H), 4.48–4.40 (m, 1H), 4.14 (dd, J=7, 5 Hz, 1H), 3.89 (dd, J=9, 5 Hz, 1H), 3.71 (s, 3H), 3.71–3.64 (m, 1H), 3.62–3.52 (m, 1H), 3.46–3.37 (m, 1H), 3.13 (dd, J=14, 5 Hz, 1H), 2.99 (dd, J=14, 7 Hz, 1H), 2.24–2.16 (m, 2H), 2.08–1.76 (m, 6H), 1.96 (br s, 3H). FAB HRMS exact mass calcd for C$_{26}$H$_{34}$N$_3$O$_5$S: 500.221918 (MH$^+$); found 500.221414.

2(R)-{2-[1-(Naphth-2-yl)-1H-imidazol-5-ylacetyl]pyrrolidin-2(S)-ylmethoxy}-3-phenyl propionyl-methionine methyl ester hydrochloride $^1$NMR(CD$_3$OD, 400 MHz) δ8.97(0.75H, s), 8.91(0.25H, s), 7.93(1H, d, J=8.6 Hz), 7.88(2H, m), 7.80(0.75H, s), 7.72(0.25H, s), 7.56(2H, m), 7.49(1H, s), 7.38(1H, m), 7.25–7.05(5H, m), 5.57(2H, m), 4.58(0.25H, dd, J=5 and 9 Hz), 4.51(0.75H, dd, J=5 and 9 Hz), 4.00(1H, dd, J=5 and 8 Hz), 4.00–3.83(1H, m), 3.75(1.5H, m), 3.68(0.75H, s), 3.68 (0.5H, m), 3.62(2.25H, s), 3.52(0.75H, dd, J=6 and 10 Hz), 3.49–3.32(1.25H, m), 3.42(0.75H, dd, 6 and 10 Hz), 3.23 (1H, m), 3.03(0.75H, dd, J=5.5 and 14.5 Hz), 2.97(0.25H, dd, J=5.5 and 14.5 Hz), 2.89(0.75, dd, J=7.5 and 14.5 Hz), 2.83(0.25H, dd, J=7.5 and 14.5 Hz), 2.4–1.63(8H, m), 2.01(0.75H, s) and 1.98(2.25H, s)ppm. FAB HRMS exact mass calcd for C$_{36}$H$_{43}$N$_4$O$_5$S 643.295418 (MH+), found 643.29568.

Anal. Calcd for C$_{36}$H$_{42}$N$_4$O$_5$S.2.6HCl: C, 58.62; H,6.09; N, 7.60. Found: C, 58.63; H, 5.95; N, 7.92.

2(S)-[1-(1H-Imidazol-4-ylacetyl)pyrrolidin-3(S)-ethyl-2(S)-ylmethyloxyl]-3-phenylpropionyl-methionine methyl ester trifluoroacetate

FAB MS 531 (M+1)

2(R)-{2-[1-(4-Cyanobenzyl)-1H-imidazol-5-ylacetyl]pyrrolidin-2(S)-ylmethoxy}-3-phenyl propionyl-methionine methyl ester hydrochloride Anal. Calcd for C$_{33}$H$_{39}$N$_5$O$_5$S.2.45 HCl.1.8 H$_2$O: C, 53.60; H, 6.14; N, 9.47; Found: C, 53.59; H, 6.15; N, 9.39.

2(R)-{2-[1-(4-Nitrobenzyl)-1H-imidazol-5-ylacetyl]pyrrolidin-2(S)-ylmethoxy}-3-phenyl propionyl-methionine methyl ester hydrochloride Anal. Calcd for C$_{33}$H$_{39}$N$_5$O$_7$S.2.15 HCl: C, 53.67; H, 5.70; N, 9.78; Found: C, 53.46; H, 5.81; N, 10.16.

2(R)-{2-[1-(4-Methoxybenzyl)-1H-imidazol-5-ylacetyl]pyrrolidin-2(S)-ylmethoxy}-3-phenyl propionyl-methionine methyl ester hydrochloride Anal. Calcd for C$_{33}$H$_{42}$N$_4$O$_6$S.0.85 HCl.0.55 H$_2$O: C, 56.61; H, 6.47; N, 8.00; Found: C, 56.60; H, 6.47; N, 8.37.

2(R)-{2-[1-(4-Cyanobenzyl)-1H-imidazol-5-ylacetyl]pyrrolidin-3(S)-ethyl-2(S)-ylmethoxy}-3-phenyl propionyl-methionine methyl ester hydrochloride

FAB MS 646 (M+1)

Example 6

Preparation of 2(S)-[1-(2(S)-Pyroglutamyl) pyrrolidin-2(S)-ylmethyloxy]-3-phenylpropionyl-methionine trifluoroacetate salt Step A: Preparation of 2(S)-[1-(2(S)-Pyroglutamyl) pyrrolidin-2(S)-ylmethyloxy]-3-phenylpropionyl-methionine trifluoroacetate salt To a soln of the 2(S)-[N-(2(S)-pyroglutamyl)-2(S)-(pyrrolidinyl)methyloxy]-3-phenylpropionyl-methionine methyl ester (38.7 mg, 0.0765 mmol) in MeOH (2 mL) under argon was added 1.0M aq LiOH (90 μL, 0.090 mmol). After stirring at ambient temperature for 18 h, the reaction was treated with HOAc (3 drops) and purified by preparative HPLC using a Nova Prep 5000 Semi Preparative HPLC System and a Waters PrepPak cartridge (47×300 mm, C18, 15 mm, 100 A) eluting with 5–95% $CH_3CN/H_2O$ (0.1% TFA) at 100 mL/min (Chromatography A conditions) to give the title compound as a white solid after lyophilization. $^1H$ NMR ($CD_3OD$, 400 MHz) δ7.36–7.21 (m, 5H), 4.67–4.60 (m, 1.25H), 4.54 (dd, J=9, 5 Hz, 0.75H), 4.31–4.24 (m, 0.75H), 4.19–4.13 (m, 0.25H), 4.13–4.08 (m, 1H), 3.77–3.70 (m, 1H), 3.67–3.37 (m, 3H), 3.20–3.10 (m, 1H), 3.04–2.95 (m, 1H), 2.53–1.85 (m, 12H), 2.10 (s, 0.75H), 2.07 (s, 2.25). FAB HRMS exact mass Calcd for $C_{24}H_{34}N_3O_6S$: 492.216833 (MH$^+$); found 492.217898.

Anal. Calcd for $C_{24}H_{33}N_3O_6S.0.70$ TFA.0.55 $H_2O$: C, 52.48; H, 6.03; N, 7.23. Found: C, 52.45; H, 5.98; N, 7.39.

Using the procedures outlined in Example 6 the following acids were prepared:

2(S)-[1-(1H-Imidazol-4-ylacetyl)pyrrolidin-2(S)-ylmethyloxy]-3-phenylpropionyl-methionine trifluoroacetate $^1H$ NMR ($CD_3OD$, 400 MHz) δ8.86 (s, 0.7H), 8.81 (0.3H), 7.42 (s, 0.7H), 7.34–7.17 (m, 5.3H), 4.64 (dd, J=9, 5 Hz, 0.3H), 4.58 (dd, J=9, 5 Hz, 0.7H), 4.40–4.29 (m, 0.3H), 4.23–4.15 (m, 1H), 4.08 (dd, J=8, 5 Hz, 0.7H), 4.01–3.88 (m, 2H), 3.81–3.40 (m, 4H), 3.21–3.12 (m, 1H), 3.03–2.93 (m, 1H), 2.52–1.88 (m, 8H), 2.08 (s, 0.9H), 2.05 (s, 2.1H). FAB HRMS exact mass calcd for $C_{24}H_{33}N_4O_5S$: 489.217167 (MH+); found 489.217975.

Anal. Calcd for $C_{24}H_{32}N_4O_5S.1.45$ TFA.0.50 $H_2O$: C, 48.74; H, 5.24; N, 8.45. Found: C, 48.73; H, 5.25; N, 8.54.

2(S)-[1-(2(S)-Pyroglutamyl)pyrrolidin-2(S)-ylmethyloxy]-3-phenylpropionyl-methionine sulfone FAB HRMS exact mass calcd for $C_{24}H_{34}N_3O_8S$: 524.206662 (MH$^+$); found 524.207702.

Anal. Calcd for $C_{24}H_{33}N_3O_8S.0.95$ TFA.0.65 $H_2O$: C, 48.33; H, 5.52; N, 6.53. Found: C, 48.35; H, 5.39; N, 6.73.

2(S)-[1-(Pyrid-3-ylcarboxy)pyrrolidin-2(S)-ylmethyloxy]-3-phenylpropionyl-methionine trifluoroacetate $^1H$ NMR ($CD_3OD$, 400 MHz) δ8.81 (br s, 1H), 8.75 (br s, 1H), 8.23 (d, J=9 Hz, 1H), 7.80–7.73 (m, 1H), 7.30–7.18 (m, 5H), 4.55 (dd, J=9, 5 Hz, 1H), 4.48–4.40 (m, 1H), 4.13 (dd, J=7, 4 Hz, 1H), 3.89 (dd, J=10, 5 Hz, 1H), 3.69 (dd, J=10, 5 Hz, 1H), 3.62–3.52 (m, 1H), 3.45–3.35 (m, 1H), 3.14 (dd, J=14, 5 Hz, 1H), 2.99 (dd, J=14, 7 Hz, 1H), 2.28–2.14 (m, 2H), 2.12–1.76 (m, 6H), 1.96 (s, 3H). FAB HRMS exact mass calcd for $C_{25}H_{32}N_3O_5S$: 486.206268 (MH$^+$); found 486.205960.

2(R)-{2-[1-(Naphth-2-yl)-1H-imidazol-5-ylacetyl]pyrrolidin-2(S)-ylmethoxy)]-3-phenyl propionyl-methionine trifluoroacetate $^1$NMR(CD3OD, 400 MHz) δ8.92 (0.75H, s), 8.90 (0.25H, s), 7.92 (2H, d, J=8.4 Hz), 7.87 (2H, m), 7.78 (0.75H, s), 7.71 (0.25H, s), 7.55 (2H, m), 7.47 (0.75H, s), 7.36 (1.25H, m), 7.28–7.06 (4H, m), 5.55 (2H, s), 4.53 (0.25H, m), 4.48 (0.75H, m), 3.98 (0.75H, br), 3.96 (0.75H, dd, J=4.2 Hz), 3.94 (0.25H, dd, J=4 Hz), 3.87 (0.25H, br), 3.79 (1H, d, J=8 Hz), 3.73 (1H, d, J=8 Hz), 3.52 (0.75H, dd, J=5.8 Hz), 3.46 (0.25H, dd, J=5.3 Hz), 3.43–3.15 (3H, m), 3.04 (0.75H, dd, J=4.5 and 15 Hz), 2.98 (0.25H, dd, J=4.5 and 15 Hz), 2.89 (0.75H, dd, J=7.5 and 14 Hz), 2.83 (0.25H, dd, J=7.5 and 14 Hz), 2.32 (0.5H, m), 2.21 (1.5H, m), 2.01 (0.75H, s), 1.99 (2.25H, s), 1.84 (2H, m) and 1.74 (4H, m). FAB HRMS exact mass calcd for $C_{35}H_{41}N_4O_5S$ 629.279768 (MH+), found 629.27934.

Anal. Calcd for $C_{35}H_{40}N_4O_5S.1.55$ TFA.0.90 H2O: C, 55.69; H,5.32; N, 6.82. Found: C, 55.67; H, 5.31; N, 6.71.

2(S)-[1-(1H-Imidazol-4-ylacetyl)pyrrolidin-3(S)-ethyl-2(S)-ylmethyloxy]-3-phenylpropionyl-methionine lithium salt FAB MS 517 (M+1), 523 (M+1, –H, +Li)

2(R)-{2-[1-(4-Cyanobenzyl)-1H-imidazol-5-ylacetyl]pyrrolidin-2(S)-ylmethoxy}-3-phenyl propionyl-methionine trifluoroacetate Anal. Calcd for $C_{32}H_{37}N_5O_5S.2.25$ HCl.0.90 $H_2O$: C, 50.02; H, 4.72; N, 7.99; Found: C, 50.01; H, 4.74; N, 7.89.

2(R)-{2-[1-(4-Nitrobenzyl)-1H-imidazol-5-ylacetyl]pyrrolidin-2(S)-ylmethoxy}-3-phenyl propionyl-methionine trifluoroacetate Anal. Calcd for $C_{31}H_{37}N_5O_7S.1.65$ HCl.0.45 $H_2O$: C, 50.24; H, 4.86; N, 8.54; Found: C, 50.24; H, 4.82; N, 8.93.

2(R)-{2-[1-(4-Methoxybenzyl)-1H-imidazol-5-ylacetyl]pyrrolidin-2(S)-ylmethoxy}-3-phenyl propionyl-methionine trifluoroacetate Anal. Calcd for $C_{32}H_{40}N_4O_6S.2.15$ HCl.0.85 $H_2O$: C, 50.16; H, 5.08; N, 6.45; Found: C, 50.15; H, 5.08; N, 6.55.

2(R)-{2-[1-(4-Cyanobenzyl)-1H-imidazol-5-ylacetyl]pyrrolidin-3(S)-ethyl-2(S)-ylmethoxy}-3-phenyl propionyl-methionine lithium salt FAB MS 632 (M+1), 638 (M+1, –H,+Li)

Example 7

Preparation of 2(S)-[1-(Pyrid-3-ylmethyl)pyrrolidin-2(S)-ylmethyloxy]-3-phenylpropionyl-methionine methyl ester bis trifluoroacetate Step A: Preparation of 2(S)-[1-(Pyrid-3-ylmethyl)pyrrolidin-2(S)-ylmethyloxy]-3-phenylpropionyl-methionine methyl ester bis trifluoroacetate 2(S)-(Pyrrolidin-2(S)-ylmethyloxy)-3-phenylpropionyl-methionine methyl ester hydrochloride (76.5 mg, 0.177 mmol) was dissolved in 1,2-dichloroethane (1.2 mL). To this mixture were added 3-pyridinecarboxaldehyde (17 mL, 0.18 mmol), 4 A sieves (228 mg), and sodium triacetoxyborohydride (183.5 mg, 0.8658 mmol). After stirring at ambient temperature under argon for 18 h, the reaction was diluted with EtOAc (15 mL), washed with saturated aq $NaHCO_3$ (2×15 mL) and saturated aq NaCl (15 mL), dried ($Na_2SO_4$), and evaporated in vacuo. The crude product was purified by preparative HPLC (Chromatography A conditions) to give the title compound after lyophilization. $^1H$ NMR ($CD_3OD$, 400 MHz) δ8.64 (br s, 1H), 8.58 (br s, 1H), 7.98 (d, J=8 Hz, 1H), 7.49 (dd, J=8, 5 Hz, 1H), 7.20–7.06 (m, 5H), 4.66–4.61 (m, 1H), 4.54–4.45 (m, 1H), 4.22–4.14 (m, 2H), 3.75–3.68 (m, 1H), 3.66 (s, 3H), 3.62–3.56 (m, 2H), 3.15–3.04 (m, 3H), 2.89 (dd, J=14, 9 Hz, 1H), 2.54–2.38 (m, 2H), 2.19–2.07 (m, 2H), 1.99 (s, 3H), 1.99–1.79 (m, 4H). FAB HRMS exact mass calcd for $C_{26}H_{36}N_3O_4S$: 486.242654 (MH+); found 486.243425.

Example 8

Preparation of 2(S)-[1-(Pyrid-3-ylmethyl)pyrrolidin-2(S)-ylmethyloxy]-3-phenylpropionyl-methionine bis trifluoroacetate Step A: Preparation of 2(S)-[1-(Pyrid-3-ylmethyl) pyrrolidin-2(S)-ylmethyloxy]-3-phenylpropionyl-methionine bis trifluoroacetate To a solution of 2(S)-[1-(pyrid-3-ylmethyl)pyrrolidin-2(S)-ylmethyloxy]-3-phenylpropionyl-methionine methyl ester (20.7 mg, 0.0426 mmol) in MeOH (1.0 mL) at 0° C. under argon was added 1.0M aq LiOH (50 μL, 0.050 mmol). After stirring at ambient temperature for 18 h, additional MeOH (1.0 mL) and 1.0M aq LiOH (50 μL, 0.050 mmol) were added. After an additional 24 h of stirring at ambient temperature, TFA (2 drops) was added. The crude reaction mixture was purified directly by preparative HPLC (Chromatography A conditions) to give the title compound after lyophilization. $^1$H NMR (CD$_3$OD, 400 MHz) δ8.76 (br s, 1H), 8.69 (br s, 1H), 8.20–8.12 (br d, J=7 Hz, 1H), 7.67–7.59 (m, 1H), 7.32–7.15 (m, 5H), 4.68 (dd, J=9, 4 Hz, 1H), 4.65–4.55 (m, 1H), 4.33–4.26 (m, 2H), 3.85–3.66 (br, 3H), 3.28–3.14 (m, 3H), 3.00 (dd, J=14, 9 Hz, 1H), 2.66–2.47 (m, 2H), 2.30–2.18 (m, 2H), 2.11 (s, 3H), 2.10–1.89 (m, 4H). FAB HRMS exact mass calcd for C$_{25}$H$_{34}$N$_3$O$_4$S: 472.227004 (MH$^+$); found 472.225954.

Example 9

Preparation of N-((4-Imidazolyl)methyl-(2S)-pyrrolidinylmethyl)-N-(1-naphthylmethyl)glycyl-methionine methyl ester tris trifluoroacetate.

Step A: Preparation of N-((1-Trityl-4-imidazolyl)methyl-(2S)-pyrrolidinylmethyl)-N-(1-naphthylmethyl)glycyl-methionine methyl ester N-((2S)-Pyrrolidinylmethyl)-N-(1-naphthylmethyl) glycyl-methionine methyl ester hydrochloride (0.2 g, 0.387 mmol) and 1-trityl-4-imidzolecarboxaldehyde (0.133 g, 0.387 mmol) were dissolved in 1,2-dichloroethane (10 ml). Triethylamine (0.108 ml, 0.774 mmol), sodium triacetoxyborohydride (0.164 g, 0.774 mmol), and 3 Å molecular sieves were added and the mixture stirred overnight. EtOAc (60 ml) and sat. NaHCO$_3$ (30 ml) were added, the mixture filtered and the layers separated. The organics were washed with water, brine and dried (MgSO$_4$). The solvent was removed to give the title compound as an oil.

Step B: Preparation of N-((4-Imidazolyl)methyl-(2S)-pyrrolidinylmethyl)-N-(1-naphthylmethyl)glycyl-methionine methyl ester tris trifluoroacetate N-((1-Trityl-4-imidazolyl)methyl-(2S)-pyrrolidinylmethyl)-N-(1-naphthylmethyl)glycyl-methionine methyl ester (0.3 g, 0.39 mmol) was dissolved in CH$_2$Cl$_2$ (5 mL) and cooled to 0° C. Triethylsilane (0.247 ml, 1.55 mmol) and trifluoroacetic acid (2 ml) were added and the reaction stirred at rt for 1 hr. The solvent was removed and the residue partitioned between water (50 ml) and hexane (30 ml). The aqueous layer was lyophilized, prepped, and the product lyophilized to give the title compound. FAB MS 524 (M+1).

Using the procedures described in Example 9, but substituting (t-butoxy)carbonylglycinal for 1-trityl-4-imidazolecarboxaldehyde in Step A, N-[1-(2-Aminoethyl) pyrrolidin-2(S)-ylmethyl]-N-(1-naphthylmethyl)glycyl-methionine methyl ester trifluoroacetate was prepared.

Anal. Calcd for C$_{26}$H$_{38}$N$_4$O$_3$S.3.75 CF$_3$CO$_2$H: C, 44.01; H, 4.60; N, 6.13; Found: C, 43.95; H, 4.65; N, 6.32.

Example 10

Preparation of N-[1-(1H-imidazol-4-ylacetyl) pyrrolidin-2(S)-ylmethyl]-N-(1-naphthylmethyl) glycyl-(β-acetylamino)alanine methyl ester trifluoroacetate Step A: Preparation of Methyl 2(S)-benzyloxycarbonylamino-3-aminopropionate A solution of 2(S)-benzyloxycarbonylamino-3-aminopropionoic acid (2.4 g) in methanol at 0° C. was saturated with HCl gas. After stirring for 2 h at 20° C. the solution was evaporated to obtain the title compound. $^1$H NMR (300 MHz, CD$_3$OD) δ7.35 (5H, m), 5.13 (2H, s), 4.50 (1H, m), 3.77 (3H, s), 3.45 (1H, m), 3.22 (1H, m).

Step B: Preparation of Methyl 2(S)-benzyloxycarbonylamino-3-acetylaminopropionate To a solution of methyl 2(S)-benzyloxycarbonylamino-3-amino propionate (2.5 g) in methylene chloride was added pyridine (20 mL) and acetic anhydride (5 mL). After stirring for 2 h the solution was concentrated in vacuo. The residue was partitioned between ethyl acetate and water. The ethyl acetate layer was extracted w/50 mL each of 2% potassium hydrogen sulfate, saturated sodium bicarbonate, saturated sodium chloride, dried over magnesium sulfate and concentrated in vacuo. Upon evaporation pyridine hydrochloride precipitated and was removed by filtration. The filtrate was evaporated to obtain the title compound. $^1$H NMR (300 MHz, CDCl$_3$) δ7.28 (5H, s), 6.14 (1H, s), 5.97 (1H, d), 5.10 (2H, s), 4.41 (1H, m), 3.78 (3H, s), 1.93 (3H, s).

Step C: Preparation of Methyl 2(S)-amino-3-acetylaminopropionate

To a solution of methyl 2(S)-benzyloxycarbonylamino-3-acetylaminopropionate (2.2 g) in ethanolic HCl was added 10% Pd/C (0.3 g) under nitrogen atmosphere. Hydrogen was applied to the mixture at 60 psi for 16 h. The mixture was filtered and concentrated in vacuo. The residue was triturated with diethyl ether to obtain the product. NMR (300 MHz, CD$_3$OD) δ4.20 (1H, m), 3.88 (3H, s), 3.82 (1H, m), 3.60 (1H, m), 1.99 (3H, s).

Step D: Preparation of N-[1-(1H-Imidazol-4-ylacetyl) pyrrolidin-2(S)-ylmethyl]-N-(1-naphthylmethyl)glycyl-(β-acetylamino)alanine methyl ester trifluoroacetate Using the procedures outlined in Example 1, but substituting methyl 2(S)-amino-3-acetylaminopropionate for methionine methyl ester in Step D, the title compound was prepared.

Anal. Calcd for C$_{29}$H$_{36}$N$_6$O$_5$.2.9 CF$_3$CO$_2$H.0.6 H$_2$O: C, 46.96; H, 4.54; N, 9.44; Found: C, 46.90; H, 4.51; N, 9.50. FAB MS 549 (M+1).

Using the methods described in Example 10 the following compounds were prepared:

N-[1-(Glycyl) pyrrolidin-2(S)-ylmethyl]-N-(1-naphthylmethyl)glycyl-(β-acetylamino)alanine methyl ester trifluoroacetate Anal. Calcd for C$_{26}$H$_{35}$N$_5$O$_5$.2.8CF$_3$CO$_2$H.0.5 H$_2$O: C, 45.96; H, 4.74; N, 8.48; Found: C, 45.98; H, 4.70; N, 8.92. FAB MS 498 (M+1).

N-[1-(Glycyl) pyrrolidin-2(S)-ylmethyl]-N-(1-naphthylmethyl)glycyl-(2-thienyl)alanine methyl ester trifluoroacetate Anal. Calcd for C$_{28}$H$_{34}$N$_4$O$_4$S.2.5 CF$_3$CO$_2$H.0.2 H$_2$O: C, 48.85; H, 4.58; N, 6.91; Found: C, 48.84; H, 4.55; N, 6.83.

N-[1-(1H-Imidazol-4-ylacetyl)pyrrolidin-2(S)-ylmethyl]-N-(1-naphthylmethyl)glycyl-(N,N-dimethyl)glutamine methyl ester Anal. Calcd for C$_{31}$H$_{40}$N$_6$O$_5$.3.4 CF$_3$CO$_2$H.0.1 H$_2$O: C, 46.99; H, 4.55; N, 8.70; Found: C, 46.95; H, 4.55; N, 8.86.

N-[1-(1H-Imidazol-4-ylacetyl)pyrrolidin-2(S)-ylmethyl]-N-(1-naphthylmethyl)glycyl-(trifluoromethyl)alanine methyl ester Anal. Calcd for C$_{28}$H$_{32}$N$_5$O$_4$F$_3$: C, 58.05; H, 5.56; N, 12.00; Found: C, 58.17; H, 5.61; N, 12.31.

N-[1-(1H-Imidazol-4-ylacetyl)pyrrolidin-2(S)-ylmethyl]-N-(1-naphthylmethyl)glycyl-(2(S)-amino-4-acetylamino)butyric acid methyl ester Anal. Calcd for $C_{30}H_{38}N_6O_5$.2.75 $CF_3CO_2H$.1.0 $H_2O$: C, 47.68; H, 4.82; N, 9.40; Found: C, 47.69; H, 4.85; N, 9.40.

N-[1-(1H-Imidazol-4-ylpropionyl) pyrrolidin-2(S)-ylmethyl]-N-(1-naphthylmethyl)glycyl-(β-acetylamino)alanine methyl ester Anal. Calcd for $C_{30}H_{38}N_6O_5$.2.6 $CF_3CO_2H$.3.3 HCl: C, 43.17; H, 4.52; N, 8.58; Found: C, 43.19; H, 4.60; N, 8.58.

N-[1-(4-Pyridylglycyl) pyrrolidin-2(S)-ylmethyl]-N-(1-naphthylmethyl)glycyl-(β-acetylamino)alanine methyl ester Anal. Calcd for $C_{30}H_{38}N_6O_5$.4.3 HCl.1.5 $H_2O$: C, 49.09; H, 6.02; N, 11.08; Found: C, 49.13; H, 6.03; N, 11.03.

N-[1-(Glycyl) pyrrolidin-2(S)-ylmethyl]-N-(1-naphthylmethyl)glycyl-(β-acetylamino)alanine cyclohexyl ester hydrochloride Anal. Calcd for $C_{31}H_{43}N_5O_5$.3.0 HCl: C, 55.15; H, 6.87; N, 10.37; Found: C, 55.14; H, 6.89; N, 10.17.

N-[1-(1H-Imidazol-4-ylacetyl)pyrrolidin-2(S)-ylmethyl]-N-(1-naphthylmethyl)glycyl-(N-methyl) glutamine methyl ester Anal. Calcd for $C_{30}H_{38}N_6O_5$.2.0 HCl.2.2 $CF_3CO_2H$.1.8 $H_2O$: C, 44.97; H, 5.02; N, 9.15; Found: C, 44.96; H, 5.02; N, 9.10.

N-[1-(1H-Imidazol-4-ylacetyl) pyrrolidin-2(S)-ylmethyl]-N-(1-naphthylmethyl)glycyl-(β-methylcarbonylamino)alanine methyl ester Anal. Calcd for $C_{29}H_{37}N_7O_5$.2.0 HCl.2.4 $CF_3CO_2H$.1.0 $H_2O$: C, 43.74; H, 4.71; N, 10.56; Found: C, 43.76; H, 4.72; N, 9.69.

N-[1-(1H-Imidazol-4-ylacetyl)pyrrolidin-2(S)-ylmethyl]-N-(1-naphthylmethyl)glycyl-(β-methylsulfonylamino)alanine methyl ester trifluoroacetate Anal. Calcd for $C_{28}H_{36}N_6O_6S$.3.2 $CF_3CO_2H$.0.8 $H_2O$: C, 42.86; H, 4.27; N, 8.72; Found: C, 42.90; H, 4.23; N, 8.72.

N-[1-(1H-Imidazol-4-ylacetyl) pyrrolidin-2(S)-ylmethyl]-N-(1-naphthylmethyl)glycyl-(β-propionylamino)alanine methyl ester trifluoroacetate Anal. Calcd for $C_{30}H_{38}N_6O_5$.2.8 $CF_3CO_2H$.1.6 $H_2O$: C, 46.95; H, 4.87; N, 9.23; Found: C, 46.92; H, 4.87; N, 9.30.

N-[1-(1H-Imidazol-4-ylacetyl) pyrrolidin-2(S)-ylmethyl]-N-(1-naphthylmethyl)glycyl-(β-pyrrolidinon-1-ylamino)alanine methyl ester Anal. Calcd for $C_{31}H_{38}N_6O_5$.1.2 $H_2O$: C, 51.00; H, 5.18; N, 10.19; Found: C, 51.02; H, 5.21; N, 10.34.

Example 11

Using the methods described in Example 1, but substituting the appropriate aldehyde for 1-naphthaldehyde in Step B, the following compounds were prepared:

N-[1-(1H-Imidazol-4-ylacetyl)pyrrolidin-2(S)-ylmethyl]-N-(benzyl)glycyl-methionine methyl ester Anal. Calcd for $C_{25}H_{35}N_5O_4S$.2.1 $CF_3CO_2H$.1.9 HCl: C, 43.28; H, 4.85; N, 8.64; Found: C, 43.27; H, 4.85; N, 8.65.

N-[1-(Glycyl)pyrrolidin-2(S)-ylmethyl]-N-(benzyl) glycyl-methionine methyl ester bis hydrochloride Anal. Calcd for $C_{22}H_{34}N_4O_4S$.2 HCl.1.8 $CF_3CO_2H$: C, 42.19; H, 5.23; N, 7.69; Found: C, 42.13; H, 5.23; N, 7.70.

N-[1-(1H-Imidazol-4-ylacetyl)pyrrolidin-2(S)-ylmethyl]-N-(4-methoxybenzyl)glycyl-methionine methyl ester hydrochloride Anal. Calcd for $C_{26}H_{37}N_5O_5S$.2.6 HCl: C, 49.85; H, 6.37; N, 11.18; Found: C, 49.86; H, 6.34; N, 11.06.

N-[1-(1H-Imidazol-4-ylacetyl)pyrrolidin-2(S)-ylmethyl]-N-(3-methoxybenzyl)glycyl-methionine methyl ester

FAB MS 532 (M+1)

N-[1-(1H-Imidazol-4-ylacetyl)pyrrolidin-2(S)-ylmethyl]-N-(2-methoxybenzyl)glycyl-methionine methyl ester Anal. Calcd for $C_{26}H_{37}N_5O_5S$.0.5 $H_2O$: C, 57.76; H, 7.08; N, 12.95; Found: C, 57.57; H, 6.90; N, 12.73.

N-[1-(Glycyl)pyrrolidin-2(S)-ylmethyl]-N-(3-methoxybenzyl)glycyl-methionine methyl ester hydrochloride Anal. Calcd for $C_{23}H_{36}N_4O_5S$.2.95 HCl: C, 46.97; H, 6.67; N, 9.53; Found: C, 46.75; H, 6.83; N, 9.33.

N-[1-(Glycyl)pyrrolidin-2(S)-ylmethyl]-N-(2-methoxybenzyl)glycyl-methionine methyl ester Anal. Calcd for $C_{23}H_{36}N_4O_5S$.2.0 HCl.1.4 $CF_3CO_2H$.0.9 $H_2O$: C, 42.49; H, 5.69; N, 7.69; Found: C, 42.49; H, 5.69; N, 7.92.

N-[1-(1H-Imidazol-4-ylpropionyl)pyrrolidin-2(S)-ylmethyl]-N-(2-methoxybenzyl)glycyl-methionine methyl ester Anal. Calcd for $C_{27}H_{39}N_5O_5S$.2.0 HCl.1.9 $CF_3CO_2H$.0.1 $H_2O$: C, 44.19; H, 5.19; N, 8.37; Found: C, 44.17; H, 5.21; N, 8.21.

N-[1-(1H-Imidazol-4-ylacetyl)pyrrolidin-2(S)-ylmethyl]-N-(3-cyanobenzyl)glycyl-methionine methyl ester Anal. Calcd for $C_{26}H_{34}N_6O_4S$.2.0 HCl.1.4 $CF_3CO_2H$.1.6 $H_2O$: C, 43.90; H, 5.19; N, 10.66; Found: C, 43.88; H, 5.21; N, 11.02.

N-[1-(1H-Imidazol-4-ylacetyl)pyrrolidin-2(S)-ylmethyl]-N-(2-cyanobenzyl)glycyl-methionine methyl ester Anal. Calcd for $C_{26}H_{34}N_6O_4S$.2.0 HCl.1.1 $CF_3CO_2H$.0.4 $H_2O$: C, 46.26; H, 5.22; N, 11.48; Found: C, 46.29; H, 5.23; N, 11.30.

N-[1-(Glycyl)pyrrolidin-2(S)-ylmethyl]-N-(2-cyanobenzyl)glycyl-methionine methyl ester Anal. Calcd for $C_{23}H_{33}N_5O_4S$.2.0 HCl.1.2 $CF_3CO_2H$.1.2 $H_2O$: C, 43.15; H, 5.50; N, 9.91; Found: C, 43.14; H, 5.46; N, 9.87.

N-[1-(1H-Imidazol-4-ylpropionyl)pyrrolidin-2(S)-ylmethyl]-N-(2-cyanobenzyl)glycyl-methionine methyl ester Anal. Calcd for $C_{27}H_{36}N_6O_4S$.2.0 HCl.1.4 $CF_3CO_2H$.0.7 $H_2O$: C, 45.55; H, 5.23; N, 10.69; Found: C, 45.49; H, 5.21; N, 10.82.

N-[1-(1H-Imidazol-4-ylacetyl)pyrrolidin-2(S)-ylmethyl]-N-(2-methylbenzyl)glycyl-methionine methyl ester Anal. Calcd for $C_{26}H_{37}N_5O_4S.0.65\ H_2O$: C, 59.21; H, 7.32; N, 13.28; Found: C, 59.21; H, 7.12; N, 13.16.

N-[1-(1H-Imidazol-4-ylacetyl)pyrrolidin-2(S)-ylmethyl]-N-(2-trifluoromethylbenzyl)glycyl-methionine methyl ester Anal. Calcd for $C_{26}H_{34}N_5O_4F_3S.0.70\ H_2O$: C, 53.63; H, 6.13; N, 12.03; Found: C, 53.61; H, 5.93; N, 11.74.

N-[1-(1H-Imidazol-4-ylacetyl)pyrrolidin-2(S)-ylmethyl]-N-(1-naphthylsulfonyl)glycyl-methionine methyl ester Anal. Calcd for $C_{28}H_{35}N_5O_6S.0.95\ H_2O$: C, 54.34; H, 6.01; N, 11.32; Found: C, 54.14; H, 5.70; N, 11.40.

Example 12

Preparation of N-[1-(1H-Imidazol-4-ylacetyl)pyrrolidin-3(S)-ethyl-2(S)-ylmethyl]-N-(1-naphthylmethyl)glycyl-methionine methyl ester Using the procedures described in the literature for similar intermediates (J. Y. L. Chung, M. W. Holladay et al, *J. Org. Chem.*, 1990, 55, 270–275), the title compound was prepared as described below.

Step A: Diethyl 1-Acetyl-5-hydroxy-3-ethylpyrrolidine-2,2-dicarboxylate

Sodium (4.02 g, 0.175 mol) was dissolved in a stirred solution of diethyl acetamidomalonate (235.4 g, 1.19 mol) in abs EtOH (1.4 L) at ambient temperature under argon. The reaction mixture was cooled to 0° C., and trans-2-pentenal (100 g, 1.08 mol) was added dropwise maintaining the reaction temperature at <5° C. After the addition, the reaction was allowed to warm to room temperature, stirred for 4 h, then quenched with acetic acid (28 mL). The solution was concentrated in vacuo, and the residue dissolved in EtOAc (1.5 L), washed with 10% $NaHCO_3$ solution (2×300 mL), brine, and dried ($MgSO_4$). The solution was filtered and concentrated to 700 mL, then heated to reflux and treated with hexane (1 L). On cooling, the title compound precipitated and was collected to give 287 g. $^1$H NMR ($CD_3OD$) δ5.65 (d, 1H, J=5 Hz), 4.1–4.25 (m, 4H), 2.7–2.8 (m, 1H), 2.21 (s, 3H), 2.10 (dd, 1H, J=6, 13, Hz),1.86–1.97 (m, 2H), 1.27 (t, 3H, J=7 Hz), 1.23 (t, 3H, J=7 Hz), 1.1–1.25 (m, 1H), 0.97 (t, 3H, J=7 Hz).

Step B: Diethyl 1-Acetyl-3-ethylpyrrolidine-2,2-dicarboxylate

To a solution of diethyl 1-acetyl-5-hydroxy-3-ethylpyrrolidine-2,2-dicarboxylate (287 g, 0.95 mol) and triethylsilane (228 mL, 1.43 mol) in $CH_2Cl_2$ (3 L) under argon was added trifluoroacetic acid (735 mL, 9.53 mol) dropwise with stirring while maintaining the internal temperature at 25° C. by means of an ice bath. After stirring for 3 h at 23° C., the solution was concentrated in vacuo,, the residue diluted with $CH_2Cl_2$ (1.5 L), then treated with $H_2O$ (1 L) and solid $Na_2CO_3$ with vigorous stirring until the solution was basic. The organic layer was separated, dried ($Na_2SO_4$), filtered, then concentrated to give the title compound as a yellow oil (373 g) which was used without further purification.

Step C: 3-Ethylproline hydrochloride (Cis:Trans Mixture)

Diethyl 1-acetyl-3-ethylpyrrolidine-2,2-dicarboxylate (373 g, 0.95 mol) was suspended in 6N HCl (2 L) and HOAc (500 mL) and heated at reflux for 20 h. The reaction mixture was cooled, washed with EtOAc (1L), then concentrated in vacuo to give an oil which crystallized upon trituration with ether to give 170 g of the title compound. $^1$H NMR ($D_2O$) δ4.23 (d, 1H, J=8 Hz), 3.84 (d, 1H, J=8 Hz), 3.15–3.4 (m, 4H), 2.33–2.44 (m, 1H), 2.19–2.4 (m, 1H), 2.02–2.15 (m, 2H), 1.53–1.72 (m, 3H), 1.23–1.43 (m, 2H), 1.0–1.15 (m, 1H), 0.75–0.83 (m, 6H).

Step D: Preparation of N-[(tert-Butyloxy)carbonyl]-3-ethylproline methyl ester

3-Ethylproline hydrochloride (Cis:Trans Mixture) (20 g, 0.11 mol) was dissolved in $CH_3OH$ (200 mL), and the solution was saturated with HCl gas, then stirred at 23° C. for 24 h. Argon was bubbled through the solution to remove excess HCl. The solution was treated with $NaHCO_3$ (>84 g) to a pH of 8, then di-tert-butyl dicarbonate (25.1 g, 0.115 mol) dissolved in $CH_3OH$ (20 mL) was added slowly. After stirring for 18 h at 23° C., the mixture was filtered, the filtrate concentrated, and the residue triturated with EtOAc, filtered again, and concentrated to give 29.1 g of the title compound as an oil.

Step E: Preparation of N[(tert-Butyloxy)carbonyl]-trans-3-ethylproline and N-[-(tert-Butyloxy)carbonyl]-cis-3-ethylproline methyl ester N-[(tert-Butyloxy)carbonyl]-3-ethylproline methyl ester (29.1 g, 0.113 mol) was dissolved in $CH_3OH$ (114 mL) with cooling to 0° C., then treated with 1N NaOH (114 mL). After stirring for 20 h at 23° C., the solution was concentrated to remove the $CH_3OH$ and then extracted with EtOAc (3×). The organic layers were combined, dried ($MgSO_4$), filtered, and concentrated to give 12.8 g of N-[(tert-Butyloxy)carbonyl]-cis-3-ethylproline methyl ester as an oil. The aqueous layer was acidified with solid citric acid and extracted with EtOAc (2×), the organic layers combined, dried ($MgSO_4$), filtered, and concentrated to give 15.5 g of N-[(tert-Butyloxy)carbonyl]-trans-3-ethylproline as an oil. $^1$H NMR ($CD_3OD$) δ3.86 and 3.78 (2 d, 1H, J=6 Hz), 3.33–3.58 (m, 2H), 2.01–2.22 (m, 2H), 1.5–1.74 (m, 2H), 1.33–1.5 (m, 1H), 1.45 and 1.42 (2 s, 9H), 0.98 (t, 3H, J=8 Hz).

Step F: Preparation of 3(S)-Ethyl-2(S)-proline

N-[(tert-Butyloxy)carbonyl]-trans-3-ethylproline (15.5 g,) 0.064 mol), S-a-methylbenzylamine (9.03 mL, 0.070 mol), HOBT (10.73 g, 0.70 mol), and N-methylmorpholine (8 mL, 0.076 mol) were dissolved in $CH_2Cl_2$ (150 mL) with stirring in an ice-$H_2O$ bath, treated with EDC (13.4 g, 0.070 mol) stirred at 23° C. for 48 h. The reaction mixture was partitioned between EtOAc and 10% citric acid solution, the organic layer washed with satd $NaHCO_3$ solution, brine and dried ($MgSO_4$), filtered, and concentrated to give an oil. This oil was dissolved in a minimum amount of ether (10 mL) to crystallize the desired S,S,S diastereomer (4.2 g). A solution of this product in 8N HCl (87 mL) and glacial acetic acid (22 mL) was heated at reflux overnight. The solution was concentrated on a rotary evaporator, and the residue taken up in $H_2O$ and extracted with ether. The aqueous layer was concentrated to dryness to give 3.8 g of a 1:1 mixture of 3(S)-ethyl-2(S)-proline and a-methylbenzylamine.

Step G: Preparation of N-[(tert-Butyloxy)carbonyl-3(S)-ethyl-2(S)-prolinol

3(S)-Ethyl-2(S)-proline containing a-methylbenzylamine (2.0 g, 0.0128 mol) was dissolved in dioxane (10 mL) and $H_2O$ (10 mL) with stirring and cooling to 0° C. N,N-diisopropylethylamine (2.2 mL, 0.0128 mol) and di-tett-butyl-dicarbonate (2.79 g, 0.0128 mol) were added and stirring was continued at 23° C. for 48 h. The reaction mixture was partitioned between EtOAc (60 mL) and H$_2$O (30 mL), the organic layer washed with 0.5N NaOH (2×40 mL), the aqueous layers combined and washed with EtOAc (30 mL) and this layer back-extracted with 0.5N NaOH (30 mL). The aqueous layers were combined and carefully acidified at 0° C. with 1N HCl to pH 2. This mixture was extracted with EtOAc (3×40 mL), the organics combined, dried (MgSO$_4$), filtered and concentrated to give N-[(tert-Butyloxy)carbonyl- 3(S)-ethyl-2(S)-proline as a colorless oil which was used without purification.

N-[(tert-Butyloxy)carbonyl-3(S)-ethyl-2(S)-proline (1.6 g, 6.58 mmol) was dissolved in dry THF (10 mL) and treated with borane (1M in THF, 12.5 mL, 12.5 mmol) with stirring at 0 ° C. for 2 h, then 23° C. for 1 h. The solution was cooled to 0° C., treated with H$_2$O (20 mL), and extracted with EtOAc (2×30 mL). The organics were washed with brine, satd NaHCO$_3$, H$_2$O, dried (MgSO$_4$), filtered and concentrated to give a viscous oil. The oil was dissolved in CH$_2$Cl$_2$, filtered through dry SiO$_2$, and the filtrate concentrated to give the title compound as an oil. $^1$H NMR (CDCl$_3$) δ4.97 (d, 1H, J=7 Hz), 3.71 (t, 1H, J=8 Hz), 3.51–3.62 (m, 3H), 3.18–3.26 (m, 1H), 1.9–2.0 (m, 1H), 1.53–1.7 (m, 2H), 1.47 (s, 9H), 1.26–1.43 (m, 2H), 0.95 (t, 3H, J=7 Hz).

Step H: Preparation of N-[(t-Butyloxy)carbonyl]-3(S)-ethyl-2(S)-prolinal

N-[(t-Butyloxy)carbonyl-3(S)-ethyl-2(S)-prolinol (0.638 g, 2.78 mmol) and Et$_3$N (1.4 mL, 9.74 mmol) were dissolved in dry CH$_2$Cl$_2$ (10 mL) with stirring and cooling to −10° C. and treated dropwise with a solution of SO$_3$.pyr (1.33 g, 8.35 mmol) in dry DMSO (5 mL) keeping the reaction mixture temperature at <0° C. The mixture was stirred at 0° C. for 20 min then at 5° C. for 20 min, and at 15° C. for 1 h, then poured into ice-cold 0.5N HCl and the layers separated. The aqueous layer was extracted with CH$_2$Cl$_2$ (3×20 mL), organics combined, washed with H$_2$O, aq satd NaHCO$_3$ solution, brine, and dried (Na$_2$SO$_4$). Filtration and concentration to dryness gave the title compound which was used without purification.

Step I: Preparation of N-[1-(1H-Imidazol-4-ylacetyl) pyrrolidin-3(S)-ethyl -2(S)-ylmethyl]-N-(1-naphthylmethyl)glycyl-methionine methyl ester Using the procedures described in Example 1, but substituting N-[(t-Butyloxy)carbonyl]-3(S)-ethyl-2(S)-prolinal for N-[(t-Butyloxy)carbonyl]- 2(S)-prolinal in Step A, the title compound was prepared.

Anal. Calcd for C$_{31}$H$_{41}$N$_5$O$_4$S.3.4 CF$_3$CO$_2$H: C, 46.93; H, 4.63; N, 7.24; Found: C, 46.87; H, 4.75; N, 7.56.

Using the procedures described in Example 12, the following compounds were prepared:

N-[1-(Glycyl) pyrrolidin-3(S)-ethyl-2(S)-ylmethyl]-N-(1-naphthylmethyl)glycyl-methionine methyl ester bis hydrochloride

FAB MS 529 (M+1).

N-[1-(1H-Imidazol-4-ylacetyl)pyrrolidin-3(S)-ethyl-2(S)-ylmethyl]-N-(benzyl)glycyl-methionine methyl ester Anal. Calcd for C$_{27}$H$_{39}$N$_5$O$_4$S.3 HCl: C, 50.74; H, 6.62; N, 10.96; Found: C, 50.57; H, 6.65; N, 10.89.

N-[1-(Glycyl) pyrrolidin-3(S)-ethyl-2(S)-ylmethyl]-N-(benzyl)glycyl-methionine methyl ester bis hydrochloride Anal. Calcd for C$_{24}$H$_{38}$N$_4$O$_4$S.2 HCl: C, 51.42; H, 7.37; N, 10.00; Found: C, 51.23; H, 7.10; N, 9.81.

Example 13

Preparation of N-[1-(1H-Imidazol-4-ylacetyl) pyrrolidin-2(S)-ylmethyl]-N-(1-naphthylmethyl) glycyl-methionine isopropyl ester Step. A: Preparation of N-(t-Butoxycarbonyl methionine isopropyl ester N-(t-Butoxycarbonyl methionine (25 g, 0.1 mol), EDC (21.1 g, 0.15 mol), 4-dimethylaminopyridine (1.22 g, 0.01 mol), and isopropanol (11.5 mL, 0.11 mol) were dissolved in dichloromethane (400 mL) with stirring in an ice-H$_2$O bath. The mixture was stirred at ambient temperature for 16 h then concentrated to dryness and partitioned between EtOAc and H$_2$O. After standard workup the crude product was chromatographed (SiO$_2$, hexane: EtOAc, 5:1) to give the title compound.

Step B: Preparation of Methionine isopropyl ester hydrochloride

HCl gas was bubbled into a solution of N-(t-Butoxycarbonyl methionine isopropyl ester (20.5 g, 0.07 mol) in EtOAc (200 mL) with stirring and cooling to −20° C. for 10 min. The flask was stoppered and stirred at −20° C. for 1 h, argon was bubbled into the solution to remove excess HCl, then the solution was concentrated to dryness to give a white solid which was used without further purification.

Step C: Preparation of N-[1-(1H-imidazol-4-ylacetyl) pyrrolidin-2(S)-ylmethyl]-N-(1-naphthylmethyl)glycyl-methionine isopropyl ester Using the methods described in Example 1, but substituting methionine isopropyl ester hydrochloride for methionine methyl ester in Step D, the title compound was prepared.

Anal. Calcd for C$_{31}$H$_{41}$N$_5$O$_4$S.0.5 H$_2$O: C, 63.24; H, 7.19; N, 11.89; Found: C, 63.22; H, 6.91; N, 11.86.

Using the methods outlined in Examples 1 and 13, the following esters were prepared:

N-[1-(1H-Imidazol-4-ylacetyl)pyrrolidin-2(S)-ylmethyl]-N-(1-naphthylmethyl)glycyl-methionine sulfone isopropyl ester Anal. Calcd for C$_{31}$H$_{41}$N$_5$O$_6$S.0.35 CH$_2$Cl$_2$: C, 58.70; H, 6.55; N, 10.92; Found: C, 58.59; H, 6.47; N, 11.05.

N-[1-(Glycyl) pyrrolidin-2(S)-ylmethyl]-N-(1-naphthylmethyl)glycyl-methionine isopropyl ester bis hydrochloride Anal. Calcd for C$_{28}$H$_{40}$N$_4$O$_4$S.2.5 HCl: C, 54.26; H, 6.91; N, 9.04; Found: C, 54.31; H, 6.98; N, 8.93.

N-[1-(Glycyl) pyrrolidin-2(S)-ylmethyl]-N-(1-naphthylmethyl)glycyl-methionine cyclohexyl ester hydrochloride Anal. Calcd for C$_{31}$ H$_{44}$N$_4$O$_4$S.2.8 HCl: C, 55.50; H, 7.03; N, 8.35; Found: C, 55.55; H, 6.95; N, 8.10.

N-[1-(Glycyl) pyrrolidin-2(S)-ylmethyl]-N-(1-naphthylmethyl)glycyl-methionine benzyl ester hydrochloride Anal. Calcd for C$_{32}$H$_{40}$N$_4$O$_4$S.2.4 HCl 0.1 H$_2$O: C, 57.71; H, 6.45; N, 8.41; Found: C, 57.75; H, 6.40; N, 8.34.

N-[1-(Glycyl) pyrrolidin-2(S)-ylmethyl]-N-(1-naphthylmethyl)glycyl-methionine ethyl ester bis hydrochloride Anal. Calcd for C$_{27}$H$_{38}$N$_4$O$_4$S.2 HCl.0.7 H$_2$O: C, 54.03; H, 6.95; N, 9.33; Found: C, 54.07; H, 6.75; N, 9.19.

N-[1-(Sarcosyl) pyrrolidin-2(S)-ylmethyl]-N-(1-naphthylmethyl)glycyl-methionine isopropyl ester bis hydrochloride

FAB MS 543 (M+1)

N-[1-(N,N-Dimethylglycyl) pyrrolidin-2(S)-ylmethyl]-N-(1-naphthylmethyl)glycyl-methionine isopropyl ester hydrochloride Anal. Calcd for $C_{30}H_{44}N_4O_4S \cdot 2.6$ HCl: C, 55.30; H, 7.21; N, 8.60; Found: C, 55.28; H, 7.30; N, 8.57.

N-[1-(Glycyl) pyrrolidin-2(S)-ylmethyl]-N-(1-naphthylmethyl)glycyl-methionine (2-pyridylmethyl) ester hydrochloride Anal. Calcd for $C_{31}H_{39}N_5O_4S \cdot 3.35$ HCl $\cdot 0.95$ EtOAc: C, 53.34; H, 6.43; N, 8.94; Found: C, 53.40; H, 6.59; N, 8.58.

N-[1-(Glycyl) pyrrolidin-2(S)-ylmethyl]-N-(1-naphthylmethyl)glycyl-methionine (1-glyceryl) ester trifluoroacetate Anal. Calcd for $C_{28}H_{40}N_4O_6S \cdot 2.80$ $CF_3CO_2H \cdot 1.5$ $H_2O$: C, 44.50; H, 5.09; N, 6.18; Found: C, 44.51; H, 5.08; N, 6.40.

N-[1-(Glycyl) pyrrolidin-2(S)-ylmethyl]-N-(1-naphthylmethyl)glycyl-methionine 4-N-methylpiperidinyl ester tris hydrochloride Anal. Calcd for $C_{31}H_{45}N_5O_4S \cdot 3.85$ HCl $\cdot 0.45$ EtOAc: C, 51.58; H, 6.92; N, 9.17; Found: C, 51.58; H, 7.02; N, 9.16.

N-[1-(Glycyl) pyrrolidin-2(S)-ylmethyl]-N-(1-naphthylmethyl)glycyl-methionine tert-butyl ester bis hydrochloride Anal. Calcd for $C_{29}H_{42}N_4O_4S \cdot 2.5$ HCl $\cdot 1.1$ $H_2O$: C, 53.28; H, 7.20; N, 8.57; Found: C, 53.34; H, 7.22; N, 8.57.

N-[1-(Glycyl) pyrrolidin-2(S)-ylmethyl]-N-(1-naphthylmethyl)glycyl-methionine 3-pentyl ester bis hydrochloride Anal. Calcd for $C_{30}H_{44}N_4O_4S \cdot 2.0$ HCl $\cdot 1.0$ $H_2O$: C, 55.63; H, 7.47; N, 8.65; Found: C, 55.93; H, 7.38; N, 8.57.

N-[1-(4-Pyridylglycyl) pyrrolidin-2(S)-ylmethyl]-N-(1-naphthylmethyl)glycyl-methionine isopropyl ester hydrochloride Anal. Calcd for $C_{33}H_{43}N_5O_4S \cdot 2.95$ HCl: C, 55.56; H, 6.49; N, 9.82; Found: C, 55.63; H, 6.78; N, 9.52.

N-[1-(1H-Imidazol-4-ylpropionyl)pyrrolidin-2(S)-ylmethyl]-N-(11-naphthylmethyl)glycyl-methionine isopropyl ester trifluoroacetate Anal. Calcd for $C_{32}H_{43}N_5O_4S \cdot 3.4$ $CF_3CO_2H$: C, 47.48; H, 4.77; N, 7.14; Found: C, 47.38; H, 4.93; N, 7.41.

Example 14

Preparation of N-[1-(1H-Imidazol-4-ylacetyl) piperidin-2(S)-ylmethyl]-N-(1-naphthylmethyl) glycyl-methionine methyl ester Step A: N-(t-Butoxycarbonyl)piperidine-2(S)-carboxylic acid 2(S)-Piperidinecarboxylic acid (3.0 g, 0.023 mol) was dissolved in dioxane (30 mL) water (30 mL) with stirring and cooling in an ice-water bath, and the solution brought to pH 8 with diisopropylethylamine. The resulting solution was treated alternately with di-tert-butyl dicarbonate (11 mL, 0.048 mol) and diisopropylethylamine (total of 15 mL, 0.086 mol ) then stirred at ambient temperature for 16 h. The reaction mixture was treated with 0.1N NaOH solution (200 mL) and extracted with EtOAc (3×100 mL). The organics were combined, washed with brine and dried ($MgSO_4$). Filtration and concentration to dryness gave the title compound which was used without further purification.

Step B: N-(t-Butoxycarbonyl)piperidinyl-2(S)-methanol

N-(t-Butoxycarbonyl)piperidine-2(S)-carboxylic acid (3.2 g, 0.014 mol) dissolved in THF (20 mL) and cooled in an ice-water bath, was treated dropwise with borane in THF (1M 28 mL, 0.028 mol) maintaining the reaction temperature at <10° C. The solution was stirred at 4° C. for 2 h, then at 25° C. for 1 h, then cooled to 0° C. and treated carefully with water (50 mL). The reaction mixture was extracted with EtOAc (3×50 mL), the organics combined, washed with water, aq satd $NaHCO_3$ solution, brine, and dried ($MgSO_4$). Filtration and concentration to dryness, followed by chromatography ($SiO_2$, $CH_2Cl_2$: $CH_3OH$, 95:5) gave the title compound. $^1H$ NMR ($CDCl_3$) δ4.25–4.35(m, 1H), 3.9–4.0 (m, 1H), 3.79–3.89 (m, 1H), 3.56–3.65 (m, 1H) 2.81–2.93 (m, 1H), 2.03 (br s, 1H), 1.53–1.72 (m, 5H), 1.46(s, 9H), 1.38–1.52 (m, 3H).

Step C: N-(t-Butoxycarbonyl)piperidine-2(S)-carboxaldehyde

N-(t-Butoxycarbonyl)piperidinyl-2(S)-methanol (2.64 g, 0.01 mol) was dissolved in anhydrous DMSO (50 mL), treated with $Et_3N$ (4.8 mL, 0.035 mol), stirred for 10 min, then cooled to 15° C. in an ice-water bath, and pyridine.$SO_3$ complex (5.5 g, 0.035 mol) was added portionwise. After 2.5 h, the reaction mixture was treated with ice (50 g), and extracted with $CH_2Cl_2$ (3×75 mL). The organics were combined, washed with 10% citric acid solution, $H_2O$, aq satd $NaHCO_3$ solution, brine, and dried ($MgSO_4$). Filtration and concentration to dryness gave the title compound as an oil. $^1H$ NMR ($CDCl_3$) δ9.59 (s, 1H), 4.43–4.67 (m, 1H), 3.83–4.06 (m, 1H), 2.81–3.0 (m, 1H), 2.12–2.3 (m, 1H), 1.53–1.72 (m, 3H), 1.47(s, 9H), 1.45–1.53 (m, 1H), 1.20–1.34 (m, 1H).

Step D: (1-Naphthylmethyl)glycine methyl ester hydrochloride

1-Naphthylmethanol (5.0 g, 0.0316 mol) was dissolved in dry $CH_2Cl_2$ (30 mL), diisopropylethylamine (6.6 mL, 0.0379 mol) was added, and the solution was cooled to 0° C. in an ice-water bath under Ar. Methanesulfonyl chloride (3.2 mL, 0.0316 mol) was added dropwise. After stirring cold for 30 min, additional diisopropylethylamine (1.6 mL) and methanesulfonyl chloride (0.8 mL) were added, and the reaction mixture was stirred and allowed to warm to 25 ° C. over 2.5 h. This solution was added alternately dropwise with diisopropylethylamine (22.5 m, 0.129 mol) to a slurry of glycine methyl ester hydrochloride (19.8 g, 0.158 mol) and diisopropylethylamine (5 mL, 0.028 mol) in dry DMF (30 mL) at 0° C. The reaction mixture was left to warm to ambient temperature overnight. Solvent was removed, and the residue treated with $H_2O$ (200 mL) and extracted with EtOAc (3×150 mL). The organics were washed with $H_2O$, brine, and dried ($MgSO_4$ and DARCO), filtered and concentrated to give a yellow oil. The oil was dissolved in EtOAc (200 mL), cooled to 0° C., and treated with HCl gas to precipitate the title compound as a tan solid. $^1H$ NMR ($CDCl_3$) δ10.48 (br s, 2H), 8.23 (d, 1H, J=8.6 Hz), 7.85–7.9 (m, 3H), 7.65 (td, 1H, J=1, 10 Hz), 7.47–7.58 (m, 2H), 4.84 (s, 2H), 3.67 (s, 3H), 3.65 (s, 2H).

Step E: N-(t-Butoxycarbonylpiperidin-2(S)-ylmethyl)-N-(1-naphthylmethyl) glycine methyl ester N-(t-Butoxycarbonyl)piperidine-2(S)-carboxaldehyde (2.19 g, 0.01 mol), (1-naphthylmethyl)glycine methyl ester hydrochloride (2.66 g, 0.01 mol) and Et$_3$N (1.4 mL, 0.01 mol) were dissolved in 1,2-dichloroethane (50 mL) with stirring under Ar in an ice-H$_2$O bath. Sodium triacetoxyborohydride (3.18 g, 0.015 mol) was added in one portion, the bath was removed, and the reaction mixture left to stir overnight at ambient temperature. The mixture was partitioned between EtOAc and aq satd NaHCO$_3$ solution, the basic layer washed with EtOAc (2×50 mL), the organics combined, washed with brine, and dried (MgSO$_4$). Filtration and concentration to dryness gave the title compound as a pale yellow oil after chromatography (SiO$_2$, EtOAc: hexane, 1:6). $^1$H NMR (CDCl$_3$) δ8.27–8.35 (m, 1H), 7.82 (d, 1H, J=8 Hz), 7.76 (d, 1H, J=8 Hz), 7.34–7.53 (m, 4H), 4.36 (d, 1H, J=13 Hz), 4.20 (d, 1H, J=13 Hz), 4.2–4.35 (m, 1H), 3.7–3.9 (m, 1H), 3.69 (s, 3H), 3.53 (d, 1H, J=17 Hz), 3.37 (d, 1H, J=17 Hz), 2.7–2.9 (m, 2H), 2.35–2.45 (m, 1H), 1.6–1.7 (m, 1H), 1.34–1.48 (m, 2H), 1.43 (s, 9H), 1.2–1.3 (m, 2H), 0.9–1.0 (m, 1H).

Step F: N-(t-Butoxycarbonylpiperidin-2(S)-ylmethyl)-N-(1-naphthylmethyl) glycine N-(t-Butoxycarbonylpiperidin-2(S)-ylmethyl)-N-(1-naphthylmethyl)glycine methyl ester (3.71 g, 8.7 mmol) was dissolved in MeOH (130 ml) in an ice-H$_2$O bath, and 1N NaOH (43.5 ml, 43.5 mmol) was added. The mixture was stirred at ambient temperature for 5 h and concentrated. The resulting residue was dissolved in H$_2$O (50 ml) and neutralized with 1N HCl (43.5 ml). The aqueous layer was washed with EtOAc (3×75 ml). The organic layers were combined, dried (MgSO$_4$), filtered, and concentrated to give the title compound as a white foam.

Step G: Preparation of N-(t-Butoxycarbonylpiperidin-2(S)-ylmethyl)-N-(1-naphthylmethyl)glycine-methionine methyl ester N-(t-Butoxycarbonylpiperidin-2(S)-ylmethyl)-N-(1-naphthylmethyl)glycine (2.00 g, 5.0 mmol), dissolved in CH$_2$Cl$_2$ (50 mL), was treated with HOBT (0.743 g, 5.5 mmol), EDC (1.05 g, 5.5 mmol), and methionine methyl ester hydrochloride (1.20 g, 6.0 mmol). The pH was adjusted to 7.5 with Et$_3$N (2.1 mL, 15 mmol) and the mixture was stirred at ambient temperature for 18 h. The mixture was diluted with EtOAc (50 mL), washed with 10% citric acid solution, water, and saturated NaHCO$_3$ solution, brine and dried (MgSO$_4$). Filtration and concentration gave the title compound. $^1$H NMR (CDCl$_3$); δ8.21 (d, 1H, J=8 Hz), 7.87 (d, 1H, J=8 Hz), 7.80 (d, 1H, J=8 Hz), 7.35–7.6 (m, 5H), 4.33–4.5 (m, 2H), 3.85–4.05 (m, 2H), 3.26 (s, 3H), 3.15–3.33 (m, 2H), 2.62–2.96 (m, 1H), 2.53–2.65 (m, 1H), 2.17 (s, 3H), 1.78–2.05 (m, 4H), 1.15–1.72 (m, 8H), 1.48 (s. 9H).

Step H: Preparation of N-(Piperidin-2(S)-ylmethyl)-N-(1-naphthylmethyl)-glycyl-methionine methyl ester hydrochloride N-(t-Butoxycarbonylpiperidin-2(S)-ylmethyl)-N-(1-naphthylmethyl)-glycyl-methionine methyl ester (3.23 g, 5.79 mmol) was dissolved in EtOAc (50 mL) and cooled to 0° C. HCl was bubbled through the mixture for 5 min, then the solution was stirred at 0° C. for 1.5 h. Argon was bubbled through the mixture to remove excess HCl and the mixture was then concentrated to give the title compound. $^1$H NMR (CD$_3$OD) δ8.24 (d, 1H, J=8 Hz), 7.82–7.91 (m, 2H), 7.42–7.57 (m, 4H), 4.53–4.58 (m, 1H), 4.31 (d, 1H, J=13 Hz), 4.13 (d, 1H, J=13 Hz), 3.68 (s, 3H), 3.45 (ABq, 2H), 3.14–3.21 (m, 1H), 2.95–3.06 (m, 1H), 2.80 (d, 2H, J=8 Hz), 2.65–2.75 (m, 1H), 2.36–2.54 (m, 2H), 2.01–2.13 (m, 1H), 2.05 (s, 3H), 1.72–1.92 (m, 4H), 1.47–1.6 (m, 2H), 1.19–1.31 (m, 1H).

Step I: Preparation of N-[1-(1H-Imidazol-4-ylacetyl) piperidin-2(S)-ylmethyl]-N-(1-naphthylmethyl)glycyl-methionine methyl ester N-(Piperidin-2(S)-ylmethyl)-N-(1-naphthylmethyl) glycyl-methionine methyl ester hydrochloride (2.1 g, 4 mmol), 4-imidazoleacetic acid hydrochloride (0.975 g, 6 mmol), hydroxybenzotriazole hydrate (0.811 g, 6 mmol), EDC hydrochloride (1.15 g, 6 mmol) and TEA (2.23 mL, 16 mmol) were dissolved in dry DMF (25 mL) and stirred under Ar for 18 h. The mixture was concentrated in vacuo and the residue taken up in aq satd NaHCO$_3$ soln and extracted with EtOAc (2×100 mL). The organics were washed with H$_2$O and brine, dried over MgSO$_4$, filtered and the solvent removed in vacuo to give an oil which was chromatographed on silica gel (5:95 MeOH:CH$_2$Cl$_2$), then further purified by preparative RPLC to give the title compound as the trifluoroacetate salt. $^1$H NMR (CD$_3$OD) δ8.87 (d, 1H, J=1.5 Hz), 8.30–8.36 (m, 1H), 7.93–8.0 (m, 2H), 7.6–7.7 (m, 1H), 7.47–7.6 (m, 3H), 7.40 (s, 1H), 4.95–5.05 (m, 1H), 4.4–4.8 (m, 2H), 3.95–4.05 (m, 1H), 3.76–3.88 (m, 2H), 3.71 (s, 3H), 2.9–3.7 (m, 6H), 2.28–2.5 (m, 2H), 2.0 (s, 3H), 1.95–2.1 (m, 1H), 1.75–1.9 (m, 1H), 1.6–1.75 (m, 2H), 1.5–1.6 (m, 2H), 1.3–1.5 (m, 2H).

MS 566 (M+1).

Anal. Calcd for C$_{30}$H$_{39}$N$_5$O$_4$S.2.5 CF$_3$CO$_2$H: C, 49.44; H, 4.92; N, 8.24. Found: C, 49.26; H, 4.98; N, 8.32.

Example 15

Preparation of N-[1-(1H-Imidazol-4-ylacetyl) piperidin-2(S)-ylmethyl]-N-(1-naphthylmethyl) glycyl-methionine Step A: N-[1-(1H-Imidazol-4-ylacetyl)piperidin-2(S)-ylmethyl]-N-(1-naphthylmethyl)glycyl-methionine N-[1-(1H-Imidazol-4-ylacetyl)piperidin-2(S)-ylmethyl]-N-(1-naphthylmethyl) glycyl-methionine (0.025 g, 0.032 mmol) was dissolved in CH$_3$OH (1 mL) at ambient temperature, treated with 1N NaOH solution (0.128 mL, 0.128 mmol) and stirred for 5 h. The solution was treated with 1N HCl (0.128 mL, 0.128 mmol) and purified by preparative RP HPLC on a VYDAC column eluting with 1%TFA:H$_2$O/1%TFA:CH$_3$CN, 95:5 to 5:95 gradient to give the title compound as the trifluoroacetate salt. $^1$H NMR (CD$_3$OD) δ8.87 (d, 1H, J=1.5 Hz), 8.30–8.35(m, 1H), 7.93–8.02 (m, 2H), 7.66–7.73 (m, 1H), 7.49–7.6 (m, 3H), 7.40 (s, 1H), 5.02–5.1 (m, 1H), 4.55–4.75 (m, 1H), 4.45–4.55 (m, 1H), 3.4–4.1 (m, 8H), 3.05–3.25 (m, 1H), 2.3–2.5 (m, 2H), 2.02 (s, 3H), 1.95–2.12 (m, 1H), 1.75–1.95 (m, 1H), 1.2–1.75 (m, 6H).

MS 552 (M+1).

Anal. Calcd for C$_{29}$H$_{37}$N$_5$O$_4$S.2 CF$_3$CO$_2$H.1.15 CH$_2$Cl$_2$: C, 46.74; H, 4.74; N, 7.98. Found: C, 46.60; H, 4.75; N, 8.35.

Example 16

Preparation of N-[1-(1H-Imidazol-4-ylacetyl) piperidin-2(S)-ylmethyl]-N-(1-naphthylmethyl) glycyl-methionine isopropyl ester Following the procedures described in Example 1, but substituting methionine isopropyl ester hydrochloride for methionine methyl ester in Step G, the title compound was prepared.

MS 594 (M+1).

Anal. Calcd for $C_{32}H_{43}N_5O_4S\cdot2.8\ CF_3CO_2H\cdot0.3\ H_2O$: C, 49.17; H, 5.09; N, 7.63. Found: C, 49.16; H, 5.09; N, 7.51.

Example 17

Preparation of N-[1-(1H-Imidazol-4-ylacetyl) piperidin-2(S)-ylmethyl]-N-(2-methoxybenzyl) glycyl-methionine Following the procedures outlined in Examples 1 and 2, but substituting 2-methoxybenzylalcohol for 1-naphthylmethanol in Example 1, Step D, the title compound was prepared.

MS 532 (M+1).

Anal. Calcd for $C_{26}H_{37}N_5O_5S\cdot3.25\ CF_3CO_2H$: C, 43.26; H, 4.50; N, 7.76. Found: C, 43.23; H, 4.61; N, 7.86.

Example 18

Preparation of N-[1-(1H-Imidazol-4-ylacetyl) piperidin-2(S)-ylmethyl]-N-(2-methoxybenzyl) glycyl-methionine isopropyl ester Following the procedures outlined in Example 1, but substituting 2-methoxybenzyl alcohol for 1-naphthylmethanol in Step D, and methionine isopropyl ester hydrochloride for the methyl ester in Step G, the title compound was prepared.

MS 574 (M+1).

Anal. Calcd for $C_{29}H_{43}N_5O_5S\cdot2.35\ CF_3CO_2H$: C, 48.08; H, 5.43; N, 8.32. Found: C, 48.12; H, 5.06; N, 8.58.

Example 19

Preparation of N-[1-(1H-Imidazol-4-ylpropionyl) piperidin-2(S)-ylmethyl]-N-(2-methoxybenzyl) glycyl-methionine methyl ester Following the procedures outlined in Example 1, but substituting 2-methoxybenzyl alcohol for 1-naphthylmethanol in Step D and 4-imidazolepropionic acid for 4-imidazoleacetic acid in Step F, the title compound was prepared.

MS 560 (M+1).

Anal. Calcd for $C_{28}H_{41}N_5O_5S$: C, 60.08; H, 7.38; N, 12.51. Found: C, 60.00; H, 7.25; N, 12.25.

Example 20

Preparation of N-[1-(1H-Imidazol-4-ylpropionyl) piperidin-2(S)-ylmethyl]-N-(2-methoxybenzyl) glycyl-methionine Following the procedures outlined in Example 2, but using the product from Example 6, the title compound was prepared.

MS 546 (M+1).

Anal. Calcd for $C_{27}H_{39}N_5O_5S\cdot3.0\ CF_3CO_2H$: C, 44.65; H, 4.77; N, 7.89. Found: C, 44.41; H, 4.77; N, 8.19.

Example 21

In vitro inhibition of ras farnesyl transferase

Assays of farnesyl-protein transferase. Partially purified bovine FPTase and Ras peptides (Ras-CVLS, Ras-CVIM and RAS-CAIL) were prepared as described by Schaber et al., *J. Biol. Chem.* 265:14701–14704 (1990), Pompliano, et al., *Biochemistry* 31:3800 (1992) and Gibbs et al., PNAS U.S.A. 86:6630–6634 (1989), respectively. Bovine FPTase was assayed in a volume of 100 µl containing 100 mM N-(2-hydroxy ethyl) piperazine-N'-(2-ethane sulfonic acid) (HEPES), pH 7.4, 5 mM $MgCl_2$, 5 mM dithiothreitol (DTT), 100 mM [$^3$H]-farnesyl diphosphate ([$^3$H]-FPP; 740 CBq/mmol, New England Nuclear), 650 nM Ras-CVLS and 10 µg/ml FPTase at 31° C. for 60 min. Reactions were initiated with FPTase and stopped with 1 ml of 1.0M HCL in ethanol. Precipitates were collected onto filter-mats using a TomTec Mach II cell harvestor, washed with 100% ethanol, dried and counted in an LKB β-plate counter. The assay was linear with respect to both substrates, FPTase levels and time; less than 10% of the [$^3$H]-FPP was utilized during the reaction period. Purified compounds were dissolved in 100% dimethyl sulfoxide (DMSO) and were diluted 20-fold into the assay. Percentage inhibition is measured by the amount of incorporation of radioactivity in the presence of the test compound when compared to the amount of incorporation in the absence of the test compound.

Human FPTase was prepared as described by Omer et al., *Biochemistry* 32:5167–5176 (1993). Human FPTase activity was assayed as described above with the exception that 0.1% (w/v) polyethylene glycol 20,000, 10 µM $ZnCl_2$ and 100 nM Ras-CVIM were added to the reaction mixture. Reactions were performed for 30 min., stopped with 100 µl of 30% (v/v) trichloroacetic acid (TCA) in ethanol and processed as described above for the bovine enzyme.

The compounds of the instant invention were tested for inhibitory activity against human FPTase by the assay described above and were found to have $IC_{50}$ of <10 µM.

Example 22

In vivo ras farnesylation assay

The cell line used in this assay is a v-ras line derived from either Rat1 or NIH3T3 cells, which expressed viral Ha-ras p21. The assay is performed essentially as described in DeClue, J. E. et al., *Cancer Research* 51:712–717, (1991). Cells in 10 cm dishes at 50–75% confluency are treated with the test compound (final concentration of solvent, methanol or dimethyl sulfoxide, is 0.1%). After 4 hours at 37° C., the cells are labelled in 3 ml methionine-free DMEM supplemeted with 10% regular DMEM, 2% fetal bovine serum and 400 mCi[$^{35}$S]methionine (1000 Ci/mmol). After an additional 20 hours, the cells are lysed in 1 ml lysis buffer (1% NP40/20 mM HEPES, pH 7.5/5 mM $MgCl_2$/1 mM DTT/10 mg/ml aprotinen/2 mg/ml leupeptin/2 mg/ml antipain/0.5 mM PMSF) and the lysates cleared by centrifugation at 100,000 xg for 45 min. Aliquots of lysates containing equal numbers of acid-precipitable counts are bought to 1 ml with IP buffer (lysis buffer lacking DTT) and immunoprecipitated with the ras-specific monoclonal antibody Y13–259 (Furth, M. E. et al., *J. Virol.* 43:294–304, (1982)). Following a 2 hour antibody incubation at 4° C., 200 ml of a 25% suspension of protein A-Sepharose coated with rabbit anti rat IgG is added for 45 min. The immunoprecipitates are washed four times with IP buffer (20 nM HEPES, pH 7.5/1 mM EDTA/1% Triton X-100.0.5% deoxycholate/0.1%/SDS/0.1M NaCI) boiled in SDS-PAGE sample buffer and loaded on 13% acrylamide gels. When the dye front reached the bottom, the gel is fixed, soaked in Enlightening, dried and autoradiographed. The intensities of the bands corresponding to farnesylated and nonfarnesylated ras proteins are compared to determine the percent inhibition of farnesyl transfer to protein.

Example 23

In vivo growth inhibition assay

To determine the biological consequences of FPTase inhibition, the effect of the compounds of the instant invention on the anchorage-independent growth of Rat1 cells transformed with either a v-ras, v-raf, or v-mos oncogene is tested. Cells transformed by v-Raf and v-Mos maybe included in the analysis to evaluate the specificity of instant compounds for Ras-induced cell transformation.

Rat 1 cells transformed with either v-ras, v-raf, or v-mos are seeded at a density of $1 \times 10^4$ cells per plate (35 mm in diameter) in a 0.3% top agarose layer in medium A (Dulbecco's modified Eagle's medium supplemented with 10% fetal bovine serum) over a bottom agarose layer (0.6%). Both layers contain 0.1% methanol or an appropriate concentration of the instant compound (dissolved in methanol at 1000 times the final concentration used in the assay). The cells are fed twice weekly with 0.5 ml of medium A containing 0.1% methanol or the concentration of the instant compound. Photomicrographs are taken 16 days after the cultures are seeded and comparisons are made.

What is claimed is:

1. A compound which inhibits farnesyl-protein transferase having the Formula I:

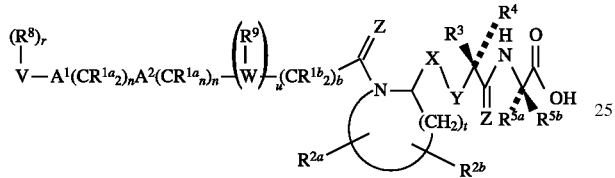

wherein:

$R^{1a}$ and $R^{1b}$ are independently selected from:
a) hydrogen,
b) aryl, heterocycle, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, CN, NO$_2$, $(R^{10})_2N$—C(NR$^{10}$)—, $R^{10}C(O)$—, $R^{10}OC(O)$—, N$_3$, —N(R$^{10}$)$_2$, or $R^{11}OC(O)NR^{10}$—,
c) $C_1$–$C_6$ alkyl unsubstituted or substituted by aryl, heterocyclic, $C_3$–$C_{10}$ cycloalkyl, $C_2$–$C_6$ alkenyl, $C_2$–$C_6$ alkynl, $R^{10}O$—, $R^{11}S(O)_m$—, $R^{10}C(O)NR^{10}$—, CN, $(R^{10})_2N$—C(NR$^{10}$)—, $R^{10}C(O)$—, $R^{10}OC(O)$—, N$_3$, —N(R$^{10}$)$_2$, or $R^{11}OC(O)NR^{10}$—;

$R^{2a}$ and $R^{2b}$ are independently selected from:
a) hydrogen,
b) $C_1$–$C_6$ alkyl unsubstituted or substituted by $C_2$–$C_6$ alkenyl, $R^{10}O$—, $R^{11}S(O)_m$—, $R^{10}C(O)NR^{10}$—, CN, N$_3$, $(R^{10})_2N$—C(NR$^{10}$)—, $R^{10}C(O)$—, $R^{10}OC(O)$—, —N(R$^{10}$)$_2$, or $R^{11}OC(O)NR^{10}$—,
c) aryl, heterocycle, $C_3$–$C_{10}$ cycloalkyl, $C_2$–$C_6$ alkenyl, $R^{10}O$—, $R^{11}S(O)_m$—, $R^{10}C(O)NR^{10}$—, CN, NO$_2$, $(R^{10})_2N$—C(NR$^{10}$)—, $R^{10}C(O)$—, $R^{10}OC(O)$—, N$_3$, —N(R$^{10}$)$_2$, or $R^{11}OC(O)NR^{10}$—, and
d) $C_1$–$C_6$ alkyl substituted with an unsubstituted or substituted group selected from aryl, heterocyclic and $C_3$–$C_{10}$ cycloalkyl;

$R^3$ and $R^4$ are independently selected from:
a) a side chain of a naturally occurring amino acid,
b) an oxidized form of a side chain of a naturally occurring amino acid which is:
i) methionine sulfoxide, or
ii) methionine sulfone, and
c) substituted or unsubstituted $C_1$–$C_{20}$ alkyl, $C_2$–$C_{20}$ alkenyl, $C_3$–$C_{10}$ cycloalkyl, aryl or heterocyclic group,
wherein the substituent is selected from F, Cl, Br, N(R$^{10}$)$_2$, NO$_2$, $R^{10}O$—, $R^{11}S(O)_m$—, $R^{10}C(O)NR^{10}$—, CN, $(R^{10})_2N$—C(NR$^{10}$)—, $R^{10}C(O)$—, $R^{10}OC(O)$—, N$_3$, —N(R$^{10}$)$_2$, $R^{11}OC(O)NR^{10}$— and $C_1$–$C_{20}$ alkyl, and
d) $C_1$–$C_6$ alkyl substituted with an unsubstituted or substituted group selected from aryl, heterocycle and $C_3$–$C_{10}$ cycloalkyl; or $R^3$ and $R^4$ are combined to form —(CH$_2$)$_s$—;

$R^{5a}$ and $R^{5b}$ are independently selected from:
a) a side chain of a naturally occurring amino acid,
b) an oxidized form of a side chain of a naturally occurring amino acid which is:
i) methionine sulfoxide, or
ii) methionine sulfone,
c) substituted or unsubstituted $C_1$–$C_{20}$ alkyl, $C_2$–$C_{20}$ alkenyl, $C_3$–$C_{10}$ cycloalkyl, aryl or heterocycle group,
wherein the substituent is selected from F, Cl, Br, CF$_3$, N(R$^{10}$)$_2$, NO$_2$, $R^{10}O$—, $R^{11}S(O)_m$—, $R^{10}C(O)NR^{10}$—, CN, $(R^{10})_2N$—C(NR$^{10}$)—, $R^{10}C(O)$—, $R^{10}OC(O)$—, N$_3$, —N(R$^{10}$)$_2$, $R^{11}OC(O)NR^{10}$— and $C_1$–$C_{20}$ alkyl,
d) $C_1$–$C_6$ alkyl substituted with an unsubstituted or substituted group selected from aryl, heterocycle and $C_3$–$C_{10}$ cycloalkyl; or $R^{5a}$ and $R^{5b}$ are combined to form —(CH$_2$)$_s$— wherein one of the carbon atoms is optionally replaced by a moiety selected from: O, S(O)$_m$, —NC(O)—, and —N(COR$^{10}$)—;

X—Y is a) 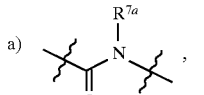

b) 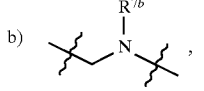

c) 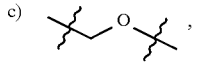

d) 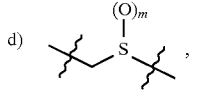

e) 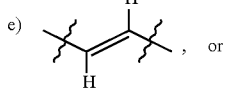, or f) —CH$_2$—CH$_2$—;

$R^{7a}$ is selected from
a) hydrogen,
b) unsubstituted or substituted aryl,
c) unsubstituted or substituted heterocycle,
d) unsubstituted or substituted $C_3$–$C_{10}$ cycloalkyl, and
e) $C_1$–$C_6$ alkyl substituted with hydrogen or an unsubstituted or substituted group selected from aryl, heterocycle and $C_3$–$C_{10}$ cycloalkyl;

$R^{7b}$ is selected from
a) hydrogen,
b) unsubstituted or substituted aryl,
c) unsubstituted or substituted heterocycle,
d) unsubstituted or substituted $C_3$–$C_{10}$ cycloalkyl,
e) $C_1$–$C_6$ alkyl substituted with hydrogen or an unsubstituted or substituted group selected from aryl, heterocycle and $C_3$–$C_{10}$ cycloalkyl, f) a carbonyl group which is bonded to an unsubstituted or substituted group selected from aryl, heterocycle, $C_3$–$C_{10}$ cycloalkyl and $C_1$–$C_6$ alkyl substituted with hydrogen or an unsubstituted or substituted group selected from aryl, heterocycle and $C_3$–$C_{10}$ cycloalkyl, and g) a sulfonyl group which is bonded to an unsubstituted or substituted group selected from aryl, heterocycle, $C_3$–$C_{10}$ cycloalkyl and $C_1$–$C_6$ alkyl substituted with hydrogen or an unsubstituted or substituted group selected from aryl, heterocycle and $C_3$–$C_{10}$ cycloalkyl;

$R^8$ is independently selected from:
a) hydrogen,
b) aryl, heterocycle, $C_3$–$C_{10}$ cycloalkyl, $C_2$–$C_6$ alkenyl, $C_2$–$C_6$ alkynyl, perfluoroalkyl, F, Cl, Br, $R^{10}O$—, $R^{11}S(O)_m$—, $R^{10}C(O)NR^{10}$—, CN, NO$_2$, $R^{10}{}_2N$—$C(NR^{10})$—, $R^{10}C(O)$—, $R^{10}OC(O)$—, $N_3$, —$N(R^{10})_2$, or $R^{11}OC(O)NR^{10}$—, and
c) $C_1$–$C_6$ alkyl unsubstituted or substituted by aryl, heterocycle, $C_3$–$C_{10}$ cycloalkyl, $C_2$–$C_6$ alkenyl, $C_2$–$C_6$ alkynyl, perfluoroalkyl, F, Cl, Br, $R^{10}O$—, $R^{11}S(O)_m$—, $R^{10}C(O)NH$—, CN, $H_2N$—$C(NH)$—, $R^{10}C(O)$—, $R^{10}OC(O)$—, $N_3$, —$N(R^{10})_2$, or $R^{10}OC(O)NH$—;

$R^9$ is selected from:
a) hydrogen,
b) $C_2$–$C_6$ alkenyl, $C_2$–$C_6$ alkynyl, perfluoroalkyl, F, Cl, Br, $R^{10}O$—, $R^{11}S(O)_m$—, $R^{10}C(O)NR^{10}$—, CN, NO$_2$, $(R^{10})_2N$—$C(NR^{10})$—, $R^{10}C(O)$—, $R^{10}OC(O)$—, $N_3$, —$N(R^{10})_2$, or $R^{11}OC(O)NR^{10}$—, and
c) $C_1$–$C_6$ alkyl unsubstituted or substituted by perfluoroalkyl, F, Cl, Br, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, $N_3$, —$N(R^{10})_2$, or $R^{11}OC(O)NR^{10}$—;

$R^{10}$ is independently selected from H, $C_1$–$C_6$ alkyl, benzyl, substituted aryl and $C_1$–$C_6$ alkyl substituted with substituted aryl;

$R^{11}$ is independently selected from $C_1$–$C_6$ alkyl and aryl;

$A^1$ and $A^2$ are independently selected from: a bond, —CH=CH—, —C≡C—, —C(O)—, —C(O)NR$^{10}$—, —NR$^{10}$C(O)—, O, —N(R$^{10}$)—, —S(O)$_2$N(R$^{10}$)—, —N(R$^{10}$)S(O)$_2$—, or S(O)$_m$;

V is selected from:
a) hydrogen,
b) heterocycle,
c) aryl,
d) $C_1$–$C_{20}$ alkyl wherein from 0 to 4 carbon atoms are replaced with a a heteroatom selected from O, S, and N, and
e) $C_2$–$C_{20}$ alkenyl, provided that V is not hydrogen if $A^1$ is $S(O)_m$ and V is not hydrogen if $A^1$ is a bond, n is 0 and $A^2$ is $S(O)_m$;

W is a heterocycle;

Z is independently $H_2$ or O;

m is     0, 1 or 2;
n is     0, 1, 2, 3 or 4;
p is     0, 1, 2, 3 or 4;
r is     0 to 5, provided that r is 0 when V is hydrogen;
s is     4 or 5;
t is     4; and
u is     0 or 1;

or a pharmaceutically acceptable salt thereof.

2. A prodrug of a compound having the Formula II:

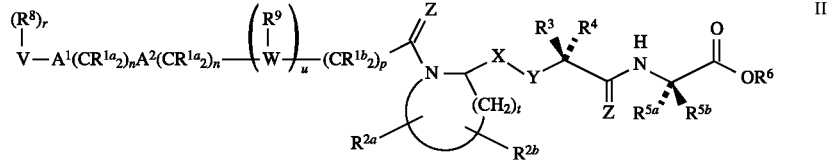

wherein:

$R^{1a}$ and $R^{1b}$ are independently selected from:
a) hydrogen,
b) aryl, heterocycle, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, CN, NO$_2$, $(R^{10})_2N$—$C(NR^{10})$—, $R^{10}C(O)$—, $R^{10}OC(O)$—, $N_3$, —$N(R^{10})_2$, or $R^{11}OC(O)NR^{10}$—,
c) $C_1$–$C_6$ alkyl unsubstituted or substituted by aryl, heterocyclic, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, $N_3$, —$N(R^{10})_2$, or $R^{11}OC(O)NR^{10}$—;

$R^{2a}$ and $R^{2b}$ are independently selected from:
a) hydrogen,
b) $C_1$–$C_6$ alkyl unsubstituted or substituted by $C_2$–$C_6$ alkenyl, $R^{10}O$—, $R^{11}S(O)_m$—, $R^{10}C(O)NR^{10}$—, CN, $N_3$, $(R^{10})_2N$—$C(NR^{10})$—, $R^{10}C(O)$—, $R^{10}OC(O)$—, —$N(R^{10})_2$, or $R^{11}OC(O)NR^{10}$—,
c) aryl, heterocycle, $C_3$–$C_{10}$ cycloalkyl, $C_2$–$C_6$ alkenyl, $R^{10}O$—, $R^{11}S(O)_m$—, $R^{10}C(O)NR^{10}$—, CN, NO$_2$, $(R^{10})_2N$—$C(NR^{10})$—, $R^{10}C(O)$—, $R^{10}OC(O)$—, $N_3$, —$N(R^{10})_2$, or $R^{11}OC(O)NR^{10}$—, and
d) $C_1$–$C_6$ alkyl substituted with an unsubstituted or substituted group selected from aryl, heterocyclic and $C_3$–$C_{10}$ cycloalkyl;

$R^3$ and $R^4$ are independently selected from:
a) a side chain of a naturally occurring amino acid,
b) an oxidized form of a side chain of a naturally occurring amino acid which is:
  i) methionine sulfoxide, or
  ii) methionine sulfone,
c) substituted or unsubstituted $C_1$–$C_{20}$ alkyl, $C_2$–$C_{20}$ alkenyl, $C_3$–$C_{10}$ cycloalkyl, aryl or heterocyclic group,
wherein the substituent is selected from F, Cl, Br, $N(R^{10})_2$, NO$_2$, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, $N_3$, —$N(R^{10})_2$, $R^{11}OC(O)NR^{10}$— and $C_1$–$C_{20}$ alkyl, and
d) $C_1$–$C_6$ alkyl substituted with an unsubstituted or substituted group selected from aryl, heterocycle and $C_3$–$C_{10}$ cycloalkyl; or $R^3$ and $R^4$ are combined to form —(CH$_2$)$_s$—;

$R^{5a}$ and $R^{5b}$ are independently selected from:
a) a side chain of a naturally occurring amino acid,
b) an oxidized form of a side chain of a naturally occurring amino acid which is:

i) methionine sulfoxide, or
ii) methionine sulfone,
c) substituted or unsubstituted $C_1$–$C_{20}$ alkyl, $C_2$–$C_{20}$ alkenyl, $C_3$–$C_{10}$ cycloalkyl, aryl or heterocycle group,
wherein the substituent is selected from F, Cl, Br, $CF_3$, $N(R^{10})_2$, $NO_2$, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, $N_3$, —$N(R^{10})_2$, $R^{11}OC(O)NR^{10}$— and $C_1$–$C_{20}$ alkyl, and
d) $C_1$–$C_6$ alkyl substituted with an unsubstituted or substituted group selected from aryl, heterocycle and $C_3$–$C_{10}$ cycloalkyl; or $R^{5a}$ and $R^{5b}$ are combined to form —$(CH_2)_s$— wherein one of the carbon atoms is optionally replaced by a moiety selected from: O, $S(O)_m$, —NC(O)—, and —$N(COR^{10})$—;

$R^6$ is
a) substituted or unsubstituted $C_1$–$C_8$ alkyl, substituted or unsubstituted $C_5$–$C_8$ cycloalkyl, or substituted or unsubstituted cyclic amine, wherein the substituted alkyl, cycloalkyl or cyclic amine is substituted with 1 or 2 substituents independently selected from:
1) $C_1$–$C_6$ alkyl,
2) aryl,
3) heterocycle,
4) —$N(R^{11})_2$,
5) —$OR^{10}$, or
b)

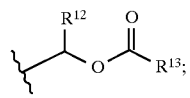

X—Y is a) 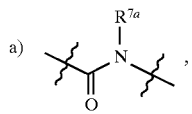

b) 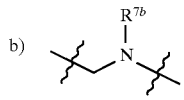

c) 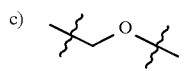

d) 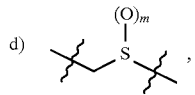

e) 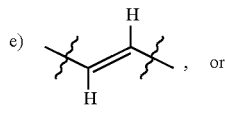, or f) —$CH_2$—$CH_2$—;

$R^{7a}$ is selected from
a) hydrogen,
b) unsubstituted or substituted aryl,
c) unsubstituted or substituted heterocycle,
d) unsubstituted or substituted $C_3$–$C_{10}$ cycloalkyl, and
e) $C_1$–$C_6$ alkyl substituted with hydrogen or an unsubstituted or substituted group selected from aryl, heterocycle and $C_3$–$C_{10}$ cycloalkyl;

$R^{7b}$ is selected from
a) hydrogen,
b) unsubstituted or substituted aryl,
c) unsubstituted or substituted heterocycle,
d) unsubstituted or substituted $C_3$–$C_{10}$ cycloalkyl,
e) $C_1$–$C_6$ alkyl substituted with hydrogen or an unsubstituted or substituted group selected from aryl, heterocycle and $C_3$–$C_{10}$ cycloalkyl,
f) a carbonyl group which is bonded to an unsubstituted or substituted group selected from aryl, heterocycle, $C_3$–$C_{10}$ cycloalkyl and $C_1$–$C_6$ alkyl substituted with hydrogen or an unsubstituted or substituted group selected from aryl, heterocycle and $C_3$–$C_{10}$ cycloalkyl, and
g) a sulfonyl group which is bonded to an unsubstituted or substituted group selected from aryl, heterocycle, $C_3$–$C_{10}$ cycloalkyl and $C_1$–$C_6$ alkyl substituted with hydrogen or an unsubstituted or substituted group selected from aryl, heterocycle and $C_3$–$C_{10}$ cycloalkyl;

$R^8$ is independently selected from:
a) hydrogen,
b) aryl, heterocycle, $C_3$–$C_{10}$ cycloalkyl, $C_2$–$C_6$ alkenyl, $C_2$–$C_6$ alkynyl, perfluoroalkyl, F, Cl, Br, $R^{10}O$—, $R^{11}S(O)_m$—, $R^{10}C(O)NR^{10}$—, CN, $NO_2$, $R^{10}_2N$—$C(NR^{10})$—, $R^{10}C(O)$—, $R^{10}OC(O)$—, $N_3$, —$N(R^{10})_2$, or $R^{11}OC(O)NR^{10}$—, and
c) $C_1$–$C_6$ alkyl unsubstituted or substituted by aryl, heterocycle, $C_3$–$C_{10}$ cycloalkyl, $C_2$–$C_6$ alkenyl, $C_2$–$C_6$ alkynyl, perfluoroalkyl, F, Cl, Br, $R^{10}O$—, $R^{11}S(O)_m$—, $R^{10}C(O)NH$—, CN, $H_2N$—$C(NH)$—, $R^{10}C(O)$—, $R^{10}OC(O)$—, $N_3$, —$N(R^{10})_2$, or $R^{10}OC(O)NH$—;

$R^9$ is selected from:
a) hydrogen,
b) $C_2$–$C_6$ alkenyl, $C_2$–$C_6$ alkynyl, perfluoroalkyl, F, Cl, Br, $R^{10}O$—, $R^{11}S(O)_m$—, $R^{10}C(O)NR^{10}$—, CN, $NO_2$, $(R^{10})_2N$—$C(NR^{10})$—, $R^{10}C(O)$—, $R^{10}OC(O)$—, $N_3$, —$N(R^{10})_2$, or $R^{11}OC(O)NR^{10}$—, and
c) $C_1$–$C_6$ alkyl unsubstituted or substituted by perfluoroalkyl, F, Cl, Br, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, $N_3$, —$N(R^{10})_2$, or $R^{11}OC(O)NR^{10}$—;

$R^{10}$ is independently selected from H, $C_1$–$C_6$ alkyl, benzyl, substituted aryl and $C_1$–$C_6$ alkyl substituted with substituted aryl;

$R^{11}$ is independently selected from $C_1$–$C_6$ alkyl and aryl;

$R^{12}$ is hydrogen or $C_1$–$C_6$ alkyl;

$R^{13}$ is $C_1$–$C_6$ alkyl;

$A^1$ and $A^2$ are independently selected from: a bond, —CH=CH—, —C≡C—, —C(O)—, —$C(O)NR^{10}$—, —$NR^{10}C(O)$—, O, —$N(R^{10})$—, —$S(O)_2N(R^{10})$—, —$N(R^{10})S(O)_2$—, or $S(O)_m$;

V is selected from:
a) hydrogen,
b) heterocycle,
c) aryl,
d) $C_1$–$C_{20}$ alkyl wherein from 0 to 4 carbon atoms are replaced with a a heteroatom selected from O, S, and N, and
e) $C_2$–$C_{20}$ alkenyl, provided that V is not hydrogen if $A^1$ is $S(O)_m$ and V is not hydrogen if $A^1$ is a bond, n is 0 and $A^2$ is $S(O)_m$;

W is a heterocycle;

Z is independently $H_2$ or O;

m is 0, 1 or 2;
n is 0, 1, 2, 3 or 4;
p is 0, 1, 2, 3 or 4;
r is 0 to 5, provided that r is 0 when V is hydrogen;
s is 4 or 5;
t is 4; and
u is 0 or 1;

or a pharmaceutically acceptable salt thereof.

3. A compound which inhibits farnesyl-protein transferase having the Formula III:

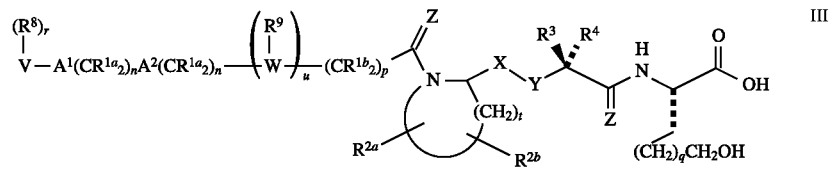

wherein:
  $R^{1a}$ and $R^{1b}$ are independently selected from:
   a) hydrogen,
   b) aryl, heterocycle, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, CN, $NO_2$, $(R^{10})_2N$—$C(NR^{10})$—, $R^{10}C(O)$—, $R^{10}OC(O)$—, $N_3$, —$N(R^{10})_2$, or $R^{11}OC(O)NR^{10}$—,
   c) $C_1$–$C_6$ alkyl unsubstituted or substituted by aryl, heterocyclic, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, $N_3$, —$N(R^{10})_2$, or $R^{11}OC(O)NR^{10}$—;

$R^{2a}$ and $R^{2b}$ are independently selected from:
   a) hydrogen,
   b) $C_1$–$C_6$ alkyl unsubstituted or substituted by $C_2$–$C_6$ alkenyl, $R^{10}O$—, $R^{11}S(O)_m$—, $R^{10}C(O)NR^{10}$—, CN, $N_3$, $(R^{10})_2N$—$C(NR^{10})$—, $R^{10}C(O)$—, $R^{10}OC(O)$—, —$N(R^{10})_2$, or $R^{11}OC(O)NR^{10}$—,
   c) aryl, heterocycle, $C_3$–$C_{10}$ cycloalkyl, $C_2$–$C_6$ alkenyl, $R^{10}O$—, $R^{11}S(O)_m$—, $R^{10}C(O)NR^{10}$—, CN, $NO_2$, $(R^{10})_2N$—$C(NR^{10})$—, $R^{10}C(O)$—, $R^{10}OC(O)$—, $N_3$, —$N(R^{10})_2$, or $R^{11}OC(O)NR^{10}$—, and
   d) $C_1$–$C_6$ alkyl substituted with an unsubstituted or substituted group selected from aryl, heterocyclic and $C_3$–$C_{10}$ cycloalkyl;

$R^3$ and $R^4$ are independently selected from:
   a) a side chain of a naturally occurring amino acid,
   b) an oxidized form of a side chain of a naturally occurring amino acid which is:
    i) methionine sulfoxide, or
    ii) methionine sulfone, and
   c) substituted or unsubstituted $C_1$–$C_{20}$ alkyl, $C_2$–$C_{20}$ alkenyl, $C_3$–$C_{10}$ cycloalkyl, aryl or heterocyclic group,
    wherein the substituent is selected from F, Cl, Br, $N(R^{10})_2$, $NO_2$, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, $N_3$, —$N(R^{10})_2$, $R^{11}OC(O)NR^{10}$— and $C_1$–$C_{20}$ alkyl, and
   d) $C_1$–$C_6$ alkyl substituted with an unsubstituted or substituted group selected from aryl, heterocycle and $C_3$–$C_{10}$ cycloalkyl; or
  $R^3$ and $R^4$ are combined to form —$(CH_2)_s$—;

X—Y is a) 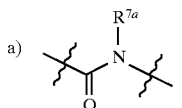, b) 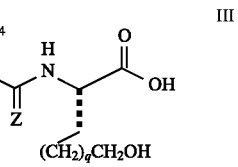, c) 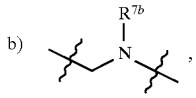, d) 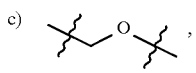, e) 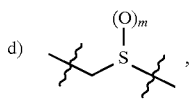, or f) —$CH_2$—$CH_2$—;

$R^{7a}$ is selected from
  a) hydrogen,
  b) unsubstituted or substituted aryl,
  c) unsubstituted or substituted heterocycle,
  d) unsubstituted or substituted $C_3$–$C_{10}$ cycloalkyl, and
  e) $C_1$–$C_6$ alkyl substituted with hydrogen or an unsubstituted or substituted group selected from aryl, heterocycle and $C_3$–$C_{10}$ cycloalkyl;

$R^{7b}$ is selected from
  a) hydrogen,
  b) unsubstituted or substituted aryl,
  c) unsubstituted or substituted heterocycle,
  d) unsubstituted or substituted $C_3$–$C_{10}$ cycloalkyl,
  e) $C_1$–$C_6$ alkyl substituted with hydrogen or an unsubstituted or substituted group selected from aryl, heterocycle and $C_3$–$C_{10}$ cycloalkyl,
  f) a carbonyl group which is bonded to an unsubstituted or substituted group selected from aryl, heterocycle, $C_3$–$C_{10}$ cycloalkyl and $C_1$–$C_6$ alkyl substituted with hydrogen or an unsubstituted or substituted group selected from aryl, heterocycle and $C_3$–$C_{10}$ cycloalkyl, and
  g) a sulfonyl group which is bonded to an unsubstituted or substituted group selected from aryl, heterocycle, $C_3$–$C_{10}$ cycloalkyl and $C_1$–$C_6$ alkyl substituted with hydrogen or an unsubstituted or substituted group selected from aryl, heterocycle and $C_3$–$C_{10}$ cycloalkyl;

$R^8$ is independently selected from:

4. A prodrug of a compound of claim 3 of the Formula IV:

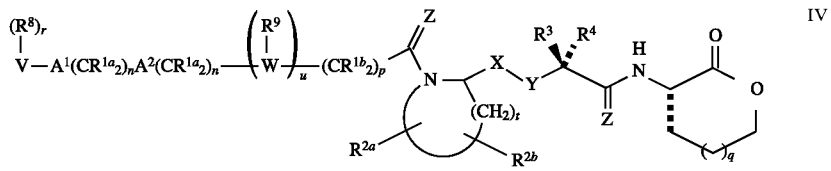

IV a) hydrogen,
b) aryl, heterocycle, $C_3$–$C_{10}$ cycloalkyl, $C_2$–$C_6$ alkenyl, $C_2$–$C_6$ alkynyl, perfluoroalkyl, F, Cl, Br, $R^{10}$O—, $R^{11}$S(O)$_m$—, $R^{10}$C(O)NR$^{10}$—, CN, NO$_2$, $R^{10}{}_2$N—C(NR$^{10}$)—, $R^{10}$C(O)—, $R^{10}$OC(O)—, N$_3$, —N(R$^{10}$)$_2$, or $R^{11}$OC(O)NR$^{10}$—, and
c) $C_1$–$C_6$ alkyl unsubstituted or substituted by aryl, heterocycle, $C_3$–$C_{10}$ cycloalkyl, $C_2$–$C_6$ alkenyl, $C_2$–$C_6$ alkynyl, perfluoroalkyl, F, Cl, Br, $R^{10}$O—, $R^{11}$S(O)$_m$—, $R^{10}$C(O)NH—, CN, H$_2$N—C(NH)—, $R^{10}$C(O)—, $R^{10}$OC(O)—, N$_3$, —N(R$^{10}$)$_2$, or $R^{10}$OC(O)NH—;

$R^9$ is selected from:
a) hydrogen,
b) $C_2$–$C_6$ alkenyl, $C_2$–$C_6$ alkynyl, perfluoroalkyl, F, Cl, Br, $R^{10}$O—, $R^{11}$S(O)$_m$—, $R^{10}$C(O)NR$^{10}$—, CN, NO$_2$, (R$^{10}$)$_2$N—C—(NR$^{10}$)—, $R^{10}$C(O)—, $R^{10}$OC(O)—, N$_3$, —N(R$^{10}$)$_2$, or $R^{11}$OC(O)NR$^{10}$—, and
c) $C_1$–$C_6$ alkyl unsubstituted or substituted by perfluoroalkyl, F, Cl, Br, $R^{10}$O—, $R^{11}$S(O)$_m$—, $R^{10}$C(O)NR$^{10}$—, CN, (R$^{10}$)$_2$N—C(NR$^{10}$)—, $R^{10}$C(O)—, $R^{10}$OC(O)—, N$_3$, —N(R$^{10}$)$_2$, or $R^{11}$OC(O)NR$^{10}$—;

$R^{10}$ is independently selected from H, $C_1$–$C_6$ alkyl, benzyl, substituted aryl and $C_1$–$C_6$ alkyl substituted with substituted aryl;

$R^{11}$ is independently selected from $C_1$–$C_6$ alkyl and aryl;

$R^{12}$ is hydrogen or $C_1$–$C_6$ alkyl;

$R^{13}$ is $C_1$–$C_6$ alkyl;

$A^1$ and $A^2$ are independently selected from: a bond, —CH=CH—, —C≡C—, —C(O)—, —C(O)NR$^{10}$—, —NR$^{10}$C(O)—, O, —N(R$^{10}$)—, —S(O)$_2$N(R$^{10}$)—, —N(R$^{10}$)S(O)$_2$—, or S(O)$_m$;

V is selected from:
a) hydrogen,
b) heterocycle,
c) aryl,
d) $C_1$–$C_{20}$ alkyl wherein from 0 to 4 carbon atoms are replaced with a a heteroatom selected from O, S, and N, and
e) $C_2$–$C_{20}$ alkenyl, provided that V is not hydrogen if $A^1$ is S(O)$_m$ and V is not hydrogen if $A^1$ is a bond, n is 0 and $A^2$ is S(O)$_m$;

W is a heterocycle;

Z is independently H$_2$ or O;

m is 0, 1 or 2;
n is 0, 1, 2, 3 or 4;
p is 0, 1, 2, 3 or 4;
q is 0, 1 or 2;
r is 0 to 5, provided that r is 0 when V is hydrogen;
s is 4 or 5;
t is 4; and
u is 0 or 1;

or a pharmaceutically acceptable salt thereof.

wherein:

$R^{1a}$ and $R^{1b}$ are independently selected from:
a) hydrogen,
b) aryl, heterocycle, $C_3$–$C_{10}$ cycloalkyl, $C_2$–$C_6$ alkenyl, $C_2$–$C_6$ alkynyl, $R^{10}$O—, $R^{11}$S(O)$_m$—, $R^{10}$C(O)NR$^{10}$—, CN, NO$_2$, (R$^{10}$)$_2$N—C(NR$^{10}$)—, $R^{10}$C(O)—, $R^{10}$OC(O)—, N$_3$, —N(R$^{10}$)$_2$, or $R^{11}$OC(O)NR$^{10}$—,
c) $C_1$–$C_6$ alkyl unsubstituted or substituted by aryl, heterocycle, $C_3$–$C_{10}$ cycloalkyl, $C_2$–$C_6$ alkenyl, $C_2$–$C_6$ alkynyl, $R^{10}$O—, $R^{11}$S(O)$_m$—, $R^{10}$C(O)NR$^{10}$—, CN, (R$^{10}$)$_2$N—C(NR$^{10}$)—, $R^{10}$C(O)—, $R^{10}$OC(O)—, N$_3$, —N(R$^{10}$)$_2$, or $R^{11}$OC(O)—NR$^{10}$—;

$R^{2a}$ and $R^{2b}$ are independently selected from:
a) hydrogen,
b) $C_1$–$C_6$ alkyl unsubstituted or substituted by $C_2$–$C_6$ alkenyl, $R^{10}$O—, $R^{11}$S(O)$_m$—, $R^{10}$C(O)NR$^{10}$—, CN, N$_3$, (R$^{10}$)$_2$N—C(NR$^{10}$)—, $R^{10}$C(O)—, $R^{10}$OC(O)—, —N(R$^{10}$)$_2$, or $R^{11}$OC(O)NR$^{10}$—;
c) aryl, heterocycle, $C_3$–$C_{10}$ cycloalkyl, $C_2$–$C_6$ alkenyl, $R^{10}$O—, $R^{11}$S(O)$_m$—, $R^{10}$C(O)NR$^{10}$—, CN, NO$_2$, (R$^{10}$)$_2$N—C(NR$^{10}$)—, $R^{10}$C(O)—, $R^{10}$OC(O)—, N$_3$, —N(R$^{10}$)$_2$, or $R^{11}$OC(O)NR$^{10}$—, and
d) $C_1$–$C_6$ alkyl substituted with an unsubstituted or substituted group selected from aryl, heterocyclic and $C_3$–$C_{10}$ cycloalkyl;

$R^3$ and $R^4$ are independently selected from:
a) a side chain of a naturally occurring amino acid,
b) an oxidized form of a side chain of a naturally occurring amino acid which is:
  i) methionine sulfoxide, or
  ii) methionine sulfone,
c) substituted or unsubstituted $C_1$–$C_{20}$ alkyl, $C_2$–$C_{20}$ alkenyl, $C_3$–$C_{10}$ cycloalkyl, aryl or heterocycle group, wherein the substituent is selected from F, Cl, Br, N(R$^{10}$)$_2$, NO$_2$, $R^{10}$O—, $R^{11}$S(O)$_m$—, $R^{10}$C(O)NR$^{10}$—, CN, (R$^{10}$)$_2$N—C(NR$^{10}$)—, $R^{10}$C(O)—, $R^{10}$OC(O)—, N$_3$, —N(R$^{10}$)$_2$, $R^{11}$OC(O)NR$^{10}$— and $C_1$–$C_{20}$ alkyl, and d) $C_1$–$C_6$ alkyl substituted with an unsubstituted or substituted group selected from aryl, heterocycle and $C_3$–$C_{10}$ cycloalkyl; or $R^3$ and $R^4$ are combined to form —(CH$_2$)$_s$—;

X—Y is a) 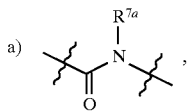

-continued

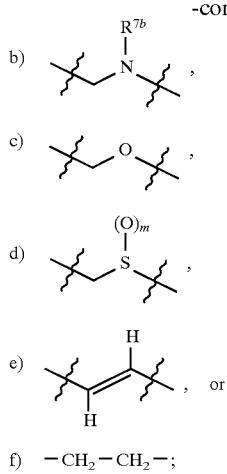

b)

c)

d)

e)

f) $-CH_2-CH_2-$;

$R^{7a}$ is selected from
a) hydrogen,
b) unsubstituted or substituted aryl,
c) unsubstituted or substituted heterocycle,
d) unsubstituted or substituted $C_3-C_{10}$ cycloalkyl, and
e) $C_1-C_6$ alkyl substituted with hydrogen or an unsubstituted or substituted group selected from aryl, heterocycle and $C_3-C_{10}$ cycloalkyl;

$R^{7b}$ is selected from
a) hydrogen,
b) unsubstituted or substituted aryl,
c) unsubstituted or substituted heterocycle,
d) unsubstituted or substituted $C_3-C_{10}$ cycloalkyl,
e) $C_1-C_6$ alkyl substituted with hydrogen or an unsubstituted or substituted group selected from aryl, heterocycle and $C_3-C_{10}$ cycloalkyl,
f) a carbonyl group which is bonded to an unsubstituted or substituted group selected from aryl, heterocycle, $C_3-C_{10}$ cycloalkyl and $C_1-C_6$ alkyl substituted with hydrogen or an unsubstituted or substituted group selected from aryl, heterocycle and $C_3-C_{10}$ cycloalkyl, and
g) a sulfonyl group which is bonded to an unsubstituted or substituted group selected from aryl, heterocycle, $C_3-C_{10}$ cycloalkyl and $C_1-C_6$ alkyl substituted with hydrogen or an unsubstituted or substituted group selected from aryl, heterocycle and $C_3-C_{10}$ cycloalkyl;

$R^8$ is independently selected from:
a) hydrogen,
b) aryl, heterocycle, $C_3-C_{10}$ cycloalkyl, $C_2-C_6$ alkenyl, $C_2-C_6$ alkynyl, perfluoroalkyl, F, Cl, Br, $R^{10}O-$, $R^{11}S(O)_m-$, $R^{10}C(O)NR^{10}-$, CN, $NO_2$, $R^{10}{}_2N-C(NR^{10})-$, $R^{10}C(O)-$, $R^{10}OC(O)-$, $N_3$, $-N(R^{10})_2$, or $R^{11}OC(O)NR^{10}-$, and
c) $C_1-C_6$ alkyl unsubstituted or substituted by aryl, heterocycle, $C_3-C_{10}$ cycloalkyl, $C_2-C_6$ alkenyl, $C_2-C_6$ alkynyl, perfluoroalkyl, F, Cl, Br, $R^{10}O-$, $R^{11}S(O)_m-$, $R^{10}C(O)NH-$, CN, $H_2N-C(NH)-$, $R^{10}C(O)-$, $R^{10}OC(O)-$, $N_3$, $-N(R^{10})_2$, or $R^{10}OC(O)NH-$;

$R^9$ is selected from:
a) hydrogen,
b) $C_2-C_6$ alkenyl, $C_2-C_6$ alkynyl, perfluoroalkyl, F, Cl, Br, $R^{10}O-$, $R^{11}S(O)_m-$, $R^{10}C(O)NR^{10}-$, CN, $NO_2$, $(R^{10})_2N-C(NR^{10})-$, $R^{10}C(O)-$, $R^{10}OC(O)-$, $N_3$, $-N(R^{10})_2$, or $R^{11}OC(O)NR^{10}-$, and
c) $C_1-C_6$ alkyl unsubstituted or substituted by perfluoroalkyl, F, Cl, Br, $R^{10}O-$, $R^{11}S(O)_m-$, $R^{10}C(O)NR^{10}-$, CN, $(R^{10})_2N-C(NR^{10})-$, $R^{10}C(O)-$, $R^{10}OC(O)-$, $N_3$, $-N(R^{10})_2$, or $R^{11}OC(O)NR^{10}-$;

$R^{10}$ is independently selected from H, $C_1-C_6$ alkyl, benzyl, substituted aryl and $C_1-C_6$ alkyl substituted with substituted aryl;

$R^{11}$ is independently selected from $C_1-C_6$ alkyl and aryl;

$R^{12}$ is hydrogen or $C_1-C_6$ alkyl;

$R^{13}$ is $C_1-C_6$ alkyl;

$A^1$ and $A^2$ are independently selected from: a bond, $-CH=CH-$, $-C\equiv C-$, $-C(O)-$, $-C(O)NR^{10}-$, $-NR^{10}C(O)-$, O, $-N(R^{10})-$, $-S(O)_2N(R^{10})-$, $-N(R^{10})S(O)_2-$, or $S(O)_m$;

V is selected from:
a) hydrogen,
b) heterocycle,
c) aryl,
d) $C_1-C_{20}$ alkyl wherein from 0 to 4 carbon atoms are replaced with a a heteroatom selected from O, S, and N, and
e) $C_2-C_{20}$ alkenyl,
provided that V is not hydrogen if $A^1$ is $S(O)_m$ and V is not hydrogen if
$A^1$ is a bond, n is 0 and $A^2$ is $S(O)_m$;

W is a heterocycle;

Z is independently $H_2$ or O;

| | |
|---|---|
| m is | 0, 1 or 2; |
| n is | 0, 1, 2, 3 or 4; |
| p is | 0, 1, 2, 3 or 4; |
| q is | 0, 1 or 2; |
| r is | 0 to 5, provided that r is 0 when V is hydrogen; |
| s is | 4 or 5; |
| t is | 4; and |
| u is | 0 or 1; | or a pharmaceutically acceptable salt thereof.

5. The compound according to claim 1 of the formula I:

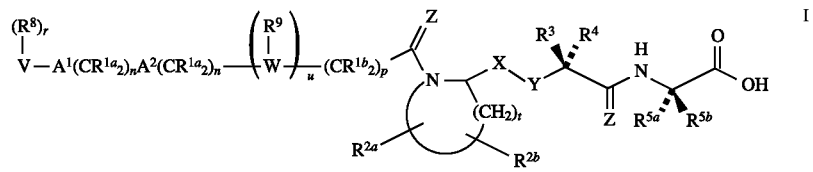

wherein:

$R^{1a}$ is independently selected from: hydrogen or $C_1-C_6$ alkyl;

$R^{1b}$ is independently selected from:
a) hydrogen,
b) aryl, heterocycle, $C_3-C_{10}$ cycloalkyl, $R^{10}O-$, $-N(R^{10})_2$ or alkenyl,
c) $C_1-C_6$ alkyl unsubstituted or substituted by aryl, heterocycle, cycloalkyl, alkenyl, $R^{10}O-$, or $-N(R^{10})_2$;

$R^{2a}$ is selected from:

a) hydrogen,
b) $C_1$–$C_6$ alkyl unsubstituted or substituted by $C_2$–$C_6$ alkenyl, $R^{10}O$—, $R^{11}S(O)_m$—, $R^{10}C(O)NR^{10}$—, CN, $N_3$, $(R^{10})_2N$—$C(NR^{10})$—, $R^{10}C(O)$—, $R^{10}OC(O)$—, —$N(R^{10})_2$, or $R^{11}OC(O)NR^{10}$—,
c) aryl, heterocycle, $C_3$–$C_{10}$ cycloalkyl, $C_2$–$C_6$ alkenyl, $R^{10}O$—, $R^{11}S(O)_m$—, $R^{10}C(O)NR^{10}$—, CN, $NO_2$, $(R^{10})_2N$—$C(NR^{10})$—, $R^{10}C(O)$—, $R^{10}OC(O)$—, $N_3$, —$N(R^{10})_2$, or $R^{11}OC(O)NR^{10}$—, and
d) $C_1$–$C_6$ alkyl substituted with an unsubstituted or substituted group selected from aryl, heterocyclic and $C_3$–$C_{10}$ cycloalkyl;

$R^{2b}$ is hydrogen;

$R^3$ and $R^4$ are independently selected from:
a) a side chain of a naturally occurring amino acid,
b) an oxidized form of a side chain of a naturally occurring amino acid which is:
  i) methionine sulfoxide, or
  ii) methionine sulfone,
c) substituted or unsubstituted $C_1$–$C_{10}$ alkyl, $C_2$–$C_{10}$ alkenyl, $C_3$–$C_{10}$ cycloalkyl, aryl or heterocyclic group,
  wherein the substituent is selected from F, Cl, Br, $NO_2$, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, $N_3$, —$N(R^{10})_2$, $R^{11}OC(O)NR^{10}$— and $C_1$–$C_{20}$ alkyl, and
d) $C_1$–$C_6$ alkyl substituted with an unsubstituted or substituted group selected from aryl, heterocycle and $C_3$–$C_{10}$ cycloalkyl;

$R^{5a}$ is selected from:
a) a side chain of a naturally occurring amino acid, wherein the amino acid is selected from methionine and glutamine,
b) an oxidized form of a side chain of a naturally occurring amino acid which is:
  i) methionine sulfoxide, or
  ii) methionine sulfone, and
c) substituted or unsubstituted $C_1$–$C_{10}$ alkyl, $C_2$–$C_{10}$ alkenyl, $C_3$–$C_{10}$ cycloalkyl, aryl or heterocyclic group,
wherein the substituent is selected from F, Cl, Br, $CF_3$, $NO_2$, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, $N_3$, —$N(R^{10})_2$, $R^{11}OC(O)NR^{10}$— and $C_1$–$C_{20}$ alkyl, and
d) $C_1$–$C_6$ alkyl substituted with an unsubstituted or substituted group selected from aryl, heterocycle and $C_3$–$C_{10}$ cycloalkyl;

$R^{5b}$ is selected from:
a) hydrogen, and
b) $C_1$–$C_3$ alkyl;

X—Y is

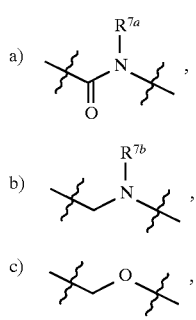

d) 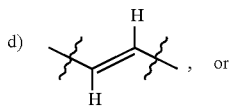, or e) —$CH_2$—$CH_2$—;

$R^{7a}$ is selected from
a) hydrogen,
b) unsubstituted or substituted aryl,
c) unsubstituted or substituted heterocycle,
d) unsubstituted or substituted $C_3$–$C_{10}$ cycloalkyl, and
e) $C_1$–$C_6$ alkyl substituted with hydrogen or an unsubstituted or substituted group selected from aryl, heterocycle and $C_3$–$C_{10}$ cycloalkyl;
  wherein heterocycle is selected from pyrrolidinyl, imidazolyl, pyridinyl, thiazolyl, pyridonyl, 2-oxopiperidinyl, indolyl, quinolinyl, isoquinolinyl, and thienyl;

$R^{7b}$ is selected from
a) hydrogen,
b) unsubstituted or substituted aryl,
c) unsubstituted or substituted heterocycle,
d) unsubstituted or substituted $C_3$–$C_{10}$ cycloalkyl,
e) $C_1$–$C_6$ alkyl substituted with hydrogen or an unsubstituted or substituted group selected from aryl, heterocycle and $C_3$–$C_{10}$ cycloalkyl,
f) a carbonyl group which is bonded to an unsubstituted or substituted group selected from aryl, heterocycle, $C_3$–$C_{10}$ cycloalkyl and $C_1$–$C_6$ alkyl substituted with hydrogen or an unsubstituted or substituted group selected from aryl, heterocycle and $C_3$–$C_{10}$ cycloalkyl, and
g) a sulfonyl group which is bonded to an unsubstituted or substituted group selected from aryl, heterocycle, $C_3$–$C_{10}$ cycloalkyl and $C_1$–$C_6$ alkyl substituted with hydrogen or an unsubstituted or substituted group selected from aryl, heterocycle and $C_3$–$C_{10}$ cycloalkyl;
wherein heterocycle is selected from pyrrolidinyl, imidazolyl, pyridinyl, thiazolyl, pyridonyl, 2-oxopiperidinyl, indolyl, quinolinyl, isoquinolinyl, and thienyl;

$R^8$ is independently selected from:
a) hydrogen,
b) $C_1$–$C_6$ alkyl, $C_2$–$C_6$ alkenyl, $C_2$–$C_6$ alkynyl, $C_1$–$C_6$ perfluoroalkyl, F, Cl, $R^{10}O$—, $R^{10}C(O)NR^{10}$—, CN, $NO_2$, $(R^{10})_2N$—$C(NR^{10})$—, $R^{10}C(O)$—, $R^{10}OC(O)$—, —$N(R^{10})_2$, or $R^{11}OC(O)NR^{10}$—, and
c) $C_1$–$C_6$ alkyl substituted by $C_1$–$C_6$ perfluoroalkyl, $R^{10}O$—, $R^{10}C(O)NR^{10}$—, $(R^{10})_2N$—$C(NR^{10})$—, $R^{10}C(O)$—, $R^{10}OC(O)$—, —$N(R^{10})_2$, or $R^{11}OC(O)NR^{10}$—;

$R^9$ is selected from:
a) hydrogen,
b) $C_2$–$C_6$ alkenyl, $C_2$–$C_6$ alkynyl, $C_1$–$C_6$ perfluoroalkyl, F, Cl, $R^{10}O$—, $R^{11}S(O)_m$—, $R^{10}C(O)NR^{10}$—, CN, $NO_2$, $(R^{10})_2N$—$C(NR^{10})$—, $R^{10}C(O)$—, $R^{10}OC(O)$—, —$N(R^{10})_2$, or $R^{11}OC(O)NR^{10}$—, and
c) $C_1$–$C_6$ alkyl unsubstituted or substituted by $C_1$–$C_6$ perfluoroalkyl, F, Cl, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, —$N(R^{10})_2$, or $R^{11}OC(O)NR^{10}$—;

$R^{10}$ is independently selected from hydrogen, $C_1$–$C_6$ alkyl, benzyl and aryl;

$R^{11}$ is independently selected from $C_1$–$C_6$ alkyl and aryl;

$A^1$ and $A^2$ are independently selected from: a bond, —CH=CH—, —C≡C—, —C(O)—, —C(O)NR$^{10}$—, O, —N(R$^{10}$)—, or S(O)$_m$;

V is selected from:
  a) hydrogen,
  b) heterocycle selected from pyrrolidinyl, imidazolyl, pyridinyl, thiazolyl, pyridonyl, 2-oxopiperidinyl, indolyl, quinolinyl, isoquinolinyl, and thienyl,
  c) aryl,
  d) $C_1$–$C_{20}$ alkyl wherein from 0 to 4 carbon atoms are replaced with a a heteroatom selected from O, S, and N, and
  e) $C_2$–$C_{20}$ alkenyl, and provided that V is not hydrogen if $A^1$ is S(O)$_m$ and V is not hydrogen if $A^1$ is a bond, n is 0 and $A^2$ is S(O)$_m$;

W is a heterocycle selected from pyrrolidinyl, imidazolyl, pyridinyl, thiazolyl, pyridonyl, 2-oxopiperidinyl, indolyl, quinolinyl, or isoquinolinyl;

Z is independently $H_2$ or O;

| | |
|---|---|
| m is | 0, 1 or 2; |
| n is | 0, 1, 2, 3 or 4; |
| p is | 0, 1, 2, 3 or 4; |
| r is | 0 to 5, provided that r is 0 when V is hydrogen; |
| t is | 4; and |
| u is | 0 or 1; | or a pharmaceutically acceptable salt thereof.

6. The compound according to claim 1 of the formula I:

i) methionine sulfoxide, or
  ii) methionine sulfone,
  c) substituted or unsubstituted $C_1$–$C_{10}$ alkyl, $C_2$–$C_{10}$ alkenyl, $C_3$–$C_{10}$ cycloalkyl, aryl or heterocyclic group,
    wherein the substituent is selected from F, Cl, Br, NO$_2$, R$^{10}$O—, R$^{11}$S(O)$_m$—, R$^{10}$C(O)NR$^{10}$—, CN, (R$^{10}$)$_2$N—C(NR$^{10}$)—, R$^{10}$C(O)—, R$^{10}$OC(O)—, N$_3$, —N(R$^{10}$)$_2$, R$^{11}$OC(O)NR$^{10}$— and $C_1$–$C_{20}$ alkyl, and
  d) $C_1$–$C_6$ alkyl substituted with an unsubstituted or substituted group selected from aryl, heterocycle and $C_3$–$C_{10}$ cycloalkyl;

$R^{5a}$ is selected from:
  a) a side chain of a naturally occurring amino acid, wherein the amino acid is selected from methionine and glutamine,
  b) an oxidized form of a side chain of a naturally occurring amino acid which is:
    i) methionine sulfoxide, or
    ii) methionine sulfone, and
  c) substituted or unsubstituted $C_1$–$C_{10}$ alkyl, $C_2$–$C_{10}$ alkenyl, $C_3$–$C_{10}$ cycloalkyl, aryl or heterocyclic group,
    wherein the substituent is selected from F, Cl, Br, CF$_3$, NO$_2$, R$^{10}$O—, R$^{11}$S(O)$_m$—, R$^{10}$C(O)NR$^{10}$—, CN, (R$^{10}$)$_2$N—C(NR$^{10}$)—, R$^{10}$C(O)—, R$^{10}$OC(O)—, N$_3$, —N(R$^{10}$)$_2$, R$^{11}$OC(O)NR$^{10}$— and $C_1$–$C_{20}$ alkyl, and
  d) $C_1$–$C_6$ alkyl substituted with an unsubstituted or substituted group selected from aryl, heterocycle and $C_3$–$C_{10}$ cycloalkyl;

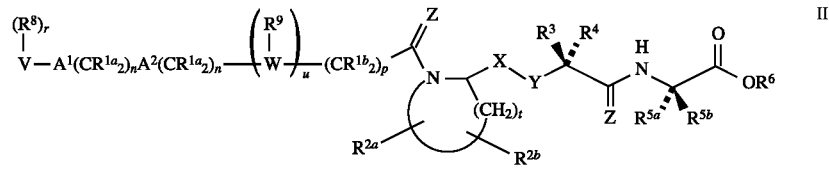

wherein:
  $R^{1a}$ is independently selected from: hydrogen or $C_1$–$C_6$ alkyl;
  $R^{1b}$ is independently selected from:
    a) hydrogen,
    b) aryl, heterocycle, $C_3$–$C_{10}$ cycloalkyl, R$^{10}$O—, —N(R$^{10}$)$_2$ or $C_2$–$C_6$ alkenyl,
    c) $C_1$–$C_6$ alkyl unsubstituted or substituted by aryl, heterocycle, $C_3$–$C_{10}$ cycloalkyl, $C_2$–$C_6$ alkenyl, R$^{10}$O—, or —N(R$^{10}$)$_2$;
  $R^{2a}$ is selected from:
    a) hydrogen,
    b) $C_1$–$C_6$ alkyl unsubstituted or substituted by $C_2$–$C_6$ alkenyl, R$^{10}$O—, R$^{11}$S(O)$_m$—, R$^{10}$C(O)NR$^{10}$—, CN, N$_3$, (R$^{10}$)$_2$N—C(NR$^{10}$)—, R$^{10}$C(O)—, R$^{10}$OC(O)—, —N(R$^{10}$)$_2$, or R$^{11}$OC(O)NR$^{10}$—,
    c) aryl, heterocycle, $C_3$–$C_{10}$ cycloalkyl, $C_2$–$C_6$ alkenyl, R$^{10}$O—, R$^{11}$S(O)$_m$—, R$^{10}$C(O)NR$^{10}$—, CN, NO$_2$, (R$^{10}$)$_2$N—C(NR$^{10}$)—, R$^{10}$C(O)—, R$^{10}$OC(O)—, N$_3$, —N(R$^{10}$)$_2$, or R$^{11}$OC(O)NR$^{10}$—, and
    d) $C_1$–$C_6$ alkyl substituted with an unsubstituted or substituted group selected from aryl, heterocyclic and $C_3$–$C_{10}$ cycloalkyl;
  $R^{2b}$ is hydrogen;
  $R^3$ and $R^4$ are independently selected from:
    a) a side chain of a naturally occurring amino acid,
    b) an oxidized form of a side chain of a naturally occurring amino acid which is:

$R^{5b}$ is selected from:
  a) hydrogen, and
  b) $C_1$–$C_3$ alkyl;

$R^6$ is
  a) substituted or unsubstituted $C_1$–$C_8$ alkyl, substituted or unsubstituted $C_5$–$C_8$ cycloalkyl, or substituted or unsubstituted cyclic amine, wherein the substituted alkyl, cycloalkyl or cyclic amine is substituted with 1 or 2 substituents independently selected from:
    1) $C_1$–$C_6$ alkyl,
    2) aryl,
    3) heterocycle,
    4) —N(R$^{11}$)$_2$,
    5) —OR$^{10}$, or b) 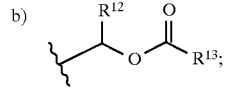

X—Y is a) 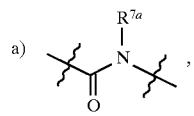

-continued b) 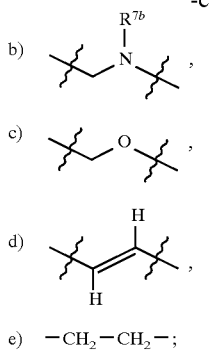

c) (structure shown)

d) (structure shown), or e) —CH$_2$—CH$_2$—;

R$^{7a}$ is selected from
a) hydrogen,
b) unsubstituted or substituted aryl,
c) unsubstituted or substituted heterocycle,
d) unsubstituted or substituted C$_3$–C$_{10}$ cycloalkyl, and
e) C$_1$–C$_6$ alkyl substituted with hydrogen or an unsubstituted or substituted group selected from aryl, heterocycle and C$_3$–C$_{10}$ cycloalkyl;
  wherein heterocycle is selected from pyrrolidinyl, imidazolyl, pyridinyl, thiazolyl, pyridonyl, 2-oxopiperidinyl, indolyl, quinolinyl, isoquinolinyl, and thienyl;

R$^{7b}$ is selected from
a) hydrogen,
b) unsubstituted or substituted aryl,
c) unsubstituted or substituted heterocycle,
d) unsubstituted or substituted C$_3$–C$_{10}$ cycloalkyl,
e) C$_1$–C$_6$ alkyl substituted with hydrogen or an unsubstituted or substituted group selected from aryl, heterocycle and C$_3$–C$_{10}$ cycloalkyl,
f) a carbonyl group which is bonded to an unsubstituted or substituted group selected from aryl, heterocycle, C$_3$–C$_{10}$ cycloalkyl and C$_1$–C$_6$ alkyl substituted with hydrogen or an unsubstituted or substituted group selected from aryl, heterocycle and C$_3$–C$_{10}$ cycloalkyl, and
g) a sulfonyl group which is bonded to an unsubstituted or substituted group selected from aryl, heterocycle, C$_3$–C$_{10}$ cycloalkyl and C$_1$–C$_6$ alkyl substituted with hydrogen or an unsubstituted or substituted group selected from aryl, heterocycle and C$_3$–C$_{10}$ cycloalkyl;
  wherein heterocycle is selected from pyrrolidinyl, imidazolyl, pyridinyl, thiazolyl, pyridonyl, 2-oxopiperidinyl, indolyl, quinolinyl, isoquinolinyl, and thienyl;

R$^8$ is independently selected from:
a) hydrogen,
b) C$_1$–C$_6$ alkyl, C$_2$–C$_6$ alkenyl, C$_2$–C$_6$ alkynyl, C$_1$–C$_6$ perfluoroalkyl, F, Cl, R$^{10}$O—, R$^{10}$C(O)NR$^{10}$—, CN, NO$_2$, (R$^{10}$)$_2$N—C(NR$^{10}$)—, R$^{10}$C(O)—, R$^{10}$OC(O)—, —N(R$^{10}$)$_2$, or R$^{11}$OC(O)NR$^{10}$—, and
c) C$_1$–C$_6$ alkyl substituted by C$_1$–C$_6$ perfluoroalkyl, R$^{10}$O—, R$^{10}$C(O)NR$^{10}$—, (R$^{10}$)$_2$N—C(NR$^{10}$)—, R$^{10}$C(O)—, R$^{10}$OC(O)—, —N(R$^{10}$)$_2$, or R$^{11}$OC(O)NR$^{10}$—;

R$^9$ is selected from:
a) hydrogen,
b) C$_2$–C$_6$ alkenyl, C$_2$–C$_6$ alkynyl, C$_1$–C$_6$ perfluoroalkyl, F, Cl, R$^{10}$O—, R$^{11}$S(O)$_m$—, R$^{10}$C(O)NR$^{10}$—, CN, NO$_2$, (R$^{10}$)$_2$N—C(NR$^{10}$)—, R$^{10}$C(O)—, R$^{10}$OC(O)—, —N(R$^{10}$)$_2$, or R$^{11}$OC(O)NR$^{10}$—, and
c) C$_1$–C$_6$ alkyl unsubstituted or substituted by C$_1$–C$_6$ perfluoroalkyl, F, Cl, R$^{10}$O—, R$^{11}$S(O)$_m$—, R$^{10}$C(O)NR$^{10}$—, CN, (R$^{10}$)$_2$N—C(NR$^{10}$)—, R$^{10}$C(O)—, R$^{10}$OC(O)—, —N(R$^{10}$)$_2$, or R$^{11}$OC(O)NR$^{10}$—;

R$^{10}$ is independently selected from hydrogen, C$_1$–C$_6$ alkyl, benzyl and aryl;

R$^{11}$ is independently selected from C$_1$–C$_6$ alkyl and aryl;

R$^{12}$ is hydrogen or C$_1$–C$_6$ alkyl;

R$^{13}$ is 1,1-dimethylethyl;

A$^1$ and A$^2$ are independently selected from: a bond, —CH=CH—, —C≡C—, —C(O)—, —C(O)NR$^{10}$—, O, —N(R$^{10}$)—, or S(O)$_m$;

V is selected from:
a) hydrogen,
b) heterocycle selected from pyrrolidinyl, imidazolyl, pyridinyl, thiazolyl, pyridonyl, 2-oxopiperidinyl, indolyl, quinolinyl, isoquinolinyl, and thienyl,
c) aryl,
d) C$_1$–C$_{20}$ alkyl wherein from 0 to 4 carbon atoms are replaced with a a heteroatom selected from O, S, and N,
e) C$_2$–C$_{20}$ alkenyl, and
provided that V is not hydrogen if A$^1$ is S(O)$_m$ and V is not hydrogen if
A$^1$ is a bond, n is 0 and A$^2$ is S(O)$_m$;

W is a heterocycle selected from pyrrolidinyl, imidazolyl, pyridinyl, thiazolyl, pyridonyl, 2-oxopiperidinyl, indolyl, quinolinyl, or isoquinolinyl;

Z is independently H$_2$ or O;

m is 0, 1 or 2;
n is 0, 1, 2, 3 or 4;
p is 0, 1, 2, 3 or 4;
r is 0 to 5, provided that r is 0 when V is hydrogen;
t is 4; and
u is 0 or 1;

or a pharmaceutically acceptable salt thereof.

7. The compound according to claim 1 of the formula I:

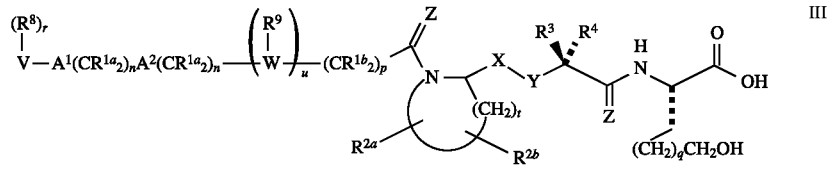

wherein:

R$^{1a}$ is independently selected from: hydrogen or C$_1$–C$_6$ alkyl;

R$^{1b}$ is independently selected from:
a) hydrogen,
b) aryl, heterocycle, C$_3$–C$_{10}$ cycloalkyl, R$^{10}$O—, —N(R$^{10}$)$_2$ or C$_2$–C$_6$ alkenyl, c) $C_1$–$C_6$ alkyl unsubstituted or substituted by aryl, heterocycle, cycloalkyl, alkenyl, $R^{10}O$—, or —$N(R^{10})_2$;

$R^{2a}$ is selected from:
a) hydrogen,
b) $C_1$–$C_6$ alkyl unsubstituted or substituted by $C_2$–$C_6$ alkenyl, $R^{10}O$—, $R^{11}S(O)_m$—, $R^{10}C(O)NR^{10}$—, CN, $N_3$, $(R^{10})_2N$—$C(NR^{10})$—, $R^{10}C(O)$—, $R^{10}OC(O)$—, —$N(R^{10})_2$, or $R^{11}OC(O)NR^{10}$—,
c) aryl, heterocycle, $C_3$–$C_{10}$ cycloalkyl, $C_2$–$C_6$ alkenyl, $R^{10}O$—, $R^{11}S(O)_m$—, $R^{10}C(O)NR^{10}$—, CN, $NO_2$, $(R^{10})_2N$—$C(NR^{10})$—, $R^{10}C(O)$—, $R^{10}OC(O)$—, $N_3$, —$N(R^{10})_2$, or $R^{11}OC(O)NR^{10}$—, and
d) $C_1$–$C_6$ alkyl substituted with an unsubstituted or substituted group selected from aryl, heterocyclic and $C_3$–$C_{10}$ cycloalkyl;

$R^{2b}$ is hydrogen;

$R^3$ and $R^4$ are independently selected from:
a) a side chain of a naturally occurring amino acid,
b) an oxidized form of a side chain of a naturally occurring amino acid which is:
  i) methionine sulfoxide, or
  ii) methionine sulfone,
c) substituted or unsubstituted $C_1$–$C_{10}$ alkyl, $C_2$–$C_{10}$ alkenyl, $C_3$–$C_{10}$ cycloalkyl, aryl or heterocycle group,
  wherein the substituent is selected from F, Cl, Br, —$NO_2$, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, $N_3$, —$N(R^{10})_2$, $R^{11}OC(O)NR^{10}$— and $C_1$–$C_{20}$ alkyl, and
d) $C_1$–$C_6$ alkyl substituted with an unsubstituted or substituted group selected from aryl, heterocycle and $C_3$–$C_{10}$ cycloalkyl;

X—Y is

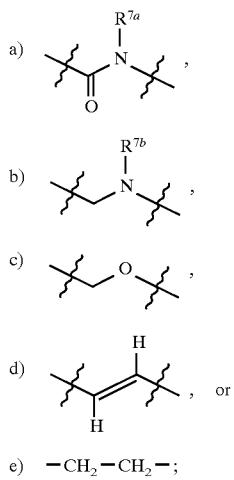

e) —$CH_2$—$CH_2$—;

$R^{7a}$ is selected from
a) hydrogen,
b) unsubstituted or substituted aryl,
c) unsubstituted or substituted heterocycle,
d) unsubstituted or substituted $C_3$–$C_{10}$ cycloalkyl, and
e) $C_1$–$C_6$ alkyl substituted with hydrogen or an unsubstituted or substituted group selected from aryl, heterocycle and $C_3$–$C_{10}$ cycloalkyl;
  wherein heterocycle is selected from pyrrolidinyl, imidazolyl, pyridinyl, thiazolyl, pyridonyl, 2-oxopiperidinyl, indolyl, quinolinyl, isoquinolinyl, and thienyl;

$R^{7b}$ is selected from
a) hydrogen,
b) unsubstituted or substituted aryl,
c) unsubstituted or substituted heterocycle,
d) unsubstituted or substituted $C_3$–$C_{10}$ cycloalkyl,
e) $C_1$–$C_6$ alkyl substituted with hydrogen or an unsubstituted or substituted group selected from aryl, heterocycle and $C_3$–$C_{10}$ cycloalkyl,
f) a carbonyl group which is bonded to an unsubstituted or substituted group selected from aryl, heterocycle, $C_3$–$C_{10}$ cycloalkyl and $C_1$–$C_6$ alkyl substituted with hydrogen or an unsubstituted or substituted group selected from aryl, heterocycle and $C_3$–$C_{10}$ cycloalkyl, and
g) a sulfonyl group which is bonded to an unsubstituted or substituted group selected from aryl, heterocycle, $C_3$–$C_{10}$ cycloalkyl and $C_1$–$C_6$ alkyl substituted with hydrogen or an unsubstituted or substituted group selected from aryl, heterocycle and $C_3$–$C_{10}$ cycloalkyl;
  wherein heterocycle is selected from pyrrolidinyl, imidazolyl, pyridinyl, thiazolyl, pyridonyl, 2-oxopiperidinyl, indolyl, quinolinyl, isoquinolinyl, and thienyl;

$R^8$ is independently selected from:
a) hydrogen,
b) $C_1$–$C_6$ alkyl, $C_2$–$C_6$ alkenyl, $C_2$–$C_6$ alkynyl, $C_1$–$C_6$ perfluoroalkyl, F, Cl, $R^{10}O$—, $R^{10}C(O)NR^{10}$—, CN, $NO_2$, $(R^{10})_2N$—$C(NR^{10})$—, $R^{10}C(O)$—, $R^{10}OC(O)$—, —$N(R^{10})_2$, or $R^{11}OC(O)NR^{10}$—, and
c) $C_1$–$C_6$ alkyl substituted by $C_1$–$C_6$ perfluoroalkyl, $R^{10}O$—, $R^{10}C(O)NR^{10}$—, $(R^{10})_2N$—$C(NR^{10})$—, $R^{10}C(O)$—, $R^{10}OC(O)$—, —$N(R^{10})_2$, or $R^{11}OC(O)NR^{10}$—;

$R^9$ is selected from:
a) hydrogen,
b) $C_2$–$C_6$ alkenyl, $C_2$–$C_6$ alkynyl, $C_1$–$C_6$ perfluoroalkyl, F, Cl, $R^{10}O$—, $R^{11}S(O)_m$—, $R^{10}C(O)NR^{10}$—, CN, $NO_2$, $(R^{10})_2N$—$C(NR^{10})$—, $R^{10}C(O)$—, $R^{10}OC(O)$—, —$N(R^{10})_2$, or $R^{11}OC(O)NR^{10}$—, and
c) $C_1$–$C_6$ alkyl unsubstituted or substituted by $C_1$–$C_6$ perfluoroalkyl, F, Cl, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, —$N(R^{10})_2$, or $R^{11}OC(O)NR^{10}$—;

$R^{10}$ is independently selected from hydrogen, $C_1$–$C_6$ alkyl, benzyl and aryl;

$R^{11}$ is independently selected from $C_1$–$C_6$ alkyl and aryl;

$A^1$ and $A^2$ are independently selected from: a bond, —CH=CH—, —C≡C—, —C(O)—, —C(O)NR$^{10}$—, O, —N(R$^{10}$)—, or S(O)$_m$;

V is selected from:
a) hydrogen,
b) heterocycle selected from pyrrolidinyl, imidazolyl, pyridinyl, thiazolyl, pyridonyl, 2-oxopiperidinyl, indolyl, quinolinyl, isoquinolinyl, and thienyl,
c) aryl,
d) $C_1$–$C_{20}$ alkyl wherein from 0 to 4 carbon atoms are replaced with a a heteroatom selected from O, S, and N, and
e) $C_2$–$C_{20}$ alkenyl, and
provided that V is not hydrogen if $A^1$ is $S(O)_m$ and V is not hydrogen if
  $A^1$ is a bond, n is 0 and $A^2$ is $S(O)_m$;

W is a heterocycle selected from pyrrolidinyl, imidazolyl, pyridinyl, thiazolyl, pyridonyl, 2-oxopiperidinyl, indolyl, quinolinyl, or isoquinolinyl;

Z is independently H₂ or O;

m is    0, 1 or 2;
n is    0, 1, 2, 3 or 4;
p is    0, 1, 2, 3 or 4;
q is    0, 1 or 2;
r is    0 to 5, provided that r is 0 when V is hydrogen;
t is    4; and
u is    0 or 1;

or a pharmaceutically acceptable salt thereof.

8. A compound of formula IV:

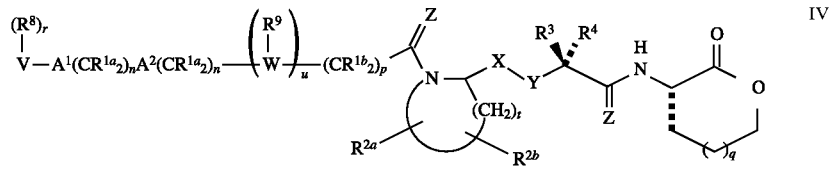

wherein:

$R^{1a}$ is independently selected from: hydrogen or $C_1$–$C_6$ alkyl;

$R^{1b}$ is independently selected from:
   a) hydrogen,
   b) aryl, heterocycle, $C_3$–$C_{10}$ cycloalkyl, $R^{10}O$—, —N($R^{10}$)$_2$ or $C_2$–$C_6$ alkenyl,
   c) $C_1$–$C_6$ alkyl unsubstituted or substituted by aryl, heterocycle, $C_3$–$C_{10}$ cycloalkyl, $C_2$–$C_6$ alkenyl, $R^{10}O$—, or —N($R^{10}$)$_2$;

$R^{2a}$ is selected from:
   a) hydrogen,
   b) $C_1$–$C_6$ alkyl unsubstituted or substituted by $C_2$–$C_6$ alkenyl, $R^{10}O$—, $R^{11}S(O)_m$—, $R^{10}C(O)NR^{10}$—, CN, N$_3$, ($R^{10}$)$_2$N—C(NR$^{10}$)—, $R^{10}C(O)$—, $R^{10}OC(O)$—, —N($R^{10}$)$_2$, or $R^{11}OC(O)NR^{10}$—,
   c) aryl, heterocycle, $C_3$–$C_{10}$ cycloalkyl, $C_2$–$C_6$ alkenyl, $R^{10}O$—, $R^{11}S(O)_m$—, $R^{10}C(O)NR^{10}$—, CN, NO$_2$, ($R^{10}$)$_2$N—C(NR$^{10}$)—, $R^{10}C(O)$—, $R^{10}OC(O)$—, N$_3$, —N($R^{10}$)$_2$, or $R^{11}OC(O)NR^{10}$—, and
   d) $C_1$–$C_6$ alkyl substituted with an unsubstituted or substituted group selected from aryl, heterocyclic and $C_3$–$C_{10}$cycloalkyl;

$R^{2b}$ is hydrogen;

$R^3$ and $R^4$ are independently selected from:
   a) a side chain of a naturally occurring amino acid,
   b) an oxidized form of a side chain of a naturally occurring amino acid which is:
      i) methionine sulfoxide, or
      ii) methionine sulfone,
   c) substituted or unsubstituted $C_1$–$C_{10}$ alkyl, $C_2$–$C_{10}$ alkenyl, $C_3$–$C_{10}$ cycloalkyl, aryl or heterocycle group,
      wherein the substituent is selected from F, Cl, Br, NO$_2$, $R^{10}O$—, $R^{11}S(O)_m$—, $R^{10}C(O)NR^{10}$—, CN, ($R^{10}$)$_2$N—C(NR$^{10}$)—, $R^{10}C(O)$—, $R^{10}OC(O)$—, N$_3$, —N($R^{10}$)$_2$, $R^{11}OC(O)NR^{10}$— and $C_1$–$C_{20}$ alkyl, and
   d) $C_1$–$C_6$ alkyl substituted with an unsubstituted or substituted group selected from aryl, heterocycle and $C_3$–$C_{10}$ cycloalkyl;

X—Y is a) 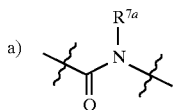

-continued b) 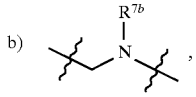

c) 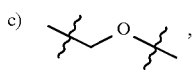

d) 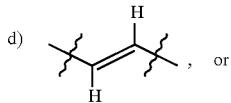, or e) —CH$_2$—CH$_2$—;

$R^{7a}$ is selected from
   a) hydrogen,
   b) unsubstituted or substituted aryl,
   c) unsubstituted or substituted heterocycle,
   d) unsubstituted or substituted $C_3$–$C_{10}$ cycloalkyl, and
   e) $C_1$–$C_6$ alkyl substituted with hydrogen or an unsubstituted or substituted group selected from aryl, heterocycle and $C_3$–$C_{10}$ cycloalkyl;
      wherein heterocycle is selected from pyrrolidinyl, imidazolyl, pyridinyl, thiazolyl, pyridonyl, 2-oxopiperidinyl, indolyl, quinolinyl, isoquinolinyl, and thienyl;

$R^{7b}$ is selected from
   a) hydrogen,
   b) unsubstituted or substituted aryl,
   c) unsubstituted or substituted heterocycle,
   d) unsubstituted or substituted $C_3$–$C_{10}$ cycloalkyl,
   e) $C_1$–$C_6$ alkyl substituted with hydrogen or an unsubstituted or substituted group selected from aryl, heterocycle and $C_3$–$C_{10}$ cycloalkyl,
   f) a carbonyl group which is bonded to an unsubstituted or substituted group selected from aryl, heterocycle, $C_3$–$C_{10}$ cycloalkyl and $C_1$–$C_6$ alkyl substituted with hydrogen or an unsubstituted or substituted group selected from aryl, heterocycle and $C_3$–$C_{10}$ cycloalkyl, and
   g) a sulfonyl group which is bonded to an unsubstituted or substituted group selected from aryl, heterocycle, $C_3$–$C_{10}$ cycloalkyl and $C_1$–$C_6$ alkyl substituted with hydrogen or an unsubstituted or substituted group selected from aryl, heterocycle and $C_3$–$C_{10}$ cycloalkyl;
      wherein heterocycle is selected from pyrrolidinyl, imidazolyl, pyridinyl, thiazolyl, pyridonyl, 2-oxopiperidinyl, indolyl, quinolinyl, isoquinolinyl, and thienyl;

$R^8$ is independently selected from:
a) hydrogen,
b) $C_1$–$C_6$ alkyl, $C_2$–$C_6$ alkenyl, $C_2$–$C_6$ alkynyl, $C_1$–$C_6$ perfluoroalkyl, F, Cl, $R^{10}$O—, $R^{10}$C(O)$NR^{10}$—, CN, $NO_2$, $(R^{10})_2$N—C($NR^{10}$)—, $R^{10}$C(O)—, $R^{10}$OC(O)—, —$N(R^{10})_2$, or $R^{11}$OC(O)$NR^{10}$—, and
c) $C_1$–$C_6$ alkyl substituted by $C_1$–$C_6$ perfluoroalkyl, $R^{10}$O—, $R^{10}$C(O)$NR^{10}$—, $(R^{10})_2$N—C($NR^{10}$)—, $R^{10}$C(O)—, $R^{10}$OC(O)—, —$N(R^{10})_2$, or $R^{11}$OC(O)$NR^{10}$—;

$R^9$ is selected from:
a) hydrogen,
b) $C_2$–$C_6$ alkenyl, $C_2$–$C_6$ alkynyl, $C_1$–$C_6$ perfluoroalkyl, F, Cl, $R^{10}$O—, $R^{11}$S(O)$_m$—, $R^{10}$C(O)$NR^{10}$—, CN, $NO_2$, $(R^{10})_2$N—C($NR^{10}$)—, $R^{10}$C(O)—, $R^{10}$OC(O)—, —$N(R^{10})_2$, or $R^{11}$OC(O)$NR^{10}$—, and
c) $C_1$–$C_6$ alkyl unsubstituted or substituted by $C_1$–$C_6$ perfluoroalkyl, F, Cl, $R^{10}$O—, $R^{11}$S(O)$_m$—, $R^{10}$C(O)$NR^{10}$—, CN, $(R^{10})_2$N—C($NR^{10}$)—, $R^{10}$C(O)—, $R^{10}$OC(O)—, —$N(R^{10})_2$, or $R^{11}$OC(O)$NR^{10}$—;

$R^{10}$ is independently selected from hydrogen, $C_1$–$C_6$ alkyl, benzyl and aryl;

$R^{11}$ is independently selected from $C_1$–$C_6$ alkyl and aryl;

$A^1$ and $A^2$ are independently selected from: a bond, —CH=CH—, —C≡C—, —C(O)—, —C(O)$NR^{10}$—, O, —$N(R^{10})$—, or S(O)$_m$;

V is selected from:
a) hydrogen,
b) heterocycle selected from pyrrolidinyl, imidazolyl, pyridinyl, thiazolyl, pyridonyl, 2-oxopiperidinyl, indolyl, quinolinyl, isoquinolinyl, and thienyl,
c) aryl,
d) $C_1$–$C_{20}$ alkyl wherein from 0 to 4 carbon atoms are replaced with a a heteroatom selected from O, S, and N, and
e) $C_2$–$C_{20}$ alkenyl, and
provided that V is not hydrogen if $A^1$ is S(O)$_m$ and V is not hydrogen if $A^1$ is a bond, n is 0 and $A^2$ is S(O)$_m$;

W is a heterocycle selected from pyrrolidinyl, imidazolyl, pyridinyl, thiazolyl, pyridonyl, 2-oxopiperidinyl, indolyl, quinolinyl, or isoquinolinyl;

Z is independently $H_2$ or O;

m is 0, 1 or 2;

n is 0, 1, 2, 3 or 4;

p is 0, 1, 2, 3 or 4;

q is 0, 1 or 2;

r is 0 to 5, provided that r is 0 when V is hydrogen;

t is 4; and u is 0 or 1;

or a pharmaceutically acceptable salt thereof.

9. A compound which inhibits farnesyl-protein transferase which is:

N-[1-(1H-Imidazol-4-ylacetyl)piperidin-2(S)-ylmethyl]-N-(1-naphthylmethyl)glycyl-methionine methyl ester;

N-[1-(1H-Imidazol-4-ylacetyl)piperidin-2(S)-ylmethyl]-N-(1-naphthylmethyl)glycyl-methionine;

N-[1-(1H-Imidazol-4-ylacetyl)piperidin-2(S)-ylmethyl]-N-(1-naphthylmethyl)glycyl-methionine isopropyl ester;

N-[1-(1H-Imidazol-4-ylacetyl)piperidin-2(S)-ylmethyl]-N-(2-methoxybenzyl)glycyl-methionine;

N-[1-(1H-Imidazol-4-ylacetyl)piperidin-2(S)-ylmethyl]-N-(2-methoxybenzyl)glycyl-methionine isopropyl ester;

N-[1-(1H-Imidazol-4-ylpropionyl)piperidin-2(S)-ylmethyl]-N-(2-methoxybenzyl)glycyl-methionine methyl ester;

N-[1-(1H-Imidazol-4-ylpropionyl)piperidin-2(S)-ylmethyl]-N-(2-methoxybenzyl)glycyl-methionine;

or a pharmaceutically acceptable salt thereof.

10. The compound according to claim 9 which inhibits farnesyl-protein transferase which is:

N-[1-(1H-Imidazol-4-ylacetyl)piperidin-2(S)-ylmethyl]-N-(2-methoxybenzyl)glycyl-methionine

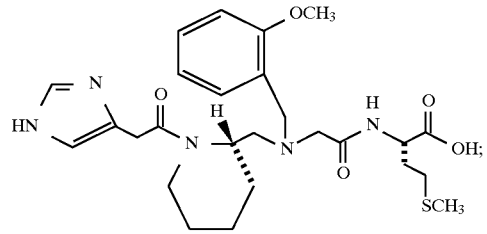

or a pharmaceutically acceptable salt thereof.

11. The compound according to claim 9 which inhibits farnesyl-protein transferase which is:

N-[1-(1H-Imidazol-4-ylacetyl)piperidin-2(S)-ylmethyl]-N-(2-methoxybenzyl)glycyl-methionine isopropyl ester

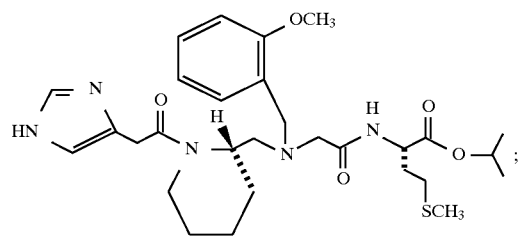

or a pharmaceutically acceptable salt thereof.

12. A pharmaceutical composition comprising a pharmaceutical carrier, and dispersed therein, a therapeutically effective amount of a compound of claim 1.

13. A pharmaceutical composition comprising a pharmaceutical carrier, and dispersed therein, a therapeutically effective amount of a compound of claim 2.

14. A pharmaceutical composition comprising a pharmaceutical carrier, and dispersed therein, a therapeutically effective amount of a compound of claim 3.

15. A pharmaceutical composition comprising a pharmaceutical carrier, and dispersed therein, a therapeutically effective amount of a compound of claim 4.

16. A pharmaceutical composition comprising a pharmaceutical carrier, and dispersed therein, a therapeutically effective amount of a compound of claim 9.

17. A method for inhibiting farnesyl-protein transferase which comprises administering to a mammal in need thereof a therapeutically effective amount of the composition of claim 12.

18. A method for inhibiting farnesyl-protein transferase which comprises administering to a mammal in need thereof a therapeutically effective amount of the composition of claim 13.

19. A method for inhibiting farnesyl-protein transferase which comprises administering to a mammal in need thereof a therapeutically effective amount of the composition of claim 14.

20. A method for inhibiting farnesyl-protein transferase which comprises administering to a mammal in need thereof a therapeutically effective amount of the composition of claim 15.

21. A method for inhibiting farnesyl-protein transferase which comprises administering to a mammal in need thereof a therapeutically effective amount of the composition of claim 16.

22. A method for treating cancer which comprises administering to a mammal in need thereof a therapeutically effective amount of a composition of claim 12.

23. A method for treating cancer which comprises administering to a mammal in need thereof a therapeutically effective amount of a composition of claim 13.

24. A method for treating cancer which comprises administering to a mammal in need thereof a therapeutically effective amount of a composition of claim 14.

25. A method for treating cancer which comprises administering to a mammal in need thereof a therapeutically effective amount of a composition of claim 16.

26. A method for treating cancer which comprises administering to a mammal in need thereof a therapeutically effective amount of a composition of claim 16.

* * * * *

UNITED STATES PATENT AND TRADEMARK OFFICE
CERTIFICATE OF CORRECTION

PATENT NO. : 5,872,135
DATED : February 16, 1999
INVENTOR(S) : S. Jane deSolms

It is certified that error appears in the above-identified patent and that said Letters Patent is hereby corrected as shown below:

On the cover page, item [73] entitled "Assignee," Merk & Co., Inc., Rahway, N.J. should read Merck & Co., Inc., Rahway, N.J.

(1) At claim 1, column 97, at lines 21-28, the structure should be:

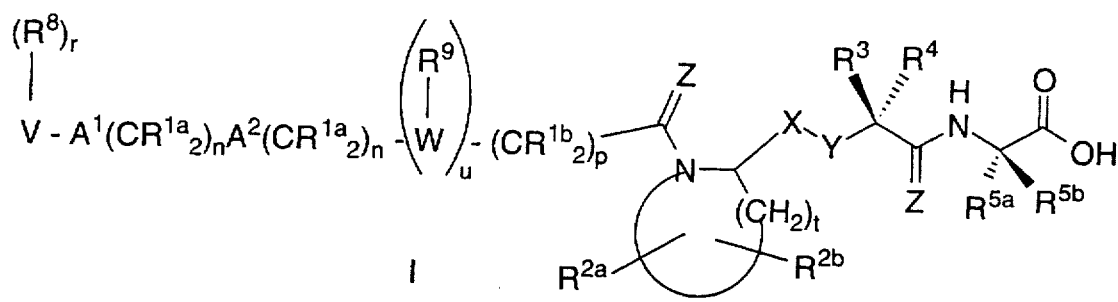

Signed and Sealed this

Thirteenth Day of July, 1999

Attest:

Q. TODD DICKINSON

Attesting Officer

Acting Commissioner of Patents and Trademarks

UNITED STATES PATENT AND TRADEMARK OFFICE
CERTIFICATE OF CORRECTION

PATENT NO. : 5,872,135
DATED : February 16, 1999
INVENTOR(S) : S. Jane deSolms

It is certified that error appears in the above-identified patent and that said Letters Patent is hereby corrected as shown below:

In Column 44, at lines 58-63, the structure should be:

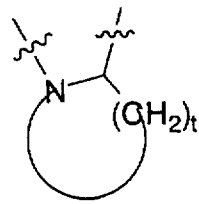

Signed and Sealed this

Twenty-fourth Day of August, 1999

Attest:

Q. TODD DICKINSON

*Attesting Officer*       *Acting Commissioner of Patents and Trademarks*